US012766200B2

(12) United States Patent
Qiao et al.

(10) Patent No.: US 12,766,200 B2
(45) **Date of Patent: *Oct. 20, 2026**

(54) TREATMENT OF DYSTROPHINOPATHIES WITH MICRODYSTROPHIN GENE THERAPY CONSTRUCTS

(71) Applicant: REGENXBIO INC., Rockville, MD (US)

(72) Inventors: Chunping Qiao, Rockville, MD (US); Devin McDougald, Boston, MA (US); Ye Liu, Clarksville, MD (US); Olivier Danos, Princeton, NJ (US)

(73) Assignee: REGENXBIO INC., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/234,245

(22) Filed: Jun. 10, 2025

(65) Prior Publication Data

US 2025/0367327 A1 Dec. 4, 2025

Related U.S. Application Data

(63) Continuation of application No. 17/778,651, filed as application No. PCT/US2020/062484 on Nov. 27, 2020, now Pat. No. 12,697,399.

(60) Provisional application No. 63/024,933, filed on May 14, 2020, provisional application No. 62/941,719, filed on Nov. 28, 2019.

(51) Int. Cl.

| | |
|---|---|
| ***A61K 48/00*** | (2006.01) |
| ***A61P 21/00*** | (2006.01) |
| ***C07K 14/47*** | (2006.01) |
| ***C12N 15/86*** | (2006.01) |

(52) U.S. Cl.

CPC .......... *A61K 48/0058* (2013.01); *A61P 21/00* (2018.01); *C07K 14/4708* (2013.01); *C12N 15/86* (2013.01); *C12N 2750/14143* (2013.01); *C12N 2750/14151* (2013.01); *C12N 2750/14171* (2013.01)

(58) Field of Classification Search

CPC . A61K 48/0058; A61P 21/00; C07K 14/4708; C12N 15/86; C12N 2750/14143

See application file for complete search history.

(56) References Cited

U.S. PATENT DOCUMENTS

| | | | | |
|---|---|---|---|---|
| 6,596,535 | B1 | 7/2003 | Carter | |
| 6,869,777 | B2 | 3/2005 | Chamberlain et al. | |
| 7,001,761 | B2 | 2/2006 | Xiao | |
| 7,125,717 | B2 | 10/2006 | Carter | |
| 7,282,199 | B2 | 10/2007 | Gao et al. | |
| 7,456,683 | B2 | 11/2008 | Takano et al. | |
| 7,510,867 | B2 | 3/2009 | Xiao | |
| 7,790,449 | B2 | 9/2010 | Gao et al. | |
| 7,892,824 | B2 | 2/2011 | Duan et al. | |
| 7,906,111 | B2 | 3/2011 | Wilson et al. | |
| 8,236,557 | B2 | 8/2012 | Dongsheng et al. | |
| 8,318,480 | B2 | 11/2012 | Gao et al. | |
| 8,501,920 | B2 | 8/2013 | Chamberlain et al. | |
| 8,524,446 | B2 | 9/2013 | Gao et al. | |
| 8,628,966 | B2 | 1/2014 | Chatterjee et al. | |
| 8,734,809 | B2 | 5/2014 | Gao et al. | |
| 8,927,514 | B2 | 1/2015 | Chatterjee et al. | |
| 8,962,332 | B2 | 2/2015 | Gao et al. | |
| 8,999,678 | B2 | 4/2015 | Vandenberghe et al. | |
| 9,169,299 | B2 | 10/2015 | Lisowski et al. | |
| 9,193,956 | B2 | 11/2015 | Schaffer et al. | |
| 9,266,964 | B2 | 2/2016 | Sexton et al. | |
| 9,284,357 | B2 | 3/2016 | Gao et al. | |
| 9,409,953 | B2 | 8/2016 | Asokan et al. | |
| 9,458,517 | B2 | 10/2016 | Schaffer et al. | |
| 9,585,971 | B2 | 3/2017 | Deverman et al. | |
| 9,587,282 | B2 | 3/2017 | Schaffer et al. | |
| 9,624,282 | B2 | 4/2017 | Lai et al. | |
| 9,840,719 | B2 | 12/2017 | High et al. | |
| 9,923,120 | B2 | 3/2018 | Minato | |
| 10,166,272 | B2 | 1/2019 | Dickson et al. | |
| 10,351,611 | B2 | 7/2019 | Lai et al. | |
| 10,428,158 | B2 | 10/2019 | Conley et al. | |
| 10,479,821 | B2 | 11/2019 | Chamberlain et al. | |
| 10,647,751 | B2 * | 5/2020 | Dickson | C12N 15/861 |
| 10,786,546 | B2 | 9/2020 | Dickson et al. | |
| 11,547,765 | B2 | 1/2023 | Xiao et al. | |
| 2003/0138772 | A1 * | 7/2003 | Gao | C07K 14/005 435/456 |

(Continued)

FOREIGN PATENT DOCUMENTS

| | | |
|---|---|---|
| WO | 0183695 | 4/2001 |
| WO | 200229056 | 10/2001 |

(Continued)

OTHER PUBLICATIONS

Duan (Hum Gene Ther. Jul. 1, 2018;29(7):733-736. doi: 10.1089/hum.2018.012) (Year: 2018).*

Banks et al. (PLoS Genet. May 20, 2010;6(5):e1000958. doi: 10.1371/journal.pgen.1000958.) (Year: 2010).*

Ramos et al. (Mol Ther. Mar. 6, 2019;27(3):623-635. doi: 10.1016/j.ymthe.2019.01.002. Epub Feb. 1, 2019.) (Year: 2019).*

Adams ME, Kramarcy N, Krall SP, et al. Absence of alpha-syntrophin leads to structurally aberrant neuromuscular synapses deficient in utrophin. J Cell Biol Sep. 18, 2000;150(6):1385-98. doi: 10.1083/jcb.150.6.1385.

Ahmad, A., Brinson, M., Hodges, B.L., Chamberlain, U.S., and Amalfitano, A. (2000). Mdx mice inducibly expressing dystrophin provide insights into the potential of gene therapy for duchenne muscular dystrophy. Hum Mol Genet 9, 2507-15.

(Continued)

*Primary Examiner* — Fereydoun G Sajjadi
*Assistant Examiner* — Joel D Levin
(74) *Attorney, Agent, or Firm* — Ballard Spahr LLP

(57) ABSTRACT

Provided are gene constructs that encode a microdystrophin protein for use in gene therapy. The microdystrophin gene constructs and expression cassettes were engineered for improved therapy with respect to efficacy, potency and safety to the subject when expressed by a viral vector in muscle cells and/or CNS cells.

46 Claims, 34 Drawing Sheets

Figure 1A:
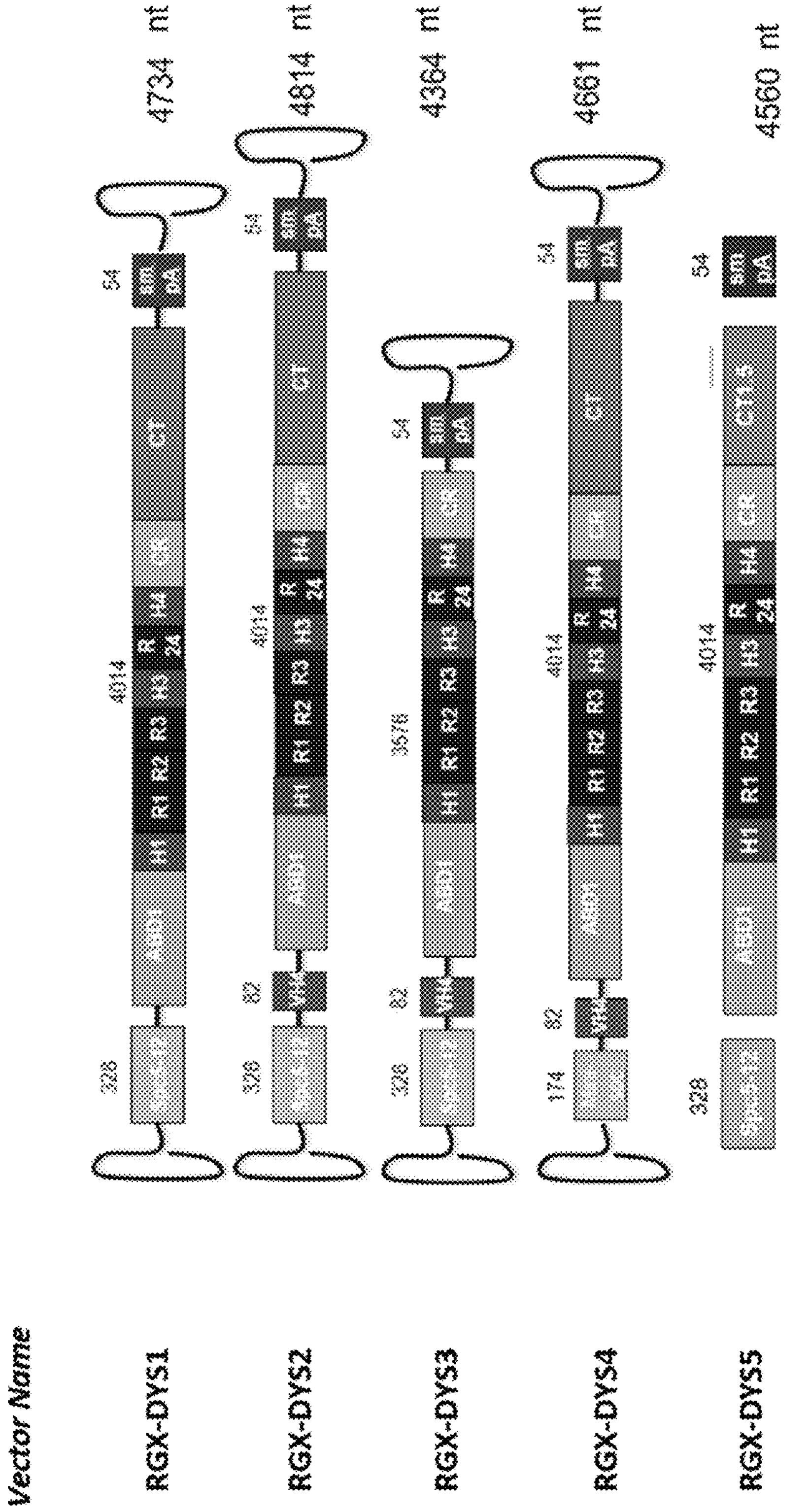

Specification includes a Sequence Listing.

(56) References Cited

U.S. PATENT DOCUMENTS

| | | | |
|---|---|---|---|
| 2007/0036760 | A1* | 2/2007 | Wilson ................. C07K 14/705 435/235.1 |
| 2008/0249052 | A1 | 10/2008 | Duan et al. |
| 2013/0224836 | A1 | 8/2013 | Muramatsu |
| 2015/0023924 | A1 | 1/2015 | High et al. |
| 2015/0126588 | A1 | 5/2015 | Nakai et al. |
| 2015/0362493 | A1 | 12/2015 | Sexton et al. |
| 2015/0374803 | A1 | 12/2015 | Wolfe |
| 2016/0017055 | A1 | 1/2016 | Nixon et al. |
| 2016/0215024 | A1 | 7/2016 | Vandenberghe et al. |
| 2016/0376323 | A1 | 12/2016 | Schaffer et al. |
| 2017/0002094 | A1 | 1/2017 | Sexton et al. |
| 2017/0051257 | A1 | 2/2017 | Vandenberghe et al. |
| 2017/0067908 | A1 | 3/2017 | Nakai et al. |
| 2017/0368198 | A1 | 12/2017 | Xiao et al. |
| 2018/0118851 | A1 | 5/2018 | Comeau et al. |
| 2018/0298110 | A1 | 10/2018 | Chyung et al. |
| 2018/0362664 | A1 | 12/2018 | Adelman et al. |
| 2019/0055581 | A1 | 2/2019 | Rodino-Klapac et al. |
| 2019/0060489 | A1 | 2/2019 | Rodino-Klapac et al. |
| 2019/0184033 | A1 | 6/2019 | Duan et al. |
| 2019/0185580 | A1 | 6/2019 | Nixon et al. |
| 2019/0194713 | A1 | 6/2019 | Mandell et al. |
| 2019/0241961 | A1 | 8/2019 | Sexton et al. |
| 2019/0361036 | A1 | 11/2019 | Sexton et al. |
| 2020/0031890 | A1 | 1/2020 | Chamberlain et al. |
| 2020/0078473 | A1 | 3/2020 | Lochmuller et al. |
| 2020/0093939 | A1 | 3/2020 | Danos et al. |
| 2020/0095298 | A1 | 3/2020 | Chamberlain et al. |
| 2020/0109214 | A1 | 4/2020 | Lu et al. |
| 2020/0199621 | A1 | 6/2020 | Rodino-Klapac et al. |
| 2020/0317815 | A1 | 10/2020 | Mendivil Medina |
| 2020/0354449 | A1 | 11/2020 | Grawunder et al. |
| 2020/0376141 | A1 | 12/2020 | Xiao et al. |
| 2020/0393464 | A1 | 12/2020 | Joseph et al. |
| 2020/0405810 | A1 | 12/2020 | Dickson et al. |
| 2021/0155956 | A1 | 5/2021 | Stedman |
| 2022/0204574 | A1 | 6/2022 | Richard et al. |

FOREIGN PATENT DOCUMENTS

| | | | |
|---|---|---|---|
| WO | 2003042397 | | 5/2003 |
| WO | 2003052051 | | 6/2003 |
| WO | 2005033321 | A2 | 4/2005 |
| WO | 2006110689 | A2 | 10/2006 |
| WO | 2008088895 | A2 | 7/2008 |
| WO | 2009104964 | A1 | 8/2009 |
| WO | 2010080833 | A1 | 7/2010 |
| WO | 2010127097 | A1 | 11/2010 |
| WO | 2014172669 | A1 | 10/2014 |
| WO | 2015013313 | A2 | 1/2015 |
| WO | 2015082570 | A1 | 6/2015 |
| WO | 2015121501 | A1 | 8/2015 |
| WO | 2015191508 | A1 | 12/2015 |
| WO | 2015197232 | A1 | 12/2015 |
| WO | 2015197869 | A1 | 12/2015 |
| WO | 2016049230 | A1 | 3/2016 |
| WO | 2016115543 | A2 | 7/2016 |
| WO | 2016177911 | A1 | 11/2016 |
| WO | 2017070170 | A1 | 4/2017 |
| WO | 2017070491 | A1 | 4/2017 |
| WO | 2017181011 | A1 | 10/2017 |
| WO | 2017181014 | A1 | 10/2017 |
| WO | 2017181015 | A1 | 10/2017 |
| WO | 2017186928 | A1 | 11/2017 |
| WO | 2017189959 | A1 | 11/2017 |
| WO | 2017221145 | A1 | 12/2017 |
| WO | 2017223128 | A1 | 12/2017 |
| WO | 2018053244 | A1 | 3/2018 |
| WO | 2019012336 | | 3/2018 |
| WO | 2018170408 | A1 | 9/2018 |
| WO | 2019154939 | A1 | 8/2019 |
| WO | 2019161059 | A1 | 8/2019 |
| WO | 2019195362 | A1 | 10/2019 |
| WO | 2019245973 | A1 | 12/2019 |
| WO | 2020086844 | A1 | 4/2020 |
| WO | 2020113164 | A1 | 6/2020 |
| WO | 2020212710 | A1 | 10/2020 |
| WO | 2020219868 | A1 | 10/2020 |
| WO | 2020227515 | A1 | 11/2020 |
| WO | 2020252136 | A1 | 12/2020 |
| WO | 2020261178 | A1 | 12/2020 |
| WO | 2021021661 | A1 | 2/2021 |
| WO | 2022232141 | A1 | 11/2022 |
| WO | 2022241030 | A1 | 11/2022 |
| WO | 2023004331 | A1 | 1/2023 |

OTHER PUBLICATIONS

Ahn, A.H., and Kunkel, L.M. (1995). Syntrophin binds to an alternatively spliced exon of dystrophin. J Cell Biol 128, 363-71.

Athanasopoulos T, Foster H, Foster K, Dickson G. Codon optimization of the microdystrophin gene for Duchene muscular dystrophy gene therapy. Methods Mol Biol 2011;709:21-37. doi: 10.1007/978-1-61737-982-6_2.

Beekman C, Janson AA, Baghat A, et al. Use of capillary Western immunoassay (Wes) for quantification of dystrophin levels in skeletal muscle of healthy controls and individuals with Becker and Duchenne muscular dystrophy. PLoS One Apr. 11, 2018;13(4):e0195850. doi: 10.1371/journal.pone.0195850.

Blake, D.J., Tinsley, J.M., Davies, K.E., Knight, A.E., Winder, S.J., and Kendrick-Jones, J. (1995). Coiled-coil regions in the carboxy-terminal domains of dystrophin and related proteins: potentials for protein-protein interactions. Trends Biochem Sci 20, 133-5.

Ehmsen J., Poon E., Davies K., The dystrophin-associated protein complex. J Cell Sci 2002; 115: 2801-2803.

England, S.B., Nicholson, L.V., Johnson, M.A., Forrest, S.M., Love, D.R., Zubrzycka-Gaarn, E.E., Bulman, D.E., Harris, J.B., and Davies, K.E. (1990). Very mi ld muscular dystrophy associated with the deletion of 46% of dystrophin. Nature 343, 180-2.

Finder J, Mayer OH, Sheehan D, Sawnani H, Abresch RT, Benditt J, Birnkrant DJ, Duong T, Henricson E, Kinnett K, McDonald CM, Connolly AM. Pulmonary Endpoints in Duchenne Muscular Dystrophy. A Workshop Summary. Am J Respir Crit Care ed. Aug. 15, 2017;196(4):512-519. doi: 10.1164/rccm.201703-0507WS.

Godfrey, C, Muses, S., McClorey, G., Well S, K.E., Coursindel, T., Terry, R.L., Betts, C, Hammond, S., O'Donovan, L., Hildyard, J., et al. (2015). How much dystrophin is enough: the physiological consequences of different levels of dystrophin in the mdx mouse. Hum Mol Genet 24, 4225-37.

Grady RM, Grange RW, Lau KS, et al. Role for alpha-dystrobrevin in the pathogenesis of dystrophin-dependent muscular dystrophies. Nat Cell Biol Aug. 1999;1(4):215-20. doi: 10.1038/12034.

Hoffman EP, Brown RH Jr, Kunkel LM. Dystrophin: the protein product of the Duchenne muscular dystrophy locus. Cell. 1987;51(6):919-928. doi:10.1016/0092-8674(87)90579-4.

Hosaka Y, Yokota T, Miyagoe-Suzuki Y, et al. Alpha1-syntrophin-deficient skeletal muscle exhibits hypertrophy and aberrant formation of neuromuscular junctions during regeneration. J Cell Biol Sep. 16, 2002, 158(6):1097-107. doi: 10.1083/jcb.200204076.

Jung, D., Yang, B., Meyer, J., Chamberlain, J.S., and Campbell, K.P. (1995). Identification and characterization of the dystrophin anchoring site on beta-dystroglycan. J Biol Chem 270, 27305-10.

Kieny P, Chollet S, Delalande P, Le Fort M, Magot A, Pereon Y, Perrouin Verbe B. Evolution of life expectancy of patients with Duchenne muscular dystrophy at AFM Yolaine de Kepper centre between 1981 and 2011. Ann Phys Rehabil Med. Sep. 2013;56(6):443-454. :10.1016/j.rehab.2013.06.002.

Koenig M, Hoffman EP, Bertelson CJ, Monaco AP, Feener C, Kunkel LM. Complete cloning of the Duchenne muscular dystrophy (DMD) cDNA and preliminary genomic organization of the DMD gene in normal and affected individuals. Cell. 1987;50(3):509-517. doi:10.1016/0092-8674(87)90504-6.

Mah JK, Korngut L, Dykeman J, Day L, Pringsheim T, Jette N. A systematic review and metaanalysis on the epidemiology of Duchenne and Becker muscular dystrophy. Neuromuscul Disord. 2014;24(6):482-491. doi:10.1016/j.nmd.2014.03.008.

(56) References Cited

OTHER PUBLICATIONS

Matsumura, K., Burghes, A.H., Mora, M., Tome, F.M., Morandi, L., Cornelio, F., Leturcq, F., Jeanpierre, M., Kaplan, J.C., and Reinert, P. (1994). Immunohistochemical analysis of dystrophin-associated proteins in Becker/Duchenne muscular dystrophy with huge in-frame deletions in the NH2-terminal and rod domains of dystrophin. J Clin Invest 93, 99-105.

Maurissen JP, Marable BR, Andrus AK, Stebbins KE. Factors affecting grip strength testing. Neurotoxicol Teratol. 2003;25(5):543-553. doi:10.1016/s0892-0362(03)00073-4.

Mayhew AG, Coratti G, Mazzone ES, Klingels K, James M, Pane M, Straub V, Goemans N, Mercuri E; Pul Working Group. Performance of Upper Limb module for Duchenne muscular dystrophy. Dev Med Child Neurol. May 2020;62(5):633-639. doi: 10.1111/dmcn.14361. Epub Sep. 19, 2019.

Mendell JR, Sahenk Z, Lehman K, Nease C, Lowes LP, Miller NF, lammarino MA, Alfano LN, Nicholl A, Al-Zaidy S, Lewis S, Church K, Shell R, Cripe LH, Potter RA, Griffin DA, Pozsgai E, Dugar A, Hogan M, Rodino-Klapac LR. Assessment of Systemic Delivery of rAAVrh74.MHCK7.micro-dystrophin in Children With Duchenne Muscular Dystrophy: A Nonrandomized Controlled Trial. JAMA Neurol. Sep. 1, 2020;77(9):1122-1131.

Mercuri, E., Bonnemann, C.G., and Muntoni, F. (2019). Muscular dystrophies. Lancet 394, 2025-2038.

Meyer OA, Tilson HA, Byrd WC, Riley Mt. A method for the routine assessment of fore-and hindlimb grip strength of rats and mice. Neurobehav Toxicol. 1979;1(3):233-236.

Mingozzi F, Hasbrouck NC, Basner-Tschakarjan E, Edmonson SA, Hui DJ, Sabatino DE, Zhou S, Wright JF, Jiang H, Pierce GF, Arruda VR, High KA. Modulation of tolerance to the transgene product in a nonhuman primate model of AAV-mediated gene transfer to liver. Blood. Oct. 1, 2007;110(7):2334-41. doi: 10.1182/blood-2007-03-080093. Epub Jul. 3, 2007.

Moens P, Baatsen PH, Maréchal G. Increased susceptibility of EDL muscles from mdx mice to damage induced by contractions with stretch. J Muscle Res Cell Motil. Aug. 1993;14(4):446-51. doi: 10.1007/BF00121296. PMID: 7693747.

Moorwood C, Liu M, Tian Z, Barton ER. Isometric and eccentric force generation assessment of skeletal muscles isolated from murine models of muscular dystrophies. J Vis Exp. 2013;(71):e50036. Published Jan. 31, 2013. doi: 10.3791/50036.

Newey, S.E., Benson, M.A., Ponting, C.P., Davies, K.E., and Blake, D.J. (2000). Alternative splicing of dystrobrevin regulates the stoichiometry of syntrophin binding to the dystrophin protein complex. Curr Biol 10, 1295-8.

Petrof, B.J., Shrager, J.B., Stedman, H.H., Kel ly, A.M., and Sweeney, H.L. (1993). Dystrophin protects the sarcolemma from stresses developed during muscle contraction. Proc Natl Acad Sci US A 90, 3710-4.

Phelps, S.F., Hauser, M.A., Cole, N.M., Rafael, J.A., Hinkle, R.T., Faulkner, J.A., and Chamberlain, U.S. (1995). Expression of full-length and truncated dystrophin mini-genes in transgenic mdx mice. Hum Mol Genet 4, 1251-8.

Putten, M.v., Hulsker, M., Young, C., Nadarajah, V.D., Heemskerk, H., Weerd, L.v.d., Hoen, P.A.C.', Ommen, G.-J.B. V., Aartsma-Rus, A.M. (2013). Low dystrophin levels increase survival and improve muscle pathology and function in dystrophin/utrophin double-knockout mice. FASEB J 27, 2484-95.

Ramaswamy, K.S., Palmer, M.L., Meulen, J.H.v.d., Renoux, A., Kostrominova, T.Y., Michele, D. E., and Faulkner, J.A. (2011). Lateral transmission of force is impaired in skeletal muscles of dystrophic mice and very old rats. J Physiol 589, 1195-208.

Rodrigues M, Echigoya Y, Fukada SI, Yokota T. Current Translational Research and Murine Models For Duchenne Muscular Dystrophy. J Neuromuscul Dis. 2016;3(1):29-48. doi:10.3233/JND-150113.

Rybakova, I.N., Patel, J.R., and Ervasti, J.M. (2000). The dystrophin complex forms a mechanically strong link between the sarcolemma and costameric actin. J Cell Biol 150, 1209-14.

Sakamoto, Miki, et al. "Micro-dystrophin cDNA ameliorates dystrophic phenotypes when introduced into mdx mice as a transgene." Biochemical and biophysical research communications 293.4 (2002): 1265-1272.

Sancar F, Touroutine D, Gao S, et al. The dystrophin-associated protein complex maintains muscle excitability by regulating Ca(2+ )-dependent K(+) (BK) channel localization. J Biol Chem. 2011;286(38):33501-33510. doi:10.1074/jbc.M111.227678.

Sicinski P, Geng Y, Ryder-Cook AS, et al. The molecular basis of muscular dystrophy in the mdx mouse: a point mutation. Science Jun. 30, 1989;244(4912):1578-80. oi:10.1126/science.2662404.

Smith JP, Hicks PS, Ortiz LR, Martinez MJ, Mandler RN. Quantitative measurement of muscle strength in the mouse. J Neurosci Methods. 1995;62(1-2):15-19. loi:10.1016/0165-0270(95)00049-6.

Suzuki, A., Yoshida, M., Hayashi, K., Mizuno, Y., Hagiwara, Y., and Ozawa, E. (1994). Molecular organization at the glycoprotein-complex-binding site of dystrophin. Three dystrophin-associated proteins bind directly to the carboxy-terminal portion of dystrophin. Eur J Biochem 220, 283-92.

Turk R, Sterrenburg E, de Meijer EJ, van Ommen GJ, den Dunnen JT, 't Hoen PA. Muscle regeneration in dystrophin-deficient mdx mice studied by gene expression profiling. BMC Genomics. 2005;6:98. Published Jul. 13, 2005. doi: 10.1186/1471-164-6- 98.

Uaesoontrachoon K, Srinivassane S, Warford J, et al. Orthogonal analysis of dystrophin protein and mRNA as a surrogate outcome for drug development. Biomark Med Oct. 2019;13(14):1209-1225. doi: 10.2217/bmm-2019-0242.

Vincent, N., Ragot, T., Gilgenkrantz, H., Couton, D., Chafey, P., Gregoire, A., Briand, P., Kaplan, J.C., Kahn, A., and Perricaudet, M. (1993) Long-term correction of mouse dystrophic degeneration by adenovirus-mediated transfer of a minidystrophin gene. Nat Genet 5, 130-4.

Wells, D.J Wells, K.E., Walsh, F.S., Davies, K.E., Goldspink, G., Love, D.R., Chan-Thomas, P., Dunckley, M.G., Piper, T., and Dickson, G. (1992). Human dystrophin expression corrects the myopathic phenotype in transgenic mdx mice. Hum Mol Genet 1, 35-40.

Winnard, A.V., Klein, C.J., Coovert, D.D., Prior, T., Papp, A., Snyder, P., Bulman, D.E., Ray, P.N., McAndrew, P., and King, W. (1993). Characterization of translational frame exception patients in Duchenne/Becker muscular dystrophy. Hum Mol Genet 2, 737-44.

Yang, L., Lochmuller, H., Luo, J., Massie, B., Nalbantoglu, J., Karpati, G., and Petrof, B.J. (1998). Adenovirus-mediated dystrophin minigene transfer improves muscle strength in adult dystrophic (MDX) mice. Gene Ther 5, 369-79.

Zatz M, Rapaport D, Vainzof M, Passos-Bueno MR, Bortolini ER, Pavanello Rde C, Peres CA. Serum creatine-kinase (CK) and pyruvate-kinase (PK) activities in Duchenne (DMD) as compared with Becker (BMD) muscular dystrophy. J Neurol Sci. Apr. 1991; 102:190-196. doi: 10.1016/0022-510x(91)90068.

Abdelrahim Abdrabou Sadek, et al, Evaluation of cardiac functions in children with Duchenne Muscular Dystrophy: A prospective case-control study. Electron Physician Nov. 2017; 9(11): 5732-5739.

Allen, et al. Absence Of Dystrophin Disrupts Skeletal Muscle Signaling: Roles Of $Ca^2$ , Reactive Oxygen Species, And Nitric Oxide In The Development Of Muscular Dystrophy, Physiol Rev 96: 253-305, 2016.

Auricchio et al., Exchange of surface proteins impacts on viral vector cellular specificity and transduction characteristics: the retina as a model, Hum. Molec. Genet. 10:3075-3081, (2001).

Banerji et al., Inhibiting Plasma Kallikrein for Hereditary Angioedema Prophylaxis, N Engl J Med 2017;376:717-28. DOI: 10.1056/NEJMoa1605767.

Banks et al, The Polyproline Site in Hinge 2 Influences the Functional Capacity of Truncated Dystrophins, PLOS Genetics, May 2010; 6(5):e1000958.

Banks et al., The Functional Capacity of AR4-R23 Microdystrophin Is Improved by Switching Hinge 2 with Hinge 3, Molecular Therapy, New Developments in Bone, Joint and Muscle Disease Gene/Cell Therapy, vol. 16, Suppl. 1, S131-S132 (Abstract#349), May 2008.

(56) References Cited

OTHER PUBLICATIONS

Barthelemey and Wein, Personalized gene and cell therapy for Duchenne Muscular Dystrophy, Neuromuscular Disorders 28: 803-824, 2018.
Bhat, et al., ABC of multifaceted dystrophin glycoprotein complex (DGC), J Cell Physiol. 233:5142-5159, 2017.
Blake, D. et al, Function and Genetics of Dystrophin and Dystrophin-Related Proteins in Muscle. Physiol. Rev. 82: 291-329, 2002.
Bottomly and Mosier, Mice whose B cells cannot produce the T15 idiotype also lack an antigen-specific helper T cell required for T15 expression, 1979, 150; 1399-409.
Burakiewicz, J. et al., Quantifying fat replacement of muscle by quantitative MRI in muscular dystrophy, Journal of Neurology, 264 : 2053-2067, 2017.
Clemens et al, Recombinant Truncated Dystrophin Minigenes: Construction, Expression, and Adenoviral Delivery, Hum. Gene Ther. 6:1477 (1995).
Crawford, et al. Assembly of the Dystrophin-associated Protein Complex Does Not Require the Dystrophin COOH-terminal Domain, The Journal of Cell Biology, vol. 150, No. 6, pp. 1399-1409, 2000.
Duan et al., Enhancement of muscle gene delivery with pseudotyped adeno- associated virus type 5 correlates with myoblast differentiation, J. Virol., 75:7662-7671 (2001).
Duan, Micro-Dystrophin Gene Therapy Goes Systemic in Duchenne Muscular Dystrophy Patients, Human Gene Therapy, 29(7): 733-736, 2018.
Duan, Systemic AAV Micro-dystrophin Gene Therapy for Duchenne Muscular Dystrophy, Molecular Therapy, 26(10): 1-20, 2018.
Faust, S.M., et al., CpG-depleted adeno-associated virus vectors evade immune detection. J Clin Invest, 2013. 123(7): p. 2994-3001.
Foster et al, Codon and mRNA Sequence Optimization of Microdystrophin Transgenes Improves Expression and Physiological Outcome in Dystrophic mdx Mice Following AAV2/8 Gene Transfer, Mol Ther 16(11): 1825-1832, 2008.
Gao and McNally, The Dystrophin Complex: structure, function and implications for therapy, Compr Physiol. 5(3): 1223-1239, 2015.
Georgiadis et al., Correction: Development of an optimized AAV2/5 gene therapy vector for Leber congenital amaurosis owing to defects in RPE65, Gene Therapy 25: 450, 2018.
Georgiadis et al., Development of an optimized AAV2/5 gene therapy vector for Leber congenital amaurosis owing to defects in RPE65, Gene Therapy 23: 857-862, 2016.
Gieseler, et al. In vitro interactions of Caenorhabditis elegans dystrophin with dystrobrevin and syntrophin, FEBS Letters 461: 59-62, 1999.
Goyenvalle et al. Therapeutic approaches to muscular dystrophy. Human Molecular Genetics, Apr. 15, 2011: 20(R1):R69-R78.
Guo, et al. Natural History of Cardiomyopathy in Adult Dogs With Golden Retriever Muscular Dystrophy, J Am Heart Assoc. 8:e012443. DOI: 10.1161/JAHA.119.012443, 2019.
Hakim, et al., A Five-Repeat Micro-Dystrophin Gene Ameliorated Dystrophic Phenotype in the Severe DBA/2J-mdx Model of Duchenne Muscular Dystrophy, Molecular Therapy, Methods & Clin Dev, 6(15):216-230, 2017.
Halbert et al., Repeat transduction in the mouse lung by using adeno-associated virus vectors with different serotypes, J. Virol., 74:1524-1532 (2000).
Koo et al, "Delivery of AAV2/9-Microdystrophin Genes Incorporating Helix 1 of the Coiled-Coil Motif in the C-Terminal Domain of Dystrophin Improves Muscle Pathology and Restores the Level of [alpha]1-Syntrophin and [alpha]-Dystrobrevin in Skeletal Muscles of mdx Mice", Human Gene Therapy, vol. 22, No. 11, Nov. 1, 2011, p. 1379-1388.
International Search Report and Written Opinion for International Application No. PCT/US2020/062484 mailed Jun. 4, 2021.
Harper, et al., Modular flexibility of dystrophin: Implications for gene therapy of Duchenne muscular dystrophy, Nature Medicine 8(3): 253, 2002.
Hemperly et al., Recent Advances in the Management of Hereditary Angioedema, J Am Osteopath Assoc.; 113 (7):546-555, doi:10.7556/jaoa.2013.006, 2013.
Judge, Dissecting the signaling and mechanical functions of the dystrophin-glycoprotein complex in skeletal muscle, 2006 PhD Dissertation, University of Washington.
Kamdar and Garry, Dystrophin-Deficient Cardiomyopathy, JACC 67(21): 2533-46, 2016.
Kenniston et al. Inhibition of Plasma Kallikrein by a Highly Specific Active Site Blocking Antibody, The Journal of Biological Chemistry vol. 289, No. 34, pp. 23596-23608, Aug. 22, 2014.
Koenig and Kunkel, Detailed analysis of the repeat domain of dystrophin reveals four potential hinge segments that may confer flexibility, J Biol Chem, 265(6):4560-4566, 1990.
Koo, et al., Long-term functional adeno-associated virus-microdystrophin expression in the dystrophic CXMDj dog, J Gene Med 13: 497-506, 2011.
Kornegay, J.N., et al, The golden retriever model of Duchenne muscular dystrophy. Skelet Muscle. 2017; 7: 9.
Kornegay, J.N., et al., Widespread muscle expression of an AAV9 human mini-dystrophin vector after intravenous injection in neonatal dystrophin-deficient dogs. Mol Ther, 2010. 18(8): p. 1501-8.
Le Guiner, C. et al. Assessment of efficacy of a rAAV9-mini-dystrophin gene therapy candidate (PF-06939926) administered to aged DMDmdx rats, Neuromuscular Disorders, vol. 28, S93, Oct. 2018.
Le Guiner, et al., Long-term microdystrophin gene therapy is effective in a canine model of Duchenne muscular dystrophy, Nature Communications 8:16105. DOI: 10.1038/ncomms16105, 2017.
Li, X. et al. Synthetic muscle promoters: activities exceeding naturally occurring regulatory sequences, Nat Biotechnology vol. 17, pp. 241-245, 1999.
Magrath, P. et al, Cardiac MRI biomarkers for Duchenne muscular dystrophy. Biomarkers in Medicine (2018) vol. 12, No. 11.
Maurer AC and Weitzman MD, Adeno-Associated Virus Genome Interactions Important for Vector Production and Transduction, 2020, Hum Gene Ther, 31: 499-511.
Mazzone et al, North Star Ambulatory Assessment, 6-minute walk test and timed items in ambulant boys with Duchenne muscular dystrophy, Neuromuscular Disorders 20 (2010) 712-716.
McCarty et al., 2001, Self-complementary recombinant adeno-associated virus (scAAV) vectors promote efficient transduction independently of DNA synthesis, Gene Therapy, vol. 8, No. 16, pp. 1248-1254.
McCourt et al. In vitro stability of therapeutically relevant, internally truncated dystrophins. Skeletal Muscle 5, 13 (2015).
Mendell, J.R., et al., Dystrophin immunity in Duchenne's muscular dystrophy. N Engl J Med, 2010. 363(15): p. 1429-37.
Pane, M. et al, Upper limb function in Duchenne muscular dystrophy: 24 month longitudinal data. PLoS One. Jun. 20, 2018; 13(6):e0199223.
Pereira and Muzyczka, The adeno-associated virus type 2 p40 promoter requires a proximal Spl interaction and a pl9 CArG-like element to facilitate Rep transactivation, Journal of Virology, Jun. 1997, 71(6):4300-4309.
Pfizer Clinical Trial NCT03362502, study start date: Jan. 23, 2018, https://clinicaltrials.gov/ct2/show/NCT03362502?term=NCT03362502&rank=l.
Pilgram et al., The Roles of the Dystrophin-Associated Glycoprotein Complex at the Synapse, Mol Neurobiol 41:1-21, 2010.
Puzzo et al., Rescue of Pompe disease in mice by AAV-mediated liver delivery of secretable acid a-glucosidase, 2017, Sci. Transí. Med. 29(9): 418.
Rabinowitz, J., Y.K. Chan, and R.J. Samulski, Adeno-associated Virus (AAV) versus Immune Response. Viruses, 2019.11(2).
Rafael, et al., Forced Expression of Dystrophin Deletion Constructs Reveals Structure-Function Correlations, The Journal of Cell Biology, vol. 134, No. 1, pp. 93-102, 1996.
Ramos JN, Development of Novel Micro-dystrophins with Enhanced Functionality, Mol Ther, 2019, 27; 623-635.

(56) References Cited

OTHER PUBLICATIONS

Recan, et al., Are Cysteine-rich and COCH-Terminal Domains of Dystrophin Critical for Sarcolemmal Localization?, J Clin Invest, vol. 89, pp. 712-716, 1992.
Rodino-Klapac, A translational approach for limb vascular delivery of the microdystrophin gene without high volume or high pressure for treatment of Duchenne muscular dystrophy, Journal of Translational Medicine, 5(45): 1-12; doi:10.1186/1479-5876-5-45, 2007.
Sadoulet-Puccio, H.M., et al., Dystrobrevin and dystrophin: an interaction through coiled-coil motifs. (1997) Proc Natl Acad Sci USA 94:12413-8.
Sambrook, J. et al., Molecular Cloning: A laboratory Manual (2nd ed.), Cold Spring Harbor Laboratory Press, Cold Spring Harbor, N.Y. (1989).
Sexton, et al., Discovery and characterization of a fully human monoclonal antibody inhibitor of plasma kallikrein for the treatment of plasma kallikrein-mediated edema. Journal of Allergy and Clinical Immunology, 131(2), p. AB32, 2013.
Shin, et al., Microdystrophin Ameliorates Muscular Dystrophy in the Canine Model of Duchenne Muscular Dystrophy, Molecular Therapy 21(4):750-757, 2013.
Stevenson, S., et al., Spatial relationship of the C-terminal domains of dystrophin and beta-dystroglycan in cardiac muscle support a direct molecular interaction at the plasma membrane interface. Circ Res, 82(1): p. 82-93, 1998.
Suzuki, et al. Mammalian alpha 1-and beta 1-syntrophin bind to the alternative splice-prone region of the dystrophin COOH terminus, The Journal of Cell Biology, vol. 128, No. 3, pp. 373-381, 1995.
Tandon, A., et al., Dystrophin genotype-cardiac phenotype correlations in Duchenne and Becker muscular dystrophies using cardiac magnetic resonance imaging. Am J Cardiol, 115(7): p. 967-71, 2015.
Uaesoontrachoon et al, Long-term treatment with naproxcinod significantly improves skeletal and cardiac disease phenotype in the mdx mouse model of dystrophy, Human Molecular Genetics, 23; 3239-49, 2014.
Van Westering, Current understanding of molecular pathology and treatment of cardiomyopathy in duchenne muscular dystrophy, Molecules, 20, 8823-8855, 2015.
Wang et al., Systemic human minidystrophin gene transfer improves functions and life span of dystrophin and dystrophin/utrophin-deficient mice, J Orhtop Res, 27: 421-6, 2009.
Wang, D., P.W.L. Tai, and G. Gao, Adeno-associated virus vector as a platform for gene therapy delivery. Nat Rev Drug Discov, 18(5): p. 358-378, 2019.
Wang, et al., Adeno-associated virus vector carrying human minidystrophin genes effectively ameliorates muscular dystrophy in mdx mouse model, PNAS, 97 (25): 13714-13719, 2000.
Wehling-Henricks et al, Cardiomyopathy in dystrophin-deficient hearts is prevented by expression of a neuronal nitric oxide synthase transgene in the myocardium, Human Molecular Genetics, 2005, 14: 1921-33.
Wu, 2007, Self-complementary recombinant adeno-associated viral vectors: packaging capacity and the role of rep proteins in vector purity, Human Gene Therapy, 18(2):171-82, 2007.
Yang et al., Identification of alpha-syntrophin binding to syntrophin triplet, dystrophin, and utrophin, J Biol Chern, 270; 4975-8, 1995.
Yoshimura, et al., AAV Vector-Mediated Microdystrophin Expression in a Relatively Small Percentage of mdx Myofibers Improved the mdx Phenotype, Molecular Therapy 10(5):821, 2004.
Yuasa et al, Effective restoration of dystrophin-associated proteins in vivo by adenovirus-mediated transfer of truncated dystrophin cDNAs, FEBS Letters 425:329-336(1998).
Yucel, N., et al, Humanizing the mdx mouse model of DMD: the long and the short of it, NPJ Regenerative Medicine 3: 4 (2018).
Zolotukhin etal., Production and purification of serotype 1, 2, and 5 recombinant adeno-associated viral vectors, Methods 28:158-167 (2002).

* cited by examiner

Wild-type Dystrophin and DAPC RGX-DYS1 and DAPC

C

B

C

D

E

B

C

E

C.

SEQUENCE LISTING

```
Sequence total quantity: 127
SEQ ID NO: 1          moltype = AA  length = 1337
```

-continued

```
FEATURE                Location/Qualifiers
REGION                 1..1337
                       note = synthetic construct; micro dystrophin protein
source                 1..1337
                       mol_type = protein
                       organism = synthetic construct
SEQUENCE: 1
MLWWEEVEDC YEREDVQKKT FTKWVNAQFS KFGKQHIENL FSDLQDGRRL LDLLEGLTGQ  60
KLPKEKGSTR VHALNNVNKA LRVLQNNNVD LVNIGSTDIV DGNHKLTLGL IWNIILHWQV  120
KNVMKNIMAG LQQTNSEKIL LSWVRQSTRN YPQVNVINFT TSWSDGLALN ALIHSHRPDL  180
FDWNSVVCQQ SATQRLEHAF NIARYQLGIE KLLDPEDVDT TYPDKKSILM YITSLFQVLP  240
QQVSIEAIQE VEMLPRPPKV TKEEHFQLHH QMHYSQQITV SLAQGYERTS SPKPRFKSYA  300
YTQAAYVTTS DPTRSPFPSQ HLEAPEDKSF GSSLMESEVN LDRYQTALEE VLSWLLSAED  360
TLQAQGEISN DVEVVKDQFH THEGYMMDLT AHQGRVGNIL QLGSKLIGTG KLSEDEETEV  420
QEQMNLLNSR WECLRVASME KQSNLHRVLM DLQNQKLKEL NDWLTKTEER TRKMEEEPLG  480
PDLEDLKRQV QQHKVLQEDL EQEQVRVNSL THMVVVVDES SGDHATAALE EQLKVLGDRW  540
ANICRWTEDR WVLLQDILLK WQRLTEEQCL FSAWLSEKED AVNKIHTTGF KDQNEMLSSL  600
QKLAVLKADL EKKKQSMGKL YSLKQDLLST LKNKSVTQKT EAWLDNFARC WDNLVQKLEK  660
STAQISQQPD LAPGLTTIGA SPTQTVTLVT QPVVTKETAI SKLEMPSSLM LEVPTLERLQ  720
ELQEATDELD LKLRQAEVIK GSWQPVGDLL IDSLQDHLEK VKALRGEIAP LKENVSHVND  780
LARQLTTLGI QLSPYNLSTL EDLNTRWKLL QVAVEDRVRQ LHEAHRDFGP ASQHFLSTSV  840
QGPWERAISP NKVPYYINHE TQTTCWDHPK MTELYQSLAD LNNVRFSAYR TAMKLRRLQK  900
ALCLDLLSLS AACDALDQHN LKQNDQPMDI LQIINCLTTI YDRLEQEHNN LVNVPLCVDM  960
CLNWLLNVYD TGRTGRIRVL SFKTGIISLC KAHLEDKYRY LFKQVASSTG FCDQRRLGLL  1020
LHDSIQIPRQ LGEVASFGGS NIEPSVRSCF QFANNKPEIE AALFLDWMRL EPQSMVWLPV  1080
LHRVAAAETA KHQAKCNICK ECPIIGFRYR SLKHFNYDIC QSCFFSGRVA KGHKMHYPMV  1140
EYCTPTTSGE DVRDFAKVLK NKFRTKRYFA KHPRMGYLPV QTVLEGDNME TPVTLINFWP  1200
VDSAPASSPQ LSHDDTHSRI EHYASRLAEM ENSNGSYLND SISPNESIDD EHLLIQHYCQ  1260
SLNQDSPLSQ PRSPAQILIS LESEERGELE RILADLEEEN RNLQAEYDRL KQQHEHKGLS  1320
PLPSPPEMMP TSPQSPR                                                 1337

SEQ ID NO: 2           moltype = AA  length = 1191
FEATURE                Location/Qualifiers
REGION                 1..1191
                       note = synthetic construct; micro dystrophin protein
source                 1..1191
                       mol_type = protein
                       organism = synthetic construct
SEQUENCE: 2
MLWWEEVEDC YEREDVQKKT FTKWVNAQFS KFGKQHIENL FSDLQDGRRL LDLLEGLTGQ  60
KLPKEKGSTR VHALNNVNKA LRVLQNNNVD LVNIGSTDIV DGNHKLTLGL IWNIILHWQV  120
KNVMKNIMAG LQQTNSEKIL LSWVRQSTRN YPQVNVINFT TSWSDGLALN ALIHSHRPDL  180
FDWNSVVCQQ SATQRLEHAF NIARYQLGIE KLLDPEDVDT TYPDKKSILM YITSLFQVLP  240
QQVSIEAIQE VEMLPRPPKV TKEEHFQLHH QMHYSQQITV SLAQGYERTS SPKPRFKSYA  300
YTQAAYVTTS DPTRSPFPSQ HLEAPEDKSF GSSLMESEVN LDRYQTALEE VLSWLLSAED  360
TLQAQGEISN DVEVVKDQFH THEGYMMDLT AHQGRVGNIL QLGSKLIGTG KLSEDEETEV  420
QEQMNLLNSR WECLRVASME KQSNLHRVLM DLQNQKLKEL NDWLTKTEER TRKMEEEPLG  480
PDLEDLKRQV QQHKVLQEDL EQEQVRVNSL THMVVVVDES SGDHATAALE EQLKVLGDRW  540
ANICRWTEDR WVLLQDILLK WQRLTEEQCL FSAWLSEKED AVNKIHTTGF KDQNEMLSSL  600
QKLAVLKADL EKKKQSMGKL YSLKQDLLST LKNKSVTQKT EAWLDNFARC WDNLVQKLEK  660
STAQISQQPD LAPGLTTIGA SPTQTVTLVT QPVVTKETAI SKLEMPSSLM LEVPTLERLQ  720
ELQEATDELD LKLRQAEVIK GSWQPVGDLL IDSLQDHLEK VKALRGEIAP LKENVSHVND  780
LARQLTTLGI QLSPYNLSTL EDLNTRWKLL QVAVEDRVRQ LHEAHRDFGP ASQHFLSTSV  840
QGPWERAISP NKVPYYINHE TQTTCWDHPK MTELYQSLAD LNNVRFSAYR TAMKLRRLQK  900
ALCLDLLSLS AACDALDQHN LKQNDQPMDI LQIINCLTTI YDRLEQEHNN LVNVPLCVDM  960
CLNWLLNVYD TGRTGRIRVL SFKTGIISLC KAHLEDKYRY LFKQVASSTG FCDQRRLGLL  1020
LHDSIQIPRQ LGEVASFGGS NIEPSVRSCF QFANNKPEIE AALFLDWMRL EPQSMVWLPV  1080
LHRVAAAETA KHQAKCNICK ECPIIGFRYR SLKHFNYDIC QSCFFSGRVA KGHKMHYPMV  1140
EYCTPTTSGE DVRDFAKVLK NKFRTKRYFA KHPRMGYLPV QTVLEGDNME T           1191

SEQ ID NO: 3           moltype = AA  length = 240
FEATURE                Location/Qualifiers
REGION                 1..240
                       note = synthetic construct; microdystrophin segment
source                 1..240
                       mol_type = protein
                       organism = synthetic construct
SEQUENCE: 3
MLWWEEVEDC YEREDVQKKT FTKWVNAQFS KFGKQHIENL FSDLQDGRRL LDLLEGLTGQ  60
KLPKEKGSTR VHALNNVNKA LRVLQNNNVD LVNIGSTDIV DGNHKLTLGL IWNIILHWQV  120
KNVMKNIMAG LQQTNSEKIL LSWVRQSTRN YPQVNVINFT TSWSDGLALN ALIHSHRPDL  180
FDWNSVVCQQ SATQRLEHAF NIARYQLGIE KLLDPEDVDT TYPDKKSILM YITSLFQVLP  240

SEQ ID NO: 4           moltype = AA  length = 12
FEATURE                Location/Qualifiers
REGION                 1..12
                       note = synthetic construct; linker
source                 1..12
                       mol_type = protein
```

```
                         organism = synthetic construct
SEQUENCE: 4
QQVSIEAIQE VE                                                     12

SEQ ID NO: 5             moltype = AA  length = 75
FEATURE                  Location/Qualifiers
REGION                   1..75
                         note = synthetic construct; microdystrophin segment
source                   1..75
                         mol_type = protein
                         organism = synthetic construct
SEQUENCE: 5
MLPRPPKVTK EEHFQLHHQM HYSQQITVSL AQGYERTSSP KPRFKSYAYT QAAYVTTSDP  60
TRSPFPSQHL EAPED                                                   75

SEQ ID NO: 6             moltype = AA  length = 9
FEATURE                  Location/Qualifiers
REGION                   1..9
                         note = synthetic construct; linker
source                   1..9
                         mol_type = protein
                         organism = synthetic construct
SEQUENCE: 6
KSFGSSLME                                                          9

SEQ ID NO: 7             moltype = AA  length = 111
FEATURE                  Location/Qualifiers
REGION                   1..111
                         note = synthetic construct; microdystrophin segment
source                   1..111
                         mol_type = protein
                         organism = synthetic construct
SEQUENCE: 7
SEVNLDRYQT ALEEVLSWLL SAEDTLQAQG EISNDVEVVK DQFHTHEGYM MDLTAHQGRV  60
GNILQLGSKL IGTGKLSEDE ETEVQEQMNL LNSRWECLRV ASMEKQSNLH R           111

SEQ ID NO: 8             moltype = AA  length = 109
FEATURE                  Location/Qualifiers
REGION                   1..109
                         note = synthetic construct; microdystrophin segment
source                   1..109
                         mol_type = protein
                         organism = synthetic construct
SEQUENCE: 8
VLMDLQNQKL KELNDWLTKT EERTRKMEEE PLGPDLEDLK RQVQQHKVLQ EDLEQEQVRV  60
NSLTHMVVVV DESSGDHATA ALEEQLKVLG DRWANICRWT EDRWVLLQD             109

SEQ ID NO: 9             moltype =   length =
SEQUENCE: 9
000

SEQ ID NO: 10            moltype = AA  length = 109
FEATURE                  Location/Qualifiers
REGION                   1..109
                         note = synthetic construct; microdystrophin segment
source                   1..109
                         mol_type = protein
                         organism = synthetic construct
SEQUENCE: 10
LKWQRLTEEQ CLFSAWLSEK EDAVNKIHTT GFKDQNEMLS SLQKLAVLKA DLEKKKQSMG  60
KLYSLKQDLL STLKNKSVTQ KTEAWLDNFA RCWDNLVQKL EKSTAQISQ             109

SEQ ID NO: 11            moltype = AA  length = 47
FEATURE                  Location/Qualifiers
REGION                   1..47
                         note = synthetic construct; microdystrophin segment
source                   1..47
                         mol_type = protein
                         organism = synthetic construct
SEQUENCE: 11
QPDLAPGLTT IGASPTQTVT LVTQPVVTKE TAISKLEMPS SLMLEVP                47

SEQ ID NO: 12            moltype =   length =
SEQUENCE: 12
000

SEQ ID NO: 13            moltype = AA  length = 106
FEATURE                  Location/Qualifiers
REGION                   1..106
```

```
                        note = synthetic construct; microdystrophin segment
source                  1..106
                        mol_type = protein
                        organism = synthetic construct
SEQUENCE: 13
RLQELQEATD ELDLKLRQAE VIKGSWQPVG DLLIDSLQDH LEKVKALRGE IAPLKENVSH  60
VNDLARQLTT LGIQLSPYNL STLEDLNTRW KLLQVAVEDR VRQLHE                 106

SEQ ID NO: 14           moltype = AA  length = 72
FEATURE                 Location/Qualifiers
REGION                  1..72
                        note = synthetic construct; microdystrophin segment
source                  1..72
                        mol_type = protein
                        organism = synthetic construct
SEQUENCE: 14
AHRDFGPASQ HFLSTSVQGP WERAISPNKV PYYINHETQT TCWDHPKMTE LYQSLADLNN  60
VRFSAYRTAM KL                                                      72

SEQ ID NO: 15           moltype = AA  length = 248
FEATURE                 Location/Qualifiers
REGION                  1..248
                        note = synthetic construct; microdystrophin segment
source                  1..248
                        mol_type = protein
                        organism = synthetic construct
SEQUENCE: 15
RRLQKALCLD LLSLSAACDA LDQHNLKQND QPMDILQIIN CLTTIYDRLE QEHNNLVNVP  60
LCVDMCLNWL LNVYDTGRTG RIRVLSFKTG IISLCKAHLE DKYRYLFKQV ASSTGFCDQR  120
RLGLLLHDSI QIPRQLGEVA SFGGSNIEPS VRSCFQFANN KPEIEAALFL DWMRLEPQSM  180
VWLPVLHRVA AAETAKHQAK CNICKECPII GFRYRSLKHF NYDICQSCFF SGRVAKGHKM  240
HYPMVEYC                                                           248

SEQ ID NO: 16           moltype = AA  length = 194
FEATURE                 Location/Qualifiers
REGION                  1..194
                        note = synthetic construct; microdystrophin segment
source                  1..194
                        mol_type = protein
                        organism = synthetic construct
SEQUENCE: 16
TPTTSGEDVR DFAKVLKNKF RTKRYFAKHP RMGYLPVQTV LEGDNMETPV TLINFWPVDS  60
APASSPQLSH DDTHSRIEHY ASRLAEMENS NGSYLNDSIS PNESIDDEHL LIQHYCQSLN  120
QDSPLSQPRS PAQILISLES EERGELERIL ADLEEENRNL QAEYDRLKQQ HEHKGLSPLP  180
SPPEMMPTSP QSPR                                                    194

SEQ ID NO: 17           moltype = AA  length = 4
FEATURE                 Location/Qualifiers
REGION                  1..4
                        note = synthetic construct; linker
source                  1..4
                        mol_type = protein
                        organism = synthetic construct
SEQUENCE: 17
ETLE                                                               4

SEQ ID NO: 18           moltype =   length =
SEQUENCE: 18
000

SEQ ID NO: 19           moltype = AA  length = 44
FEATURE                 Location/Qualifiers
REGION                  1..44
                        note = synthetic construct; microdystrophin segment
source                  1..44
                        mol_type = protein
                        organism = synthetic construct
SEQUENCE: 19
PSLTQTTVME TVTTVTTREQ ILVKHAQEEL PPPPPQKKRQ ITVD                   44

SEQ ID NO: 20           moltype = DNA  length = 4017
FEATURE                 Location/Qualifiers
misc_feature            1..4017
                        note = synthetic construct; dystrophin
source                  1..4017
                        mol_type = other DNA
                        organism = synthetic construct
SEQUENCE: 20
atgctttggt gggaagaggt ggaagattgc tatgagaggg aagatgtgca gaagaaaacc  60
```

-continued

```
ttcaccaaat gggtcaatgc ccagttcagc aagtttggca agcagcacat tgagaacctg  120
ttcagtgacc tgcaggatgg cagaaggctg ctggatctgc tggaaggcct gacaggccag  180
aagctgccta aagagaaggg cagcacaaga gtgcatgccc tgaacaatgt gaacaaggcc  240
ctgagagtgc tgcagaacaa caatgtggac ctggtcaata ttggcagcac agacattgtg  300
gatggcaacc acaagctgac cctgggcctg atctggaaca tcatcctgca ctggcaagtg  360
aagaatgtga tgaagaacat catggctggc ctgcagcaga ccaactctga gaagatcctg  420
ctgagctggg tcagacagag caccagaaac taccctcaag tgaatgtgat caacttcacc  480
acctcttgga gtgatggact ggccctgaat gccctgatcc acagccacag acctgacctg  540
tttgactgga actctgttgt gtgccagcag tctgccacac agagactgga acatgccttc  600
aacattgcca gataccagct gggaattgag aaactgctgg accctgagga tgtggacacc  660
acctatcctg acaagaaatc catcctcatg tacatcacca gcctgttcca ggtgctgccc  720
cagcaagtgt ccattgaggc cattcaagag gttgagatgc tgcccagacc tcctaaagtg  780
accaaagagg aacacttcca gctgcaccac cagatgcact actctcagca gatcacagtg  840
tctctggccc agggatatga gagaacaagc agccccaagc ctaggttcaa gagctatgcc  900
tacacacagg ctgcctatgt gaccacatct gaccccacaa gaagcccatt tccaagccag  960
catctggaag cccctgagga caagagcttt ggcagcagcc tgatggaatc tgaagtgaac  1020
ctggatagat accagacagc cctggaagaa gtgctgtcct ggctgctgtc tgctgaggat  1080
acactgcagg ctcagggtga aatcagcaat gatgtggaag tggtcaagga ccagtttcac  1140
acccatgagg gctacatgat ggacctgaca gcccaccagg gcagagtggg aaatatcctg  1200
cagctgggct ccaagctgat tggcacaggc aagctgtctg aggatgaaga gacagaggtg  1260
caagagcaga tgaacctgct gaacagcaga tgggagtgtc tgagagtggc cagcatggaa  1320
aagcagagca acctgcacag agtgctcatg gacctgcaga atcagaaact gaaagaactg  1380
aatgactggc tgaccaagac agaagaaagg actaggaaga tggaagagga acctctggga  1440
ccagacctgg aagatctgaa aagacaggtg cagcagcata aggtgctgca agaggacctt  1500
gagcaagagc aagtcagagt gaacagcctg acacacatgg tggtggttgt ggatgagtcc  1560
tctggggatc atgccacagc tgctctggaa gaacagctga aggtgctggg agacagatgg  1620
gccaacatct gtaggtggac agaggataga tgggtgctgc tccaggacat tctgctgaag  1680
tggcagagac tgacagagga acagtgcctg ttttctgcct ggctctctga gaaagaggat  1740
gctgtcaaca agatccatac cacaggcttc aaggatcaga atgagatgct cagctccctg  1800
cagaaactgg ctgtgctgaa ggctgacctg gaaaagaaaa agcagtccat gggcaagctc  1860
tacagcctga agcaggacct gctgtctacc ctgaagaaca agtctgtgac ccagaaaact  1920
gaggcctggc tggacaactt tgctagatgc tgggacaacc tggtgcagaa gctggaaaag  1980
tctacagccc agatcagcca gcaacctgat cttgcccctg gcctgaccac aattggagcc  2040
tctccaacac agactgtgac cctggttacc cagccagtgg tcaccaaaga gacagccatc  2100
agcaaactgg aaatgcccag ctctctgatg ctggaagtcc ccacactgga aaggctgcaa  2160
gaacttcaag aggccacaga tgagctggac ctgaagctga gacaggctga agtgatcaaa  2220
ggcagctggc agccagttgg ggacctgctc attgatagcc tgcaggacca tctggaaaaa  2280
gtgaaagccc tgaggggaga gattgcccct ctgaaagaaa atgtgtccca tgtgaatgac  2340
ctggccagac agctgaccac actgggaatc cagctgagcc cctacaacct gagcacccctt  2400
gaggacctga acaccaggtg gaagctcctc caggtggcag tggaagatag agtcaggcag  2460
ctgcatgagg cccacagaga ttttggacca gccagccagc actttctgtc tacctctgtg  2520
caaggcccct gggagagagc tatctctcct aacaaggtgc cctactacat caaccatgag  2580
acacagacca cctgttggga tcaccccaag atgacagagc tgtaccagag tctggcagac  2640
ctcaacaatg tcagattcag tgcctacagg actgccatga agctcagaag gctccagaaa  2700
gctctgtgcc tggacctgct ttccctgagt gcagcttgtg atgccctgga ccagcacaat  2760
ctgaagcaga atgaccagcc tatggacatc ctccagatca tcaactgcct caccaccatc  2820
tatgataggc tggaacaaga gcacaacaat ctggtcaatg tgcccctgtg tgtggacatg  2880
tgcctgaatt ggctgctgaa tgtgtatgac acaggcagaa caggcaggat cagagtcctg  2940
tccttcaaga caggcatcat ctccctgtgc aaagcccact tggaggacaa gtacagatac  3000
ctgttcaagc aagtggcctc cagcacaggc ttttgtgacc agagaaggct gggcctgctc  3060
ctgcatgaca gcattcagat ccctagacag ctgggagaag tggcttcctt tggaggcagc  3120
aatattgagc catcagtcag gtcctgtttt cagtttgcca acaacaagcc tgagattgag  3180
gctgccctgt tcctggactg gatgagactt gagcctcaga gcatggtctg gctgcctgtg  3240
cttcatagag tggctgctgc tgagactgcc aagcaccagg ccaagtgcaa catctgcaaa  3300
gagtgcccca tcattggctt cagatacaga tccctgaagc acttcaacta tgatatctgc  3360
cagagctgct tctttagtgg cagggttgcc aagggccaca aaatgcacta ccccatggtg  3420
gaatactgca ccccaacaac ctctggggaa gatgttagag actttgccaa ggtgctgaaa  3480
aacaagttca ggaccaagag atactttgct aagcacccca gaatgggcta cctgcctgtc  3540
cagacagtgc ttgagggtga caacatggaa acccctgtga cactgatcaa tttctggcca  3600
gtggactctg cccctgcctc aagtccacag ctgtcccatg atgacaccca cagcagaatt  3660
gagcactatg cctccagact ggcagagatg gaaaacagca atggcagcta cctgaatgat  3720
agcatcagcc ccaatgagag cattgatgat gagcatctgc tgatccagca ctactgtcag  3780
tccctgaacc aggactctcc actgagccag cctagaagcc ctgctcagat cctgatcagc  3840
cttgagtctg aggaaagggg agagctggaa agaatcctgg cagatcttga ggaagagaac  3900
agaaacctgc aggcagagta tgacaggctc aaacagcagc atgagcacaa gggactgagc  3960
cctctgcctt ctcctcctga aatgatgccc acctctccac agtctccaag gtgatga     4017
```

```
SEQ ID NO: 21          moltype = DNA  length = 3573
FEATURE                Location/Qualifiers
misc_feature           1..3573
                       note = synthetic construct; dystrophin
source                 1..3573
                       mol_type = other DNA
                       organism = synthetic construct
SEQUENCE: 21
atgctttggt gggaagaggt ggaagattgc tatgagaggg aagatgtgca gaagaaaacc  60
ttcaccaaat gggtcaatgc ccagttcagc aagtttggca agcagcacat tgagaacctg  120
ttcagtgacc tgcaggatgg cagaaggctg ctggatctgc tggaaggcct gacaggccag  180
aagctgccta aagagaaggg cagcacaaga gtgcatgccc tgaacaatgt gaacaaggcc  240
```

-continued

```
ctgagagtgc tgcagaacaa caatgtggac ctggtcaata ttggcagcac agacattgtg  300
gatggcaacc acaagctgac cctgggcctg atctggaaca tcatcctgca ctggcaagtg  360
aagaatgtga tgaagaacat catggctggc ctgcagcaga ccaactctga gaagatcctg  420
ctgagctggg tcagacagag caccagaaac taccctcaag tgaatgtgat caacttcacc  480
acctcttgga gtgatggact ggccctgaat gccctgatcc acagccacag acctgacctg  540
tttgactgga actctgttgt gtgccagcag tctgccacac agagactgga acatgccttc  600
aacattgcca gataccagct gggaattgag aaactgctgg accctgagga tgtggacacc  660
acctatcctg acaagaaatc catcctcatg tacatcacca gcctgttcca ggtgctgccc  720
cagcaagtgt ccattgaggc cattcaagag gttgagatgc tgcccagacc tcctaaagtg  780
accaaagagg aacacttcca gctgcaccac cagatgcact actctcagca gatcacagtg  840
tctctggccc agggatatga gagaacaagc agccccaagc ctaggttcaa gagctatgcc  900
tacacacagg ctgcctatgt gaccacatct gaccccacaa gaagcccatt tccaagccag  960
catctggaag cccctgagga caagagcttt ggcagcagcc tgatggaatc tgaagtgaac  1020
ctggatagat accagacagc cctggaagaa gtgctgtcct ggctgctgtc tgctgaggat  1080
acactgcagg ctcagggtga aatcagcaat gatgtggaag tggtcaagga ccagtttcac  1140
acccatgagg gctacatgat ggacctgaca gcccaccagg gcagagtggg aaatatcctg  1200
cagctgggct ccaagctgat tggcacaggc aagctgtctg aggatgaaga gacagaggtg  1260
caagagcaga tgaacctgct gaacagcaga tgggagtgtc tgagagtggc cagcatggaa  1320
aagcagagca acctgcacag agtgctcatg gacctgcaga atcagaaact gaaagaactg  1380
aatgactggc tgaccaagac agaagaaagg actaggaaga tggaagagga acctctggga  1440
ccagacctgg aagatctgaa aagacaggtg cagcagcata aggtgctgca agaggacctt  1500
gagcaagagc aagtcagagt gaacagcctg acacacatgg tggtggttgt ggatgagtcc  1560
tctggggatc atgccacagc tgctctggaa gaacagctga aggtgctggg agacagatgg  1620
gccaacatct gtaggtggac agaggataga tgggtgctgc tccaggacat tctgctgaag  1680
tggcagagac tgacagagga acagtgcctg ttttctgcct ggctctctga gaaagaggat  1740
gctgtcaaca agatccatac cacaggcttc aaggatcaga atgagatgct cagctccctg  1800
cagaaactgg ctgtgctgaa ggctgacctg gaaaagaaaa agcagtccat gggcaagctc  1860
tacagcctga agcaggacct gctgtctacc ctgaagaaca agtctgtgac ccagaaaact  1920
gaggcctggc tggacaactt tgctagatgc tgggacaacc tggtgcagaa gctggaaaag  1980
tctacagccc agatcagcca gcaacctgat cttgcccctg gcctgaccac aattggagcc  2040
tctccaacac agactgtgac cctggttacc cagccagtgg tcaccaaaga gacagccatc  2100
agcaaactgg aaatgcccag ctctctgatg ctggaagtcc ccacactgga aaggctgcaa  2160
gaacttcaag aggccacaga tgagctggac ctgaagctga gacaggctga agtgatcaaa  2220
ggcagctggc agccagttgg ggacctgctc attgatagcc tgcaggacca tctggaaaaa  2280
gtgaaagccc tgaggggaga gattgcccct ctgaaagaaa atgtgtccca tgtgaatgac  2340
ctggccagac agctgaccac actgggaatc cagctgagcc cctacaacct gagcaccctt  2400
gaggacctga acaccaggtg gaagctcctc caggtggcag tggaagatag agtcaggcag  2460
ctgcatgagg cccacagaga ttttggacca gccagccagc actttctgtc tacctctgtg  2520
caaggcccct gggagagagc tatctctcct aacaaggtgc cctactacat caaccatgag  2580
acacagacca cctgttggga tcaccccaag atgacagagc tgtaccagag tctggcagac  2640
ctcaacaatg tcagattcag tgcctacagg actgccatga agctcagaag gctccagaaa  2700
gctctgtgcc tggacctgct ttccctgagt gcagcttgtg atgccctgga ccagcacaat  2760
ctgaagcaga atgaccagcc tatggacatc ctccagatca tcaactgcct caccaccatc  2820
tatgataggc tggaacaaga gcacaacaat ctggtcaatg tgcccctgtg tgtggacatg  2880
tgcctgaatt ggctgctgaa tgtgtatgac acaggcagaa caggcaggat cagagtcctg  2940
tccttcaaga caggcatcat ctccctgtgc aaagcccact tggaggacaa gtacagatac  3000
ctgttcaagc aagtggcctc cagcacaggc ttttgtgacc agagaaggct gggcctgctc  3060
ctgcatgaca gcattcagat ccctagacag ctgggagaag tggcttcctt tggaggcagc  3120
aatattgagc catcagtcag gtcctgtttt cagtttgcca acaacaagcc tgagattgag  3180
gctgccctgt tcctggactg gatgagactt gagcctcaga gcatggtctg gctgcctgtg  3240
cttcatagag tggctgctgc tgagactgcc aagcaccagg ccaagtgcaa catctgcaaa  3300
gagtgcccca tcattggctt cagatacaga tccctgaagc acttcaacta tgatatctgc  3360
cagagctgct tctttagtgg cagggttgcc aagggccaca aaatgcacta ccccatggtg  3420
gaatactgca ccccaacaac ctctggggaa gatgttagag actttgccaa ggtgctgaaa  3480
aacaagttca ggaccaagag atactttgct aagcacccca gaatgggcta cctgcctgtc  3540
cagacagtgc ttgagggtga caacatggaa acc                               3573
```

```
SEQ ID NO: 22          moltype = DNA  length = 720
FEATURE                Location/Qualifiers
misc_feature           1..720
                       note = synthetic construct; dystrophin segment
source                 1..720
                       mol_type = other DNA
                       organism = synthetic construct
SEQUENCE: 22
atgctttggt gggaagaagt agaggactgt tatgaaagag aagatgttca aaagaaaaca  60
ttcacaaaat gggtaaatgc acaattttct aagtttggga agcagcatat tgagaacctc  120
ttcagtgacc tacaggatgg gaggcgcctc ctagacctcc tcgaaggcct gacagggcaa  180
aaactgccaa aagaaaaagg atccacaaga gttcatgccc tgaacaatgt caacaaggca  240
ctgcgggttt tgcagaacaa taatgttgat ttagtgaata ttggaagtac tgacatcgta  300
gatggaaatc ataaactgac tcttggtttg atttggaata taatcctcca ctggcaggtc  360
aaaaatgtaa tgaaaaatat catggctgga ttgcaacaaa ccaacagtga aaagattctc  420
ctgagctggg tccgacaatc aactcgtaat tatccacagg ttaatgtaat caacttcacc  480
accagctggt ctgatggcct ggctttgaat gctctcatcc atagtcatag gccagaccta  540
tttgactgga atagtgtggt ttgccagcag tcagccacac aacgactgga acatgcattc  600
aacatcgcca gatatcaatt aggcatagag aaactactcg atcctgaaga tgttgatacc  660
acctatccag ataagaagtc catcttaatg tacatcacat cactcttcca agttttgcct  720

SEQ ID NO: 23          moltype = DNA  length = 36
```

```
FEATURE                Location/Qualifiers
misc_feature           1..36
                       note = synthetic construct; linker
source                 1..36
                       mol_type = other DNA
                       organism = synthetic construct
SEQUENCE: 23
caacaagtga gcattgaagc catccaggaa gtggaa                              36

SEQ ID NO: 24          moltype = DNA  length = 225
FEATURE                Location/Qualifiers
misc_feature           1..225
                       note = synthetic construct; microdystrophin segment
source                 1..225
                       mol_type = other DNA
                       organism = synthetic construct
SEQUENCE: 24
atgttgccaa ggccacctaa agtgactaaa gaagaacatt ttcagttaca tcatcaaatg  60
cactattctc aacagatcac ggtcagtcta gcacagggat atgagagaac ttcttcccct  120
aagcctcgat tcaagagcta tgcctacaca caggctgctt atgtcaccac ctctgaccct  180
acacggagcc catttccttc acagcatttg gaagctcctg aagac                  225

SEQ ID NO: 25          moltype = DNA  length = 27
FEATURE                Location/Qualifiers
misc_feature           1..27
                       note = synthetic construct; linker
source                 1..27
                       mol_type = other DNA
                       organism = synthetic construct
SEQUENCE: 25
aagtcatttg gcagttcatt gatggag                                        27

SEQ ID NO: 26          moltype = DNA  length = 333
FEATURE                Location/Qualifiers
misc_feature           1..333
                       note = synthetic construct; microdystrophin segment
source                 1..333
                       mol_type = other DNA
                       organism = synthetic construct
SEQUENCE: 26
agtgaagtaa acctggaccg ttatcaaaca gctttagaag aagtattatc gtggcttctt  60
tctgctgagg acacattgca agcacaagga gagatttcta atgatgtgga agtggtgaaa  120
gaccagtttc atactcatga ggggtacatg atggatttga cagcccatca gggccgggtt  180
ggtaatattc tacaattggg aagtaagctg attggaacag gaaaattatc agaagatgaa  240
gaaactgaag tacaagagca gatgaatctc ctaaattcaa gatgggaatg cctcagggta  300
gctagcatgg aaaaacaaag caatttacat aga                               333

SEQ ID NO: 27          moltype = DNA  length = 327
FEATURE                Location/Qualifiers
misc_feature           1..327
                       note = synthetic construct; microdystrophin segment
source                 1..327
                       mol_type = other DNA
                       organism = synthetic construct
SEQUENCE: 27
gttttaatgg atctccagaa tcagaaactg aaagagttga atgactggct aacaaaaaca  60
gaagaaagaa caaggaaaat ggaggaagag cctcttggac ctgatcttga agacctaaaa  120
cgccaagtac aacaacataa ggtgcttcaa gaagatctag aacaagaaca agtcagggtc  180
aattctctca ctcacatggt ggtggtagtt gatgaatcta gtggagatca cgcaactgct  240
gctttggaag aacaacttaa ggtattggga gatcgatggg caaacatctg tagatggaca  300
gaagaccgct gggttctttt acaagac                                      327

SEQ ID NO: 28          moltype =   length =
SEQUENCE: 28
000

SEQ ID NO: 29          moltype = DNA  length = 327
FEATURE                Location/Qualifiers
misc_feature           1..327
                       note = synthetic construct; microdystrophin segment
source                 1..327
                       mol_type = other DNA
                       organism = synthetic construct
SEQUENCE: 29
ctcaaatggc aacgtcttac tgaagaacag tgcctttttta gtgcatggct ttcagaaaaa  60
gaagatgcag tgaacaagat tcacacaact ggctttaaag atcaaaatga aatgttatca  120
agtcttcaaa aactggccgt tttaaaagcg gatctagaaa agaaaaagca atccatgggc  180
aaactgtatt cactcaaaca agatcttctt tcaacactga agaataagtc agtgacccag  240
aagacggaag catggctgga taactttgcc cggtgttggg ataatttagt ccaaaaactt  300
```

```
gaaaagagta cagcacagat ttcacag                                     327

SEQ ID NO: 30          moltype = DNA  length = 141
FEATURE                Location/Qualifiers
misc_feature           1..141
                       note = synthetic construct; microdystrophin segment
source                 1..141
                       mol_type = other DNA
                       organism = synthetic construct
SEQUENCE: 30
cagcctgacc tagctcctgg actgaccact attggagcct ctcctactca gactgttact  60
ctggtgacac aacctgtggt tactaaggaa actgccatct ccaaactaga aatgccatct  120
tccttgatgt tggaggtacc t                                           141

SEQ ID NO: 31          moltype =   length =
SEQUENCE: 31
000

SEQ ID NO: 32          moltype = DNA  length = 315
FEATURE                Location/Qualifiers
misc_feature           1..315
                       note = synthetic construct; microdystrophin segment
source                 1..315
                       mol_type = other DNA
                       organism = synthetic construct
SEQUENCE: 32
agactccaac ttcaagaggc cacggatgag ctggacctca agctgcgcca agctgaggtg  60
atcaagggat cctggcagcc cgtgggcgat ctcctcattg actctctcca agatcacctc  120
gagaaagtca aggcacttcg aggagaaatt gcgcctctga aagagaacgt gagccacgtc  180
aatgaccttg ctcgccagct taccactttg ggcattcagc tctcaccgta taacctcagc  240
actctggaag acctgaacac cagatggaag cttctgcagg tggccgtcga ggaccgagtc  300
aggcagctgc atgaa                                                  315

SEQ ID NO: 33          moltype = DNA  length = 216
FEATURE                Location/Qualifiers
misc_feature           1..216
                       note = synthetic construct; microdystrophin segment
source                 1..216
                       mol_type = other DNA
                       organism = synthetic construct
SEQUENCE: 33
gcccacaggg actttggtcc agcatctcag cactttcttt ccacgtctgt ccagggtccc  60
tgggagagag ccatctcgcc aaacaaagtg ccctactata tcaaccacga gactcaaaca  120
acttgctggg accatcccaa aatgacagag ctctaccagt ctttagctga cctgaataat  180
gtcagattct cagcttatag gactgccatg aaactc                           216

SEQ ID NO: 34          moltype = DNA  length = 744
FEATURE                Location/Qualifiers
misc_feature           1..744
                       note = synthetic construct; microdystrophin segment
source                 1..744
                       mol_type = other DNA
                       organism = synthetic construct
SEQUENCE: 34
cgaagactgc agaaggccct ttgcttggat ctcttgagcc tgtcagctgc atgtgatgcc  60
ttggaccagc acaacctcaa gcaaaatgac cagcccatgg atatcctgca gattattaat  120
tgtttgacca ctatttatga ccgcctggag caagagcaca acaatttggt caacgtccct  180
ctctgcgtgg atatgtgtct gaactggctg ctgaatgttt atgatacggg acgaacaggg  240
aggatccgtg tcctgtcttt taaaactggc atcatttccc tgtgtaaagc acatttggaa  300
gacaagtaca gataccttttt caagcaagtg gcaagttcaa caggattttg tgaccagcgc  360
aggctgggcc tccttctgca tgattctatc caaattccaa gacagttggg tgaagttgca  420
tcctttgggg gcagtaacat tgagccaagt gtccggagct gcttccaatt tgctaataat  480
aagccagaga tcgaagcggc cctcttccta gactggatga gactggaacc ccagtccatg  540
gtgtggctgc ccgtcctgca cagagtggct gctgcagaaa ctgccaagca tcaggccaaa  600
tgtaacatct gcaaagagtg tccaatcatt ggattcaggt acaggagtct aaagcacttt  660
aattatgaca tctgccaaag ctgctttttt tctggtcgag ttgcaaaagg ccataaaatg  720
cactatccca tggtggaata ttgc                                        744

SEQ ID NO: 35          moltype = DNA  length = 582
FEATURE                Location/Qualifiers
misc_feature           1..582
                       note = synthetic construct; microdystrophin segment
source                 1..582
                       mol_type = other DNA
                       organism = synthetic construct
SEQUENCE: 35
actccgacta catcaggaga agatgttcga gactttgcca aggtactaaa aaacaaattt  60
cgaaccaaaa ggtattttgc gaagcatccc cgaatgggct acctgccagt gcagactgtc  120
ttagaggggg acaacatgga aactcccgtt actctgatca acttctggcc agtagattct  180
```

```
gcgcctgcct cgtcccctca gctttcacac gatgatactc attcacgcat tgaacattat  240
gctagcaggc tagcagaaat ggaaaacagc aatggatctt atctaaatga tagcatctct  300
cctaatgaga gcatagatga tgaacatttg ttaatccagc attactgcca aagtttgaac  360
caggactccc ccctgagcca gcctcgtagt cctgcccaga tcttgatttc cttagagagt  420
gaggaaagag gggagctaga gagaatccta gcagatcttg aggaagaaaa caggaatctg  480
caagcagaat atgaccgtct aaagcagcag cacgaacata aaggcctgtc cccactgccg  540
tcccctcctg aaatgatgcc cacctctccc cagagtcccc gg                    582

SEQ ID NO: 36          moltype = DNA  length = 12
FEATURE                Location/Qualifiers
misc_feature           1..12
                       note = synthetic construct; linker
source                 1..12
                       mol_type = other DNA
                       organism = synthetic construct
SEQUENCE: 36
gagacccttg aa                                                      12

SEQ ID NO: 37          moltype =   length =
SEQUENCE: 37
000

SEQ ID NO: 38          moltype = DNA  length = 132
FEATURE                Location/Qualifiers
misc_feature           1..132
                       note = synthetic construct; microdystrophin segment
source                 1..132
                       mol_type = other DNA
                       organism = synthetic construct
SEQUENCE: 38
ccatcactaa cacagacaac tgtaatggaa acagtaacta cggtgaccac aagggaacag  60
atcctggtaa agcatgctca agaggaactt ccaccaccac ctccccaaaa gaagaggcag  120
attactgtgg at                                                      132

SEQ ID NO: 39          moltype = DNA  length = 328
FEATURE                Location/Qualifiers
misc_feature           1..328
                       note = synthetic construct; promoter
source                 1..328
                       mol_type = other DNA
                       organism = synthetic construct
SEQUENCE: 39
ggccgtccgc cctcggcacc atcctcacga cacccaaata tggcgacggg tgaggaatgg  60
tggggagtta tttttagagc ggtgaggaag gtgggcaggc agcaggtgtt ggcgctctaa  120
aaataactcc cgggagttat ttttagagcg gaggaatggt ggacacccaa atatggcgac  180
ggttcctcac ccgtcgccat atttgggtgt ccgccctcgg ccggggccgc attcctgggg  240
gccgggcggt gctcccgccc gcctcgataa aaggctccgg ggccggcggc ggcccacgag  300
ctacccggag gagcgggagg cgccaagc                                     328

SEQ ID NO: 40          moltype = DNA  length = 173
FEATURE                Location/Qualifiers
misc_feature           1..173
                       note = synthetic construct; promoter
source                 1..173
                       mol_type = other DNA
                       organism = synthetic construct
SEQUENCE: 40
aatggtggac acccaaatat ggcgacggtt cctcacccgt cgccatattt gggtgtccgc  60
cctcggccgg ggccgcattc ctgggggccg ggcggtgctc ccgcccgcct cgataaaagg  120
ctccggggcc ggcggcggcc cacgagctac ccggaggagc gggaggcgcc aag         173

SEQ ID NO: 41          moltype = DNA  length = 50
FEATURE                Location/Qualifiers
misc_feature           1..50
                       note = synthetic construct; intron
source                 1..50
                       mol_type = other DNA
                       organism = synthetic construct
SEQUENCE: 41
gtgagtatct cagggatcca gacatgggga tatgggaggt gcctctgatc             50

SEQ ID NO: 42          moltype = DNA  length = 50
FEATURE                Location/Qualifiers
misc_feature           1..50
                       note = synthetic construct; poly A
source                 1..50
                       mol_type = other DNA
                       organism = synthetic construct
SEQUENCE: 42
```

```
aggcctaata aagagctcag atgcatcgat cagagtgtgt tggtttttg            50

SEQ ID NO: 43          moltype = DNA  length = 25
FEATURE                Location/Qualifiers
misc_feature           1..25
                       note = synthetic construct; primer
source                 1..25
                       mol_type = other DNA
                       organism = synthetic construct
SEQUENCE: 43
tgactcgaga ggcctaataa agagc                                      25

SEQ ID NO: 44          moltype = DNA  length = 22
FEATURE                Location/Qualifiers
misc_feature           1..22
                       note = synthetic construct; primer
source                 1..22
                       mol_type = other DNA
                       organism = synthetic construct
SEQUENCE: 44
gtggagaggt gtcagaggtt cc                                         22

SEQ ID NO: 45          moltype = DNA  length = 20
FEATURE                Location/Qualifiers
misc_feature           1..20
                       note = synthetic construct; primer
source                 1..20
                       mol_type = other DNA
                       organism = synthetic construct
SEQUENCE: 45
ggcccacgag ctacccggag                                            20

SEQ ID NO: 46          moltype = DNA  length = 21
FEATURE                Location/Qualifiers
misc_feature           1..21
                       note = synthetic construct; primer
source                 1..21
                       mol_type = other DNA
                       organism = synthetic construct
SEQUENCE: 46
cttccagcag atccagcagc c                                          21

SEQ ID NO: 47          moltype = DNA  length = 23
FEATURE                Location/Qualifiers
misc_feature           1..23
                       note = synthetic construct; primer
source                 1..23
                       mol_type = other DNA
                       organism = synthetic construct
SEQUENCE: 47
aagggacctt taccagtgat gtg                                        23

SEQ ID NO: 48          moltype = DNA  length = 21
FEATURE                Location/Qualifiers
misc_feature           1..21
                       note = synthetic construct; primer
source                 1..21
                       mol_type = other DNA
                       organism = synthetic construct
SEQUENCE: 48
acttactctc gccttcctcg g                                          21

SEQ ID NO: 49          moltype = DNA  length = 15
FEATURE                Location/Qualifiers
misc_feature           1..15
                       note = synthetic construct; probe
source                 1..15
                       mol_type = other DNA
                       organism = synthetic construct
SEQUENCE: 49
cagcaaagga attca                                                 15

SEQ ID NO: 50          moltype = DNA  length = 18
FEATURE                Location/Qualifiers
misc_feature           1..18
                       note = synthetic construct; primer
source                 1..18
                       mol_type = other DNA
                       organism = synthetic construct
```

```
SEQUENCE: 50
tgggcctgct cctgcatg                                              18

SEQ ID NO: 51          moltype = DNA  length = 18
FEATURE                Location/Qualifiers
misc_feature           1..18
                       note = synthetic construct; primer
source                 1..18
                       mol_type = other DNA
                       organism = synthetic construct
SEQUENCE: 51
atctcaggct tggcaaac                                              18

SEQ ID NO: 52          moltype = DNA  length = 19
FEATURE                Location/Qualifiers
misc_feature           1..19
                       note = synthetic construct; proble
source                 1..19
                       mol_type = other DNA
                       organism = synthetic construct
SEQUENCE: 52
caatattgag ccatcagtc                                             19

SEQ ID NO: 53          moltype = DNA  length = 4734
FEATURE                Location/Qualifiers
misc_feature           1..4734
                       note = synthetic construct; dystrophin cassette
source                 1..4734
                       mol_type = other DNA
                       organism = synthetic construct
SEQUENCE: 53
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct catatgcagg gtaatgggga tcctctagag gccgtccgcc ctcggcacca  180
tcctcacgac acccaaatat ggcgacgggt gaggaatggt ggggagttat ttttagagcg  240
gtgaggaagg tgggcaggca gcaggtgttg gcgctctaaa aataactccc gggagttatt  300
tttagagcgg aggaatggtg gacacccaaa tatggcgacg gttcctcacc cgtcgccata  360
tttgggtgtc cgccctcggc cgggccgca ttcctgggg ccgggcggtg ctcccgcccg  420
cctcgataaa aggctccggg gccggcggcg gcccacgagc tacccggagg agcgggaggc  480
gccaagcgga attcgccacc atgctttggt gggaagaggt ggaagattgc tatgagaggg  540
aagatgtgca gaagaaaacc ttcaccaaat gggtcaatgc ccagttcagc aagtttggca  600
agcagcacat tgagaacctg ttcagtgacc tgcaggatgg cagaaggctg ctggatctgc  660
tggaaggcct gacaggccag aagctgccta aagagaaggg cagcacaaga gtgcatgccc  720
tgaacaatgt gaacaaggcc ctgagagtgc tgcagaacaa caatgtggac ctggtcaata  780
ttggcagcac agacattgtg gatggcaacc acaagctgac cctgggcctg atctggaaca  840
tcatcctgca ctggcaagtg aagaatgtga tgaagaacat catggctggc ctgcagcaga  900
ccaactctga gaagatcctg ctgagctggg tcagacagag caccagaaac taccctcaag  960
tgaatgtgat caacttcacc acctcttgga gtgatggact ggccctgaat gccctgatcc  1020
acagccacag acctgacctg tttgactgga actctgttgt gtgccagcag tctgccacac  1080
agagactgga acatgccttc aacattgcca gataccagct gggaattgag aaactgctgg  1140
accctgagga tgtggacacc acctatcctg acaagaaatc catcctcatg tacatcacca  1200
gcctgttcca ggtgctgccc cagcaagtgt ccattgaggc cattcaagag gttgagatgc  1260
tgcccagacc tcctaaagtg accaaagagg aacacttcca gctgcaccac cagatgcact  1320
actctcagca gatcacagtg tctctggccc agggatatga gagaacaagc agccccaagc  1380
ctaggttcaa gagctatgcc tacacacagg ctgcctatgt gaccacatct gaccccacaa  1440
gaagcccatt tccaagccag catctggaag cccctgagga caagagcttt ggcagcagcc  1500
tgatggaatc tgaagtgaac ctggatagat accagacagc cctggaagaa gtgctgtcct  1560
ggctgctgtc tgctgaggat acactgcagg ctcagggtga aatcagcaat gatgtggaag  1620
tggtcaagga ccagtttcac acccatgagg gctacatgat ggacctgaca gcccaccagg  1680
gcagagtggg aaatatcctg cagctgggct ccaagctgat tggcacaggc aagctgtctg  1740
aggatgaaga gacagaggtg caagagcaga tgaacctgct gaacagcaga tgggagtgtc  1800
tgagagtggc cagcatggaa aagcagagca acctgcacag agtgctcatg gacctgcaga  1860
atcagaaact gaaagaactg aatgactggc tgaccaagac agaagaaagg actaggaaga  1920
tggaagagga acctctggga ccagacctgg aagatctgaa aagacaggtg cagcagcata  1980
aggtgctgca agaggacctt gagcaagagc aagtcagagt gaacagcctg acacacatgg  2040
tggtggttgt ggatgagtcc tctggggatc atgccacagc tgctctggaa gaacagctga  2100
aggtgctggg agacagatgg gccaacatct gtaggtggac agaggataga tgggtgctgc  2160
tccaggacat tctgctgaag tggcagagac tgacagagga acagtgcctg ttttctgcct  2220
ggctctctga gaaagaggat gctgtcaaca agatccatac cacaggcttc aaggatcaga  2280
atgagatgct cagctccctg cagaaactgg ctgtgctgaa ggctgacctg gaaaagaaaa  2340
agcagtccat gggcaagctc tacagcctga agcaggacct gctgtctacc ctgaagaaca  2400
agtctgtgac ccagaaaact gaggcctggc tggacaactt tgctagatgc tgggacaacc  2460
tggtgcagaa gctggaaaag tctacagccc agatcagcca gcaacctgat cttgcccctg  2520
gcctgaccac aattggagcc tctccaacac agactgtgac cctggttacc cagccagtgg  2580
tcaccaaaga gacagccatc agcaaactgg aaatgcccag ctctctgatg ctggaagtcc  2640
ccacactgga aaggctgcaa gaacttcaag aggccacaga tgagctggac ctgaagctga  2700
gacaggctga agtgatcaaa ggcagctggc agccagttgg ggacctgctc attgatagcc  2760
tgcaggacca tctggaaaaa gtgaaagccc tgaggggaga gattgcccct ctgaaagaaa  2820
atgtgtccca tgtgaatgac ctggccagac agctgaccac actgggaatc cagctgagcc  2880
```

-continued

```
cctacaacct gagcaccctt gaggacctga acaccaggtg gaagctcctc caggtggcag  2940
tggaagatag agtcaggcag ctgcatgagg cccacagaga ttttggacca gccagccagc  3000
actttctgtc tacctctgtg caaggcccct gggagagagc tatctctcct aacaaggtgc  3060
cctactacat caaccatgag acacagacca cctgttggga tcaccccaag atgacagagc  3120
tgtaccagag tctggcagac ctcaacaatg tcagattcag tgcctacagg actgccatga  3180
agctcagaag gctccagaaa gctctgtgcc tggacctgct ttccctgagt gcagcttgtg  3240
atgccctgga ccagcacaat ctgaagcaga atgaccagcc tatggacatc ctccagatca  3300
tcaactgcct caccaccatc tatgataggc tggaacaaga gcacaacaat ctggtcaatg  3360
tgcccctgtg tgtggacatg tgcctgaatt ggctgctgaa tgtgtatgac acaggcagaa  3420
caggcaggat cagagtcctg tccttcaaga caggcatcat ctccctgtgc aaagcccact  3480
tggaggacaa gtacagatac ctgttcaagc aagtggcctc cagcacaggc ttttgtgacc  3540
agagaaggct gggcctgctc ctgcatgaca gcattcagat ccctagacag ctgggagaag  3600
tggcttcctt tggaggcagc aatattgagc catcagtcag gtcctgtttt cagtttgcca  3660
acaacaagcc tgagattgag gctgccctgt tcctggactg gatgagactt gagcctcaga  3720
gcatggtctg gctgcctgtg cttcatagag tggctgctgc tgagactgcc aagcaccagg  3780
ccaagtgcaa catctgcaaa gagtgcccca tcattggctt cagatacaga tccctgaagc  3840
acttcaacta tgatatctgc cagagctgct tctttagtgg caggttgcc aagggccaca  3900
aaatgcacta ccccatggtg gaatactgca ccccaacaac ctctggggaa gatgttagag  3960
actttgccaa ggtgctgaaa aacaagttca ggaccaagag atactttgct aagcacccca  4020
gaatgggcta cctgcctgtc cagacagtgc ttgagggtga caacatggaa acccctgtga  4080
cactgatcaa tttctggcca gtggactctg cccctgcctc aagtccacag ctgtcccatg  4140
atgacaccca cagcagaatt gagcactatg cctccagact ggcagagatg gaaaacagca  4200
atggcagcta cctgaatgat agcatcagcc ccaatgagag cattgatgat gagcatctgc  4260
tgatccagca ctactgtcag tccctgaacc aggactctcc actgagccag cctagaagcc  4320
ctgctcagat cctgatcagc cttgagtctg aggaaagggg agagctggaa agaatcctgg  4380
cagatcttga ggaagagaac agaaacctgc aggcagagta tgacaggctc aaacagcagc  4440
atgagcacaa gggactgagc cctctgcctt ctcctcctga aatgatgccc acctctccac  4500
agtctccaag gtgatgactc gagaggccta ataaagagct cagatgcatc gatcagagtg  4560
tgttggtttt ttgtgtgcca gggtaatggg ctagctgcgg ccgcaggaac ccctagtgat  4620
ggagttggcc actccctctc tgcgcgctcg ctcgctcact gaggccgggc gaccaaaggt  4680
cgcccgacgc ccgggctttg cccgggcggc ctcagtgagc gagcgagcgc gcag        4734
```

```
SEQ ID NO: 54          moltype = DNA  length = 4814
FEATURE                Location/Qualifiers
misc_feature           1..4814
                       note = synthetic construct; dystrophin cassette
source                 1..4814
                       mol_type = other DNA
                       organism = synthetic construct
SEQUENCE: 54
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct catatgcagg gtaatgggga tcctctagag gccgtccgcc ctcggcacca  180
tcctcacgac acccaaatat ggcgacgggt gaggaatggt ggggagttat ttttagagcg  240
gtgaggaagg tgggcaggca gcaggtgttg gcgctctaaa aataactccc gggagttatt  300
tttagagcgg aggaatggtg gacacccaaa tatggcgacg gttcctcacc cgtcgccata  360
tttgggtgtc cgccctcggc cggggccgca ttcctggggg ccgggcggtg ctcccgcccg  420
cctcgataaa aggctccggg gccggcggcg gcccacgagc tacccggagg agcgggaggc  480
gccaaggtga gtatctcagg gatccagaca tggggatatg ggaggtgcct ctgatcccag  540
ggctcactgt gggtctctct gttcacagga attcgccacc atgctttggt gggaagaggt  600
ggaagattgc tatgagaggg aagatgtgca gaagaaaacc ttcaccaaat gggtcaatgc  660
ccagttcagc aagtttggca agcagcacat tgagaacctg ttcagtgacc tgcaggatgg  720
cagaaggctg ctggatctgc tggaaggcct gacaggccag aagctgccta aagagaaggg  780
cagcacaaga gtgcatgccc tgaacaatgt gaacaaggcc ctgagagtgc tgcagaacaa  840
caatgtggac ctggtcaata ttggcagcac agacattgtg gatggcaacc acaagctgac  900
cctgggcctg atctggaaca tcatcctgca ctggcaagtg aagaatgtga tgaagaacat  960
catggctggc ctgcagcaga ccaactctga gaagatcctg ctgagctggg tcagacagag  1020
caccagaaac taccctcaag tgaatgtgat caacttcacc acctcttgga gtgatggact  1080
ggccctgaat gccctgatcc acagccacag acctgacctg tttgactgga actctgttgt  1140
gtgccagcag tctgccacac agagactgga acatgccttc aacattgcca gataccagct  1200
gggaattgag aaactgctgg accctgagga tgtggacacc acctatcctg acaagaaatc  1260
catcctcatg tacatcacca gcctgttcca ggtgctgccc cagcaagtgt ccattgaggc  1320
cattcaagag gttgagatgc tgcccagacc tcctaaagtg accaaagagg aacacttcca  1380
gctgcaccac cagatgcact actctcagca gatcacagtg tctctggccc agggatatga  1440
gagaacaagc agccccaagc ctaggttcaa gagctatgcc tacacacagg ctgcctatgt  1500
gaccacatct gaccccacaa gaagcccatt tccaagccag catctggaag cccctgagga  1560
caagagcttt ggcagcagcc tgatggaatc tgaagtgaac ctggatagat accagacagc  1620
cctggaagaa gtgctgtcct ggctgctgtc tgctgaggat acactgcagg ctcagggtga  1680
aatcagcaat gatgtggaag tggtcaagga ccagtttcac acccatgagg gctacatgat  1740
ggacctgaca gcccaccagg gcagagtggg aaatatcctg cagctgggct ccaagctgat  1800
tggcacaggc aagctgtctg aggatgaaga gacagaggtg caagagcaga tgaacctgct  1860
gaacagcaga tgggagtgtc tgagagtggc cagcatggaa aagcagagca acctgcacag  1920
agtgctcatg gacctgcaga atcagaaact gaaagaactg aatgactggc tgaccaagac  1980
agaagaaagg actaggaaga tggaagagga acctctggga ccagacctgg aagatctgaa  2040
aagacaggtg cagcagcata aggtgctgca agaggacctt gagcaagagc aagtcagagt  2100
gaacagcctg acacacatgg tggtggttgt ggatgagtcc tctggggatc atgccacagc  2160
tgctctggaa gaacagctga aggtgctggg agacagatgg gccaacatct gtaggtggac  2220
agaggataga tgggtgctgc tccaggacat tctgctgaag tggcagagac tgacagagga  2280
acagtgcctg ttttctgcct ggctctctga gaaagaggat gctgtcaaca agatccatac  2340
```

```
cacaggcttc aaggatcaga atgagatgct cagctccctg cagaaactgg ctgtgctgaa  2400
ggctgacctg gaaaagaaaa agcagtccat gggcaagctc tacagcctga agcaggacct  2460
gctgtctacc ctgaagaaca agtctgtgac ccagaaaact gaggcctggc tggacaactt  2520
tgctagatgc tgggacaacc tggtgcagaa gctggaaaag tctacagccc agatcagcca  2580
gcaacctgat cttgcccctg gcctgaccac aattggagcc tctccaacac agactgtgac  2640
cctggttacc cagccagtgg tcaccaaaga gacagccatc agcaaactgg aaatgcccag  2700
ctctctgatg ctggaagtcc ccacactgga aaggctgcaa gaacttcaag aggccacaga  2760
tgagctggac ctgaagctga gacaggctga agtgatcaaa ggcagctggc agccagttgg  2820
ggacctgctc attgatagcc tgcaggacca tctggaaaaa gtgaaagccc tgaggggaga  2880
gattgcccct ctgaaagaaa atgtgtccca tgtgaatgac ctggccagac agctgaccac  2940
actgggaatc cagctgagcc cctacaacct gagcaccctt gaggacctga acaccaggtg  3000
gaagctcctc caggtggcag tggaagatag agtcaggcag ctgcatgagg cccacagaga  3060
ttttggacca gccagccagc actttctgtc tacctctgtg caaggcccct gggagagagc  3120
tatctctcct aacaaggtgc cctactacat caaccatgag acacagacca cctgttggga  3180
tcaccccaag atgacagagc tgtaccagag tctggcagac ctcaacaatg tcagattcag  3240
tgcctacagg actgccatga agctcagaag gctccagaaa gctctgtgcc tggacctgct  3300
ttccctgagt gcagcttgtg atgccctgga ccagcacaat ctgaagcaga atgaccagcc  3360
tatggacatc ctccagatca tcaactgcct caccaccatc tatgataggc tggaacaaga  3420
gcacaacaat ctggtcaatg tgcccctgtg tgtggacatg tgcctgaatt ggctgctgaa  3480
tgtgtatgac acaggcagaa caggcaggat cagagtcctg tccttcaaga caggcatcat  3540
ctccctgtgc aaagcccact tggaggacaa gtacagatac ctgttcaagc aagtggcctc  3600
cagcacaggc ttttgtgacc agagaaggct gggcctgctc ctgcatgaca gcattcagat  3660
ccctagacag ctgggagaag tggcttcctt tggaggcagc aatattgagc catcagtcag  3720
gtcctgtttt cagtttgcca acaacaagcc tgagattgag gctgccctgt tcctggactg  3780
gatgagactt gagcctcaga gcatggtctg gctgcctgtg cttcatagag tggctgctgc  3840
tgagactgcc aagcaccagg ccaagtgcaa catctgcaaa gagtgcccca tcattggctt  3900
cagatacaga tccctgaagc acttcaacta tgatatctgc cagagctgct tctttagtgg  3960
cagggttgcc aagggccaca aaatgcacta ccccatggtg gaatactgca ccccaacaac  4020
ctctggggaa gatgttagag actttgccaa ggtgctgaaa aacaagttca ggaccaagag  4080
atactttgct aagcacccca gaatgggcta cctgcctgtc cagacagtgc ttgagggtga  4140
caacatggaa acccctgtga cactgatcaa tttctggcca gtggactctg cccctgcctc  4200
aagtccacag ctgtcccatg atgacaccca cagcagaatt gagcactatg cctccagact  4260
ggcagagatg gaaaacagca atggcagcta cctgaatgat agcatcagcc ccaatgagag  4320
cattgatgat gagcatctgc tgatccagca ctactgtcag tccctgaacc aggactctcc  4380
actgagccag cctagaagcc ctgctcagat cctgatcagc cttgagtctg aggaaagggg  4440
agagctggaa agaatcctgg cagatcttga ggaagagaac agaaacctgc aggcagagta  4500
tgacaggctc aaacagcagc atgagcacaa gggactgagc cctctgcctt ctcctcctga  4560
aatgatgccc acctctccac agtctccaag gtgatgactc gagaggccta ataaagagct  4620
cagatgcatc gatcagagtg tgttggtttt ttgtgtgcca gggtaatggg ctagctgcgg  4680
ccgcaggaac ccctagtgat ggagttggcc actccctctc tgcgcgctcg ctcgctcact  4740
gaggccgggc gaccaaaggt cgcccgacgc ccgggctttg cccgggcggc ctcagtgagc  4800
gagcgagcgc gcag                                                    4814
```

```
SEQ ID NO: 55          moltype = DNA  length = 4364
FEATURE                Location/Qualifiers
misc_feature           1..4364
                       note = synthetic construct; dystrophin cassette
source                 1..4364
                       mol_type = other DNA
                       organism = synthetic construct
SEQUENCE: 55
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct catatgcagg gtaatgggga tcctctagag gccgtccgcc ctcggcacca  180
tcctcacgac acccaaatat ggcgacgggt gaggaatggt ggggagttat ttttagagcg  240
gtgaggaagg tgggcaggca gcaggtgttg gcgctctaaa aataactccc gggagttatt  300
tttagagcgg aggaatggtg gacacccaaa tatggcgacg gttcctcacc cgtcgccata  360
tttgggtgtc cgccctcggc cggggccgca ttcctggggg ccgggcggtg ctcccgcccg  420
cctcgataaa aggctccggg gccggcggcg gcccacgagc tacccggagg agcgggaggc  480
gccaaggtga gtatctcagg gatccagaca tggggatatg ggaggtgcct ctgatcccag  540
ggctcactgt gggtctctct gttcacagga attcgccacc atgctttggt gggaagaggt  600
ggaagattgc tatgagaggg aagatgtgca gaagaaaacc ttcaccaaat gggtcaatgc  660
ccagttcagc aagtttggca agcagcacat tgagaacctg ttcagtgacc tgcaggatgg  720
cagaaggctg ctggatctgc tggaaggcct gacaggccag aagctgccta aagagaaggg  780
cagcacaaga gtgcatgccc tgaacaatgt gaacaaggcc ctgagagtgc tgcagaacaa  840
caatgtggac ctggtcaata ttggcagcac agacattgtg gatggcaacc acaagctgac  900
cctgggcctg atctggaaca tcatcctgca ctggcaagtg aagaatgtga tgaagaacat  960
catggctggc ctgcagcaga ccaactctga gaagatcctg ctgagctggg tcagacagag  1020
caccagaaac taccctcaag tgaatgtgat caacttcacc acctcttgga gtgatggact  1080
ggccctgaat gccctgatcc acagccacag acctgacctg tttgactgga actctgttgt  1140
gtgccagcag tctgccacac agagactgga acatgccttc aacattgcca gataccagct  1200
gggaattgag aaactgctgg accctgagga tgtggacacc acctatcctg acaagaaatc  1260
catcctcatg tacatcacca gcctgttcca ggtgctgccc cagcaagtgt ccattgaggc  1320
cattcaagag gttgagatgc tgcccagacc tcctaaagtg accaaagagg aacacttcca  1380
gctgcaccac cagatgcact actctcagca gatcacagtg tctctggccc agggatatga  1440
gagaacaagc agccccaagc ctaggttcaa gagctatgcc tacacacagg ctgcctatgt  1500
gaccacatct gaccccacaa gaagcccatt tccaagccag catctggaag cccctgagga  1560
caagagcttt ggcagcagcc tgatggaatc tgaagtgaac ctggatagat accagacagc  1620
cctggaagaa gtgctgtcct ggctgctgtc tgctgaggat acactgcagg ctcagggtga  1680
```

```
aatcagcaat gatgtggaag tggtcaagga ccagtttcac acccatgagg gctacatgat  1740
ggacctgaca gcccaccagg gcagagtggg aaatatcctg cagctgggct ccaagctgat  1800
tggcacaggc aagctgtctg aggatgaaga gacagaggtg caagagcaga tgaacctgct  1860
gaacagcaga tgggagtgtc tgagagtggc cagcatggaa aagcagagca acctgcacag  1920
agtgctcatg gacctgcaga atcagaaact gaaagaactg aatgactggc tgaccaagac  1980
agaagaaagg actaggaaga tggaagagga acctctggga ccagacctgg aagatctgaa  2040
aagacaggtg cagcagcata aggtgctgca agaggacctt gagcaagagc aagtcagagt  2100
gaacagcctg acacacatgg tggtggttgt ggatgagtcc tctggggatc atgccacagc  2160
tgctctggaa gaacagctga aggtgctggg agacagatgg gccaacatct gtaggtggac  2220
agaggataga tgggtgctgc tccaggacat tctgctgaag tggcagagac tgacagagga  2280
acagtgcctg ttttctgcct ggctctctga gaaagaggat gctgtcaaca agatccatac  2340
cacaggcttc aaggatcaga atgagatgct cagctccctg cagaaactgg ctgtgctgaa  2400
ggctgacctg gaaaagaaaa agcagtccat gggcaagctc tacagcctga agcaggacct  2460
gctgtctacc ctgaagaaca agtctgtgac ccagaaaact gaggcctggc tggacaactt  2520
tgctagatgc tgggacaacc tggtgcagaa gctggaaaag tctacagccc agatcagcca  2580
gcaacctgat cttgcccctg gcctgaccac aattggagcc tctccaacac agactgtgac  2640
cctggttacc cagccagtgg tcaccaaaga gacagccatc agcaaactgg aaatgcccag  2700
ctctctgatg ctggaagtcc ccacactgga aaggctgcaa gaacttcaag aggccacaga  2760
tgagctggac ctgaagctga gacaggctga agtgatcaaa ggcagctggc agccagttgg  2820
ggacctgctc attgatagcc tgcaggacca tctggaaaaa gtgaaagccc tgaggggaga  2880
gattgcccct ctgaaagaaa atgtgtccca tgtgaatgac ctggccagac agctgaccac  2940
actgggaatc cagctgagcc cctacaacct gagcaccctt gaggacctga acaccaggtg  3000
gaagctcctc caggtggcag tggaagatag agtcaggcag ctgcatgagg cccacagaga  3060
ttttggacca gccagccagc actttctgtc tacctctgtg caaggcccct gggagagagc  3120
tatctctcct aacaaggtgc cctactacat caaccatgag acacagacca cctgttggga  3180
tcaccccaag atgacagagc tgtaccagag tctggcagac ctcaacaatg tcagattcag  3240
tgcctacagg actgccatga agctcagaag gctccagaaa gctctgtgcc tggacctgct  3300
ttccctgagt gcagcttgtg atgccctgga ccagcacaat ctgaagcaga atgaccagcc  3360
tatggacatc ctccagatca tcaactgcct caccaccatc tatgataggc tggaacaaga  3420
gcacaacaat ctggtcaatg tgcccctgtg tgtggacatg tgcctgaatt ggctgctgaa  3480
tgtgtatgac acaggcagaa caggcaggat cagagtcctg tccttcaaga caggcatcat  3540
ctccctgtgc aaagcccact tggaggacaa gtacagatac ctgttcaagc aagtggcctc  3600
cagcacaggc ttttgtgacc agagaaggct gggcctgctc ctgcatgaca gcattcagat  3660
ccctagacag ctgggagaag tggcttcctt tggaggcagc aatattgagc catcagtcag  3720
gtcctgtttt cagtttgcca acaacaagcc tgagattgag gctgccctgt tcctggactg  3780
gatgagactt gagcctcaga gcatggtctg gctgcctgtg cttcatagag tggctgctgc  3840
tgagactgcc aagcaccagg ccaagtgcaa catctgcaaa gagtgcccca tcattggctt  3900
cagatacaga tccctgaagc acttcaacta tgatatctgc cagagctgct tctttagtgg  3960
cagggttgcc aagggccaca aaatgcacta ccccatggtg gaatactgca ccccaacaac  4020
ctctggggaa gatgttagag actttgccaa ggtgctgaaa aacaagttca ggaccaagag  4080
atactttgct aagcacccca gaatgggcta cctgcctgtc cagacagtgc ttgagggtga  4140
caacatggaa acctgatgag tcgacaggcc taataaagag ctcagatgca tcgatcagag  4200
tgtgttggtt ttttgtgtgg ctagctgcgg ccgcaggaac ccctagtgat ggagttggcc  4260
actccctctc tgcgcgctcg ctcgctcact gaggccgggc gaccaaaggt cgcccgacgc  4320
ccgggctttg cccgggcggc ctcagtgagc gagcgagcgc gcag                  4364
```

```
SEQ ID NO: 56          moltype = DNA  length = 4661
FEATURE                Location/Qualifiers
misc_feature           1..4661
                       note = synthetic construct; dystrophin cassette
source                 1..4661
                       mol_type = other DNA
                       organism = synthetic construct
SEQUENCE: 56
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct catatgcagg gtaatgggga tcctctagag aatggtggac acccaaatat  180
ggcgacggtt cctcacccgt cgccatattt gggtgtccgc cctcggccgg ggccgcattc  240
ctgggggccg ggcggtgctc ccgcccgcct cgataaaagg ctccggggcc ggcggcggcc  300
cacgagctac ccggaggagc gggaggcgcc aaggtgagta tctcagggat ccagacatgg  360
ggatatggga ggtgcctctg atcccagggc tcactgtggg tctctctgtt cacaggaatt  420
cgccaccatg ctttggtggg aagaggtgga agattgctat gagagggaag atgtgcagaa  480
gaaaaccttc accaaatggg tcaatgccca gttcagcaag tttggcaagc agcacattga  540
gaacctgttc agtgacctgc aggatggcag aaggctgctg gatctgctgg aaggcctgac  600
aggccagaag ctgcctaaag agaagggcag cacaagagtg catgccctga acaatgtgaa  660
caaggccctg agagtgctgc agaacaacaa tgtggacctg gtcaatattg gcagcacaga  720
cattgtggat ggcaaccaca agctgaccct gggcctgatc tggaacatca tcctgcactg  780
gcaagtgaag aatgtgatga agaacatcat ggctggcctg cagcagacca actctgagaa  840
gatcctgctg agctgggtca gacagagcac cagaaactac cctcaagtga atgtgatcaa  900
cttcaccacc tcttggagtg atggactggc cctgaatgcc ctgatccaca gccacagacc  960
tgacctgttt gactggaact ctgttgtgtg ccagcagtct gccacacaga gactggaaca  1020
tgccttcaac attgccagat accagctggg aattgagaaa ctgctggacc ctgaggatgt  1080
ggacaccacc tatcctgaca agaaatccat cctcatgtac atcaccagcc tgttccaggt  1140
gctgccccag caagtgtcca ttgaggccat tcaagaggtt gagatgctgc ccagacctcc  1200
taaagtgacc aaagaggaac acttccagct gcaccaccag atgcactact ctcagcagat  1260
cacagtgtct ctggcccagg gatatgagag aacaagcagc cccaagccta ggttcaagag  1320
ctatgcctac acacaggctg cctatgtgac cacatctgac ccccacaagaa gcccatttcc  1380
aagccagcat ctggaagccc ctgaggacaa gagctttggc agcagcctga tggaatctga  1440
agtgaacctg gatagatacc agacagccct ggaagaagtg ctgtcctggc tgctgtctgc  1500
```

```
tgaggataca ctgcaggctc agggtgaaat cagcaatgat gtggaagtgg tcaaggacca  1560
gtttcacacc catgagggct acatgatgga cctgacagcc caccagggca gagtgggaaa  1620
tatcctgcag ctgggctcca agctgattgg cacaggcaag ctgtctgagg atgaagagac  1680
agaggtgcaa gagcagatga acctgctgaa cagcagatgg gagtgtctga gagtggccag  1740
catggaaaag cagagcaacc tgcacagagt gctcatggac ctgcagaatc agaaactgaa  1800
agaactgaat gactggctga ccaagacaga agaaaggact aggaagatgg aagaggaacc  1860
tctgggacca gacctggaag atctgaaaag acaggtgcag cagcataagg tgctgcaaga  1920
ggaccttgag caagagcaag tcagagtgaa cagcctgaca cacatggtgg tggttgtgga  1980
tgagtcctct ggggatcatg ccacagctgc tctggaagaa cagctgaagg tgctgggaga  2040
cagatgggcc aacatctgta ggtggacaga ggatagatgg gtgctgctcc aggacattct  2100
gctgaagtgg cagagactga cagaggaaca gtgcctgttt tctgcctggc tctctgagaa  2160
agaggatgct gtcaacaaga tccataccac aggcttcaag gatcagaatg agatgctcag  2220
ctccctgcag aaactggctg tgctgaaggc tgacctggaa aagaaaaagc agtccatggg  2280
caagctctac agcctgaagc aggacctgct gtctaccctg aagaacaagt ctgtgaccca  2340
gaaaactgag gcctggctgg acaactttgc tagatgctgg gacaacctgg tgcagaagct  2400
ggaaaagtct acagcccaga tcagccagca acctgatctt gcccctggcc tgaccacaat  2460
tggagcctct ccaacacaga ctgtgaccct ggttacccag ccagtggtca ccaaagagac  2520
agccatcagc aaactggaaa tgcccagctc tctgatgctg gaagtcccca cactggaaag  2580
gctgcaagaa cttcaagagg ccacagatga gctggacctg aagctgagac aggctgaagt  2640
gatcaaaggc agctggcagc cagttgggga cctgctcatt gatagcctgc aggaccatct  2700
ggaaaaagtg aaagccctga ggggagagat tgcccctctg aaagaaaatg tgtcccatgt  2760
gaatgacctg gccagacagc tgaccacact gggaatccag ctgagcccct acaacctgag  2820
caccettgag gacctgaaca ccaggtggaa gctcctccag gtggcagtgg aagatagagt  2880
caggcagctg catgaggccc acagagattt tggaccagcc agccagcact ttctgtctac  2940
ctctgtgcaa ggcccctggg agagagctat ctctcctaac aaggtgccct actacatcaa  3000
ccatgagaca cagaccacct gttgggatca ccccaagatg acagagctgt accagagtct  3060
ggcagacctc aacaatgtca gattcagtgc ctacaggact gccatgaagc tcagaaggct  3120
ccagaaagct ctgtgcctgg acctgctttc cctgagtgca gcttgtgatg ccctggacca  3180
gcacaatctg aagcagaatg accagcctat ggacatcctc cagatcatca actgcctcac  3240
caccatctat gataggctgg aacaagagca caacaatctg gtcaatgtgc ccctgtgtgt  3300
ggacatgtgc ctgaattggc tgctgaatgt gtatgacaca ggcagaacag gcaggatcag  3360
agtcctgtcc ttcaagacag gcatcatctc cctgtgcaaa gcccacttgg aggacaagta  3420
cagatacctg ttcaagcaag tggcctccag cacaggcttt tgtgaccaga gaaggctggg  3480
cctgctcctg catgacagca ttcagatccc tagacagctg ggagaagtgg cttcctttgg  3540
aggcagcaat attgagccat cagtcaggtc ctgttttcag tttgccaaca acaagcctga  3600
gattgaggct gccctgttcc tggactggat gagacttgag cctcagagca tggtctggct  3660
gcctgtgctt catagagtgg ctgctgctga gactgccaag caccaggcca agtgcaacat  3720
ctgcaaagag tgccccatca ttggcttcag atacagatcc ctgaagcact tcaactatga  3780
tatctgccag agctgcttct ttagtggcag ggttgccaag ggccacaaaa tgcactaccc  3840
catggtggaa tactgcaccc caacaacctc tggggaagat gttagagact ttgccaaggt  3900
gctgaaaaac aagttcagga ccaagagata ctttgctaag caccccagaa tgggctacct  3960
gcctgtccag acagtgcttg agggtgacaa catggaaacc cctgtgacac tgatcaattt  4020
ctggccagtg gactctgccc ctgcctcaag tccacagctg tcccatgatg acacccacag  4080
cagaattgag cactatgcct ccagactggc agagatggaa aacagcaatg gcagctacct  4140
gaatgatagc atcagcccca atgagagcat tgatgatgag catctgctga tccagcacta  4200
ctgtcagtcc ctgaaccagg actctccact gagccagcct agaagccctg ctcagatcct  4260
gatcagcctt gagtctgagg aaaggggaga gctggaaaga atcctggcag atcttgagga  4320
agagaacaga aacctgcagg cagagtatga caggctcaaa cagcagcatg agcacaaggg  4380
actgagccct ctgccttctc ctcctgaaat gatgcccacc tctccacagt ctccaaggtg  4440
atgactcgag aggcctaata aagagctcag atgcatcgat cagagtgtgt tggtttttttg  4500
tgtgccaggg taatgggcta gctgcggccg caggaacccc tagtgatgga gttggccact  4560
ccctctctgc gcgctcgctc gctcactgag gccgggcgac caaaggtcgc ccgacgcccg  4620
ggctttgccc gggcggcctc agtgagcgag cgagcgcgca g                     4661
```

```
SEQ ID NO: 57           moltype = DNA  length = 720
FEATURE                 Location/Qualifiers
misc_feature            1..720
                        note = synthetic construct; dystrophin segment
source                  1..720
                        mol_type = other DNA
                        organism = synthetic construct
SEQUENCE: 57
atgctttggt gggaagaggt ggaagattgc tatgagaggg aagatgtgca gaagaaaacc  60
ttcaccaaat gggtcaatgc ccagttcagc aagtttggca agcagcacat tgagaacctg  120
ttcagtgacc tgcaggatgg cagaaggctg ctggatctgc tggaaggcct gacaggccag  180
aagctgccta aagagaaggg cagcacaaga gtgcatgccc tgaacaatgt gaacaaggcc  240
ctgagagtgc tgcagaacaa caatgtggac ctggtcaata ttggcagcac agacattgtg  300
gatggcaacc acaagctgac cctgggcctg atctggaaca tcatcctgca ctggcaagtg  360
aagaatgtga tgaagaacat catggctggc ctgcagcaga ccaactctga gaagatcctg  420
ctgagctggg tcagacagag caccagaaac taccctcaag tgaatgtgat caacttcacc  480
acctcttgga gtgatggact ggccctgaat gccctgatcc acagccacag acctgacctg  540
tttgactgga actctgttgt gtgccagcag tctgccacac agagactgga acatgccttc  600
aacattgcca gataccagct gggaattgag aaactgctgg accctgagga tgtggacacc  660
acctatcctg acaagaaatc catcctcatg tacatcacca gcctgttcca ggtgctgccc  720
```

```
SEQ ID NO: 58           moltype = DNA  length = 36
FEATURE                 Location/Qualifiers
misc_feature            1..36
                        note = synthetic construct; linker
```

-continued

```
source                  1..36
                        mol_type = other DNA
                        organism = synthetic construct
SEQUENCE: 58
cagcaagtgt ccattgaggc cattcaagag gttgag                             36

SEQ ID NO: 59           moltype = DNA  length = 225
FEATURE                 Location/Qualifiers
misc_feature            1..225
                        note = synthetic construct; dystrophin segment
source                  1..225
                        mol_type = other DNA
                        organism = synthetic construct
SEQUENCE: 59
atgctgccca gacctcctaa agtgaccaaa gaggaacact tccagctgca ccaccagatg  60
cactactctc agcagatcac agtgtctctg gcccagggat atgagagaac aagcagcccc  120
aagcctaggt tcaagagcta tgcctacaca caggctgcct atgtgaccac atctgacccc  180
acaagaagcc catttccaag ccagcatctg gaagcccctg aggac                  225

SEQ ID NO: 60           moltype = DNA  length = 27
FEATURE                 Location/Qualifiers
misc_feature            1..27
                        note = synthetic construct; linker
source                  1..27
                        mol_type = other DNA
                        organism = synthetic construct
SEQUENCE: 60
aagagctttg gcagcagcct gatggaa                                       27

SEQ ID NO: 61           moltype = DNA  length = 333
FEATURE                 Location/Qualifiers
misc_feature            1..333
                        note = synthetic construct; dystrophin segment
source                  1..333
                        mol_type = other DNA
                        organism = synthetic construct
SEQUENCE: 61
tctgaagtga acctggatag ataccagaca gccctggaag aagtgctgtc ctggctgctg  60
tctgctgagg atacactgca ggctcagggt gaaatcagca atgatgtgga agtggtcaag  120
gaccagtttc acacccatga gggctacatg atggacctga cagcccacca gggcagagtg  180
ggaaatatcc tgcagctggg ctccaagctg attggcacag gcaagctgtc tgaggatgaa  240
gagacagagg tgcaagagca gatgaacctg ctgaacagca gatgggagtg tctgagagtg  300
gccagcatgg aaaagcagag caacctgcac aga                                333

SEQ ID NO: 62           moltype = DNA  length = 327
FEATURE                 Location/Qualifiers
misc_feature            1..327
                        note = synthetic construct; dystrophin segment
source                  1..327
                        mol_type = other DNA
                        organism = synthetic construct
SEQUENCE: 62
gtgctcatgg acctgcagaa tcagaaactg aaagaactga atgactggct gaccaagaca  60
gaagaaagga ctaggaagat ggaagaggaa cctctgggac cagacctgga agatctgaaa  120
agacaggtgc agcagcataa ggtgctgcaa gaggaccttg agcaagagca agtcagagtg  180
aacagcctga cacacatggt ggtggttgtg gatgagtcct ctggggatca tgccacagct  240
gctctggaag aacagctgaa ggtgctggga gacagatggg ccaacatctg taggtggaca  300
gaggatagat gggtgctgct ccaggac                                      327

SEQ ID NO: 63           moltype =   length =
SEQUENCE: 63
000

SEQ ID NO: 64           moltype = DNA  length = 327
FEATURE                 Location/Qualifiers
misc_feature            1..327
                        note = synthetic construct; dystrophin segment
source                  1..327
                        mol_type = other DNA
                        organism = synthetic construct
SEQUENCE: 64
ctgaagtggc agagactgac agaggaacag tgcctgtttt ctgcctggct ctctgagaaa  60
gaggatgctg tcaacaagat ccataccaca ggcttcaagg atcagaatga gatgctcagc  120
tccctgcaga aactggctgt gctgaaggct gacctggaaa agaaaaagca gtccatgggc  180
aagctctaca gcctgaagca ggacctgctg tctaccctga agaacaagtc tgtgacccag  240
aaaactgagg cctggctgga caactttgct agatgctggg acaacctggt gcagaagctg  300
gaaaagtcta cagcccagat cagccag                                      327

SEQ ID NO: 65           moltype = DNA  length = 141
```

```
FEATURE                Location/Qualifiers
misc_feature           1..141
                       note = synthetic construct; dystrophin segment
source                 1..141
                       mol_type = other DNA
                       organism = synthetic construct
SEQUENCE: 65
caacctgatc ttgcccctgg cctgaccaca attggagcct ctccaacaca gactgtgacc  60
ctggttaccc agccagtggt caccaaagag acagccatca gcaaactgga aatgcccagc  120
tctctgatgc tggaagtccc c                                           141

SEQ ID NO: 66          moltype =   length =
SEQUENCE: 66
000

SEQ ID NO: 67          moltype = DNA  length = 318
FEATURE                Location/Qualifiers
misc_feature           1..318
                       note = synthetic construct; dystrophin segment
source                 1..318
                       mol_type = other DNA
                       organism = synthetic construct
SEQUENCE: 67
aggctgcaag aacttcaaga ggccacagat gagctggacc tgaagctgag acaggctgaa  60
gtgatcaaag gcagctggca gccagttggg gacctgctca ttgatagcct gcaggaccat  120
ctggaaaaag tgaaagccct gaggggagag attgcccctc tgaaagaaaa tgtgtcccat  180
gtgaatgacc tggccagaca gctgaccaca ctgggaatcc agctgagccc ctacaacctg  240
agcacccttg aggacctgaa caccaggtgg aagctcctcc aggtggcagt ggaagataga  300
gtcaggcagc tgcatgag                                               318

SEQ ID NO: 68          moltype = DNA  length = 216
FEATURE                Location/Qualifiers
misc_feature           1..216
                       note = synthetic construct; dystrophin segment
source                 1..216
                       mol_type = other DNA
                       organism = synthetic construct
SEQUENCE: 68
gcccacagag attttggacc agccagccag cactttctgt ctacctctgt gcaaggcccc  60
tgggagagag ctatctctcc taacaaggtg ccctactaca tcaaccatga gacacagacc  120
acctgttggg atcaccccaa gatgacagag ctgtaccaga gtctggcaga cctcaacaat  180
gtcagattca gtgcctacag gactgccatg aagctc                           216

SEQ ID NO: 69          moltype = DNA  length = 744
FEATURE                Location/Qualifiers
misc_feature           1..744
                       note = synthetic construct; dystrophin segment
source                 1..744
                       mol_type = other DNA
                       organism = synthetic construct
SEQUENCE: 69
agaaggctcc agaaagctct gtgcctggac ctgctttccc tgagtgcagc ttgtgatgcc  60
ctggaccagc acaatctgaa gcagaatgac cagcctatgg acatcctcca gatcatcaac  120
tgcctcacca ccatctatga taggctggaa caagagcaca acaatctggt caatgtgccc  180
ctgtgtgtgg acatgtgcct gaattggctg ctgaatgtgt atgacacagg cagaacaggc  240
aggatcagag tcctgtcctt caagacaggc atcatctccc tgtgcaaagc ccacttggag  300
gacaagtaca gatacctgtt caagcaagtg gcctccagca caggcttttg tgaccagaga  360
aggctgggcc tgctcctgca tgacagcatt cagatcccta gacagctggg agaagtggct  420
tcctttggag gcagcaatat tgagccatca gtcaggtcct gttttcagtt tgccaacaac  480
aagcctgaga ttgaggctgc cctgttcctg gactggatga gacttgagcc tcagagcatg  540
gtctggctgc ctgtgcttca tagagtggct gctgctgaga ctgccaagca ccaggccaag  600
tgcaacatct gcaaagagtg ccccatcatt ggcttcagat acagatccct gaagcacttc  660
aactatgata tctgccagag ctgcttcttt agtggcaggg ttgccaaggg ccacaaaatg  720
cactacccca tggtggaata ctgc                                        744

SEQ ID NO: 70          moltype = DNA  length = 588
FEATURE                Location/Qualifiers
misc_feature           1..588
                       note = synthetic construct; dystrophin segment
source                 1..588
                       mol_type = other DNA
                       organism = synthetic construct
SEQUENCE: 70
accccaacaa cctctgggga agatgttaga gactttgcca aggtgctgaa aaacaagttc  60
aggaccaaga gatactttgc taagcacccc agaatgggct acctgcctgt ccagacagtg  120
cttgagggtg acaacatgga aacccctgtg acactgatca atttctggcc agtggactct  180
gcccctgcct caagtccaca gctgtcccat gatgacaccc acagcagaat tgagcactat  240
gcctccagac tggcagagat ggaaaacagc aatggcagct acctgaatga tagcatcagc  300
cccaatgaga gcattgatga tgagcatctg ctgatccagc actactgtca gtccctgaac  360
```

-continued

```
caggactctc cactgagcca gcctagaagc cctgctcaga tcctgatcag ccttgagtct  420
gaggaaaggg gagagctgga aagaatcctg gcagatcttg aggaagagaa cagaaacctg  480
caggcagagt atgacaggct caaacagcag catgagcaca agggactgag ccctctgcct  540
tctcctcctg aaatgatgcc cacctctcca cagtctccaa ggtgatga              588

SEQ ID NO: 71          moltype = DNA  length = 12
FEATURE                Location/Qualifiers
misc_feature           1..12
                       note = synthetic construct; linker
source                 1..12
                       mol_type = other DNA
                       organism = synthetic construct
SEQUENCE: 71
gaaacactgg aa                                                     12

SEQ ID NO: 72          moltype =   length =
SEQUENCE: 72
000

SEQ ID NO: 73          moltype = DNA  length = 129
FEATURE                Location/Qualifiers
misc_feature           1..129
                       note = synthetic construct; viral peptide
source                 1..129
                       mol_type = other DNA
                       organism = synthetic construct
SEQUENCE: 73
cgcgcgctcg ctcgctcact gaggccgccc gggcaaagcc cgggcgtcgg gcgacctttg  60
gtcgcccggc ctcagtgagc gagcgagcgc gcagagaggg agtggccaac tccatcacta  120
ggggttcct                                                         129

SEQ ID NO: 74          moltype = DNA  length = 130
FEATURE                Location/Qualifiers
misc_feature           1..130
                       note = synthetic construct; viral peptide
source                 1..130
                       mol_type = other DNA
                       organism = synthetic construct
SEQUENCE: 74
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag                                                        130

SEQ ID NO: 75          moltype = DNA  length = 133
FEATURE                Location/Qualifiers
misc_feature           1..133
                       note = synthetic construct; chimeric intron
source                 1..133
                       mol_type = other DNA
                       organism = synthetic construct
SEQUENCE: 75
gtaagtatca aggttacaag acaggtttaa ggagaccaat agaaactggg cttgtcgaga  60
cagagaagac tcttgcgttt ctgataggca cctattggtc ttactgacat ccactttgcc  120
tttctctcca cag                                                    133

SEQ ID NO: 76          moltype = DNA  length = 97
FEATURE                Location/Qualifiers
misc_feature           1..97
                       note = synthetic construct; intron
source                 1..97
                       mol_type = other DNA
                       organism = synthetic construct
SEQUENCE: 76
gtaagtttag tctttttgtc ttttatttca ggtcccggat ccggtggtgg tgcaaatcaa  60
agaactgctc ctcagtggat gttgccttta cttctag                          97

SEQ ID NO: 77          moltype = AA  length = 738
FEATURE                Location/Qualifiers
source                 1..738
                       mol_type = protein
                       organism = Adeno-associated dependoparvovirus A
SEQUENCE: 77
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
```

-continued

```
VPFHSSYAHS QSLDRLMNPL IDQYLYYLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 78          moltype = AA  length = 736
FEATURE                Location/Qualifiers
source                 1..736
                       mol_type = protein
                       organism = Adeno-associated dependoparvovirus A
SEQUENCE: 78
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 79          moltype = AA  length = 1283
FEATURE                Location/Qualifiers
REGION                 1..1283
                       note = synthetic construct; dystrophin protein
source                 1..1283
                       mol_type = protein
                       organism = synthetic construct
SEQUENCE: 79
MLWWEEVEDC YEREDVQKKT FTKWVNAQFS KFGKQHIENL FSDLQDGRRL LDLLEGLTGQ  60
KLPKEKGSTR VHALNNVNKA LRVLQNNNVD LVNIGSTDIV DGNHKLTLGL IWNIILHWQV  120
KNVMKNIMAG LQQTNSEKIL LSWVRQSTRN YPQVNVINFT TSWSDGLALN ALIHSHRPDL  180
FDWNSVVCQQ SATQRLEHAF NIARYQLGIE KLLDPEDVDT TYPDKKSILM YITSLFQVLP  240
QQVSIEAIQE VEMLPRPPKV TKEEHFQLHH QMHYSQQITV SLAQGYERTS SPKPRFKSYA  300
YTQAAYVTTS DPTRSPFPSQ HLEAPEDKSF GSSLMESEVN LDRYQTALEE VLSWLLSAED  360
TLQAQGEISN DVEVVKDQFH THEGYMMDLT AHQGRVGNIL QLGSKLIGTG KLSEDEETEV  420
QEQMNLLNSR WECLRVASME KQSNLHRVLM DLQNQKLKEL NDWLTKTEER TRKMEEEPLG  480
PDLEDLKRQV QQHKVLQEDL EQEQVRVNSL THMVVVVDES SGDHATAALE EQLKVLGDRW  540
ANICRWTEDR WVLLQDILLK WQRLTEEQCL FSAWLSEKED AVNKIHTTGF KDQNEMLSSL  600
QKLAVLKADL EKKKQSMGKL YSLKQDLLST LKNKSVTQKT EAWLDNFARC WDNLVQKLEK  660
STAQISQQPD LAPGLTTIGA SPTQTVTLVT QPVVTKETAI SKLEMPSSLM LEVPTLERLQ  720
ELQEATDELD LKLRQAEVIK GSWQPVGDLL IDSLQDHLEK VKALRGEIAP LKENVSHVND  780
LARQLTTLGI QLSPYNLSTL EDLNTRWKLL QVAVEDRVRQ LHEAHRDFGP ASQHFLSTSV  840
QGPWERAISP NKVPYYINHE TQTTCWDHPK MTELYQSLAD LNNVRFSAYR TAMKLRRLQK  900
ALCLDLLSLS AACDALDQHN LKQNDQPMDI LQIINCLTTI YDRLEQEHNN LVNVPLCVDM  960
CLNWLLNVYD TGRTGRIRVL SFKTGIISLC KAHLEDKYRY LFKQVASSTG FCDQRRLGLL  1020
LHDSIQIPRQ LGEVASFGGS NIEPSVRSCF QFANNKPEIE AALFLDWMRL EPQSMVWLPV  1080
LHRVAAAETA KHQAKCNICK ECPIIGFRYR SLKHFNYDIC QSCFFSGRVA KGHKMHYPMV  1140
EYCTPTTSGE DVRDFAKVLK NKFRTKRYFA KHPRMGYLPV QTVLEGDNME TPVTLINFWP  1200
VDSAPASSPQ LSHDDTHSRI EHYASRLAEM ENSNGSYLND SISPNESIDD EHLLIQHYCQ  1260
SLNQDSPLSQ PRSPAQILIS LES                                         1283

SEQ ID NO: 80          moltype = DNA  length = 426
FEATURE                Location/Qualifiers
misc_feature           1..426
                       note = synthetic construct; dystrophin
source                 1..426
                       mol_type = other DNA
                       organism = synthetic construct
SEQUENCE: 80
accccaacaa cctctgggga agatgttaga gactttgcca aggtgctgaa aaacaagttc  60
aggaccaaga gatactttgc taagcacccc agaatgggct acctgcctgt ccagacagtg  120
cttgagggtg acaacatgga aacccctgtg acactgatca atttctggcc agtggactct  180
gcccctgcct caagtccaca gctgtcccat gatgacaccc acagcagaat tgagcactat  240
gcctccagac tggcagagat ggaaaacagc aatggcagct acctgaatga tagcatcagc  300
cccaatgaga gcattgatga tgagcatctg ctgatccagc actactgtca gtccctgaac  360
caggactctc cactgagcca gcctagaagc cctgctcaga tcctgatcag ccttgagtct  420
tgatga                                                            426

SEQ ID NO: 81          moltype = DNA  length = 3855
FEATURE                Location/Qualifiers
misc_feature           1..3855
                       note = synthetic construct; dystrophin
```

```
source                  1..3855
                        mol_type = other DNA
                        organism = synthetic construct
SEQUENCE: 81
atgctttggt gggaagaggt ggaagattgc tatgagaggg aagatgtgca gaagaaaacc  60
ttcaccaaat gggtcaatgc ccagttcagc aagtttggca agcagcacat tgagaacctg  120
ttcagtgacc tgcaggatgg cagaaggctg ctggatctgc tggaaggcct gacaggccag  180
aagctgccta aagagaaggg cagcacaaga gtgcatgccc tgaacaatgt gaacaaggcc  240
ctgagagtgc tgcagaacaa caatgtggac ctggtcaata ttggcagcac agacattgtg  300
gatggcaacc acaagctgac cctgggcctg atctggaaca tcatcctgca ctggcaagtg  360
aagaatgtga tgaagaacat catggctggc ctgcagcaga ccaactctga gaagatcctg  420
ctgagctggg tcagacagag caccagaaac taccctcaag tgaatgtgat caacttcacc  480
acctcttgga gtgatggact ggccctgaat gccctgatcc acagccacag acctgacctg  540
tttgactgga actctgttgt gtgccagcag tctgccacac agagactgga acatgccttc  600
aacattgcca gataccagct gggaattgag aaactgctgg accctgagga tgtggacacc  660
acctatcctg acaagaaatc catcctcatg tacatcacca gcctgttcca ggtgctgccc  720
cagcaagtgt ccattgaggc cattcaagag gttgagatgc tgcccagacc tcctaaagtg  780
accaaagagg aacacttcca gctgcaccac cagatgcact actctcagca gatcacagtg  840
tctctggccc agggatatga gagaacaagc agccccaagc ctaggttcaa gagctatgcc  900
tacacacagg ctgcctatgt gaccacatct gaccccacaa gaagcccatt tccaagccag  960
catctggaag cccctgagga caagagcttt ggcagcagcc tgatggaatc tgaagtgaac  1020
ctggatagat accagacagc cctggaagaa gtgctgtcct ggctgctgtc tgctgaggat  1080
acactgcagg ctcagggtga aatcagcaat gatgtggaag tggtcaagga ccagtttcac  1140
acccatgagg gctacatgat ggacctgaca gcccaccagg gcagagtggg aaatatcctg  1200
cagctgggct ccaagctgat tggcacaggc aagctgtctg aggatgaaga gacagaggtg  1260
caagagcaga tgaacctgct gaacagcaga tgggagtgtc tgagagtggc cagcatggaa  1320
aagcagagca acctgcacag agtgctcatg gacctgcaga atcagaaact gaaagaactg  1380
aatgactggc tgaccaagac agaagaaagg actaggaaga tggaagagga acctctggga  1440
ccagacctgg aagatctgaa aagacaggtg cagcagcata aggtgctgca agaggacctt  1500
gagcaagagc aagtcagagt gaacagcctg acacacatgg tggtggttgt ggatgagtcc  1560
tctggggatc atgccacagc tgctctggaa gaacagctga aggtgctggg agacagatgg  1620
gccaacatct gtaggtggac agaggataga tgggtgctgc tccaggacat tctgctgaag  1680
tggcagagac tgacagagga acagtgcctg ttttctgcct ggctctctga gaaagaggat  1740
gctgtcaaca agatccatac cacaggcttc aaggatcaga atgagatgct cagctccctg  1800
cagaaactgg ctgtgctgaa ggctgacctg gaaaagaaaa agcagtccat gggcaagctc  1860
tacagcctga agcaggacct gctgtctacc ctgaagaaca agtctgtgac ccagaaaact  1920
gaggcctggc tggacaactt tgctagatgc tgggacaacc tggtgcagaa gctggaaaag  1980
tctacagccc agatcagcca gcaacctgat cttgcccctg gcctgaccac aattggagcc  2040
tctccaacac agactgtgac cctggttacc cagccagtgg tcaccaaaga gacagccatc  2100
agcaaactgg aaatgcccag ctctctgatg ctggaagtcc ccacactgga aaggctgcaa  2160
gaacttcaag aggccacaga tgagctggac ctgaagctga gacaggctga agtgatcaaa  2220
ggcagctggc agccagttgg ggacctgctc attgatagcc tgcaggacca tctggaaaaa  2280
gtgaaagccc tgaggggaga gattgcccct ctgaaagaaa atgtgtccca tgtgaatgac  2340
ctggccagac agctgaccac actgggaatc cagctgagcc cctacaacct gagcaccctt  2400
gaggacctga acaccaggtg gaagctcctc caggtggcag tggaagatag agtcaggcag  2460
ctgcatgagg cccacagaga ttttggacca gccagccagc actttctgtc tacctctgtg  2520
caaggcccct gggagagagc tatctctcct aacaaggtgc cctactacat caaccatgag  2580
acacagacca cctgttggga tcaccccaag atgacagagc tgtaccagag tctggcagac  2640
ctcaacaatg tcagattcag tgcctacagg actgccatga agctcagaag gctccagaaa  2700
gctctgtgcc tggacctgct ttccctgagt gcagcttgtg atgccctgga ccagcacaat  2760
ctgaagcaga atgaccagcc tatggacatc ctccagatca tcaactgcct caccaccatc  2820
tatgataggc tggaacaaga gcacaacaat ctggtcaatg tgcccctgtg tgtggacatg  2880
tgcctgaatt ggctgctgaa tgtgtatgac acaggcagaa caggcaggat cagagtcctg  2940
tccttcaaga caggcatcat ctccctgtgc aaagcccact tggaggacaa gtacagatac  3000
ctgttcaagc aagtggcctc cagcacaggc ttttgtgacc agagaaggct gggcctgctc  3060
ctgcatgaca gcattcagat ccctagacag ctgggagaag tggcttcctt tggaggcagc  3120
aatattgagc catcagtcag gtcctgtttt cagtttgcca acaacaagcc tgagattgag  3180
gctgccctgt tcctggactg gatgagactt gagcctcaga gcatggtctg gctgcctgtg  3240
cttcatagag tggctgctgc tgagactgcc aagcaccagg ccaagtgcaa catctgcaaa  3300
gagtgcccca tcattggctt cagatacaga tccctgaagc acttcaacta tgatatctgc  3360
cagagctgct tctttagtgg cagggttgcc aagggccaca aaatgcacta ccccatggtg  3420
gaatactgca ccccaacaac ctctggggaa gatgttagag actttgccaa ggtgctgaaa  3480
aacaagttca ggaccaagag atactttgct aagcacccca gaatgggcta cctgcctgtc  3540
cagacagtgc ttgagggtga caacatggaa acccctgtga cactgatcaa tttctggcca  3600
gtggactctg cccctgcctc aagtccacag ctgtcccatg atgacaccca cagcagaatt  3660
gagcactatg cctccagact ggcagagatg gaaaacagca atggcagcta cctgaatgat  3720
agcatcagcc ccaatgagag cattgatgat gagcatctgc tgatccagca ctactgtcag  3780
tccctgaacc aggactctcc actgagccag cctagaagcc ctgctcagat cctgatcagc  3840
cttgagtctt gatga                                                   3855

SEQ ID NO: 82           moltype = DNA  length = 4560
FEATURE                 Location/Qualifiers
misc_feature            1..4560
                        note = synthetic construct; dystrophin cassette
source                  1..4560
                        mol_type = other DNA
                        organism = synthetic construct
SEQUENCE: 82
ctgcgcgctc gctcgctcac tgaggccgcc cgggcaaagc ccgggcgtcg ggcgaccttt  60
```

-continued

```
ggtcgcccgg cctcagtgag cgagcgagcg cgcagagagg gagtggccaa ctccatcact  120
aggggttcct catatgcagg gtaatgggga tcctctagag gccgtccgcc ctcggcacca  180
tcctcacgac acccaaatat ggcgacgggt gaggaatggt ggggagttat ttttagagcg  240
gtgaggaagg tgggcaggca gcaggtgttg gcgctctaaa aataactccc gggagttatt  300
tttagagcgg aggaatggtg gacacccaaa tatggcgacg gttcctcacc cgtcgccata  360
tttgggtgtc cgccctcggc cggggccgca ttcctggggg ccgggcggtg ctcccgcccg  420
cctcgataaa aggctccggg gccggcggcg gcccacgagc tacccggagg agcgggaggc  480
gccaagcgga attcgccacc atgctttggt gggaagaggt ggaagattgc tatgagaggg  540
aagatgtgca gaagaaaacc ttcaccaaat gggtcaatgc ccagttcagc aagtttggca  600
agcagcacat tgagaacctg ttcagtgacc tgcaggatgg cagaaggctg ctggatctgc  660
tggaaggcct gacaggccag aagctgccta aagagaaggg cagcacaaga gtgcatgccc  720
tgaacaatgt gaacaaggcc ctgagagtgc tgcagaacaa caatgtggac ctggtcaata  780
ttggcagcac agacattgtg gatggcaacc acaagctgac cctgggcctg atctggaaca  840
tcatcctgca ctggcaagtg aagaatgtga tgaagaacat catggctggc ctgcagcaga  900
ccaactctga gaagatcctg ctgagctggg tcagacagag caccagaaac taccctcaag  960
tgaatgtgat caacttcacc acctcttgga gtgatggact ggccctgaat gccctgatcc  1020
acagccacag acctgacctg tttgactgga actctgttgt gtgccagcag tctgccacac  1080
agagactgga acatgccttc aacattgcca gataccagct gggaattgag aaactgctgg  1140
accctgagga tgtggacacc acctatcctg acaagaaatc catcctcatg tacatcacca  1200
gcctgttcca ggtgctgccc cagcaagtgt ccattgaggc cattcaagag gttgagatgc  1260
tgcccagacc tcctaaagtg accaaagagg aacacttcca gctgcaccac cagatgcact  1320
actctcagca gatcacagtg tctctggccc agggatatga gagaacaagc agccccaagc  1380
ctaggttcaa gagctatgcc tacacacagg ctgcctatgt gaccacatct gaccccacaa  1440
gaagcccatt tccaagccag catctggaag cccctgagga caagagcttt ggcagcagcc  1500
tgatggaatc tgaagtgaac ctggatagat accagacagc cctggaagaa gtgctgtcct  1560
ggctgctgtc tgctgaggat acactgcagg ctcagggtga aatcagcaat gatgtggaag  1620
tggtcaagga ccagtttcac acccatgagg gctacatgat ggacctgaca gcccaccagg  1680
gcagagtggg aaatatcctg cagctgggct ccaagctgat tggcacaggc aagctgtctg  1740
aggatgaaga gacagaggtg caagagcaga tgaacctgct gaacagcaga tgggagtgtc  1800
tgagagtggc cagcatggaa aagcagagca acctgcacag agtgctcatg gacctgcaga  1860
atcagaaact gaaagaactg aatgactggc tgaccaagac agaagaaagg actaggaaga  1920
tggaagagga acctctggga ccagacctgg aagatctgaa aagacaggtg cagcagcata  1980
aggtgctgca agaggacctt gagcaagagc aagtcagagt gaacagcctg acacacatgg  2040
tggtggttgt ggatgagtcc tctggggatc atgccacagc tgctctggaa gaacagctga  2100
aggtgctggg agacagatgg gccaacatct gtaggtggac agaggataga tgggtgctgc  2160
tccaggacat tctgctgaag tggcagagac tgacagagga acagtgcctg ttttctgcct  2220
ggctctctga gaaagaggat gctgtcaaca agatccatac cacaggcttc aaggatcaga  2280
atgagatgct cagctccctg cagaaactgg ctgtgctgaa ggctgacctg gaaaagaaaa  2340
agcagtccat gggcaagctc tacagcctga agcaggacct gctgtctacc ctgaagaaca  2400
agtctgtgac ccagaaaact gaggcctggc tggacaactt tgctagatgc tgggacaacc  2460
tggtgcagaa gctggaaaag tctacagccc agatcagcca gcaacctgat cttgcccctg  2520
gcctgaccac aattggagcc tctccaacac agactgtgac cctggttacc cagccagtgg  2580
tcaccaaaga gacagccatc agcaaactgg aaatgcccag ctctctgatg ctggaagtcc  2640
ccacactgga aaggctgcaa gaacttcaag aggccacaga tgagctggac ctgaagctga  2700
gacaggctga agtgatcaaa ggcagctggc agccagttgg ggacctgctc attgatagcc  2760
tgcaggacca tctggaaaaa gtgaaagccc tgaggggaga gattgcccct ctgaaagaaa  2820
atgtgtccca tgtgaatgac ctggccagac agctgaccac actgggaatc cagctgagcc  2880
cctacaacct gagcaccctt gaggacctga acaccaggtg gaagctcctc caggtggcag  2940
tggaagatag agtcaggcag ctgcatgagg cccacagaga ttttggacca gccagccagc  3000
actttctgtc tacctctgtg caaggcccct gggagagagc tatctctcct aacaaggtgc  3060
cctactacat caaccatgag acacagacca cctgttggga tcaccccaag atgacagagc  3120
tgtaccagag tctggcagac ctcaacaatg tcagattcag tgcctacagg actgccatga  3180
agctcagaag gctccagaaa gctctgtgcc tggacctgct ttccctgagt gcagcttgtg  3240
atgccctgga ccagcacaat ctgaagcaga atgaccagcc tatggacatc ctccagatca  3300
tcaactgcct caccaccatc tatgataggc tggaacaaga gcacaacaat ctggtcaatg  3360
tgcccctgtg tgtggacatg tgcctgaatt ggctgctgaa tgtgtatgac acaggcagaa  3420
caggcaggat cagagtcctg tccttcaaga caggcatcat ctccctgtgc aaagcccact  3480
tggaggacaa gtacagatac ctgttcaagc aagtggcctc cagcacaggc ttttgtgacc  3540
agagaaggct gggcctgctc ctgcatgaca gcattcagat ccctagacag ctgggagaag  3600
tggcttcctt tggaggcagc aatattgagc catcagtcag gtcctgtttt cagtttgcca  3660
acaacaagcc tgagattgag gctgccctgt tcctggactg gatgagactt gagcctcaga  3720
gcatggtctg gctgcctgtg cttcatagag tggctgctgc tgagactgcc aagcaccagg  3780
ccaagtgcaa catctgcaaa gagtgcccca tcattggctt cagatacaga tccctgaagc  3840
acttcaacta tgatatctgc cagagctgct tctttagtgg cagggttgcc aagggccaca  3900
aaatgcacta ccccatggtg gaatactgca ccccaacaac ctctggggaa gatgttagag  3960
actttgccaa ggtgctgaaa aacaagttca ggaccaagag atactttgct aagcacccca  4020
gaatgggcta cctgcctgtc cagacagtgc ttgagggtga caacatggaa acccctgtga  4080
cactgatcaa tttctggcca gtggactctg cccctgcctc aagtccacag ctgtcccatg  4140
atgacaccca cagcagaatt gagcactatg cctccagact ggcagagatg gaaaacagca  4200
atggcagcta cctgaatgat agcatcagcc ccaatgagag cattgatgat gagcatctgc  4260
tgatccagca ctactgtcag tccctgaacc aggactctcc actgagccag cctagaagcc  4320
ctgctcagat cctgatcagc cttgagtctt gatgagtcga caggcctaat aaagagctca  4380
gatgcatcga tcagagtgtg ttggtttttt gtgtggctag ctgcggccgc aggaacccct  4440
agtgatggag ttggccactc cctctctgcg cgctcgctcg ctcactgagg ccgggcgacc  4500
aaaggtcgcc cgacgcccgg gctttgcccg ggcggcctca gtgagcgagc gagcgcgcag  4560
```

```
SEQ ID NO: 83          moltype = AA  length = 140
FEATURE                Location/Qualifiers
REGION                 1..140
```

```
                         note = synthetic construct; microdystrophin segment
source                   1..140
                         mol_type = protein
                         organism = synthetic construct
SEQUENCE: 83
TPTTSGEDVR DFAKVLKNKF RTKRYFAKHP RMGYLPVQTV LEGDNMETPV TLINFWPVDS  60
APASSPQLSH DDTHSRIEHY ASRLAEMENS NGSYLNDSIS PNESIDDEHL LIQHYCQSLN  120
QDSPLSQPRS PAQILISLES                                              140

SEQ ID NO: 84            moltype = AA  length = 35
FEATURE                  Location/Qualifiers
REGION                   1..35
                         note = synthetic construct; minimal alpha-syntrophin
                          binding site
source                   1..35
                         mol_type = protein
                         organism = synthetic construct
SEQUENCE: 84
MENSNGSYLN DSISPNESID DEHLLIQHYC QSLNQ                             35

SEQ ID NO: 85            moltype = AA  length = 738
FEATURE                  Location/Qualifiers
REGION                   1..738
                         note = synthetic construct; capsid sequence
source                   1..738
                         mol_type = protein
                         organism = synthetic construct
SEQUENCE: 85
MAADGYLPDW LEDNLSEGIR EWWDLKPGAP KPKANQQKQD NGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVESPVKTAP GKKRPVEPSP QRSPDSSTGI GKKGQQPAKK RLNFGQTGDS  180
ESVPDPQPIG EPPAAPSGVG PNTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
RLINNNWGFR PKRLNFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYNFED  420
VPFHSSYAHS QSLDRLMNPL IDQYLYYLSR TQSTGGTAGT QQLLFSQAGP NNMSAQAKNW  480
LPGPCYRQQR VSTTLSQNNN SNFAWTGATK YHLNGRDSLV NPGVAMATHK DDEERFFPSS  540
GVLMFGKQGA GKDNVDYSSV MLTSEEEIKT TNPVATEQYG VVADNLQQQN AAPIVGAVNS  600
QGALPGMVWQ NRDVYLQGPI WAKIPHTDGN FHPSPLMGGF GLKHPPPQIL IKNTPVPADP  660
PTTFNQAKLA SFITQYSTGQ VSVEIEWELQ KENSKRWNPE IQYTSNYYKS TNVDFAVNTE  720
GTYSEPRPIG TRYLTRNL                                                738

SEQ ID NO: 86            moltype = AA  length = 110
FEATURE                  Location/Qualifiers
REGION                   1..110
                         note = synthetic construct; microdystrophin segment
source                   1..110
                         mol_type = protein
                         organism = synthetic construct
SEQUENCE: 86
EISYVPSTYL TEITHVSQAL LEVEQLLNAP DLCAKDFEDL FKQEESLKNI KDSLQQSSGR  60
IDIIHSKKTA ALQSATPVER VKLQEALSQL DFQWEKVNKM YKDRQGRFDR             110

SEQ ID NO: 87            moltype = AA  length = 105
FEATURE                  Location/Qualifiers
REGION                   1..105
                         note = synthetic construct; microdystrophin segment
source                   1..105
                         mol_type = protein
                         organism = synthetic construct
SEQUENCE: 87
EKWRRFHYDI KIFNQWLTEA EQFLRKTQIP ENWEHAKYKW YLKELQDGIG QRQTVVRTLN  60
ATGEEIIQQS SKTDASILQE KLGSLNLRWQ EVCKQLSDRK KRLEE                  105

SEQ ID NO: 88            moltype = AA  length = 216
FEATURE                  Location/Qualifiers
REGION                   1..216
                         note = synthetic construct; microdystrophin segment
source                   1..216
                         mol_type = protein
                         organism = synthetic construct
SEQUENCE: 88
ISYVPSTYLT EITHVSQALL EVEQLLNAPD LCAKDFEDLF KQEESLKNIK DSLQQSSGRI  60
DIIHSKKTAA LQSATPVERV KLQEALSQLD FQWEKVNKMY KDRQGRFDRS VEKWRRFHYD  120
IKIFNQWLTE AEQFLRKTQI PENWEHAKYK WYLKELQDGI GQRQTVVRTL NATGEEIIQQ  180
SSKTDASILQ EKLGSLNLRW QEVCKQLSDR KKRLEE                            216

SEQ ID NO: 89            moltype = AA  length = 4
FEATURE                  Location/Qualifiers
```

-continued

```
REGION                1..4
                      note = synthetic construct; linker
source                1..4
                      mol_type = protein
                      organism = synthetic construct
SEQUENCE: 89
QTLE                                                                4

SEQ ID NO: 90         moltype = AA  length = 54
FEATURE               Location/Qualifiers
REGION                1..54
                      note = synthetic construct; dystrophin segment
source                1..54
                      mol_type = protein
                      organism = synthetic construct
SEQUENCE: 90
AKHQAKCNIC KECPIIGFRY RSLKHFNYDI CQSCFFSGRV AKGHKMHYPM VEYC        54

SEQ ID NO: 91         moltype = AA  length = 1287
FEATURE               Location/Qualifiers
REGION                1..1287
                      note = synthetic construct; dystrophin
source                1..1287
                      mol_type = protein
                      organism = synthetic construct
SEQUENCE: 91
MLWWEEVEDC YEREDVQKKT FTKWVNAQFS KFGKQHIENL FSDLQDGRRL LDLLEGLTGQ  60
KLPKEKGSTR VHALNNVNKA LRVLQNNNVD LVNIGSTDIV DGNHKLTLGL IWNIILHWQV  120
KNVMKNIMAG LQQTNSEKIL LSWVRQSTRN YPQVNVINFT TSWSDGLALN ALIHSHRPDL  180
FDWNSVVCQQ SATQRLEHAF NIARYQLGIE KLLDPEDVDT TYPDKKSILM YITSLFQVLP  240
QQVSIEAIQE VEMLPRPPKV TKEEHFQLHH QMHYSQQITV SLAQGYERTS SPKPRFKSYA  300
YTQAAYVTTS DPTRSPFPSQ HLEAPEDKSF GSSLMESEVN LDRYQTALEE VLSWLLSAED  360
TLQAQGEISN DVEVVKDQFH THEGYMMDLT AHQGRVGNIL QLGSKLIGTG KLSEDEETEV  420
QEQMNLLNSR WECLRVASME KQSNLHRVLM DLQNQKLKEL NDWLTKTEER TRKMEEEPLG  480
PDLEDLKRQV QQHKVLQEDL EQEQVRVNSL THMVVVVDES SGDHATAALE EQLKVLGDRW  540
ANICRWTEDR WVLLQDILLK WQRLTEEQCL FSAWLSEKED AVNKIHTTGF KDQNEMLSSL  600
QKLAVLKADL EKKKQSMGKL YSLKQDLLST LKNKSVTQKT EAWLDNFARC WDNLVQKLEK  660
STAQISQQPD LAPGLTTIGA SPTQTVTLVT QPVVTKETAI SKLEMPSSLM LEVPTLERLQ  720
ELQEATDELD LKLRQAEVIK GSWQPVGDLL IDSLQDHLEK VKALRGEIAP LKENVSHVND  780
LARQLTTLGI QLSPYNLSTL EDLNTRWKLL QVAVEDRVRQ LHEAHRDFGP ASQHFLSTSV  840
QGPWERAISP NKVPYYINHE TQTTCWDHPK MTELYQSLAD LNNVRFSAYR TAMKLRRLQK  900
ALCLDLLSLS AACDALDQHN LKQNDQPMDI LQIINCLTTI YDRLEQEHNN LVNVPLCVDM  960
CLNWLLNVYD TGRTGRIRVL SFKTGIISLC KAHLEDKYRY LFKQVASSTG FCDQRRLGLL  1020
LHDSIQIPRQ LGEVASFGGA KHQAKCNICK ECPIIGFRYR SLKHFNYDIC QSCFFSGRVA  1080
KGHKMHYPMV EYCTPTTSGE DVRDFAKVLK NKFRTKRYFA KHPRMGYLPV QTVLEGDNME  1140
TPVTLINFWP VDSAPASSPQ LSHDDTHSRI EHYASRLAEM ENSNGSYLND SISPNESIDD  1200
EHLLIQHYCQ SLNQDSPLSQ PRSPAQILIS LESEERGELE RILADLEEEN RNLQAEYDRL  1260
KQQHEHKGLS PLPSPPEMMP TSPQSPR                                      1287

SEQ ID NO: 92         moltype = AA  length = 1345
FEATURE               Location/Qualifiers
REGION                1..1345
                      note = synthetic construct; dystrophin
source                1..1345
                      mol_type = protein
                      organism = synthetic construct
SEQUENCE: 92
MLWWEEVEDC YEREDVQKKT FTKWVNAQFS KFGKQHIENL FSDLQDGRRL LDLLEGLTGQ  60
KLPKEKGSTR VHALNNVNKA LRVLQNNNVD LVNIGSTDIV DGNHKLTLGL IWNIILHWQV  120
KNVMKNIMAG LQQTNSEKIL LSWVRQSTRN YPQVNVINFT TSWSDGLALN ALIHSHRPDL  180
FDWNSVVCQQ SATQRLEHAF NIARYQLGIE KLLDPEDVDT TYPDKKSILM YITSLFQVLP  240
QQVSIEAIQE VEMLPRPPKV TKEEHFQLHH QMHYSQQITV SLAQGYERTS SPKPRFKSYA  300
YTQAAYVTTS DPTRSPFPSQ HLEAPEDKSF GSSLMESEVN LDRYQTALEE VLSWLLSAED  360
TLQAQGEISN DVEVVKDQFH THEGYMMDLT AHQGRVGNIL QLGSKLIGTG KLSEDEETEV  420
QEQMNLLNSR WECLRVASME KQSNLHRVLM DLQNQKLKEL NDWLTKTEER TRKMEEEPLG  480
PDLEDLKRQV QQHKVLQEDL EQEQVRVNSL THMVVVVDES SGDHATAALE EQLKVLGDRW  540
ANICRWTEDR WVLLQDILEI SYVPSTYLTE ITHVSQALLE VEQLLNAPDL CAKDFEDLFK  600
QEESLKNIKD SLQQSSGRID IIHSKKTAAL QSATPVERVK LQEALSQLDF QWEKVNKMYK  660
DRQGRFDRSV EKWRRFHYDI KIFNQWLTEA EQFLRKTQIP ENWEHAKYKW YLKELQDGIG  720
QRQTVVRTLN ATGEEIIQQS SKTDASILQE KLGSLNLRWQ EVCKQLSDRK KRLEEQTLER  780
LQELQEATDE LDLKLRQAEV IKGSWQPVGD LLIDSLQDHL EKVKALRGEI APLKENVSHV  840
NDLARQLTTL GIQLSPYNLS TLEDLNTRWK LLQVAVEDRV RQLHEAHRDF GPASQHFLST  900
SVQGPWERAI SPNKVPYYIN HETQTTCWDH PKMTELYQSL ADLNNVRFSA YRTAMKLRRL  960
QKALCLDLLS LSAACDALDQ HNLKQNDQPM DILQIINCLT TIYDRLEQEH NNLVNVPLCV  1020
DMCLNWLLNV YDTGRTGRIR VLSFKTGIIS LCKAHLEDKY RYLFKQVASS TGFCDQRRLG  1080
LLLHDSIQIP RQLGEVASFG GSNIEPSVRS CFQFANNKPE IEAALFLDWM RLEPQSMVWL  1140
PVLHRVAAAE TAKHQAKCNI CKECPIIGFR YRSLKHFNYD ICQSCFFSGR VAKGHKMHYP  1200
MVEYCTPTTS GEDVRDFAKV LKNKFRTKRY FAKHPRMGYL PVQTVLEGDN METPVTLINF  1260
WPVDSAPASS PQLSHDDTHS RIEHYASRLA EMENSNGSYL NDSISPNESI DDEHLLIQHY  1320
```

```
CQSLNQDSPL SQPRSPAQIL ISLES                                 1345

SEQ ID NO: 93          moltype = AA  length = 1253
FEATURE                Location/Qualifiers
REGION                 1..1253
                       note = synthetic construct; dystrophin
source                 1..1253
                       mol_type = protein
                       organism = synthetic construct
SEQUENCE: 93
MLWWEEVEDC YEREDVQKKT FTKWVNAQFS KFGKQHIENL FSDLQDGRRL LDLLEGLTGQ  60
KLPKEKGSTR VHALNNVNKA LRVLQNNNVD LVNIGSTDIV DGNHKLTLGL IWNIILHWQV  120
KNVMKNIMAG LQQTNSEKIL LSWVRQSTRN YPQVNVINFT TSWSDGLALN ALIHSHRPDL  180
FDWNSVVCQQ SATQRLEHAF NIARYQLGIE KLLDPEDVDT TYPDKKSILM YITSLFQVLP  240
QQVSIEAIQE VEMLPRPPKV TKEEHFQLHH QMHYSQQITV SLAQGYERTS SPKPRFKSYA  300
YTQAAYVTTS DPTRSPFPSQ HLEAPEDKSF GSSLMESEVN LDRYQTALEE VLSWLLSAED  360
TLQAQGEISN DVEVVKDQFH THEGYMMDLT AHQGRVGNIL QLGSKLIGTG KLSEDEETEV  420
QEQMNLLNSR WECLRVASME KQSNLHRVLM DLQNQKLKEL NDWLTKTEER TRKMEEEPLG  480
PDLEDLKRQV QQHKVLQEDL EQEQVRVNSL THMVVVVDES SGDHATAALE EQLKVLGDRW  540
ANICRWTEDR WVLLQDILEI SYVPSTYLTE ITHVSQALLE VEQLLNAPDL CAKDFEDLFK  600
QEESLKNIKD SLQQSSGRID IIHSKKTAAL QSATPVERVK LQEALSQLDF QWEKVNKMYK  660
DRQGRFDRSV EKWRRFHYDI KIFNQWLTEA EQFLRKTQIP ENWEHAKYKW YLKELQDGIG  720
QRQTVVRTLN ATGEEIIQQS SKTDASILQE KLGSLNLRWQ EVCKQLSDRK KRLEEQTLER  780
LQELQEATDE LDLKLRQAEV IKGSWQPVGD LLIDSLQDHL EKVKALRGEI APLKENVSHV  840
NDLARQLTTL GIQLSPYNLS TLEDLNTRWK LLQVAVEDRV RQLHEAHRDF GPASQHFLST  900
SVQGPWERAI SPNKVPYYIN HETQTTCWDH PKMTELYQSL ADLNNVRFSA YRTAMKLRRL  960
QKALCLDLLS LSAACDALDQ HNLKQNDQPM DILQIINCLT TIYDRLEQEH NNLVNVPLCV  1020
DMCLNWLLNV YDTGRTGRIR VLSFKTGIIS LCKAHLEDKY RYLFKQVASS TGFCDQRRLG  1080
LLLHDSIQIP RQLGEVASFG GSNIEPSVRS CFQFANNKPE IEAALFLDWM RLEPQSMVWL  1140
PVLHRVAAAE TAKHQAKCNI CKECPIIGFR YRSLKHFNYD ICQSCFFSGR VAKGHKMHYP  1200
MVEYCTPTTS GEDVRDFAKV LKNKFRTKRY FAKHPRMGYL PVQTVLEGDN MET         1253

SEQ ID NO: 94          moltype = DNA  length = 330
FEATURE                Location/Qualifiers
misc_feature           1..330
                       note = synthetic construct; dystrophin segment
source                 1..330
                       mol_type = other DNA
                       organism = synthetic construct
SEQUENCE: 94
gaaatttctt atgtgccttc tacttatttg actgaaatca ctcatgtctc acaagcccta  60
ttagaagtgg aacaacttct caatgctcct gacctctgtg ctaaggactt tgaagatctc  120
tttaagcaag aggagtctct gaagaatata aaagatagtc tacaacaaag ctcaggtcgg  180
attgacatta ttcatagcaa gaagacagca gcattgcaaa gtgcaacgcc tgtggaaagg  240
gtgaagctac aggaagctct ctcccagctt gatttccaat gggaaaaagt taacaaaatg  300
tacaaggacc gacaagggcg atttgacaga                                330

SEQ ID NO: 95          moltype = DNA  length = 312
FEATURE                Location/Qualifiers
misc_feature           1..312
                       note = synthetic construct; dystrophin segment
source                 1..312
                       mol_type = other DNA
                       organism = synthetic construct
SEQUENCE: 95
gagaaatggc ggcgttttca ttatgatata aagatattta atcagtggct aacagaagct  60
gaacagtttc tcagaaagac acaaattcct gagaattggg aacatgctaa atacaaatgg  120
tatcttaagg aactccagga tggcattggg cagcggcaaa ctgttgtcag aacattgaat  180
gcaactgggg aagaaataat tcagcaatcc tcaaaaacag atgccagtat tctacaggaa  240
aaattgggaa gcctgaatct gcggtggcag gaggtctgca aacagctgtc agacagaaaa  300
aagaggctag aa                                                   312

SEQ ID NO: 96          moltype = DNA  length = 648
FEATURE                Location/Qualifiers
misc_feature           1..648
                       note = synthetic ocnstruct; dystrophin segment
source                 1..648
                       mol_type = other DNA
                       organism = synthetic construct
SEQUENCE: 96
gaaatttctt atgtgccttc tacttatttg actgaaatca ctcatgtctc acaagcccta  60
ttagaagtgg aacaacttct caatgctcct gacctctgtg ctaaggactt tgaagatctc  120
tttaagcaag aggagtctct gaagaatata aaagatagtc tacaacaaag ctcaggtcgg  180
attgacatta ttcatagcaa gaagacagca gcattgcaaa gtgcaacgcc tgtggaaagg  240
gtgaagctac aggaagctct ctcccagctt gatttccaat gggaaaaagt taacaaaatg  300
tacaaggacc gacaagggcg atttgacaga tctgttgaga aatggcggcg ttttcattat  360
gatataaaga tatttaatca gtggctaaca gaagctgaac agtttctcag aaagacacaa  420
attcctgaga attgggaaca tgctaaatac aaatggtatc ttaaggaact ccaggatggc  480
attgggcagc ggcaaactgt tgtcagaaca ttgaatgcaa ctggggaaga aataattcag  540
```

```
caatcctcaa aaacagatgc cagtattcta caggaaaaat tgggaagcct gaatctgcgg  600
tggcaggagg tctgcaaaca gctgtcagac agaaaaaaga ggctagaa               648

SEQ ID NO: 97          moltype = DNA  length = 330
FEATURE                Location/Qualifiers
misc_feature           1..330
                       note = synthetic construct; dystrophin segment
source                 1..330
                       mol_type = other DNA
                       organism = synthetic construct
SEQUENCE: 97
gagatcagct atgtgcccag cacctacctg acagagatca cccatgtgtc tcaggccctg  60
ctggaagtgg aacagctgct gaatgcccct gacctgtgtg ccaaggactt tgaggacctg  120
ttcaagcaag aggaaagcct gaagaacatc aaggacagcc tgcagcagtc ctctggcaga  180
attgacatca tccacagcaa gaaaacagct gccctgcagt ctgccacacc tgtggaaaga  240
gtgaagctgc aagaggccct gagccagctg gacttccagt gggagaaagt gaacaagatg  300
tacaaggaca ggcagggcag atttgataga                                   330

SEQ ID NO: 98          moltype = DNA  length = 315
FEATURE                Location/Qualifiers
misc_feature           1..315
                       note = synthetic construct; dystrophin segment
source                 1..315
                       mol_type = other DNA
                       organism = synthetic construct
SEQUENCE: 98
gaaaagtgga gaaggttcca ctatgacatc aagatcttca accagtggct gacagaggct  60
gagcagttcc tgagaaagac acagatccct gagaactggg agcatgccaa gtacaagtgg  120
tatctgaaag aactgcagga tggcattggc cagagacaga cagttgtcag aaccctgaat  180
gccacagggg aagagatcat ccagcagagc agcaagacag atgccagcat cctgcaagag  240
aagctgggca gcctgaacct gagatggcaa gaagtgtgca agcagctgtc tgacagaaag  300
aagaggctgg aagaa                                                   315

SEQ ID NO: 99          moltype = DNA  length = 651
FEATURE                Location/Qualifiers
misc_feature           1..651
                       note = synthetic construct; dystrophin segment
source                 1..651
                       mol_type = other DNA
                       organism = synthetic construct
SEQUENCE: 99
gagatcagct atgtgcccag cacctacctg acagagatca cccatgtgtc tcaggccctg  60
ctggaagtgg aacagctgct gaatgcccct gacctgtgtg ccaaggactt tgaggacctg  120
ttcaagcaag aggaaagcct gaagaacatc aaggacagcc tgcagcagtc ctctggcaga  180
attgacatca tccacagcaa gaaaacagct gccctgcagt ctgccacacc tgtggaaaga  240
gtgaagctgc aagaggccct gagccagctg gacttccagt gggagaaagt gaacaagatg  300
tacaaggaca ggcagggcag atttgataga agtgtggaaa agtggagaag gttccactat  360
gacatcaaga tcttcaacca gtggctgaca gaggctgagc agttcctgag aaagacacag  420
atccctgaga actgggagca tgccaagtac aagtggtatc tgaaagaact gcaggatggc  480
attggccaga gacagacagt tgtcagaacc ctgaatgcca caggggaaga gatcatccag  540
cagagcagca agacagatgc cagcatcctg caagagaagc tgggcagcct gaacctgaga  600
tggcaagaag tgtgcaagca gctgtctgac agaaagaaga ggctggaaga a           651

SEQ ID NO: 100         moltype = DNA  length = 162
FEATURE                Location/Qualifiers
misc_feature           1..162
                       note = synthetic construct; dystrophin segment
source                 1..162
                       mol_type = other DNA
                       organism = synthetic construct
SEQUENCE: 100
gccaagcacc aggccaagtg caacatctgc aaagagtgcc ccatcattgg cttcagatac  60
agatccctga agcacttcaa ctatgatatc tgccagagct gcttctttag tggcagggtt  120
gccaagggcc acaaaatgca ctaccccatg gtggaatact gc                     162

SEQ ID NO: 101         moltype = DNA  length = 3867
FEATURE                Location/Qualifiers
misc_feature           1..3867
                       note = synthetic construct; dystrophin
source                 1..3867
                       mol_type = other DNA
                       organism = synthetic construct
SEQUENCE: 101
atgctttggt gggaagaggt ggaagattgc tatgagaggg aagatgtgca gaagaaaacc  60
ttcaccaaat gggtcaatgc ccagttcagc aagtttggca agcagcacat tgagaacctg  120
ttcagtgacc tgcaggatgg cagaaggctg ctggatctgc tggaaggcct gacaggccag  180
aagctgccta aagagaaggg cagcacaaga gtgcatgccc tgaacaatgt gaacaaggcc  240
ctgagagtgc tgcagaacaa caatgtggac ctggtcaata ttggcagcac agacattgtg  300
gatggcaacc acaagctgac cctgggcctg atctggaaca tcatcctgca ctggcaagtg  360
```

```
aagaatgtga tgaagaacat catggctggc ctgcagcaga ccaactctga gaagatcctg  420
ctgagctggg tcagacagag caccagaaac taccctcaag tgaatgtgat caacttcacc  480
acctcttgga gtgatggact ggccctgaat gccctgatcc acagccacag acctgacctg  540
tttgactgga actctgttgt gtgccagcag tctgccacac agagactgga acatgccttc  600
aacattgcca gataccagct gggaattgag aaactgctgg accctgagga tgtggacacc  660
acctatcctg acaagaaatc catcctcatg tacatcacca gcctgttcca ggtgctgccc  720
cagcaagtgt ccattgaggc cattcaagag gttgagatgc tgcccagacc tcctaaagtg  780
accaaagagg aacacttcca gctgcaccac cagatgcact actctcagca gatcacagtg  840
tctctggccc agggatatga gagaacaagc agccccaagc ctaggttcaa gagctatgcc  900
tacacacagg ctgcctatgt gaccacatct gaccccacaa gaagcccatt tccaagccag  960
catctggaag cccctgagga caagagcttt ggcagcagcc tgatggaatc tgaagtgaac  1020
ctggatagat accagacagc cctggaagaa gtgctgtcct ggctgctgtc tgctgaggat  1080
acactgcagg ctcagggtga aatcagcaat gatgtggaag tggtcaagga ccagtttcac  1140
acccatgagg gctacatgat ggacctgaca gcccaccagg gcagagtggg aaatatcctg  1200
cagctgggct ccaagctgat tggcacaggc aagctgtctg aggatgaaga gacagaggtg  1260
caagagcaga tgaacctgct gaacagcaga tgggagtgtc tgagagtggc cagcatggaa  1320
aagcagagca acctgcacag agtgctcatg gacctgcaga atcagaaact gaaagaactg  1380
aatgactggc tgaccaagac agaagaaagg actaggaaga tggaagagga acctctggga  1440
ccagacctgg aagatctgaa aagacaggtg cagcagcata aggtgctgca agaggacctt  1500
gagcaagagc aagtcagagt gaacagcctg acacacatgg tggtggttgt ggatgagtcc  1560
tctggggatc atgccacagc tgctctggaa gaacagctga aggtgctggg agacagatgg  1620
gccaacatct gtaggtggac agaggataga tgggtgctgc tccaggacat tctgctgaag  1680
tggcagagac tgacagagga acagtgcctg ttttctgcct ggctctctga gaaagaggat  1740
gctgtcaaca agatccatac cacaggcttc aaggatcaga atgagatgct cagctccctg  1800
cagaaactgg ctgtgctgaa ggctgacctg gaaaagaaaa agcagtccat gggcaagctc  1860
tacagcctga agcaggacct gctgtctacc ctgaagaaca agtctgtgac ccagaaaact  1920
gaggcctggc tggacaactt tgctagatgc tgggacaacc tggtgcagaa gctggaaaag  1980
tctacagccc agatcagcca gcaacctgat cttgcccctg gcctgaccac aattggagcc  2040
tctccaacac agactgtgac cctggttacc cagccagtgg tcaccaaaga gacagccatc  2100
agcaaactgg aaatgcccag ctctctgatg ctggaagtcc ccacactgga aaggctgcaa  2160
gaacttcaag aggccacaga tgagctggac ctgaagctga gacaggctga agtgatcaaa  2220
ggcagctggc agccagttgg ggacctgctc attgatagcc tgcaggacca tctggaaaaa  2280
gtgaaagccc tgaggggaga gattgcccct ctgaaagaaa atgtgtccca tgtgaatgac  2340
ctggccagac agctgaccac actgggaatc cagctgagcc cctacaacct gagcaccctt  2400
gaggacctga acaccaggtg gaagctcctc caggtggcag tggaagatag agtcaggcag  2460
ctgcatgagg cccacagaga ttttggacca gccagccagc actttctgtc tacctctgtg  2520
caaggcccct gggagagagc tatctctcct aacaaggtgc cctactacat caaccatgag  2580
acacagacca cctgttggga tcaccccaag atgacagagc tgtaccagag tctggcagac  2640
ctcaacaatg tcagattcag tgcctacagg actgccatga agctcagaag gctccagaaa  2700
gctctgtgcc tggacctgct ttccctgagt gcagcttgtg atgccctgga ccagcacaat  2760
ctgaagcaga atgaccagcc tatggacatc ctccagatca tcaactgcct caccaccatc  2820
tatgataggc tggaacaaga gcacaacaat ctggtcaatg tgcccctgtg tgtggacatg  2880
tgcctgaatt ggctgctgaa tgtgtatgac acaggcagaa caggcaggat cagagtcctg  2940
tccttcaaga caggcatcat ctccctgtgc aaagcccact tggaggacaa gtacagatac  3000
ctgttcaagc aagtggcctc cagcacaggc ttttgtgacc agagaaggct gggcctgctc  3060
ctgcatgaca gcattcagat ccctagacag ctgggagaag tggcttcctt tggaggcgcc  3120
aagcaccagg ccaagtgcaa catctgcaaa gagtgcccca tcattggctt cagatacaga  3180
tccctgaagc acttcaacta tgatatctgc cagagctgct tctttagtgg cagggttgcc  3240
aagggccaca aaatgcacta ccccatggtg gaatactgca ccccaacaac ctctggggaa  3300
gatgttagag actttgccaa ggtgctgaaa aacaagttca ggaccaagag atactttgct  3360
aagcacccca gaatgggcta cctgcctgtc cagacagtgc ttgagggtga caacatggaa  3420
acccctgtga cactgatcaa tttctggcca gtggactctg cccctgcctc aagtccacag  3480
ctgtcccatg atgacaccca cagcagaatt gagcactatg cctccagact ggcagagatg  3540
gaaaacagca atggcagcta cctgaatgat agcatcagcc ccaatgagag cattgatgat  3600
gagcatctgc tgatccagca ctactgtcag tccctgaacc aggactctcc actgagccag  3660
cctagaagcc ctgctcagat cctgatcagc cttgagtctg aggaaagggg agagctggaa  3720
agaatcctgg cagatcttga ggaagagaac agaaacctgc aggcagagta tgacaggctc  3780
aaacagcagc atgagcacaa gggactgagc cctctgcctt ctcctcctga aatgatgccc  3840
acctctccac agtctccaag gtgatga                                     3867
```

```
SEQ ID NO: 102         moltype = DNA  length = 4041
FEATURE                Location/Qualifiers
misc_feature           1..4041
                       note = synthetic construct; dystrophin
source                 1..4041
                       mol_type = other DNA
                       organism = synthetic construct
SEQUENCE: 102
atgctttggt gggaagaggt ggaagattgc tatgagaggg aagatgtgca gaagaaaacc  60
ttcaccaaat gggtcaatgc ccagttcagc aagtttggca agcagcacat tgagaacctg  120
ttcagtgacc tgcaggatgg cagaaggctg ctggatctgc tggaaggcct gacaggccag  180
aagctgccta aagagaaggg cagcacaaga gtgcatgccc tgaacaatgt gaacaaggcc  240
ctgagagtgc tgcagaacaa caatgtggac ctggtcaata ttggcagcac agacattgtg  300
gatggcaacc acaagctgac cctgggcctg atctggaaca tcatcctgca ctggcaagtg  360
aagaatgtga tgaagaacat catggctggc ctgcagcaga ccaactctga gaagatcctg  420
ctgagctggg tcagacagag caccagaaac taccctcaag tgaatgtgat caacttcacc  480
acctcttgga gtgatggact ggccctgaat gccctgatcc acagccacag acctgacctg  540
tttgactgga actctgttgt gtgccagcag tctgccacac agagactgga acatgccttc  600
aacattgcca gataccagct gggaattgag aaactgctgg accctgagga tgtggacacc  660
```

-continued

```
acctatcctg acaagaaatc catcctcatg tacatcacca gcctgttcca ggtgctgccc  720
cagcaagtgt ccattgaggc cattcaagag gttgagatgc tgcccagacc tcctaaagtg  780
accaaagagg aacacttcca gctgcaccac cagatgcact actctcagca gatcacagtg  840
tctctggccc agggatatga gagaacaagc agccccaagc ctaggttcaa gagctatgcc  900
tacacacagg ctgcctatgt gaccacatct gaccccacaa gaagcccatt tccaagccag  960
catctggaag cccctgagga caagagcttt ggcagcagcc tgatggaatc tgaagtgaac  1020
ctggatagat accagacagc cctggaagaa gtgctgtcct ggctgctgtc tgctgaggat  1080
acactgcagg ctcagggtga aatcagcaat gatgtggaag tggtcaagga ccagtttcac  1140
acccatgagg gctacatgat ggacctgaca gcccaccagg gcagagtggg aaatatcctg  1200
cagctgggct ccaagctgat tggcacaggc aagctgtctg aggatgaaga gacagaggtg  1260
caagagcaga tgaacctgct gaacagcaga tgggagtgtc tgagagtggc cagcatggaa  1320
aagcagagca acctgcacag agtgctcatg gacctgcaga atcagaaact gaaagaactg  1380
aatgactggc tgaccaagac agaagaaagg actaggaaga tggaagagga acctctggga  1440
ccagacctgg aagatctgaa aagacaggtg cagcagcata aggtgctgca agaggacctt  1500
gagcaagagc aagtcagagt gaacagcctg acacacatgg tggtggttgt ggatgagtcc  1560
tctggggatc atgccacagc tgctctggaa gaacagctga aggtgctggg agacagatgg  1620
gccaacatct gtaggtggac agaggataga tgggtgctgc tccaggacat tctggagatc  1680
agctatgtgc ccagcaccta cctgacagag atcacccatg tgtctcaggc cctgctggaa  1740
gtggaacagc tgctgaatgc ccctgacctg tgtgccaagg actttgagga cctgttcaag  1800
caagaggaaa gcctgaagaa catcaaggac agcctgcagc agtcctctgg cagaattgac  1860
atcatccaca gcaagaaaac agctgccctg cagtctgcca cacctgtgga aagagtgaag  1920
ctgcaagagg ccctgagcca gctggacttc cagtgggaga aagtgaacaa gatgtacaag  1980
gacaggcagg gcagatttga tagaagtgtg gaaaagtgga gaaggttcca ctatgacatc  2040
aagatcttca accagtggct gacagaggct gagcagttcc tgagaaagac acagatccct  2100
gagaactggg agcatgccaa gtacaagtgg tatctgaaag aactgcagga tggcattggc  2160
cagagacaga cagttgtcag aaccctgaat gccacagggg aagagatcat ccagcagagc  2220
agcaagacag atgccagcat cctgcaagag aagctgggca gcctgaacct gagatggcaa  2280
gaagtgtgca agcagctgtc tgacagaaag aagaggctgg aagaacagac actggaaagg  2340
ctgcaagaac ttcaagaggc cacagatgag ctggacctga agctgagaca ggctgaagtg  2400
atcaaaggca gctggcagcc agttggggac ctgctcattg atagcctgca ggaccatctg  2460
gaaaaagtga aagccctgag gggagagatt gcccctctga aagaaaatgt gtcccatgtg  2520
aatgacctgg ccagacagct gaccacactg ggaatccagc tgagccccta caacctgagc  2580
acccttgagg acctgaacac caggtggaag ctcctccagg tggcagtgga agatagagtc  2640
aggcagctgc atgaggccca cagagatttt ggaccagcca gccagcactt tctgtctacc  2700
tctgtgcaag gcccctggga gagagctatc tctcctaaca aggtgcccta ctacatcaac  2760
catgagacac agaccacctg ttgggatcac cccaagatga cagagctgta ccagagtctg  2820
gcagacctca acaatgtcag attcagtgcc tacaggactg ccatgaagct cagaaggctc  2880
cagaaagctc tgtgcctgga cctgctttcc ctgagtgcag cttgtgatgc cctggaccag  2940
cacaatctga agcagaatga ccagcctatg gacatcctcc agatcatcaa ctgcctcacc  3000
accatctatg ataggctgga acaagagcac aacaatctgg tcaatgtgcc cctgtgtgtg  3060
gacatgtgcc tgaattggct gctgaatgtg tatgacacag gcagaacagg caggatcaga  3120
gtcctgtcct tcaagacagg catcatctcc ctgtgcaaag cccacttgga ggacaagtac  3180
agatacctgt tcaagcaagt ggcctccagc acaggctttt gtgaccagag aaggctgggc  3240
ctgctcctgc atgacagcat tcagatccct agacagctgg gagaagtggc ttcctttgga  3300
ggcagcaata ttgagcctc agtcaggtcc tgttttcagt ttgccaacaa caagcctgag  3360
attgaggctg ccctgttcct ggactggatg agacttgagc ctcagagcat ggtctggctg  3420
cctgtgcttc atagagtggc tgctgctgag actgccaagc accaggccaa gtgcaacatc  3480
tgcaaagagt gccccatcat tggcttcaga tacagatccc tgaagcactt caactatgat  3540
atctgccaga gctgcttctt tagtggcagg gttgccaagg gccacaaaat gcactacccc  3600
atggtggaat actgcacccc aacaacctct ggggaagatg ttagagactt tgccaaggtg  3660
ctgaaaaaca agttcaggac caagagatac tttgctaagc accccagaat gggctacctg  3720
cctgtccaga cagtgcttga gggtgacaac atggaaaccc ctgtgacact gatcaatttc  3780
tggccagtgg actctgcccc tgcctcaagt ccacagctgt cccatgatga cacccacagc  3840
agaattgagc actatgcctc cagactggca gagatggaaa acagcaatgg cagctacctg  3900
aatgatagca tcagccccaa tgagagcatt gatgatgagc atctgctgat ccagcactac  3960
tgtcagtccc tgaaccagga ctctccactg agccagccta gaagccctgc tcagatcctg  4020
atcagccttg agtcttgatg a                                            4041
```

```
SEQ ID NO: 103         moltype = DNA  length = 3765
FEATURE                Location/Qualifiers
misc_feature           1..3765
                       note = synthetic construct; dystrophin
source                 1..3765
                       mol_type = other DNA
                       organism = synthetic construct
SEQUENCE: 103
atgctttggt gggaagaggt ggaagattgc tatgagaggg aagatgtgca gaagaaaacc  60
ttcaccaaat gggtcaatgc ccagttcagc aagtttggca agcagcacat tgagaacctg  120
ttcagtgacc tgcaggatgg cagaaggctg ctggatctgc tggaaggcct gacaggccag  180
aagctgccta aagagaaggg cagcacaaga gtgcatgccc tgaacaatgt gaacaaggcc  240
ctgagagtgc tgcagaacaa caatgtggac ctggtcaata ttggcagcac agacattgtg  300
gatggcaacc acaagctgac cctgggcctg atctggaaca tcatcctgca ctggcaagtg  360
aagaatgtga tgaagaacat catggctggc ctgcagcaga ccaactctga gaagatcctg  420
ctgagctggg tcagacagag caccagaaac taccctcaag tgaatgtgat caacttcacc  480
acctcttgga gtgatggact ggccctgaat gccctgatcc acagccacag acctgacctg  540
tttgactgga actctgttgt gtgccagcag tctgccacac agagactgga acatgccttc  600
aacattgcca gataccagct gggaattgag aaactgctgg accctgagga tgtggacacc  660
acctatcctg acaagaaatc catcctcatg tacatcacca gcctgttcca ggtgctgccc  720
cagcaagtgt ccattgaggc cattcaagag gttgagatgc tgcccagacc tcctaaagtg  780
```

```
accaaagagg aacacttcca gctgcaccac cagatgcact actctcagca gatcacagtg  840
tctctggccc agggatatga gagaacaagc agccccaagc ctaggttcaa gagctatgcc  900
tacacacagg ctgcctatgt gaccacatct gaccccacaa gaagcccatt tccaagccag  960
catctggaag cccctgagga caagagcttt ggcagcagcc tgatggaatc tgaagtgaac  1020
ctggatagat accagacagc cctggaagaa gtgctgtcct ggctgctgtc tgctgaggat  1080
acactgcagg ctcagggtga aatcagcaat gatgtggaag tggtcaagga ccagtttcac  1140
acccatgagg gctacatgat ggacctgaca gcccaccagg gcagagtggg aaatatcctg  1200
cagctgggct ccaagctgat tggcacaggc aagctgtctg aggatgaaga gacagaggtg  1260
caagagcaga tgaacctgct gaacagcaga tgggagtgtc tgagagtggc cagcatggaa  1320
aagcagagca acctgcacag agtgctcatg gacctgcaga atcagaaact gaaagaactg  1380
aatgactggc tgaccaagac agaagaaagg actaggaaga tggaagagga acctctggga  1440
ccagacctgg aagatctgaa aagacaggtg cagcagcata aggtgctgca agaggacctt  1500
gagcaagagc aagtcagagt gaacagcctg acacacatgg tggtggttgt ggatgagtcc  1560
tctggggatc atgccacagc tgctctggaa gaacagctga aggtgctggg agacagatgg  1620
gccaacatct gtaggtggac agaggataga tgggtgctgc tccaggacat tctggagatc  1680
agctatgtgc ccagcaccta cctgacagag atcacccatg tgtctcaggc cctgctggaa  1740
gtggaacagc tgctgaatgc ccctgacctg tgtgccaagg actttgagga cctgttcaag  1800
caagaggaaa gcctgaagaa catcaaggac agcctgcagc agtcctctgg cagaattgac  1860
atcatccaca gcaagaaaac agctgccctg cagtctgcca cacctgtgga aagagtgaag  1920
ctgcaagagg ccctgagcca gctggacttc cagtgggaga aagtgaacaa gatgtacaag  1980
gacaggcagg gcagatttga tagaagtgtg gaaaagtgga gaaggttcca ctatgacatc  2040
aagatcttca accagtggct gacagaggct gagcagttcc tgagaaagac acagatccct  2100
gagaactggg agcatgccaa gtacaagtgg tatctgaaag aactgcagga tggcattggc  2160
cagagacaga cagttgtcag aaccctgaat gccacagggg aagagatcat ccagcagagc  2220
agcaagacag atgccagcat cctgcaagag aagctgggca gcctgaacct gagatggcaa  2280
gaagtgtgca agcagctgtc tgacagaaag aagaggctgg aagaacagac actggaaagg  2340
ctgcaagaac ttcaagaggc cacagatgag ctggacctga agctgagaca ggctgaagtg  2400
atcaaaggca gctggcagcc agttggggac ctgctcattg atagcctgca ggaccatctg  2460
gaaaaagtga aagccctgag gggagagatt gcccctctga aagaaaatgt gtcccatgtg  2520
aatgacctgg ccagacagct gaccacactg ggaatccagc tgagccccta caacctgagc  2580
acccttgagg acctgaacac caggtggaag ctcctccagg tggcagtgga agatagagtc  2640
aggcagctgc atgaggccca cagagatttt ggaccagcca gccagcactt tctgtctacc  2700
tctgtgcaag gcccctggga gagagctatc tctcctaaca aggtgcccta ctacatcaac  2760
catgagacac agaccacctg ttgggatcac ccccaagatga cagagctgta ccagagtctg  2820
gcagacctca acaatgtcag attcagtgcc tacaggactg ccatgaagct cagaaggctc  2880
cagaaagctc tgtgcctgga cctgctttcc ctgagtgcag cttgtgatgc cctggaccag  2940
cacaatctga agcagaatga ccagcctatg gacatcctcc agatcatcaa ctgcctcacc  3000
accatctatg ataggctgga acaagagcac aacaatctgg tcaatgtgcc cctgtgtgtg  3060
gacatgtgcc tgaattggct gctgaatgtg tatgacacag gcagaacagg caggatcaga  3120
gtcctgtcct tcaagacagg catcatctcc ctgtgcaaag cccacttgga ggacaagtac  3180
agatacctgt tcaagcaagt ggcctccagc acaggctttt gtgaccagag aaggctgggc  3240
ctgctcctgc atgacagcat tcagatccct agacagctgg gagaagtggc ttcctttgga  3300
ggcagcaata ttgagccatc agtcaggtcc tgttttcagt ttgccaacaa caagcctgag  3360
attgaggctg ccctgttcct ggactggatg agacttgagc ctcagagcat ggtctggctg  3420
cctgtgcttc atagagtggc tgctgctgag actgccaagc accaggccaa gtgcaacatc  3480
tgcaaagagt gccccatcat tggcttcaga tacagatccc tgaagcactt caactatgat  3540
atctgccaga gctgcttctt tagtggcagg gttgccaagg gccacaaaat gcactacccc  3600
atggtggaat actgcacccc aacaacctct ggggaagatg ttagagactt tgccaaggtg  3660
ctgaaaaaca agttcaggac caagagatac tttgctaagc accccagaat gggctacctg  3720
cctgtccaga cagtgcttga gggtgacaac atggaaacct gatga                 3765

SEQ ID NO: 104         moltype = DNA  length = 4584
FEATURE                Location/Qualifiers
misc_feature           1..4584
                       note = synthetic construct; dystrophin cassette
source                 1..4584
                       mol_type = other DNA
                       organism = synthetic construct
SEQUENCE: 104
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct catatgcagg gtaatgggga tcctctagag gccgtccgcc ctcggcacca  180
tcctcacgac acccaaatat ggcgacgggt gaggaatggt ggggagttat ttttagagcg  240
gtgaggaagg tgggcaggca gcaggtgttg gcgctctaaa aataactccc gggagttatt  300
tttagagcgg aggaatggtg gacacccaaa tatggcgacg gttcctcacc cgtcgccata  360
tttgggtgtc cgccctcggc cgggccgca ttcctggggg ccgggcggtg ctcccgcccg  420
cctcgataaa aggctccggg gccggcggcg gcccacgagc tacccggagg agcgggaggc  480
gccaagcgga attcgccacc atgctttggt gggaagaggt ggaagattgc tatgagaggg  540
aagatgtgca gaagaaaacc ttcaccaaat gggtcaatgc ccagttcagc aagtttggca  600
agcagcacat tgagaacctg ttcagtgacc tgcaggatgg cagaaggctg ctggatctgc  660
tggaaggcct gacaggccag aagctgccta aagagaaggg cagcacaaga gtgcatgccc  720
tgaacaatgt gaacaaggcc ctgagagtgc tgcagaacaa caatgtggac ctggtcaata  780
ttggcagcac agacattgtg gatggcaacc acaagctgac cctgggcctg atctggaaca  840
tcatcctgca ctggcaagtg aagaatgtga tgaagaacat catggctggc ctgcagcaga  900
ccaactctga gaagatcctg ctgagctggg tcagacagag caccagaaac taccctcaag  960
tgaatgtgat caacttcacc acctcttgga gtgatggact ggccctgaat gccctgatcc  1020
acagccacag acctgacctg tttgactgga actctgttgt gtgccagcag tctgccacac  1080
agagactgga acatgccttc aacattgcca gataccagct gggaattgag aaactgctgg  1140
accctgagga tgtggacacc acctatcctg acaagaaatc catcctcatg tacatcacca  1200
```

```
gcctgttcca ggtgctgccc cagcaagtgt ccattgaggc cattcaagag gttgagatgc  1260
tgcccagacc tcctaaagtg accaaagagg aacacttcca gctgcaccac cagatgcact  1320
actctcagca gatcacagtg tctctggccc agggatatga gagaacaagc agccccaagc  1380
ctaggttcaa gagctatgcc tacacacagg ctgcctatgt gaccacatct gaccccacaa  1440
gaagcccatt tccaagccag catctggaag cccctgagga caagagcttt ggcagcagcc  1500
tgatggaatc tgaagtgaac ctggatagat accagacagc cctggaagaa gtgctgtcct  1560
ggctgctgtc tgctgaggat acactgcagg ctcagggtga aatcagcaat gatgtggaag  1620
tggtcaagga ccagtttcac acccatgagg gctacatgat ggacctgaca gcccaccagg  1680
gcagagtggg aaatatcctg cagctgggct ccaagctgat tggcacaggc aagctgtctg  1740
aggatgaaga gacagaggtg caagagcaga tgaacctgct gaacagcaga tgggagtgtc  1800
tgagagtggc cagcatggaa aagcagagca acctgcacag agtgctcatg gacctgcaga  1860
atcagaaact gaaagaactg aatgactggc tgaccaagac agaagaaagg actaggaaga  1920
tggaagagga acctctggga ccagacctgg aagatctgaa aagacaggtg cagcagcata  1980
aggtgctgca agaggacctt gagcaagagc aagtcagagt gaacagcctg acacacatgg  2040
tggtggttgt ggatgagtcc tctggggatc atgccacagc tgctctggaa gaacagctga  2100
aggtgctggg agacagatgg gccaacatct gtaggtggac agaggataga tgggtgctgc  2160
tccaggacat tctgctgaag tggcagagac tgacagagga acagtgcctg ttttctgcct  2220
ggctctctga gaaagaggat gctgtcaaca agatccatac cacaggcttc aaggatcaga  2280
atgagatgct cagctccctg cagaaactgg ctgtgctgaa ggctgacctg gaaaagaaaa  2340
agcagtccat gggcaagctc tacagcctga agcaggacct gctgtctacc ctgaagaaca  2400
agtctgtgac ccagaaaact gaggcctggc tggacaactt tgctagatgc tgggacaacc  2460
tggtgcagaa gctggaaaag tctacagccc agatcagcca gcaacctgat cttgcccctg  2520
gcctgaccac aattggagcc tctccaacac agactgtgac cctggttacc cagccagtgg  2580
tcaccaaaga gacagccatc agcaaactgg aaatgcccag ctctctgatg ctggaagtcc  2640
ccacactgga aaggctgcaa gaacttcaag aggccacaga tgagctggac ctgaagctga  2700
gacaggctga agtgatcaaa ggcagctggc agccagttgg ggacctgctc attgatagcc  2760
tgcaggacca tctggaaaaa gtgaaagccc tgaggggaga gattgcccct ctgaaagaaa  2820
atgtgtccca tgtgaatgac ctggccagac agctgaccac actgggaatc cagctgagcc  2880
cctacaacct gagcaccctt gaggacctga acaccaggtg gaagctcctc caggtggcag  2940
tggaagatag agtcaggcag ctgcatgagg cccacagaga ttttggacca gccagccagc  3000
actttctgtc tacctctgtg caaggcccct gggagagagc tatctctcct aacaaggtgc  3060
cctactacat caaccatgag acacagacca cctgttggga tcaccccaag atgacagagc  3120
tgtaccagag tctggcagac ctcaacaatg tcagattcag tgcctacagg actgccatga  3180
agctcagaag gctccagaaa gctctgtgcc tggacctgct ttccctgagt gcagcttgtg  3240
atgccctgga ccagcacaat ctgaagcaga atgaccagcc tatggacatc ctccagatca  3300
tcaactgcct caccaccatc tatgataggc tggaacaaga gcacaacaat ctggtcaatg  3360
tgcccctgtg tgtggacatg tgcctgaatt ggctgctgaa tgtgtatgac acaggcagaa  3420
caggcaggat cagagtcctg tccttcaaga caggcatcat ctccctgtgc aaagcccact  3480
tggaggacaa gtacagatac ctgttcaagc aagtggcctc cagcacaggc ttttgtgacc  3540
agagaaggct gggcctgctc ctgcatgaca gcattcagat ccctagacag ctgggagaag  3600
tggcttcctt tggaggcgcc aagcaccagg ccaagtgcaa catctgcaaa gagtgcccca  3660
tcattggctt cagatacaga tccctgaagc acttcaacta tgatatctgc cagagctgct  3720
tctttagtgg cagggttgcc aagggccaca aaatgcacta ccccatggtg gaatactgca  3780
ccccaacaac ctctggggaa gatgttagag actttgccaa ggtgctgaaa aacaagttca  3840
ggaccaagag atactttgct aagcacccca gaatgggcta cctgcctgtc cagacagtgc  3900
ttgagggtga caacatggaa acccctgtga cactgatcaa tttctggcca gtggactctg  3960
cccctgcctc aagtccacag ctgtcccatg atgacaccca cagcagaatt gagcactatg  4020
cctccagact ggcagagatg gaaaacagca atggcagcta cctgaatgat agcatcagcc  4080
ccaatgagag cattgatgat gagcatctgc tgatccagca ctactgtcag tccctgaacc  4140
aggactctcc actgagccag cctagaagcc ctgctcagat cctgatcagc cttgagtctg  4200
aggaaagggg agagctggaa agaatcctgg cagatcttga ggaagagaac agaaacctgc  4260
aggcagagta tgacaggctc aaacagcagc atgagcacaa gggactgagc cctctgcctt  4320
ctcctcctga aatgatgccc acctctccac agtctccaag gtgatgactc gagaggccta  4380
ataaagagct cagatgcatc gatcagagtg tgttggtttt ttgtgtgcca gggtaatggg  4440
ctagctgcgg ccgcaggaac ccctagtgat ggagttggcc actccctctc tgcgcgctcg  4500
ctcgctcact gaggccgggc gaccaaaggt cgcccgacgc ccgggctttg cccgggcggc  4560
ctcagtgagc gagcgagcgc gcag                                        4584
```

```
SEQ ID NO: 105          moltype = DNA  length = 4746
FEATURE                 Location/Qualifiers
misc_feature            1..4746
                        note = synthetic construct; dystrophin cassette
source                  1..4746
                        mol_type = other DNA
                        organism = synthetic construct
SEQUENCE: 105
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct catatgcagg gtaatgggga tcctctagag gccgtccgcc ctcggcacca  180
tcctcacgac acccaaatat ggcgacgggt gaggaatggt ggggagttat ttttagagcg  240
gtgaggaagg tgggcaggca gcaggtgttg gcgctctaaa aataactccc gggagttatt  300
tttagagcgg aggaatggtg gacacccaaa tatggcgacg gttcctcacc cgtcgccata  360
tttgggtgtc cgccctcggc cggggccgca ttcctggggg ccgggcggtg ctcccgcccg  420
cctcgataaa aggctccggg gccggcggcg gcccacgagc tacccggagg agcgggaggc  480
gccaagcgga attcgccacc atgctttggt gggaagaggt ggaagattgc tatgagaggg  540
aagatgtgca gaagaaaacc ttcaccaaat gggtcaatgc ccagttcagc aagtttggca  600
agcagcacat tgagaacctg ttcagtgacc tgcaggatgg cagaaggctg ctggatctgc  660
tggaaggcct gacaggccag aagctgccta aagagaaggg cagcacaaga gtgcatgccc  720
tgaacaatgt gaacaaggcc ctgagagtgc tgcagaacaa caatgtggac ctggtcaata  780
```

-continued

```
ttggcagcac agacattgtg gatggcaacc acaagctgac cctgggcctg atctggaaca  840
tcatcctgca ctggcaagtg aagaatgtga tgaagaacat catggctggc ctgcagcaga  900
ccaactctga gaagatcctg ctgagctggg tcagacagag caccagaaac taccctcaag  960
tgaatgtgat caacttcacc acctcttgga gtgatggact ggccctgaat gccctgatcc  1020
acagccacag acctgacctg tttgactgga actctgttgt gtgccagcag tctgccacac  1080
agagactgga acatgccttc aacattgcca gataccagct gggaattgag aaactgctgg  1140
accctgagga tgtggacacc acctatcctg acaagaaatc catcctcatg tacatcacca  1200
gcctgttcca ggtgctgccc cagcaagtgt ccattgaggc cattcaagag gttgagatgc  1260
tgcccagacc tcctaaagtg accaaagagg aacacttcca gctgcaccac cagatgcact  1320
actctcagca gatcacagtg tctctggccc agggatatga gagaacaagc agccccaagc  1380
ctaggttcaa gagctatgcc tacacacagg ctgcctatgt gaccacatct gaccccacaa  1440
gaagcccatt tccaagccag catctggaag cccctgagga caagagcttt ggcagcagcc  1500
tgatggaatc tgaagtgaac ctggatagat accagacagc cctggaagaa gtgctgtcct  1560
ggctgctgtc tgctgaggat acactgcagg ctcagggtga aatcagcaat gatgtggaag  1620
tggtcaagga ccagtttcac acccatgagg gctacatgat ggacctgaca gcccaccagg  1680
gcagagtggg aaatatcctg cagctgggct ccaagctgat tggcacaggc aagctgtctg  1740
aggatgaaga gacagaggtg caagagcaga tgaacctgct gaacagcaga tgggagtgtc  1800
tgagagtggc cagcatggaa aagcagagca acctgcacag agtgctcatg gacctgcaga  1860
atcagaaact gaaagaactg aatgactggc tgaccaagac agaagaaagg actaggaaga  1920
tggaagagga acctctggga ccagacctgg aagatctgaa aagacaggtg cagcagcata  1980
aggtgctgca agaggacctt gagcaagagc aagtcagagt gaacagcctg acacacatgg  2040
tggtggttgt ggatgagtcc tctggggatc atgccacagc tgctctggaa gaacagctga  2100
aggtgctggg agacagatgg gccaacatct gtaggtggac agaggataga tgggtgctgc  2160
tccaggacat tctggagatc agctatgtgc ccagcaccta cctgacagag atcacccatg  2220
tgtctcaggc cctgctggaa gtggaacagc tgctgaatgc cctgacctg tgtgccaagg  2280
actttgagga cctgttcaag caagaggaaa gcctgaagaa catcaaggac agcctgcagc  2340
agtcctctgg cagaattgac atcatccaca gcaagaaaac agctgccctg cagtctgcca  2400
cacctgtgga aagagtgaag ctgcaagagg ccctgagcca gctggacttc cagtgggaga  2460
aagtgaacaa gatgtacaag gacaggcagg gcagatttga tagaagtgtg gaaaagtgga  2520
gaaggttcca ctatgacatc aagatcttca accagtggct gacagaggct gagcagttcc  2580
tgagaaagac acagatccct gagaactggg agcatgccaa gtacaagtgg tatctgaaag  2640
aactgcagga tggcattggc cagagacaga cagttgtcag aaccctgaat gccacagggg  2700
aagagatcat ccagcagagc agcaagacag atgccagcat cctgcaagag aagctgggca  2760
gcctgaacct gagatggcaa gaagtgtgca agcagctgtc tgacagaaag aagaggctgg  2820
aagaacagac actggaaagg ctgcaagaac ttcaagaggc cacagatgag ctggacctga  2880
agctgagaca ggctgaagtg atcaaaggca gctggcagcc agttggggac ctgctcattg  2940
atagcctgca ggaccatctg gaaaaagtga aagccctgag gggagagatt gcccctctga  3000
aagaaaatgt gtcccatgtg aatgacctgg ccagacagct gaccacactg ggaatccagc  3060
tgagccccta caacctgagc acccttgagg acctgaacac caggtggaag ctcctccagg  3120
tggcagtgga agatagagtc aggcagctgc atgaggccca cagagatttt ggaccagcca  3180
gccagcactt tctgtctacc tctgtgcaag gcccctggga gagagctatc tctcctaaca  3240
aggtgcccta ctacatcaac catgagacac agaccacctg ttgggatcac cccaagatga  3300
cagagctgta ccagagtctg gcagacctca acaatgtcag attcagtgcc tacaggactg  3360
ccatgaagct cagaaggctc cagaaagctc tgtgcctgga cctgctttcc ctgagtgcag  3420
cttgtgatgc cctggaccag cacaatctga agcagaatga ccagcctatg gacatcctcc  3480
agatcatcaa ctgcctcacc accatctatg ataggctgga acaagagcac aacaatctgg  3540
tcaatgtgcc cctgtgtgtg gacatgtgcc tgaattggct gctgaatgtg tatgacacag  3600
gcagaacagg caggatcaga gtcctgtcct tcaagacagg catcatctcc ctgtgcaaag  3660
cccacttgga ggacaagtac agatacctgt tcaagcaagt ggcctccagc acaggctttt  3720
gtgaccagag aaggctgggc ctgctcctgc atgacagcat tcagatccct agacagctgg  3780
gagaagtggc ttcctttgga ggcagcaata ttgagccatc agtcaggtcc tgttttcagt  3840
ttgccaacaa caagcctgag attgaggctg ccctgttcct ggactggatg agacttgagc  3900
ctcagagcat ggtctggctg cctgtgcttc atagagtggc tgctgctgag actgccaagc  3960
accaggccaa gtgcaacatc tgcaaagagt gccccatcat tggcttcaga tacagatccc  4020
tgaagcactt caactatgat atctgccaga gctgcttctt tagtggcagg gttgccaagg  4080
gccacaaaat gcactacccc atggtggaat actgcacccc aacaacctct ggggaagatg  4140
ttagagactt tgccaaggtg ctgaaaaaca agttcaggac caagagatac tttgctaagc  4200
accccagaat gggctacctg cctgtccaga cagtgcttga gggtgacaac atggaaaccc  4260
ctgtgacact gatcaatttc tggccagtgg actctgcccc tgcctcaagt ccacagctgt  4320
cccatgatga cacccacagc agaattgagc actatgcctc cagactggca gagatggaaa  4380
acagcaatgg cagctacctg aatgatagca tcagccccaa tgagagcatt gatgatgagc  4440
atctgctgat ccagcactac tgtcagtccc tgaaccagga ctctccactg agccagccta  4500
gaagccctgc tcagatcctg atcagccttg agtcttgatg agtcgacagg cctaataaag  4560
agctcagatg catcgatcag agtgtgttgg ttttttgtgt ggctagctgc ggccgcagga  4620
acccctagtg atggagttgg ccactccctc tctgcgcgct cgctcgctca ctgaggccgg  4680
gcgaccaaag gtcgcccgac gcccgggctt tgcccgggcg gcctcagtga gcgagcgagc  4740
gcgcag                                                            4746
```

```
SEQ ID NO: 106          moltype = DNA  length = 4470
FEATURE                 Location/Qualifiers
misc_feature            1..4470
                        note = synthetic construct; dystropin cassette
source                  1..4470
                        mol_type = other DNA
                        organism = synthetic construct
SEQUENCE: 106
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct catatgcagg gtaatgggga tcctctagag gccgtccgcc ctcggcacca  180
```

-continued

```
tcctcacgac acccaaatat ggcgacgggt gaggaatggt ggggagttat ttttagagcg  240
gtgaggaagg tgggcaggca gcaggtgttg gcgctctaaa aataactccc gggagttatt  300
tttagagcgg aggaatggtg gacacccaaa tatggcgacg gttcctcacc cgtcgccata  360
tttgggtgtc cgccctcggc cggggccgca ttcctggggg ccgggcggtg ctcccgcccg  420
cctcgataaa aggctccggg gccggcggcg gcccacgagc tacccggagg agcgggaggc  480
gccaagcgga attcgccacc atgctttggt gggaagaggt ggaagattgc tatgagaggg  540
aagatgtgca gaagaaaacc ttcaccaaat gggtcaatgc ccagttcagc aagtttggca  600
agcagcacat tgagaacctg ttcagtgacc tgcaggatgg cagaaggctg ctggatctgc  660
tggaaggcct gacaggccag aagctgccta aagagaaggg cagcacaaga gtgcatgccc  720
tgaacaatgt gaacaaggcc ctgagagtgc tgcagaacaa caatgtggac ctggtcaata  780
ttggcagcac agacattgtg gatggcaacc acaagctgac cctgggcctg atctggaaca  840
tcatcctgca ctggcaagtg aagaatgtga tgaagaacat catggctggc ctgcagcaga  900
ccaactctga gaagatcctg ctgagctggg tcagacagag caccagaaac taccctcaag  960
tgaatgtgat caacttcacc acctcttgga gtgatggact ggccctgaat gccctgatcc  1020
acagccacag acctgacctg tttgactgga actctgttgt gtgccagcag tctgccacac  1080
agagactgga acatgccttc aacattgcca gataccagct gggaattgag aaactgctgg  1140
accctgagga tgtggacacc acctatcctg acaagaaatc catcctcatg tacatcacca  1200
gcctgttcca ggtgctgccc cagcaagtgt ccattgaggc cattcaagag gttgagatgc  1260
tgcccagacc tcctaaagtg accaaagagg aacacttcca gctgcaccac cagatgcact  1320
actctcagca gatcacagtg tctctggccc agggatatga gagaacaagc agccccaagc  1380
ctaggttcaa gagctatgcc tacacacagg ctgcctatgt gaccacatct gaccccacaa  1440
gaagcccatt tccaagccag catctggaag cccctgagga caagagcttt ggcagcagcc  1500
tgatggaatc tgaagtgaac ctggatagat accagacagc cctggaagaa gtgctgtcct  1560
ggctgctgtc tgctgaggat acactgcagg ctcagggtga aatcagcaat gatgtggaag  1620
tggtcaagga ccagtttcac acccatgagg gctacatgat ggacctgaca gcccaccagg  1680
gcagagtggg aaatatcctg cagctgggct ccaagctgat tggcacaggc aagctgtctg  1740
aggatgaaga gacagaggtg caagagcaga tgaacctgct gaacagcaga tgggagtgtc  1800
tgagagtggc cagcatggaa aagcagagca acctgcacag agtgctcatg gacctgcaga  1860
atcagaaact gaaagaactg aatgactggc tgaccaagac agaagaaagg actaggaaga  1920
tggaagagga acctctggga ccagacctgg aagatctgaa aagacaggtg cagcagcata  1980
aggtgctgca agaggacctt gagcaagagc aagtcagagt gaacagcctg acacacatgg  2040
tggtggttgt ggatgagtcc tctggggatc atgccacagc tgctctggaa gaacagctga  2100
aggtgctggg agacagatgg gccaacatct gtaggtggac agaggataga tgggtgctgc  2160
tccaggacat tctggagatc agctatgtgc ccagcaccta cctgacagag atcacccatg  2220
tgtctcaggc cctgctggaa gtggaacagc tgctgaatgc ccctgacctg tgtgccaagg  2280
actttgagga cctgttcaag caagaggaaa gcctgaagaa catcaaggac agcctgcagc  2340
agtcctctgg cagaattgac atcatccaca gcaagaaaac agctgccctg cagtctgcca  2400
cacctgtgga aagagtgaag ctgcaagagg ccctgagcca gctggacttc cagtgggaga  2460
aagtgaacaa gatgtacaag gacaggcagg gcagatttga tagaagtgtg gaaaagtgga  2520
gaaggttcca ctatgacatc aagatcttca accagtggct gacagaggct gagcagttcc  2580
tgagaaagac acagatccct gagaactggg agcatgccaa gtacaagtgg tatctgaaag  2640
aactgcagga tggcattggc cagagacaga cagttgtcag aaccctgaat gccacagggg  2700
aagagatcat ccagcagagc agcaagacag atgccagcat cctgcaagag aagctgggca  2760
gcctgaacct gagatggcaa gaagtgtgca agcagctgtc tgacagaaag aagaggctgg  2820
aagaacagac actggaaagg ctgcaagaac ttcaagaggc cacagatgag ctggacctga  2880
agctgagaca ggctgaagtg atcaaaggca gctggcagcc agttggggac ctgctcattg  2940
atagcctgca ggaccatctg gaaaaagtga aagccctgag gggagagatt gcccctctga  3000
aagaaaatgt gtcccatgtg aatgacctgg ccagacagct gaccacactg ggaatccagc  3060
tgagccccta caacctgagc acccttgagg acctgaacac caggtggaag ctcctccagg  3120
tggcagtgga agatagagtc aggcagctgc atgaggccca cagagatttt ggaccagcca  3180
gccagcactt tctgtctacc tctgtgcaag gcccctggga gagagctatc tctcctaaca  3240
aggtgcccta ctacatcaac catgagacac agaccacctg ttgggatcac cccaagatga  3300
cagagctgta ccagagtctg gcagacctca acaatgtcag attcagtgcc tacaggactg  3360
ccatgaagct cagaaggctc cagaaagctc tgtgcctgga cctgctttcc ctgagtgcag  3420
cttgtgatgc cctggaccag cacaatctga agcagaatga ccagcctatg gacatcctcc  3480
agatcatcaa ctgcctcacc accatctatg ataggctgga acaagagcac aacaatctgg  3540
tcaatgtgcc cctgtgtgtg gacatgtgcc tgaattggct gctgaatgtg tatgacacag  3600
gcagaacagg caggatcaga gtcctgtcct tcaagacagg catcatctcc ctgtgcaaag  3660
cccacttgga ggacaagtac agatacctgt tcaagcaagt ggcctccagc acaggctttt  3720
gtgaccagag aaggctgggc ctgctcctgc atgacagcat tcagatccct agacagctgg  3780
gagaagtggc ttcctttgga ggcagcaata ttgagccatc agtcaggtcc tgtttttcagt  3840
ttgccaacaa caagcctgag attgaggctg ccctgttcct ggactggatg agacttgagc  3900
ctcagagcat ggtctggctg cctgtgcttc atagagtggc tgctgctgag actgccaagc  3960
accaggccaa gtgcaacatc tgcaaagagt gccccatcat tggcttcaga tacagatccc  4020
tgaagcactt caactatgat atctgccaga gctgcttctt tagtggcagg gttgccaagg  4080
gccacaaaat gcactacccc atggtggaat actgcacccc aacaacctct ggggaagatg  4140
ttagagactt tgccaaggtg ctgaaaaaca agttcaggac caagagatac tttgctaagc  4200
accccagaat gggctacctg cctgtccaga cagtgcttga gggtgacaac atggaaacct  4260
gatgagtcga caggcctaat aaagagctca gatgcatcga tcagagtgtg ttggtttttt  4320
gtgtggctag ctgcggccgc aggaacccct agtgatggag ttggccactc cctctctgcg  4380
cgctcgctcg ctcactgagg ccgggcgacc aaaggtcgcc cgacgcccgg gctttgcccg  4440
ggcggcctca gtgagcgagc gagcgcgcag                                 4470
```

```
SEQ ID NO: 107          moltype =   length =
SEQUENCE: 107
000

SEQ ID NO: 108          moltype = DNA  length = 12
FEATURE                 Location/Qualifiers
```

-continued

```
misc_feature          1..12
                      note = synthetic construct; linker
source                1..12
                      mol_type = other DNA
                      organism = synthetic construct
SEQUENCE: 108
gaaacccttg aa                                                        12

SEQ ID NO: 109        moltype = DNA  length = 162
FEATURE               Location/Qualifiers
misc_feature          1..162
                      note = synthetic construct; dystrophin segment
source                1..162
                      mol_type = other DNA
                      organism = synthetic construct
SEQUENCE: 109
gccaagcatc aggccaaatg taacatctgc aaagagtgtc caatcattgg attcaggtac  60
aggagtctaa agcactttaa ttatgacatc tgccaaagct gcttttttc tggtcgagtt  120
gcaaaaggcc ataaaatgca ctatcccatg gtggaatatt gc                     162

SEQ ID NO: 110        moltype =   length =
SEQUENCE: 110
000

SEQ ID NO: 111        moltype = DNA  length = 12
FEATURE               Location/Qualifiers
misc_feature          1..12
                      note = synthetic construct; linker
source                1..12
                      mol_type = other DNA
                      organism = synthetic construct
SEQUENCE: 111
gagacactgg aa                                                        12

SEQ ID NO: 112        moltype = AA  length = 738
FEATURE               Location/Qualifiers
REGION                1..738
                      note = synthetic construct; capsid sequence
source                1..738
                      mol_type = protein
                      organism = synthetic construct
SEQUENCE: 112
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEAAKTAP GKKRPVEPSP QRSPDSSTGI GKKGQQPAKK RLNFGQTGDS  180
ESVPDPQPIG EPPAGPSGLG SGTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYTFED  420
VPFHSSYAHS QSLDRLMNPL IDQYLYYLSR TQSTGGTQGT QQLLFSQAGP ANMSAQAKNW  480
LPGPCYRQQR VSTTLSQNNN SNFAWTGATK YHLNGRDSLV NPGVAMATHK DDEERFFPSS  540
GVLMFGKQGA GRDNVDYSSV MLTSEEEIKT TNPVATEQYG VVADNLQQTN TGPIVGNVNS  600
QGALPGMVWQ NRDVYLQGPI WAKIPHTDGN FHPSPLMGGF GLKHPPPQIL IKNTPVPADP  660
PTTFSQAKLA SFITQYSTGQ VSVEIEWELQ KENSKRWNPE IQYTSNYYKS TNVDFAVNTE  720
GTYSEPRPIG TRYLTRNL                                                 738

SEQ ID NO: 113        moltype = AA  length = 736
FEATURE               Location/Qualifiers
REGION                1..736
                      note = synthetic construct; capsid sequence
source                1..736
                      mol_type = protein
                      organism = synthetic construct
SEQUENCE: 113
MAADGYLPDW LEDTLSEGIR QWWKLKPGPP PPKPAERHKD DSRGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGSQPAKKK LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGGQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVSTEGV  720
YSEPRPIGTR YLTRNL                                                   736

SEQ ID NO: 114        moltype = AA  length = 740
```

-continued

```
FEATURE                Location/Qualifiers
REGION                 1..740
                       note = synthetic construct; capsid sequence
source                 1..740
                       mol_type = protein
                       organism = synthetic construct
SEQUENCE: 114
MAADGYLPDW LEDTLSEGIR QWWKLKPGPP PPKPAERHKD DSRGLVLPGY KYLGPGNGLD  60
KGEPVNAADA AALEHDKAYD GINQLKAGDN PYLKYNHADA EFQERLKEDT SFGGNLGRAV  120
FQAKKRLLEP LGLVEEAAKT APGKKRPVEQ SPQEPDSSAG IGKSGSQPAK KKLNFGQTGD  180
TESVPDPGIN PIGEPPAAPS GVGSLTMASG GGAPVADNNE GADGVGSSSG NWHCDSQWLG  240
DRVITTSTRT WALPTYNNHL YKQISNSTSG GSSNDNAYFG YSTPWGYFDF NRFHCHFSPR  300
DWQRLINNNW GFRPKRLNFK LFNIQVKEVT DNNGVKTIAN NLTSTVQVFT DSDYQLPYVL  360
GSAHEGCLPP FPADVFMIPQ YGYLTLNDGS QAVGRSSFYC LEYFPSQMLR TGNNFQFSYE  420
FENVPFHSSY AHSQSLDRLM NPLIDQYLYY LSKTINGSGQ NQQTLKFSVA GPSNMAVQGR  480
NYIPGPSYRQ QRVSTTVTQN NNSEFAWPGA SSWALNGRNS LMNPGPAMAS HKEGEDRFFP  540
LSGSLIFGKQ GTGRDNVDAD KVMITNEEEI KTTNPVATES YGQVATNHQS AQAQAQTGWV  600
QNQGILPGMV WQDRDVYLQG PIWAKIPHTD GNFHPSPLMG GFGMKHPPPQ ILIKNTPVPA  660
DPPTAFNKDK LNSFITQYST GQVSVEIEWE LQKENSKRWN PEIQYTSNYY KSNNVEFAVN  720
TEGVYSEPRP IGTRYLTRNL                                             740

SEQ ID NO: 115         moltype = DNA  length = 865
FEATURE                Location/Qualifiers
misc_feature           1..865
                       note = synthetic construct; promoter sequence
source                 1..865
                       mol_type = other DNA
                       organism = synthetic construct
SEQUENCE: 115
ccactacggg tttaggctgc ccatgtaagg aggcaaggcc tggggacacc cgagatgcct  60
ggttataatt aacccagaca tgtggctgcc cccccccccc ccaacacctg ctgcctctaa  120
aaataaccct gtccctggtg gatcccacta cgggtttagg ctgcccatgt aaggaggcaa  180
ggcctgggga cacccgagat gcctggttat aattaaccca gacatgtggc tgcccccccc  240
ccccccaaca cctgctgcct ctaaaaataa ccctgtccct ggtggatccc actacgggtt  300
taggctgccc atgtaaggag gcaaggcctg gggacacccg agatgcctgg ttataattaa  360
cccagacatg tggctgcccc cccccccccc aacacctgct gcctctaaaa ataaccctgt  420
ccctggtgga tcccctgcat gcgaagatct tcgaacaagg ctgtgggggga ctgagggcag  480
gctgtaacag gcttgggggc cagggcttat acgtgcctgg gactcccaaa gtattactgt  540
tccatgttcc cggcgaaggg ccagctgtcc cccgccagct agactcagca cttagtttag  600
gaaccagtga gcaagtcagc ccttggggca gcccatacaa ggccatgggg ctgggcaagc  660
tgcacgcctg ggtccggggt gggcacggtg cccgggcaac gagctgaaag ctcatctgct  720
ctcaggggcc cctccctggg gacagcccct cctggctagt cacaccctgt aggctcctct  780
atataaccca ggggcacagg ggctgccctc attctaccac cacctccaca gcacagacag  840
acactcagga gccagccagc gtcga                                       865

SEQ ID NO: 116         moltype = DNA  length = 1725
FEATURE                Location/Qualifiers
misc_feature           1..1725
                       note = synthetic construct; promoter sequence
source                 1..1725
                       mol_type = other DNA
                       organism = synthetic construct
SEQUENCE: 116
gacattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggagtatt tacggtaaac tgcccacttg gcagtacatc  240
aagtgtatca tatgccaagt acgcccccta ttgacgtcaa tgacggtaaa tggcccgcct  300
ggcattatgc ccagtacatg accttatggg actttcctac ttggcagtac atctacgtat  360
tagtcatcgc tattaccatg gtcgaggtga gccccacgtt ctgcttcact ctccccatct  420
cccccccctc cccaccccca attttgtatt tatttatttt ttaattattt tgtgcagcga  480
tgggggcggg gggggggggg gggcgcgcgc caggcggggc ggggcggggc gaggggcggg  540
gcggggcgag gcggagaggt gcggcggcag ccaatcagag cggcgcgctc cgaaagtttc  600
cttttatggc gaggcggcgg cggcggcggc cctataaaaa gcgaagcgcg cggcgggcgg  660
gagtcgctgc gcgctgcctt cgccccgtgc cccgctccgc cgccgcctcg cgccgcccgc  720
cccggctctg actgaccgcg ttactcccac aggtgagcgg gcgggacggc ccttctcctc  780
cgggctgtaa ttagcgcttg gtttaatgac ggcttgtttc ttttctgtgg ctgcgtgaaa  840
gccttgaggg gctccgggag ggccctttgt gcggggggag cggctcgggg ggtgcgtgcg  900
tgtgtgtgtg cgtggggagc gccgcgtgcg gctccgcgct gcccggcggc tgtgagcgct  960
gcgggcgcgg cgcggggctt tgtgcgctcc gcagtgtgcg cgaggggagc gcggccgggg  1020
gcggtgcccc gcggtgcggg gggggctgcg aggggaacaa aggctgcgtg cggggtgtgt  1080
gcgtgggggg gtgagcaggg ggtgtgggcg cgtcggtcgg gctgcaaccc cccctgcacc  1140
cccctccccg agttgctgag cacggcccgg cttcgggtgc ggggctccgt acggggcgtg  1200
gcgcggggct cgccgtgccg ggcggggggt ggcggcaggt gggggtgccg ggcggggcgg  1260
ggccgcctcg ggccggggag ggctcggggg aggggcgcgg cggcccccgg agcgccggcg  1320
gctgtcgagg cgcggcgagc cgcagccatt gccttttatg gtaatcgtgc gagagggcgc  1380
agggacttcc tttgtcccaa atctgtgcgg agccgaaatc tgggaggcgc cgccgcaccc  1440
cctctagcgg gcgcggggcg aagcggtgcg gcgccggcag gaaggaaatg ggcggggagg  1500
gccttcgtgc gtcgccgcgc cgccgtcccc ttctccctct ccagcctcgg ggctgtccgc  1560
```

-continued

```
gggggggacgg ctgccttcgg gggggacggg gcagggcggg gttcggcttc tggcgtgtga  1620
ccggcggctc tagagcctct gctaaccatg ttcatgcctt cttctttttc ctacagctcc  1680
tgggcaacgt gctggttatt gtgctgtctc atcattttgg caaag                   1725

SEQ ID NO: 117         moltype = DNA  length = 251
FEATURE                Location/Qualifiers
misc_feature           1..251
                       note = synthetic construct; promoter sequence
source                 1..251
                       mol_type = other DNA
                       organism = synthetic construct
SEQUENCE: 117
atggaggcgg tactatgtag atgagaattc aggagcaaac tgggaaaagc aactgcttcc  60
aaatatttgt gatttttaca gtgtagtttt ggaaaaactc ttagcctacc aattcttcta  120
agtgttttaa aatgtgggag ccagtacaca tgaagttata gagtgtttta atgaggctta  180
aatatttacc gtaactatga aatgctacgc atatcatgct gttcaggctc cgtggccacg  240
caactcatac t                                                       251

SEQ ID NO: 118         moltype = DNA  length = 212
FEATURE                Location/Qualifiers
misc_feature           1..212
                       note = synthetic construct; promoter sequence
source                 1..212
                       mol_type = other DNA
                       organism = synthetic construct
SEQUENCE: 118
gggcagagcg cacatcgccc acagtccccg agaagttggg gggaggggtc ggcaattgaa  60
cgggtgccta gagaaggtgg cgcggggtaa actgggaaag tgatgtcgtg tactggctcc  120
gcctttttcc cgagggtggg ggagaaccgt atataagtgc agtagtcgcc gtgaacgttc  180
tttttcgcaa cgggtttgcc gccagaacac ag                                212

SEQ ID NO: 119         moltype = DNA  length = 240
FEATURE                Location/Qualifiers
misc_feature           1..240
                       note = synthetic construct; desmin sequence
source                 1..240
                       mol_type = other DNA
                       organism = synthetic construct
SEQUENCE: 119
ctgcagacat gcttgctgcc tgccctggcg tgccctggcg aggcttgccg tcacaggacc  60
cccgctggct gactcagggg cgcaggctct tgcgggggag ctggcctccc gcccccacgg  120
ccacgggccc tttcctggca ggacagcggg atcttgcagc tgtcagggga ggggatgacg  180
ggggactgat gtcaggaggg gatacaaata gtgccgaaca aggaccggat tagatctacc  240

SEQ ID NO: 120         moltype = DNA  length = 792
FEATURE                Location/Qualifiers
misc_feature           1..792
                       note = synthetic construct; MHCK7 sequence
source                 1..792
                       mol_type = other DNA
                       organism = synthetic construct
SEQUENCE: 120
aagcttgcat gtctaagcta gacccttcag attaaaaata actgaggtaa gggcctgggt  60
aggggaggtg gtgtgagacg ctcctgtctc tcctctatct gcccatcggc cctttgggga  120
ggaggaatgt gcccaaggac taaaaaaagg ccatggagcc agaggggcga gggcaacaga  180
cctttcatgg gcaaaccttg gggccctgct gtctagcatg ccccactacg ggtctaggct  240
gcccatgtaa ggaggcaagg cctggggaca cccgagatgc ctggttataa ttaacccaga  300
catgtggctg cccccccccc cccaacacct gctgcctcta aaaataaccc tgtccctggt  360
ggatcccctg catgcgaaga tcttcgaaca aggctgtggg ggactgaggg caggctgtaa  420
caggcttggg ggccagggct tatacgtgcc tgggactccc aaagtattac tgttccatgt  480
tcccggcgaa gggccagctg tcccccgcca gctagactca gcacttagtt taggaaccag  540
tgagcaagtc agcccttggg gcagcccata caaggccatg gggctgggca agctgcacgc  600
ctgggtccgg ggtgggcacg gtgcccgggc aacgagctga aagctcatct gctctcaggg  660
gcccctccct ggggacagcc cctcctggct agtcacaccc tgtaggctcc tctatataac  720
ccaggggcac aggggctgcc ctcattctac caccacctcc acagcacaga cagacactca  780
ggagcagcca gc                                                      792

SEQ ID NO: 121         moltype = DNA  length = 714
FEATURE                Location/Qualifiers
misc_feature           1..714
                       note = synthetic construct; truncated MCK
source                 1..714
                       mol_type = other DNA
                       organism = synthetic construct
SEQUENCE: 121
ccactacggg tctaggctgc ccatgtaagg aggcaaggcc tggggacacc cgagatgcct  60
ggttataatt aaccccaaca cctgctgccc cccccccccc aacacctgct gcctgagcct  120
gagcggttac cccacccogg tgcctgggtc ttaggctctg tacaccatgg aggagaagct  180
cgctctaaaa ataaccctgt ccctggtgga tccactacgg gtctatgctg cccatgtaag  240
```

-continued

```
gaggcaaggc ctggggacac ccgagatgcc tggttataat taaccccaac acctgctgcc  300
cccccccccc caacacctgc tgcctgagcc tgagcggtta ccccaccccg gtgcctgggt  360
cttaggctct gtacaccatg gaggagaagc tcgctctaaa aataaccctg tccctggtgg  420
accactacgg gtctaggctg cccatgtaag gaggcaaggc ctggggacac ccgagatgcc  480
tggttataat taaccccaac acctgctgcc cccccccccc aacacctgct gcctgagcct  540
gagcggttac cccaccccgg tgcctgggtc ttaggctctg tacaccatgg aggagaagct  600
cgctctaaaa ataaccctgt ccctggtcct ccctggggac agcccctcct ggctagtcac  660
accctgtagg ctcctctata taacccaggg gcacaggggc tgcccccggg tcac        714

SEQ ID NO: 122         moltype = DNA  length = 25
FEATURE                Location/Qualifiers
misc_feature           1..25
                       note = synthetic construct; primer
source                 1..25
                       mol_type = other DNA
                       organism = synthetic construct
SEQUENCE: 122
acagatacct gttcaagcaa gtggc                                        25

SEQ ID NO: 123         moltype = DNA  length = 17
FEATURE                Location/Qualifiers
misc_feature           1..17
                       note = synthetic construct; primer
source                 1..17
                       mol_type = other DNA
                       organism = synthetic construct
SEQUENCE: 123
tcaatctcag gcttggc                                                 17

SEQ ID NO: 124         moltype = DNA  length = 19
FEATURE                Location/Qualifiers
misc_feature           1..19
                       note = synthetic construct; primer
source                 1..19
                       mol_type = other DNA
                       organism = synthetic construct
SEQUENCE: 124
caatattgag ccatcagtc                                               19

SEQ ID NO: 125         moltype =   length =
SEQUENCE: 125
000

SEQ ID NO: 126         moltype = DNA  length = 12
FEATURE                Location/Qualifiers
misc_feature           1..12
                       note = synthetic construct; linker
source                 1..12
                       mol_type = other DNA
                       organism = synthetic construct
SEQUENCE: 126
cagacactgg aa                                                      12

SEQ ID NO: 127         moltype = AA  length = 738
FEATURE                Location/Qualifiers
REGION                 1..738
                       note = synthetic construct; capsid sequence
source                 1..738
                       mol_type = protein
                       organism = synthetic construct
SEQUENCE: 127
MAADGYLPDW LEDNLSEGIR EWWDLKPGAP KPKANQQKQD NGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVESPVKTAP GKKRPVEPSP QRSPDSSTGI GKKGQQPAKK RLNFGQTGDS  180
ESVPDPQPIG EPPAGPSGLG SGTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
RLINNNWGFR PKRLNFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYNFED  420
VPFHSSYAHS QSLDRLMNPL IDQYLYYLSR TQSTGGTAGT QQLLFSQAGP NNMSAQAKNW  480
LPGPCYRQQR VSTTLSQNNN SNFAWTGATK YHLNGRDSLV NPGVAMATHK DDEERFFPSS  540
GVLMFGKQGA GKDNVDYSSV MLTSEEEIKT TNPVATEQYG VVADNLQQQN AAPIVGAVNS  600
QGALPGMVWQ NRDVYLQGPI WAKIPHTDGN FHPSPLMGGF GLKHPPPQIL IKNTPVPADP  660
PTTFNQAKLA SFITQYSTGQ VSVEIEWELQ KENSKRWNPE IQYTSNYYKS TNVDFAVNTE  720
GTYSEPRPIG TRYLTRNL                                                738
```

TREATMENT OF DYSTROPHINOPATHIES WITH MICRODYSTROPHIN GENE THERAPY CONSTRUCTS

0. SEQUENCE LISTING

The instant application contains a Sequence Listing which has been submitted electronically in xml format and is hereby incorporated by reference in its entirety. Said xml copy, created on Jun. 10, 2025, is named 38013_0009U5_SL.xml and is 240,352 bytes in size.

1. FIELD OF THE INVENTION

The present invention relates to novel microdystrophins and gene therapy vectors, such as recombinant AAV vectors encoding the novel microdystrophins, as well as compositions and uses thereof and methods of treatment using the same.

2. BACKGROUND

A group of neuromuscular diseases called dystrophinopathies are caused by mutations in the DMD gene. Each dystrophinopathy has a distinct phenotype, with all patients suffering from muscle weakness and ultimately cardiomyopathy with ranging severity. Duchenne muscular dystrophy (DMD) is a severe, X-linked, progressive neuromuscular disease affecting approximately one in 3,600 to 9,200 live male births. The disorder is caused by frameshift mutations in the dystrophin gene abolishing the expression of the dystrophin protein. Due to the lack of the dystrophin protein, skeletal muscle, and ultimately heart and respiratory muscles (e.g., intercostal muscles and diaphragm), degenerate causing premature death. Progressive weakness and muscle atrophy begin in childhood. Affected individuals experience breathing difficulties, respiratory infections, and swallowing problems. Almost all DMD patients will develop cardiomyopathy. Pneumonia compounded by cardiac involvement is the most frequent cause of death, which frequently occurs before the third decade.

Becker muscular dystrophy (BMD) has less severe symptoms than DMD, but still leads to premature death. Compared to DMD, BMD is characterized by later-onset skeletal muscle weakness. Whereas DMD patients are wheelchair dependent before age 13, those with BMD lose ambulation and require a wheelchair after age 16. BMD patients also exhibit preservation of neck flexor muscle strength, unlike their counterparts with DMD. Despite milder skeletal muscle involvement, heart failure from DMD-associated dilated cardiomyopathy (DCM) is a common cause of morbidity and the most common cause of death in BMD, which occurs on average in the mid-40s.

Dystrophin is a cytoplasmic protein encoded by the DMD gene, and functions to link cytoskeletal actin filaments to membrane proteins. Normally, the dystrophin protein, located primarily in skeletal and cardiac muscles, with smaller amounts expressed in the brain, acts as a shock absorber during muscle fiber contraction by linking the actin of the contractile apparatus to the layer of connective tissue that surrounds each muscle fiber. In muscle, dystrophin is localized at the cytoplasmic face of the sarcolemma membrane.

The DMD gene is the largest known human gene. The most common mutations that cause DMD or BMD are large deletion mutations of one or more exons (60-70%), but duplication mutations (5-10%), and single nucleotide variants (including small deletions or insertions, single-base changes, and splice site changes accounting for approximately 25-35% of pathogenic variants in males with DMD and about 10-20% of males with BMD), can also cause pathogenic dystrophin variants. In DMD, mutations often lead to a frame shift resulting in a premature stop codon and a truncated, non-functional or unstable protein. Nonsense point mutations can also result in premature termination codons with the same result. While mutations causing DMD can affect any exon, exons 2-20 and 45-55 are common hotspots for large deletion and duplication mutations. In-frame deletions result in the less severe Becker muscular dystrophy (BMD), in which patients express a truncated, partially functional dystrophin.

Full-length dystrophin is a large (427 kDa) protein comprising a number of subdomains that contribute to its function. These subdomains include, in order from the amino-terminus toward the carboxy-terminus, the N-terminal actin-binding domain, a central so-called "rod" domain, a cysteine-rich domain and lastly a carboxy-terminal domain or region. The rod domain is comprised of 4 proline-rich hinge domains (abbreviated H), and 24 spectrin-like repeats (abbreviated R) in the following order: a first hinge domain (H1), 3 spectrin-like repeats (R1, R2, R3), a second hinge domain (H2), 16 more spectrin-like repeats (R4, R5, R6, R7, R8, R9, R10, R11, R12, R13, R14, R15, R16, R17, R18, R19), a third hinge domain (H3), 5 more spectrin-like repeats (R20, R21, R22, R23, R24), and a fourth hinge domain (H4) (including the WW domain). Following the rod domain are the cysteine-rich domain, and the COOH (C)-terminal (CT) domain.

With advances in use of adeno-associated virus (AAV) mediated gene therapy to potentially treat a variety of rare diseases, there has been hope and interest that AAV could be used to treat DMD, BMD and less severe dystrophinopathies. Due to limits on payload size of AAV vectors, attention has focused on creating micro- or mini-dystrophins, smaller versions of dystrophin that eliminate non-essential subdomains while maintaining at least some function of the full-length protein. AAV-mediated minidystrophin gene therapy in mdx mice, an animal model for DMD, was reported as exhibiting efficient expression in muscle and improved muscle function (See, e.g., Wang et al., J. Orthop. Res. 27:421 (2009)).

Thus, there exists a need in the art for AAV vectors encoding micro- or mini-dystrophins that can be expressed at effective levels in transduced cells of subjects with DMD or BMD and preferably minimizing immune responses to the therapeutic protein.

3. SUMMARY OF THE INVENTION

Provided is an invention based, in part, on novel gene constructs that encode a microdystrophin protein for use in gene therapy. The microdystrophin gene constructs and expression cassettes were engineered for improved therapy with respect to efficacy, potency and safety to the subject when expressed by a viral vector in muscle cells and/or CNS cells. Based on in vivo therapeutic models, the microdystrophin gene therapies of the present disclosure showed measured improvements in grip strength, maximal and specific muscle force and/or reduction in organ and muscle weight. Accordingly, provided are improved gene therapy vectors, for example, recombinant AAV vectors, such as recombinant AAV8 or AAV9 vectors, comprising these constructs for gene therapy expression of the microdystrophin proteins, and methods of using these gene therapy vectors in therapeutic methods and methods of making these gene therapy vectors as described herein.

Provided are microdystrophin proteins and nucleic acid constructs encoding same that comprise the N-terminal actin binding domain and a subset of the hinge, rod and spectrin domains, followed by the cysteine-rich domain and, optionally, all or a portion, for example, a helix 1-containing portion, of the C-terminal domain. In particular embodiments, the microdystrophin has all or a portion of the C-terminal domain, or an α1-syntrophin and/or α-dystrobrevin binding portion thereof. Microdystrophins having a C-terminal domain, or an α1-syntrophin and/or α-dystrobrevin binding portion thereof, may have improved cardioprotective activity and/or result in improvement in or decrease/delay the progression of weakened cardiac muscle function.

Figure 22:
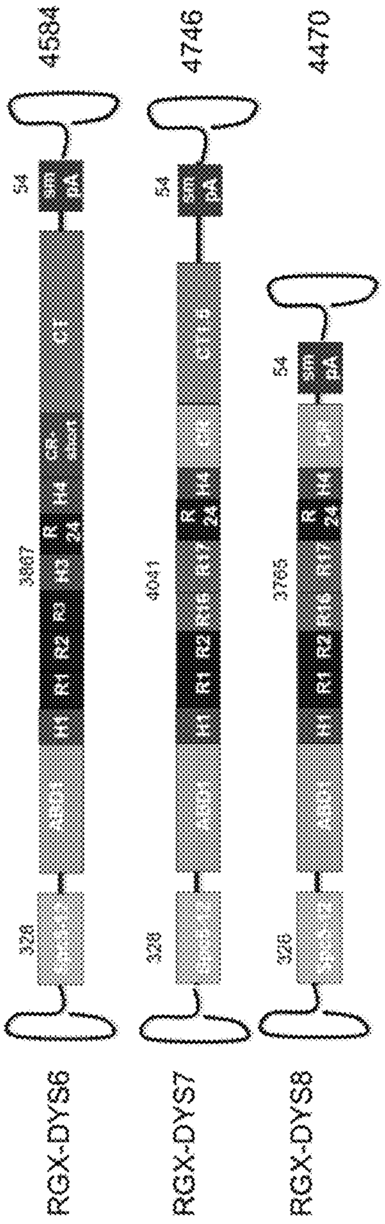

Exemplary microdystrophins encoding constructs are illustrated in FIGS. 1A and 22. Embodiments described herein are a microdystrophin protein having from amino-terminus to the carboxy terminus:

ABD—H1—R1—R2—R3—H3—R24—H4—CR,

ABD—H1—R1—R2—R3—H3—R24—H4—CR—CT

ABD—H1—R1—R2—R16—H17—R24—H4—CR—CT, or

ABD—H1—R1—R2—R16—R17—R24—H4—CR, wherein ABD is an actin-binding domain of dystrophin, H1 is a hinge 1 region of dystrophin, R1 is a spectrin 1 region of dystrophin, R2 is a spectrin 2 region of dystrophin, R3 is a spectrin 3 region of dystrophin, H3 is a hinge 3 region of dystrophin, R16 is a spectrin 16 region of dystrophin, R17 is a spectrin 17 region of dystrophin, R24 is a spectrin 24 region of dystrophin, CR is the cysteine-rich region of dystrophin or at least a portion thereof which binds β-dystroglycan, and CT is at least a portion of a C-terminal region of dystrophin, where the portion comprises a α1-syntrophin binding site and/or an α-dystrobrevin binding site. In certain embodiments, the CT domain has an amino acid sequence of SEQ ID NO: 35, 70, or 83. In certain embodiments, the H3 domain is the entire sequence of SEQ ID NO: 11. The CR domain may be the full length CR domain or a shortened CR domain, particularly a shortened CR domain which binds β-dystroglycan. In certain embodiments, the CR domain has an amino acid sequence of SEQ ID NO: 15 or 90. In certain embodiments, endogenous linker sequences link domains, for example, all or a 3 amino acid portion of the linker between R23 and R24 in the endogenous human dystrophin protein, link the H3 domain and the R24 domain. Alternatively, in some embodiments, H3 can be substituted with hinge 2 region of dystrophin (H2).

The microdystrophins provided herein exhibit dystrophin functions (see FIG. 13), such as (1) binding to one of, a combination of, or all of actin, β-dystroglycan, α1-syntrophin, α-dystrobrevin, and nNOS (including nNOS binding indirectly via α1-syntrophin); (2) promoting improved muscle function or slowing in the progression of reduction in muscle function in an animal model (for example, in the mdx mouse model described herein) or in human subjects; and/or (3) having a cardioprotective function or promoting improvement in cardiac muscle function or attenuation of cardiac dysfunction or slowing the progression of degeneration of cardiac function in animal models or human patients.

In particular embodiments, the microdystrophin has an amino acid sequence of SEQ ID NOs: 1, 2, 79, 91, 92, or 93.

Provided herein are nucleic acids encoding microdystrophins, including transgenes or gene cassettes for use in gene therapy. In embodiments, the microdystrophins are encoded by a nucleotide sequence of SEQ ID NOs: 20, 21, 81, 101, 102, or 103 or any nucleotide sequence encoding the amino acid sequence of SEQ ID NOs: 1, 2, 79, 91, 92, or 93. Exemplary constructs are illustrated in FIGS. 1A and 22. In certain embodiments, the constructs include an intron 5' of the microdystrophin encoding sequence. In some embodiments, the intron is less than 100 nucleotides in length. In particular embodiments, the constructs include the human immunoglobulin heavy chain variable region (VH) 4 (VH4) intron and the intron is located 5' of the microdystrophin encoding sequence. The presence of the VH4 intron may lead to improved expression of the microdystrophin in cells relative to expression from nucleic acid constructs not having the VH4 intron.

The transgenes provided herein contain promoters that drive expression of the microdystrophin in appropriate cell types, such as muscle cells (including skeletal muscle, cardiac muscle, and/or smooth muscle) and/or CNS cells. Reducing the size of transgenes used in gene therapy, such as with recombinant AAV vector therapy, may improve the efficacy and efficiency of the recombinant AAV vectors. Provided herein are transgenes in which the promoter is a muscle-specific promoter, CNS specific promoter, or both. In certain embodiments, the promoter is a muscle-specific promoter that is less than 350 kb in length. In some embodiments, the promoter is an SPc5-12 promoter (SEQ ID NO: 39). Provided herein are transgenes in which the promoter is a truncated SPc5-12 promoter (SEQ ID NO: 40) that directs expression of the microdystrophin and is shorter than the SPc5-12 promoter as described more fully herein. In certain embodiments, the promoter is a CNS specific promoter.

Provided also are transgenes or gene cassettes in which the microdystrophin coding sequence has been codon optimized for increased expression. In addition or alternatively, the microdystrophin coding sequences and/or the transgene sequences may be depleted of CpG to reduce immunogenicity. In some embodiments, the microdystrophin transgene has fewer than two (2) CpG islands, or one (1) CpG island (in particular, as defined herein) and in certain embodiments has no CpG islands. The transgene with fewer than 2, 1 or has 0 CpG islands has reduced immunogenicity as measured by anti-drug antibody titer compared to microdystrophin constructs having more than 2 CpG islands.

Provided herein are nucleic acids comprising nucleotide sequences of SEQ ID NO: 53, 54, 55, 56, 82, 104, 105, or 106 which encode exemplary gene cassettes or transgenes.

The recombinant vector for delivering the transgenes described herein includes non-replicating recombinant adeno-associated virus vectors (rAAV), and may be of an AAV8 or AAV9 serotype or any other serotype appropriate for delivery of the microdystrophin coding sequences to muscle cells, including both skeletal muscle and cardiac muscle, and/or CNS cells which will express the microdystrophin and provide additional benefit to the patient, and/or deliver to muscle cells.

Also provided are pharmaceutical compositions comprising the recombinant vectors encoding the microdystrophins provided herein, including with a pharmaceutically acceptable excipient and methods of treatment for any dystrophinopathy, such as for Duchenne muscular dystrophy (DMD) and Becker muscular dystrophy (BMD), X-linked dilated cardiomyopathy, as well as DMD or BMD female carriers, by administration of the gene therapy vectors described herein to a subject in need thereof. Provided are methods of treating, ameliorating the symptoms of or managing a dystrophinopathy, such as Duchenne muscular dystrophy (DMD) and Becker muscular dystrophy (BMD), X-linked dilated cardiomyopathy by administration of an rAAV containing a transgene or gene cassette described herein, by administration to a subject in need thereof such that the microdystrophin is delivered to the muscle (including skeletal muscle, cardiac muscle, and/or smooth muscle) and/or the CNS. In particular embodiments, the rAAV is administered systemically.

Also provided are methods of manufacturing the viral vectors, particularly the AAV based viral vectors, and host cells for producing same. In specific embodiments, provided are methods of producing recombinant AAVs comprising culturing a host cell containing an artificial genome comprising a cis expression cassette flanked by AAV ITRs, wherein the cis expression cassette comprises a transgene encoding a therapeutic microdystrophin operably linked to expression control elements that will control expression of the transgene in human cells; a trans expression cassette lacking AAV ITRs, wherein the trans expression cassette encodes an AAV rep and capsid protein operably linked to expression control elements that drive expression of the AAV rep and capsid proteins in the host cell in culture and supply the rep and cap proteins in trans; sufficient adenovirus helper functions to permit replication and packaging of the artificial genome by the AAV capsid proteins; and recovering recombinant AAV encapsidating the artificial genome from the cell culture.

The present inventions are illustrated by way of examples infra describing the construction and making of microdystrophin vectors and in vitro and in vivo assays demonstrating effectiveness.

EXEMPLARY EMBODIMENTS

1. A nucleic acid composition comprising a nucleic acid sequence encoding a microdystrophin protein wherein the microdystrophin protein comprises or consists of dystrophin domains arranged from amino-terminus to the carboxy terminus: ABD-H1-R1-R2-R3-H3-R24-H4-CR-CT, wherein ABD is an actin-binding domain of dystrophin, H1 is a hinge 1 region of dystrophin, R1 is a spectrin 1 region of dystrophin, R2 is a spectrin 2 region of dystrophin, R3 is a spectrin 3 region of dystrophin, H3 is a hinge 3 region of dystrophin, R24 is a spectrin 24 region of dystrophin, H4 is hinge 4 region of dystrophin, CR is the cysteine-rich region of dystrophin or a β-dystroglycan binding portion thereof, and CT is the C-terminal region of dystrophin or a portion of the C-terminal region comprising an α1-syntrophin binding site or a dystrobrevin binding site.

2. The nucleic acid composition of embodiment 1 (1) comprising a nucleic acid sequence encoding the microdystrophin protein with an amino acid sequence of SEQ ID NO: 1 or 91, or a nucleic acid sequence at least 90%, 95% or 98% identical thereto or the reverse complement thereof encoding a therapeutically functional microdystrophin protein, or (2) comprising or consisting of a nucleic acid sequence of SEQ ID NO: 20 or 100 or a nucleic acid sequence at least 90%, 95% or 98% identical thereto or the reverse complement thereof, wherein the nucleic acid sequence encodes a therapeutically functional microdystrophin protein.

3. The nucleic acid composition of embodiment 1 (1) comprising a nucleic acid sequence encoding the microdystrophin protein with an amino acid sequence of SEQ ID NO: 79 or a nucleic acid sequence at least 90%, 95% or 98% identical thereto or the reverse complement thereof encoding a therapeutically functional microdystrophin protein, or (2) comprising or consisting of a nucleic acid sequence of SEQ ID NO: 81 or a nucleic acid sequence at least 90%, 95% or 98% identical thereto or the reverse complement thereof, wherein the nucleic acid encodes a therapeutically functional microdystrophin protein.

4. A nucleic acid composition comprising a nucleic acid sequence comprising an intron (I) coupled to the 5' end of a nucleic acid sequence encoding a microdystrophin protein, wherein the microdystrophin protein comprises or consists of dystrophin domains arranged from amino-terminus to the carboxy terminus: ABD-H1-R1-R2-R3-H3-R24-H4-CR, wherein ABD is an actin-binding domain of dystrophin, H1 is a hinge 1 region of dystrophin, R1 is a spectrin 1 region of dystrophin, R2 is a spectrin 2 region of dystrophin, R3 is a spectrin 3 region of dystrophin, H3 is a hinge 3 region of dystrophin, R24 is a spectrin 24 region of dystrophin, H4 is hinge 4 region of dystrophin, CR is a cysteine-rich region of dystrophin.

5. The nucleic acid composition of embodiment 4 (1) comprising a nucleic acid sequence encoding the microdystrophin protein with an amino acid sequence of SEQ ID NO: 2 or a nucleic acid sequence at least 90%, 95% or 98% identical thereto or the reverse complement thereof or (2) comprising or consisting of a nucleic acid sequence of SEQ ID NO: 21 or a nucleic acid sequence at least 90%, 95% or 98% identical thereto or the reverse complement thereof, wherein the nucleic acid encodes a therapeutically functional dystrophin.

6. The nucleic acid composition of embodiments 1 to 3 further comprising an intron (I) coupled to the 5' end of the nucleic acid sequence encoding the microdystrophin protein.

7. The nucleic acid composition of any of embodiments 4 to 6, wherein I is the human immunoglobin heavy chain variable region (VH) 4 intron (VH4) or the SV40 intron or the chimeric intron located 5' of the microdystrophin encoding sequence.

8. The nucleic acid composition of embodiment 7, wherein the nucleic acid sequence encoding the VH4 intron comprises or consists of the nucleic acid sequence of SEQ ID NO: 41 or a nucleic acid sequence at least 90%, 95% or 98% identical thereto or the reverse complement thereof and increases microdystrophin expression relative to a reference nucleic acid lacking the VH4 intron sequence; wherein the nucleic acid sequence encoding a chimeric intron comprises or consists of the nucleic acid sequence of SEQ ID NO: 75 or a nucleic acid sequence at least 90%, 95% or 98% identical thereto or the reverse complement thereof and increases microdystrophin expression relative to a reference nucleic acid lacking the chimeric intron sequence; or wherein the nucleic acid sequence encoding a SV40 intron comprises or consists of the nucleic acid sequence of SEQ ID NO: 76 or a nucleic acid sequence at least 90%, 95% or 98% identical thereto or the reverse complement thereof and increases microdystrophin expression relative to a reference nucleic lacking the chimeric intron sequence.

9. The nucleic acid composition of any of embodiments 1-3 or 6-8, wherein the nucleic acid sequence encoding the CT domain comprises or consists of the nucleic acid sequence of SEQ ID NO: 35 or a nucleic acid sequence at least 90%, 95% or 98% identical thereto or the reverse complement thereof and increases binding of the microdystrophin to α1-syntrophin, β-syntrophin, and/or dystrobrevin relative to a reference microdystrophin lacking the CT domain sequence; wherein the nucleic acid sequence encoding the CT domain comprises or consists of the nucleic acid sequence of SEQ ID NO: 70 or a nucleic acid sequence at least 90%, 95% or 98% identical thereto or the reverse complement thereof and increases binding of the microdystrophin to α1-syntrophin, 0-syntrophin, and/or dystrobrevin relative to a reference microdystrophin lacking the CT domain sequence; or wherein the nucleic acid sequence encoding a minimal CT domain or consists of the nucleic acid sequence of SEQ ID NO: 80 or a nucleic acid sequence at least 90%, 95% or 98% identical thereto or the reverse complement thereof and increases binding of the microdystrophin to α1-syntrophin relative to a reference microdystrophin lacking the CT domain sequence.

10. The nucleic acid composition of embodiment 9 wherein the CT domain has an amino acid sequence of SEQ ID NO: 16 or 83 or comprises the amino acid sequence of SEQ ID NO: 84.

11. The nucleic acid composition of any of the foregoing embodiments, wherein the nucleic acid sequence encoding the CR domain comprises or consists of the nucleic acid sequence of SEQ ID NO: 34 or 69 or a nucleic acid sequence at least 90%, 95% or 98% identical thereto or the reverse complement thereof and increases binding of the microdystrophin to β-dystroglycan relative to a reference microdystrophin lacking the CR domain sequence; wherein the nucleic acid sequence encoding the CR domain comprises or consists of the nucleic acid sequence of SEQ ID NO: 100 or 109 or a nucleic acid sequence at least 90%, 95% or 98% identical thereto or the reverse complement thereof and increases binding of the microdystrophin to β-dystroglycan relative to a reference microdystrophin lacking the CR domain sequence.

12. The nucleic acid composition of embodiment 11, wherein the CR domain has an amino acid sequence of SEQ ID NO: 15 or 90.

13. The nucleic acid composition of any one of the foregoing embodiments, wherein the nucleic acid sequence encoding ABD consists of SEQ ID NO: 22 or 57 or a sequence with at least 75%, at least 80%, at least 85%, at least 90%, at least 95%, at least 98% or at least 99% identity to SEQ ID NO: 22 or 57; the nucleic acid sequence encoding H1 consists of SEQ ID NO: 24 or 59 or a sequence with at least 75%, at least 80%, at least 85%, at least 90%, at least 95%, at least 98% or at least 99% identity to SEQ ID NO: 24 or 59; the nucleic acid sequence encoding R1 consists of SEQ ID NO: 26 or 61 or a sequence with at least 75%, at least 80%, at least 85%, at least 90%, at least 95%, at least 98% or at least 99% identity to SEQ ID NO: 26 or 61; the nucleic acid sequence encoding R2 consists of SEQ ID NO: 27 or 62 or a sequence with at least 75%, at least 80%, at least 85%, at least 90%, at least 95%, at least 98% or at least 99% identity to SEQ ID NO: 27 or 62; the nucleic acid sequence encoding R3 consists of SEQ ID NO: 29 or 64 or a sequence with at least 75%, at least 80%, at least 85%, at least 90%, at least 95%, at least 98% or at least 99% identity to SEQ ID NO: 29 or 64; the nucleic acid sequence encoding H2 consists of SEQ ID NO: 38 or a sequence with at least 50%, at least 60%, at least 70%, at least 75%, at least 80%, at least 85%, at least 90%, at least 95%, at least 98% or at least 99% identity to SEQ ID NO: 38; the nucleic acid sequence encoding H3 consists of SEQ ID NO: 30 or 65 or a sequence with at least 75%, at least 80%, at least 85%, at least 90%, at least 95%, at least 98% or at least 99% identity to SEQ ID NO: 30 or 65; the nucleic acid sequence encoding R24 consists of SEQ ID NO: 32 or 67 or a sequence with at least 75%, at least 80%, at least 85%, at least 90%, at least 95%, at least 98% or at least 99% identity to SEQ ID NO: 32 or 67; the nucleic acid sequence encoding H4 consists of SEQ ID NO: 33 or 68 or a sequence with at least 75%, at least 80%, at least 85%, at least 90%, at least 95%, at least 98%, or at least 99% identity to SEQ ID NO: 33 or 68; the nucleic acid sequence encoding CR consists of SEQ ID NO: 34, 69, 100 or 109 or a sequence with at least 75%, at least 80%, at least 85%, at least 90%, at least 95%, at least 98% or at least 99% identity to SEQ ID NO: 34, 69, 100 or 109; the nucleic acid sequence encoding CT, if present, consists of SEQ ID NO: 35, 70, or 80 or a sequence with at least 75%, at least 80%, at least 85%, at least 90%, at least 95%, at least 98% or at least 99% identity to SEQ ID NO: 35, 70, or 80; and, optionally, the I nucleic acid sequence is a nucleic acid sequence of SEQ ID NO: 41 or a sequence with at least 75%, at least 80%, at least 85%, at least 90%, at least 95%, at least 98% or at least 99% identity to SEQ ID NO: 41 coupled at the 5' end of the nucleic acid sequence encoding the microdystrophin.

14. The nucleic acid composition of any one of the foregoing embodiments, wherein the nucleic acid sequence that encodes ABD consists of SEQ ID NO: 22 or 57; the nucleic acid sequence that encodes H1 consists of SEQ ID NO: 24 or 59; the nucleic acid sequence that encodes R1 consists of SEQ ID NO: 26 or 61; the nucleic acid sequence that encodes R2 consists of SEQ ID NO: 27 or 62; the nucleic acid sequence that encodes R3 consists of SEQ ID NO: 29 or 64; the nucleic acid sequence that encodes H2 consists of SEQ ID NO: 38; the nucleic acid sequence that encodes H3 consists of SEQ ID NO: 30 or 65; the nucleic acid sequence that encodes H4 consists of SEQ ID NO: 33 or 68; the nucleic acid sequence that encodes R24 consists of SEQ ID NO: 32 or 67; the nucleic acid sequence that encodes CR consists of SEQ ID NO: 34, 69, 100, or 109; I consists of SEQ ID NO: 41; and/or the nucleic acid sequence that encodes CT consists of SEQ ID NO: 35, 70 or 80.

15. The nucleic acid composition of any one of the foregoing embodiments, wherein the micro dystrophin protein comprises or consists of dystrophin sequences arranged from amino-terminus to the carboxy terminus: ABD-L1-H1-L2-R1-R2-L3-R3-H3-L4-R24-H4-CR-CT or ABD-L1-H1-L2-R1-R2-L3-R3-H3-L4-R24-H4-CR., wherein L1, L2, L3, and L4 are linkers.

16. The nucleic acid composition of any one of the foregoing embodiments, wherein the nucleic acid sequences encoding L1 comprise or consist of SEQ ID NO: 23 or 58, L2 comprise or consist of SEQ ID NO: 25 or 60, L3 comprise or consist of SEQ ID NO: 28 or 63, and L4 comprise or consist of SEQ ID NO: 31, 36, 37, 66, 71 or 72.

17. A nucleic acid composition comprising a nucleic acid sequence encoding a microdystrophin protein, wherein the microdystrophin protein comprises or consists of dystrophin domains arranged from amino-terminus to the carboxy terminus: ABD-H1-R1-R2-R16-R17-R24-H4-CR, wherein ABD is an actin-binding domain of dystrophin, H1 is a hinge 1 region of dystrophin, R1 is a spectrin 1 region of dystrophin, R2 is a spectrin 2 region of dystrophin, R16 is a spectrin 16 region of dystrophin, R17 is a spectrin 17 region of dystrophin, R24 is a spectrin 24 region of dystrophin, H4 is hinge 4 region of dystrophin, and CR is a cysteine-rich region of dystrophin 18. The nucleic acid composition of embodiment 17 (1) comprising a nucleic acid sequence encoding the microdystrophin protein with an amino acid sequence of SEQ ID NO: 93 or a nucleic acid sequence at least 90%, 95% or 98% identical thereto or the reverse complement thereof or (2) comprising or consisting of a nucleic acid sequence of SEQ ID NO: 103 or a nucleic acid sequence at least 90%, 95% or 98% identical thereto or the reverse complement thereof, wherein the nucleic acid encodes a therapeutically functional microdystrophin.

19. The nucleic acid composition of embodiment 17 or 18, further comprising a nucleotide sequence encoding a CT domain that comprises a α1-syntrophin binding site and/or a dystrobrevin binding site at the C-terminal end of the CR domain.

20. The nucleic acid composition of any one of embodiment 19 (1) comprising a nucleic acid sequence encoding the microdystrophin protein with an amino acid sequence of SEQ ID NO: 92 or a nucleic acid sequence at least 90%, 95% or 98% identical thereto or the reverse complement thereof or (2) comprising or consisting of a nucleic acid sequence of SEQ ID NO: 102 or a nucleic acid sequence at least 90%, 95% or 98% identical thereto or the reverse complement thereof, wherein the nucleic acid encodes a therapeutically functional microdystrophin.

21. The nucleic acid composition of embodiment 19 or 20, wherein the nucleic acid sequence encoding the CT domain comprises or consists of the nucleic acid sequence of SEQ ID NO: 35 or a nucleic acid sequence at least 90%, 95% or 98% identical thereto or the reverse complement thereof and increases binding of the microdystrophin to α1-syntrophin, 0-syntrophin, and/or dystrobrevin relative to a reference microdystrophin lacking the CT domain sequence; wherein the nucleic acid sequence encoding the CT domain comprises or consists of the nucleic acid sequence of SEQ ID NO: 70 or a nucleic acid sequence at least 90%, 95% or 98% identical thereto or the reverse complement thereof and increases binding of the microdystrophin to α1-syntrophin, β-syntrophin, and/or dystrobrevin relative to a reference microdystrophin lacking the CT domain sequence; or wherein the nucleic acid sequence encoding a minimal CT domain or consists of the nucleic acid sequence of SEQ ID NO: 80 or a nucleic acid sequence at least 90%, 95% or 98% identical thereto or the reverse complement thereof and increases binding of the microdystrophin to α1-syntrophin relative to a reference microdystrophin lacking the CT domain sequence.

22. The nucleic acid composition of any of embodiments 17 to 21, wherein the nucleic acid sequence encoding ABD consists of SEQ ID NO: 22 or 57 or a sequence with at least 75%, at least 80%, at least 85%, at least 90%, at least 95%, at least 98% or at least 99% identity to SEQ ID NO: 22 or 57; the nucleic acid sequence encoding H1 consists of SEQ ID NO: 24 or 59 or a sequence with at least 75%, at least 80%, at least 85%, at least 90%, at least 95%, at least 98% or at least 99% identity to SEQ ID NO: 24 or 59; the nucleic acid sequence encoding R1 consists of SEQ ID NO: 26 or 61 or a sequence with at least 75%, at least 80%, at least 85%, at least 90%, at least 95%, at least 98% or at least 99% identity to SEQ ID NO: 26 or 61; the nucleic acid sequence encoding R2 consists of SEQ ID NO: 27 or 62 or a sequence with at least 75%, at least 80%, at least 85%, at least 90%, at least 95%, at least 98% or at least 99% identity to SEQ ID NO: 27 or 62; the nucleic acid sequence encoding R16 consists of SEQ ID NO: 94 or 98 or a sequence with at least 75%, at least 80%, at least 85%, at least 90%, at least 95%, at least 98% or at least 99% identity to SEQ ID NO: 94 or 98; the nucleic acid sequence encoding R17 consists of SEQ ID NO: 95 or 99 or a sequence with at least 75%, at least 80%, at least 85%, at least 90%, at least 95%, at least 98% or at least 99% identity to SEQ ID NO: 95 or 99; the nucleic acid sequence encoding R24 consists of SEQ ID NO: 32 or 67 or a sequence with at least 75%, at least 80%, at least 85%, at least 90%, at least 95%, at least 98% or at least 99% identity to SEQ ID NO: 32 or 67; a nucleic acid sequence encoding H4 consists of SEQ ID NO: 33 or 68 or a sequence with at least 75%, at least 80%, at least 85%, at least 90%, at least 95%, at least 98%, or at least 99% identity to SEQ ID NO: 33 or 68; the nucleic acid sequence encoding CR consists of SEQ ID NO: 34, 69, 100 or 109 or a sequence with at least 75%, at least 80%, at least 85%, at least 90%, at least 95%, at least 98% or at least 99% identity to SEQ ID NO: 34 or 69; the nucleic acid sequence encoding CT consists of SEQ ID NO: 35, 70, or 80 or a sequence with at least 75%, at least 80%, at least 85%, at least 90%, at least 95%, at least 98% or at least 99% identity to SEQ ID NO: 35, 70, or 80 encoding a microdystrophin that has functional activity.

23. The nucleic acid composition of any one of embodiments 17 to 22, wherein the nucleic acid sequence that encodes ABD consists of SEQ ID NO: 22 or 57; the nucleic acid sequence that encodes H1 consists of SEQ ID NO: 24 or 59; the nucleic acid sequence that encodes R1 consists of SEQ ID NO: 26 or 61; the nucleic acid sequence that encodes R2 consists of SEQ ID NO: 27 or 62; the nucleic acid sequence that encodes R16 consists of SEQ ID NO: 94 or 98; the nucleic acid sequence that encodes R17 consists of SEQ ID NO: 95 or 99; the nucleic acid sequence that encodes H4 consists of SEQ ID NO: 33 or 68; R24 consists of SEQ ID NO: 32 or 67; the nucleic acid sequence that encodes CR consists of SEQ ID NO: 34, 69, 100 or 109; and, if present, the nucleic acid sequence that encodes CT consists of SEQ ID NO: 35, 70 or 80.

24. The nucleic acid composition of embodiments 17 to 23 further comprising an intron (I) coupled to the 5' end of the nucleic acid sequence encoding the microdystrophin protein.

25. The nucleic acid composition of any of embodiment 24, wherein I is the human immunoglobin heavy chain variable region (VH) 4 intron (VH4) or the SV40 intron or the chimeric intron located 5' of the microdystrophin encoding sequence.

26. The nucleic acid composition of embodiment 25, wherein the nucleic acid sequence encoding the VH4 intron comprises or consists of the nucleic acid sequence of SEQ ID NO: 41 or a nucleic acid sequence at least 90%, 95% or 98% identical thereto or the reverse complement thereof and increases microdystrophin expression relative to a reference nucleic acid lacking the VH4 intron sequence; wherein the nucleic acid sequence encoding a chimeric intron comprises or consists of the nucleic acid sequence of SEQ ID NO: 75 or a nucleic acid sequence at least 90%, 95% or 98% identical thereto or the reverse complement thereof and increases microdystrophin expression relative to a reference nucleic acid lacking the chimeric intron sequence; or wherein the nucleic acid sequence encoding a SV40 intron comprises or consists of the nucleic acid sequence of SEQ ID NO: 76 or a nucleic acid sequence at least 90%, 95% or 98% identical thereto or the reverse complement thereof and increases microdystrophin expression relative to a reference nucleic acid lacking the chimeric intron sequence.

27. The nucleic acid composition of any one of embodiments 17 to 26, wherein the microdystrophin protein comprises or consists of dystrophin sequences arranged from amino-terminus to the carboxy terminus: ABD-L1-H1-L2-R1-R2-L3-R16-L4.1-R17-L4.2-R24-H4-CR-CT or ABD-L1-H1-L2-R1-R2-L3-R16-L4.1-R17-L4.2-R24-H4-CR, wherein L1, L2, L3, L4.1 and L4.2 are linkers.

28. The nucleic acid composition of embodiment 27, wherein the nucleic acid sequence encoding L1 comprises or consists of SEQ ID NO: 23 or 58; the nucleic acid sequence encoding L2 comprises or consists of SEQ ID NO: 25 or 60; the nucleic acid sequence encoding L3 comprises or consists of SEQ ID NO: 28 or 63; the nucleic acid sequence encoding L4.1 comprises or consists of SEQ ID NO: 107 or 125; and the nucleic acid sequence encoding L4.2 comprises or consists of SEQ ID NO: 108 or 126.

29. The nucleic acid composition of any one of the foregoing embodiments, wherein the nucleic acid is a nucleic acid vector comprising a transcription regulatory element that promotes expression in muscle and/or CNS tissue operably linked to the nucleic acid sequence coding for the microdystrophin protein.

30. The nucleic acid composition of embodiment 29, wherein the transcription regulatory element comprises a muscle-specific promoter, optionally, skeletal, smooth, or/or cardiac muscle specific promoter.

31. The nucleic acid composition of embodiment 29 or 30, wherein the promoter is SPc5-12 or a transcriptionally active portion thereof.

32. The nucleic acid composition of embodiment 31, wherein the promoter consists of nucleic acid sequence of SEQ ID NO: 39 or 40.

33. The nucleic acid composition of embodiment 29, wherein the transcription regulatory element comprises a CNS-specific promoter.

34. The nucleic acid composition of embodiment 29, wherein the promoter is a CB7 promoter, cytomegalovirus (CMV) promoter, Rous sarcoma virus (RSV) promoter, MMT promoter, EF-1 alpha promoter (SEQ ID NO: 118), UB6 promoter, chicken beta-actin promoter, CAG promoter (SEQ ID NO: 116), RPE65 promoter, opsin promoter, TBG (Thyroxine-binding Globulin) promoter, APOA2 promoter, SERPINA1 (hAAT) promoter, MIR122 promoter, or an inducible promoter such as a hypoxia-inducible or rapamycin-inducible promoter.

35. The nucleic acid composition of embodiment 29 or 30, wherein the muscle-specific transcriptional regulatory element is one of a CK1 promoter, a CK4 promoter, a CK5 promoter, a CK6 promoter, a CK7 promoter, a CK8 promoter (SEQ ID NO: 115), a MCK promoter (or truncated form thereof) (SEQ ID NO: 121), a desmin promoter (SEQ ID NO: 119), a MHCK7 promoter (SEQ ID NO: 120), an enh358MCK promoter, a dMCK promoter, or a tMCK promoter.

36. The nucleic acid composition of any of the foregoing embodiments wherein the nucleotide sequence comprises a polyadenylation signal 3' of the nucleotide sequence encoding the microdystrophin.

37. The nucleic acid composition of embodiment 36, wherein the polyadenylation signal has a nucleotide sequence of SEQ ID NO: 42.

38. The nucleic acid composition of any one of the foregoing embodiments, wherein the nucleic acid comprises an AAV vector nucleotide sequence comprising from the 5' to the 3': (i) AAV ITR—transcription regulatory element-nucleic acid sequence encoding the microdystrophin domains arranged from N-terminus to C-terminus ABD-H1-R1-R2-R3-H3-R24-H4-CR-CT- polyadenylation sequence—AAV ITR; (ii) AAV ITR-transcription regulatory element—nucleic acid sequence encoding the microdystrophin domains arranged from N-terminus to C-terminus ABD-H1-R1-R2-R3-H3-R24-H4-CR—polyadenylation sequence—AAV ITR; (iii) AAV ITR—transcription regulatory element-nucleic acid sequence encoding the microdystrophin domains arranged from N-terminus to C-terminus ABD-H1-R1-R2-R16-R17-R24-H4-CR-CT- polyadenylation sequence—AAV ITR; or (iv) AAV ITR-transcription regulatory element-nucleic acid sequence encoding the microdystrophin domains arranged from N-terminus to C-terminus ABD-H1-R1-R2-R16-R17-R24-H4-CR—polyadenylation sequence—AAV ITR, wherein the AAV ITR is optionally AAV2 ITR.

39. The nucleic acid composition of any of the foregoing embodiments wherein the nucleotide sequence is codon optimized and/or depleted for CpG sequences.

40. The nucleic acid composition of any of the foregoing embodiments which has fewer than 2, or 1 CpG islands, or has no CpG islands.

41. The nucleic acid composition of embodiment 40, which exhibits reduced immunogenicity when administered to a human subject as measured by anti-drug antibody titer compared to a microdystrophin construct having more than 0 CpG islands.

42. The nucleic acid composition of any one of the foregoing embodiments comprising a nucleic acid sequence of SEQ ID NO: 53, 54, 55, 56, 82, 104, 105, or 106

43. The nucleic acid composition of any one of the foregoing embodiments comprising an AAV vector nucleotide sequence comprising an AAV ITR at the 5' and 3' ends of the nucleic acid sequence, wherein the AAV ITR is optionally AAV2 ITR.

44. The nucleic acid composition of embodiment 43, wherein the 5' ITR comprises or consists of the nucleotide sequence of SEQ ID NO: 73 and the 3' ITR comprises or consists of the nucleotide sequence of SEQ ID NO: 74

45. A rAAV particle comprising an expression cassette comprising the nucleic acid composition of any one of the foregoing embodiments.

46. The rAAV particle of embodiment 45, which has a capsid protein from at least one AAV type selected from AAV type 1 (AAV1), type 2 (AAV2), type 3 (AAV3), type 4 (AAV4), type 5 (AAV5), type 6 (AAV6), type 7 (AAV7), type 8 (AAV8), type rh8 (AAVrh8), type 9 (AAV9), type PHP.B (AAVPHP.B), type hu37 (AAV.hu37), type hu31 (AAV.hu31), type hu32 (AAV.hu32), type rh10 (AAVrh10), type rh20 (AAVrh20), type rh39 (AAVrh39), and type rh74 (AAVrh74).

47. The rAAV particle of embodiment 45 or 46, wherein said capsid protein has an amino acid sequence that is at least 95% identical to SEQ ID NO: 77 (AAV8 capsid) or has an amino acid sequence of SEQ ID NO: 77.

48. The rAAV particle of embodiment 45 or 46, wherein said capsid protein has an amino acid sequence that is at least 95% identical to SEQ ID NO 78 (AAV9 capsid) or has an amino acid sequence of SEQ ID NO: 78.

49. A pharmaceutical composition comprising a therapeutically effective amount of an rAAV particle of any one of embodiments 45 to 48 and a pharmaceutically acceptable carrier.

50. A method of delivering a transgene to a cell, said method comprising contacting said cell with the rAAV particle of any one of embodiments 45 to 49, wherein said cell is contacted with the vector.

51. A pharmaceutical composition for treating a dystrophinopathy in a human subject in need thereof, comprising a therapeutically effective amount of an rAAV particle of any one of embodiments 45 to 49, optionally wherein said rAAV particle is formulated for administration to the circulation, muscle tissue, or CNS of said subject said subject.

52. A method of treating a dystrophinopathy in a human subject in need thereof, comprising:

administering to said subject a pharmaceutical composition comprising a therapeutically effective amount of a rAAV particle of any one of embodiments 45 to 49, so that a depot is formed in the muscle of said subject that releases a microdystrophin protein.

53. A method of preventing transmission of a dystrophinopathy to progeny of a human subject in need thereof, comprising:

administering to said subject a pharmaceutical composition comprising a therapeutically effective amount of a rAAV particle of any one of embodiments 45 to 49, such that the nucleic acid encoding the microdystrophin is incorporated into the germline of said subject.

54. The pharmaceutical composition or the method of embodiments 51 to 53, wherein the dystrophinopathy is DMD, BMD, X-linked dilated cardiomyopathy or the subject is a female carrier of DMD or BMD.

55. The pharmaceutical composition or the method of embodiments 51 to 54, wherein the composition is administered with at least a second agent effective for treating the dystrophinopathy.

56. The pharmaceutical composition or the method of embodiment 55, wherein the second agent is selected from the group consisting of an antisense oligonucleotide that causes exon skipping of the DMD gene, an anti-myostatin antibody, an agent that promotes ribosomal read-through of nonsense mutations, an agent that suppresses premature stop codons, an anabolic steroid and a corticosteroid.

57. The pharmaceutical composition or the method of any one of embodiments 51 to 56, wherein said administration improves the patient's grip strength was improved, increases the maximal and specific muscle force and/or reduced organ and muscle weight.

58. The pharmaceutical composition or method of any one of embodiments 51 to 57, wherein administration of the rAAV particle improves or maintains cardiac function or slows the decline of cardiac function.

59. The pharmaceutical composition or method of any one of embodiments 51 to 58, wherein administration of the rAAV particle increases muscle mass or strength or maintains muscle mass or strength or reduces the likelihood of loss of muscle mass or strength.

60. A microdystrophin protein comprising or consisting of dystrophin domains arranged from the amino-terminus to the carboxy terminus ABD-H1-R1-R2-R3-H3-R24-H4-CR-CT, wherein ABD is an actin-binding domain of dystrophin, H1 is a hinge 1 region of dystrophin, R1 is a spectrin 1 region of dystrophin, R2 is a spectrin 2 region of dystrophin, R3 is a spectrin 3 region of dystrophin, H3 is a hinge 3 region of dystrophin, R24 is a spectrin 24 region of dystrophin, CR is a cysteine-rich region of dystrophin, and CT is at least a portion of a C-terminal region of dystrophin comprising an α1-syntrophin binding site, β-syntrophin binding site, and/or dystrobrevin site.

61. The microdystrophin protein of embodiment 60 comprising or consisting of an amino acid sequence of SEQ ID NOs: 1, 79, or 91.

62. The microdystrophin protein of embodiment 60 or 61, wherein the CT domain is a truncated CT domain which comprises an α1-syntrophin binding site.

63. The microdystrophin protein of any one of embodiments 60 to 62 wherein the CT domain comprises or consist of the amino acid sequence of SEQ ID NO: 16 or 83 or comprises the amino acid sequence of SEQ ID NO: 84.

64. The microdystrophin protein of any one of embodiments 60 to 63, wherein CR domain comprises β-dystroglycan binding site.

65. The microdystrophin protein of any one of embodiments 60 to 64 wherein the CR domain comprises or consists of the amino acid sequence of SEQ ID NO: 15 or 90.

66. The microdystrophin protein of any one embodiments 60 to 66, wherein ABD consists of SEQ ID NO: 3 or an amino acid sequence with at least 80%, at least 85%, at least 90%, at least 95%, at least 96%, at least 97%, at least 98%, or at least 99% sequence identity to SEQ ID NO: 3; H1 consists of SEQ ID NO: 5 or an amino acid sequence with at least 80%, at least 85%, at least 90%, at least 95%, at least 96%, at least 97%, at least 98%, or at least 99% sequence identity to SEQ ID NO: 5; R1 consists of SEQ ID NO: 7 or an amino acid sequence with at least 80%, at least 85%, at least 90%, at least 95%, at least 96%, at least 97%, at least 98%, or at least 99% sequence identity to SEQ ID NO: 7; R2 consists of SEQ ID NO: 8 or an amino acid sequence with at least 80%, at least 85%, at least 90%, at least 95%, at least 96%, at least 97%, at least 98%, or at least 99% sequence identity to SEQ ID NO: 8; H3 consists of SEQ ID NO: 11 or an amino acid sequence with at least 80%, at least 85%, at least 90%, at least 95%, at least 96%, at least 97%, at least 98%, or at least 99% sequence identity to SEQ ID NO: 11; R24 consists of SEQ ID NO: 13 or an amino acid sequence with at least 80%, at least 85%, at least 90%, at least 95%, at least 96%, at least 97%, at least 98%, or at least 99% sequence identity to SEQ ID NO: 13; H4 consists of SEQ ID NO: 14 or an amino acid sequence with at least 80%, at least 85%, at least 90%, at least 95%, at least 96%, at least 97%, at least 98%, or at least 99% sequence identity to SEQ ID NO: 14; CR consists of SEQ ID NO: 15 or 90 or an amino acid sequence with at least 80%, at least 85%, at least 90%, at least 95%, at least 96%, at least 97%, at least 98%, or at least 99% sequence identity to SEQ ID NO: 15 or 90; and CT consists of SEQ ID NOs: 16 or 83 or an amino acid sequence with at least 80%, at least 85%, at least 90%, at least 95%, at least 96%, at least 97%, at least 98%, or at least 99% sequence identity to SEQ ID NO: 16 or 83.

67. The microdystrophin protein of any one of embodiments 60 to 66, wherein ABD consists of SEQ ID NO: 3, H1 consists of SEQ ID NO: 5; R1 consists of SEQ ID NO: 7; R2 consists of SEQ ID NO: 8; R3 consists of SEQ ID NO: 10; H3 consists of SEQ ID NO: 11; R24 consists of SEQ ID NO: 13; H4 consists of SEQ ID NO: 14; CR consists of SEQ ID NO: 15 or 90; or CT consists of SEQ ID NO: 16 or 83.

68. The microdystrophin protein of any one of embodiments 60 to 67, comprising dystrophin domains arranged from the amino-terminus to the carboxy terminus: ABD-L1-H1-L2-R1-R2-L3-R3-H3-L4-R24-H4-CR-CT, wherein L1, L2, L3, and L4 are linkers.

69. The microdystrophin protein of embodiment 68, wherein the amino acid sequences of L1, L2, L3, and L4 consist of SEQ ID NOs: 4, 6, 9, and 12, respectively.

70. A microdystrophin protein comprising or consisting of dystrophin domains arranged from the amino-terminus to the carboxy terminus ABD-H1-R1-R2-R16-R17-R24-H4-CR, wherein ABD is an actin-binding domain of dystrophin, H1 is a hinge 1 region of dystrophin, R1 is a spectrin 1 region of dystrophin, R2 is a spectrin 2 region of dystrophin, R16 is a spectrin 16 region of dystrophin, R17 is a spectrin 17 region of dystrophin, R24 is a spectrin 24 region of dystrophin, and CR is a cysteine-rich region of dystrophin.

71. The microdystrophin protein of embodiment 70 comprising or consisting of the amino acid sequence of SEQ ID NO: 93.

72. The microdystrophin protein of embodiment 70 comprising or consisting of dystrophin domains arranged from the amino-terminus to the carboxy terminus ABD-H1-R1-

R2-R16-R17-R24-H4-CR-CT wherein CT is at least a portion of a C-terminal region of dystrophin comprising an α1-syntrophin binding site or a dystrobrevin binding site.

73. The microdystrophin protein of embodiment 72 wherein the CT domain comprises or consist of the amino acid sequence of SEQ ID NO: 16 or 83 or comprises the amino acid sequence of SEQ ID NO: 84.

74. The microdystrophin protein of embodiment 72 or 73 comprising or consisting of the amino acid sequence of SEQ ID NOS: 92.

75. The microdystrophin protein of any one of embodiments 70 to 74, wherein H4 domain comprises β-dystroglycan binding site.

76. The microdystrophin protein of any one embodiments 70 to 75, wherein ABD consists of SEQ ID NO: 3 or an amino acid sequence with at least 80%, at least 85%, at least 90%, at least 95%, at least 96%, at least 97%, at least 98%, or at least 99% sequence identity to SEQ ID NO: 3; H1 consists of SEQ ID NO: 5 or an amino acid sequence with at least 80%, at least 85%, at least 90%, at least 95%, at least 96%, at least 97%, at least 98%, or at least 99% sequence identity to SEQ ID NO: 5; R1 consists of SEQ ID NO: 7 or an amino acid sequence with at least 80%, at least 85%, at least 90%, at least 95%, at least 96%, at least 97%, at least 98%, or at least 99% sequence identity to SEQ ID NO: 7; R2 consists of SEQ ID NO: 8 or an amino acid sequence with at least 80%, at least 85%, at least 90%, at least 95%, at least 96%, at least 97%, at least 98%, or at least 99% sequence identity to SEQ ID NO: 8; R16 consists of SEQ ID NO: 86 or an amino acid sequence with at least 80%, at least 85%, at least 90%, at least 95%, at least 96%, at least 97%, at least 98%, or at least 99% sequence identity to SEQ ID NO: 86; R17 consists of SEQ ID NO: 87 or an amino acid sequence with at least 80%, at least 85%, at least 90%, at least 95%, at least 96%, at least 97%, at least 98%, or at least 99% sequence identity to SEQ ID NO: 87; R24 consists of SEQ ID NO: 13 or an amino acid sequence with at least 80%, at least 85%, at least 90%, at least 95%, at least 96%, at least 97%, at least 98%, or at least 99% sequence identity to SEQ ID NO: 13; H4 consists of SEQ ID NO: 14 or an amino acid sequence with at least 80%, at least 85%, at least 90%, at least 95%, at least 96%, at least 97%, at least 98%, or at least 99% sequence identity to SEQ ID NO: 14; and CR consists of SEQ ID NO: 15 or 90 or an amino acid sequence with at least 80%, at least 85%, at least 90%, at least 95%, at least 96%, at least 97%, at least 98%, or at least 99% sequence identity to SEQ ID NO: 15 or 90;

77. The microdystrophin protein of any of embodiments 70 to 76 comprising or consisting of a CT domain at the C terminus of the CR domain wherein the CT consists of SEQ ID NOs: 16 or 83 or an amino acid sequence with at least 80%, at least 85%, at least 90%, at least 95%, at least 96%, at least 97%, at least 98%, or at least 99% sequence identity to SEQ ID NO: 16 or 83.

78. The microdystrophin protein of any one of embodiments 70 to 77, wherein ABD consists of SEQ ID NO: 3, H1 consists of SEQ ID NO: 5; R1 consists of SEQ ID NO: 7; R2 consists of SEQ ID NO: 8; R16 consists of SEQ ID NO: 86; R17 consists of SEQ ID NO: 87; R24 consists of SEQ ID NO: 13; H4 consists of SEQ ID NO: 14; and CR consists of SEQ ID NO: 15 or 90; and/or CT consists of SEQ ID NO: 16 or 83.

79. The microdystrophin protein of any one of embodiments 70 to 78, wherein the CT consists of SEQ ID NO: 16 or 83.

80. The microdystrophin protein of any one of embodiments 70 to 80, comprising dystrophin domains arranged from the amino-terminus to the carboxy terminus: ABD-L1-H1-L2-R1-R2-L3-R16-L4.1-R17-L4.2-R24-H4-CR-CT or ABD-L1-H1-L2-R1-R2-L3-R16-L4.1-R17-L4.2-R24-H4-CR, wherein L1, L2, L3, L4.1 and L4.2 are linkers.

81. The microdystrophin protein of embodiment 80, wherein the amino acid sequences of L1, L2, L3, L4.1 and L4.2 consist of SEQ ID NOs: 4, 6, 9, 110, and 89, respectively.

82. A method of treating a dystrophinopathy in a human subject in need thereof, comprising delivering to the circulation, muscle tissue and/or cerebrospinal fluid of said human subject, a therapeutically effective amount of a microdystrophin protein according to any one of embodiments 60 to 81.

83. A pharmaceutical composition for treatment of a dystrophinopathy in a human subject comprising a therapeutically effective amount of a microdystrophin protein according to any one of embodiments 60 to 81 formulated for delivery to the circulation, muscle tissue and/or cerebrospinal fluid of said human subject.

84. The method or pharmaceutical composition of embodiment 82 or 83, wherein the dystrophinopathy is DMD, BMD or X-linked dilated cardiomyopathy.

85. The method or pharmaceutical composition of any one of embodiments 82 to 84, wherein the CT domain comprises an α1-syntrophin binding site, a β-syntrophin binding site, and/or a dystrobrevin binding site.

86. The method or pharmaceutical composition of embodiment 85, wherein the CT domain is a truncated CT domain comprising an α1-syntrophin binding site.

87. The method or pharmaceutical composition of any one of embodiments 82 to 86, wherein H4 comprises β-dystroglycan binding site.

88. A method of producing recombinant AAVs comprising:

(a) culturing a host cell containing:
  (i) an artificial genome comprising a cis expression cassette, wherein the cis expression cassette comprises a nucleic acid composition of any one of embodiments 38 to 44;
  (ii) a trans expression cassette lacking AAV ITRs, wherein the trans expression cassette encodes an AAV rep and capsid protein operably linked to expression control elements that drive expression of the AAV rep and capsid proteins in the host cell in culture and supply the rep and cap proteins in trans;
  (iii) sufficient adenovirus helper functions to permit replication and packaging of the artificial genome by the AAV capsid proteins; and
(b) recovering recombinant AAV encapsidating the artificial genome from the cell culture.

89. A host cell comprising:

a. an artificial genome comprising a cis expression cassette, wherein the cis expression cassette comprises a nucleic acid composition of any one of embodiments 38 to 44;
b. a trans expression cassette lacking AAV ITRs, wherein the trans expression cassette encodes an AAV rep and capsid protein operably linked to expression control elements that drive expression of the AAV rep and capsid proteins in the host cell in culture and supply the rep and cap proteins in trans; and
c. sufficient adenovirus helper functions to permit replication and packaging of the artificial genome by the AAV capsid proteins.

4. BRIEF DESCRIPTION OF THE FIGURES

Figure 1B:
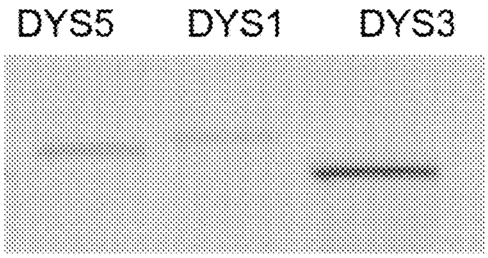
Figure 1C:
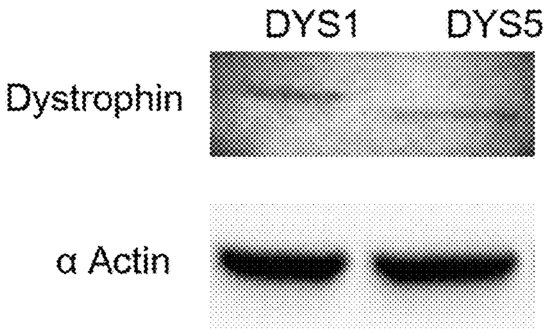
Figure 2:
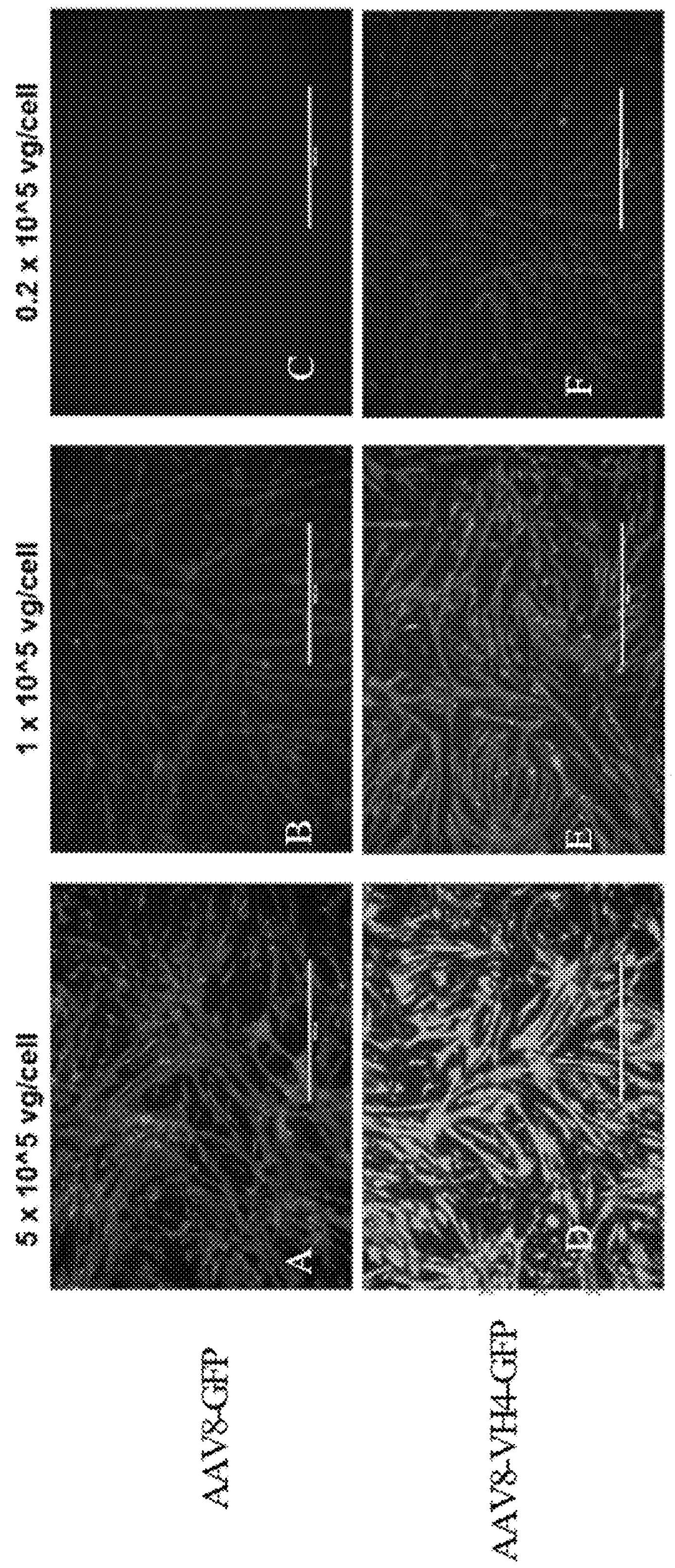

FIGS. 1A-C. FIG. 1A illustrate vector gene expression cassettes and microdystrophin constructs for use in a Cis-plasmid for gene therapy. DNA length for each component and complete transgene are listed for each construct. SPc5-12: synthetic muscle-specific promoter; Mini-SPc: truncated synthetic muscle-specific promoter; CT1.5: truncated/minimal CT domain; VH4: human immunoglobin heavy chain variable region intron; ABD: actin binding domain; H: hinge; R: rod; CR: cysteine rich domain; CT: C-terminal domain; smPA: small polyA; ABD: Actin Binding Domain 1 (ABD1). FIGS. 1B-C depict protein bands detected by Western Blot (antibody (1c7) against dystrophin) showing relative size of microdystrophin proteins expressed from plasmids RGX-DYS1, RGX-DYS3 and RGX-DYS5.

FIGS. 2A-F depict fluorescent microscopy of differentiated C2C12 cells three days post-infection with reporter AAV vectors AAV8-GFP (A-C) and AAV8-VH4-GFP (D-F) at various dosage (indicated above the images: 5x10e5 vg/cell (A, D), 1x10e5 vg/cell (B, E), 0.2x10e5 vg/cell (C, F)). Scale bar: 200 μM. vg: vector genomes.

Figure 3:
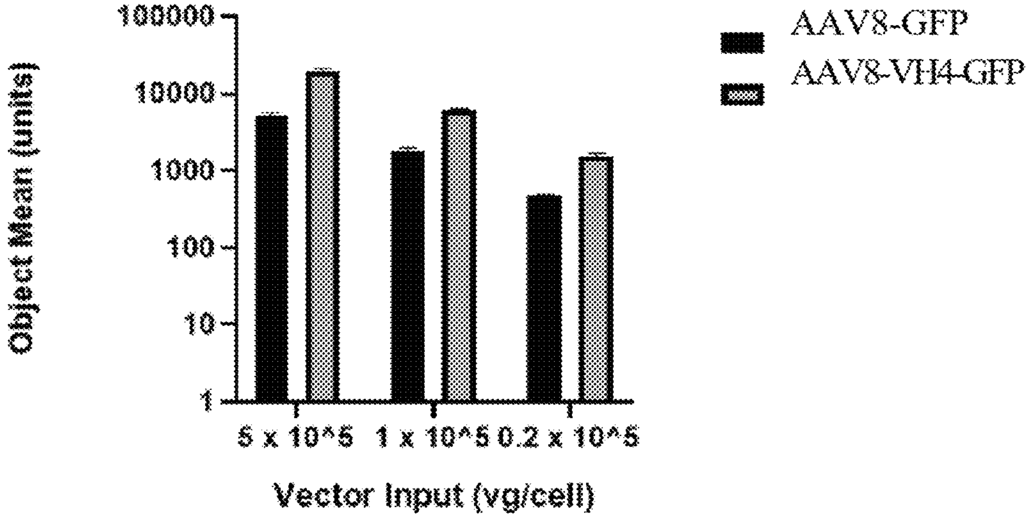

FIG. 3 shows mean fluorescence intensity (units) of transduced C2C12 cells measured three days post infection with AAV8-GFP and AAV8-VH4-GFP vectors at three different dosages: 5×10e5 vg/cell, 1×10e5 vg/cell, and 0.2×10e5 vg/cell.

Figure 4:
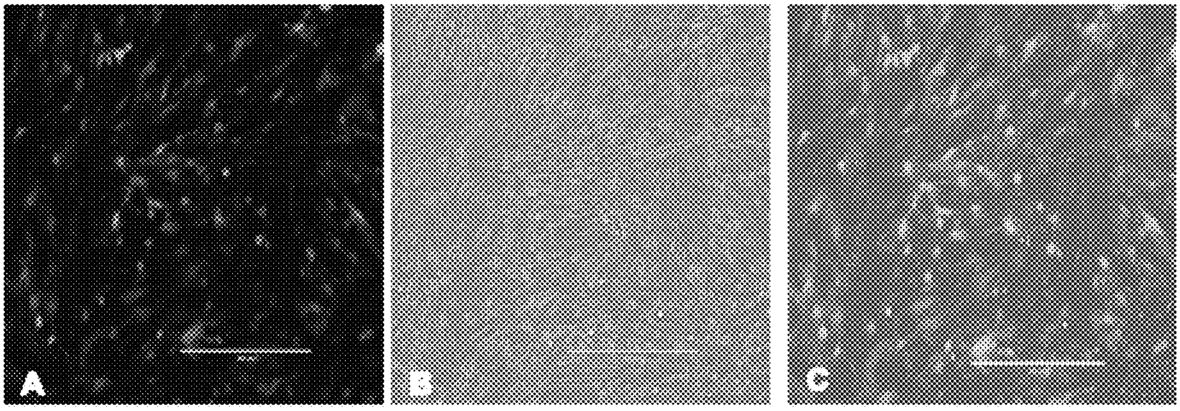
Figure 5:
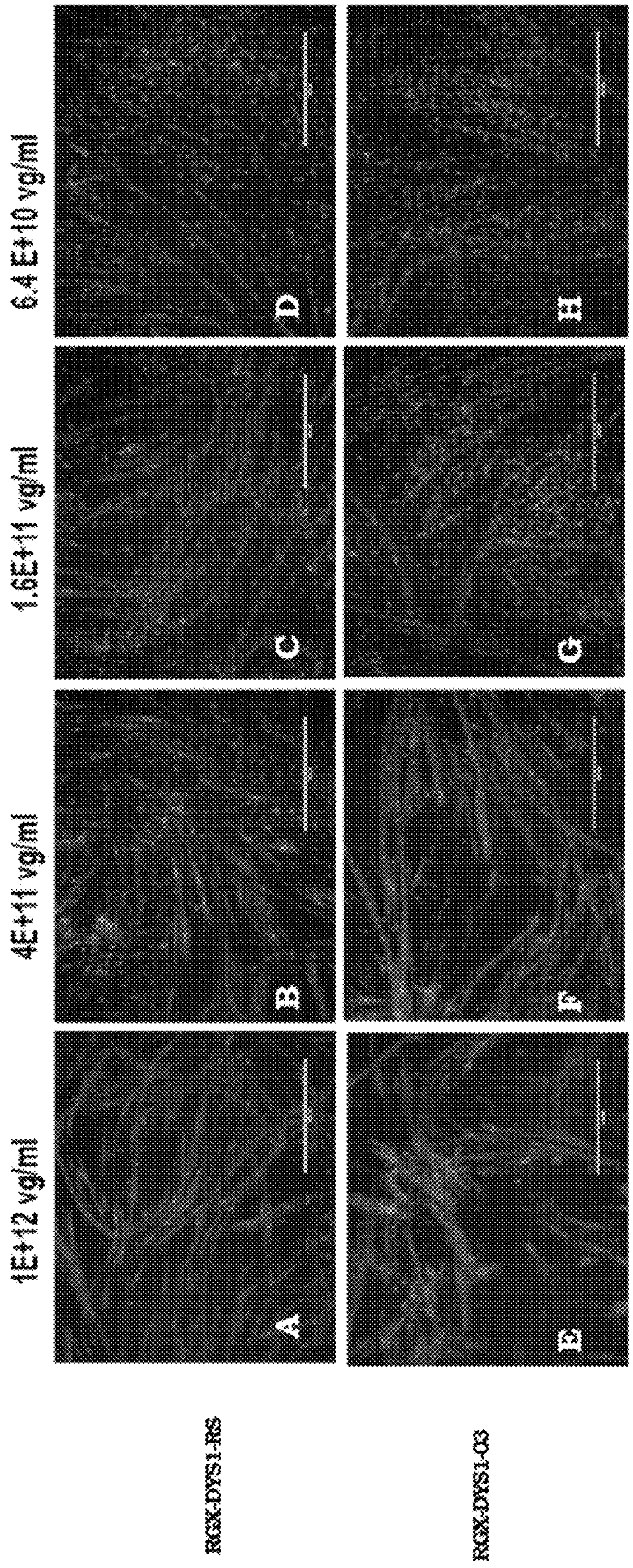

FIGS. 4A-C depict fluorescent microscopy of differentiated C2C12 cells six days post infection with AAV8-CAG-GFP. Images A-C were taken daily using an EVOS™ microscope with transmitted light and GFP channels under the same magnification: A, microscopic image set to the GFP channel; B, brightfield (or phase contrast) to observe the confluence of cells; C, merged image of A and B to observe the number of infected cells to be approximately 50%.

FIGS. 5A-H depicts in vitro potency testing of microdystrophin vector (RGX-DYS1-03, E-H) as compared to the reference control (RGX-DYS-RS, A-D) by immunofluorescent staining of dystrophin protein. There were three replicates for each dosage (indicated above respective images): 1e12 vg/ml (A, E), 4e11 vg/ml (B, F), 1.6e11 vg/ml (C, G), and 6.4e10 vg/ml (D, H).

Figure 6:
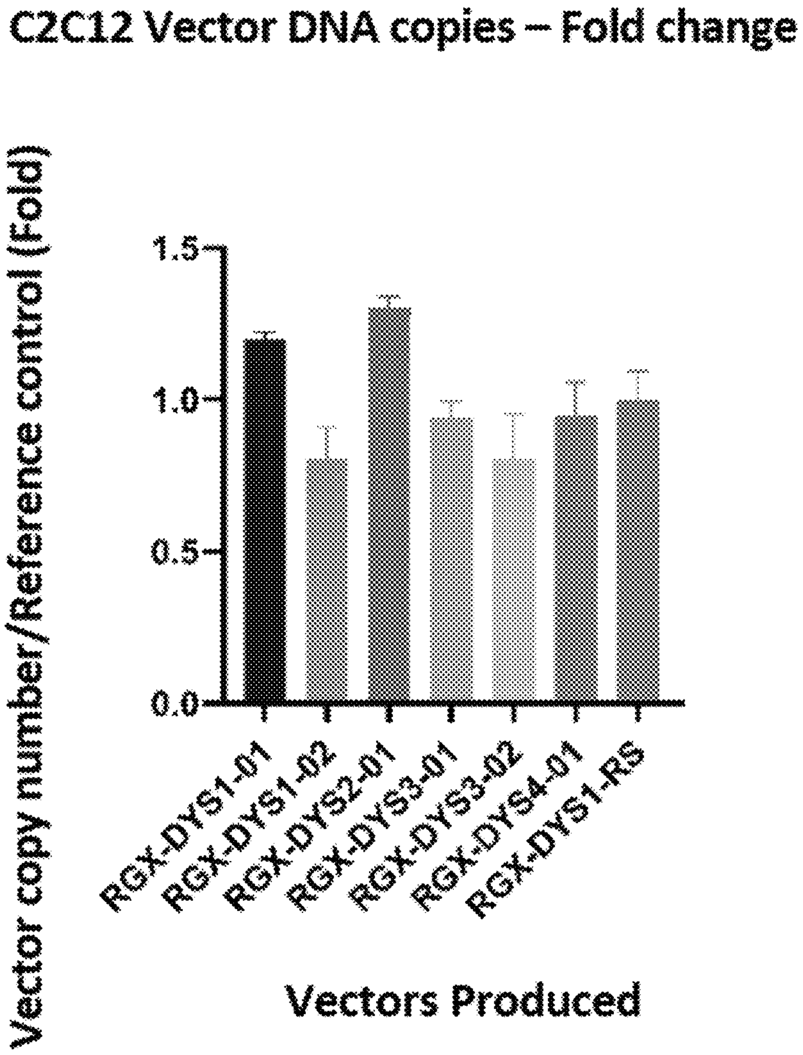

FIG. 6 provides infectivity data in mouse muscle cell line C2C12 cells for each vector, as a measure of vector potency. Normalized data (vector copy number/reference control) for each vector batch RGX-DYS1-01, RGX-DYS1-02, RGX-DYS2-01, RGX-DYS3-01, RGX-DYS3-02, RGX-DYS4-01, and RGX-DYS1-RS are shown. An internal control vector based on an earlier batch of DYS1 (RGX-DYS1-RS) was considered as reference standard (1.0).

Figure 7:
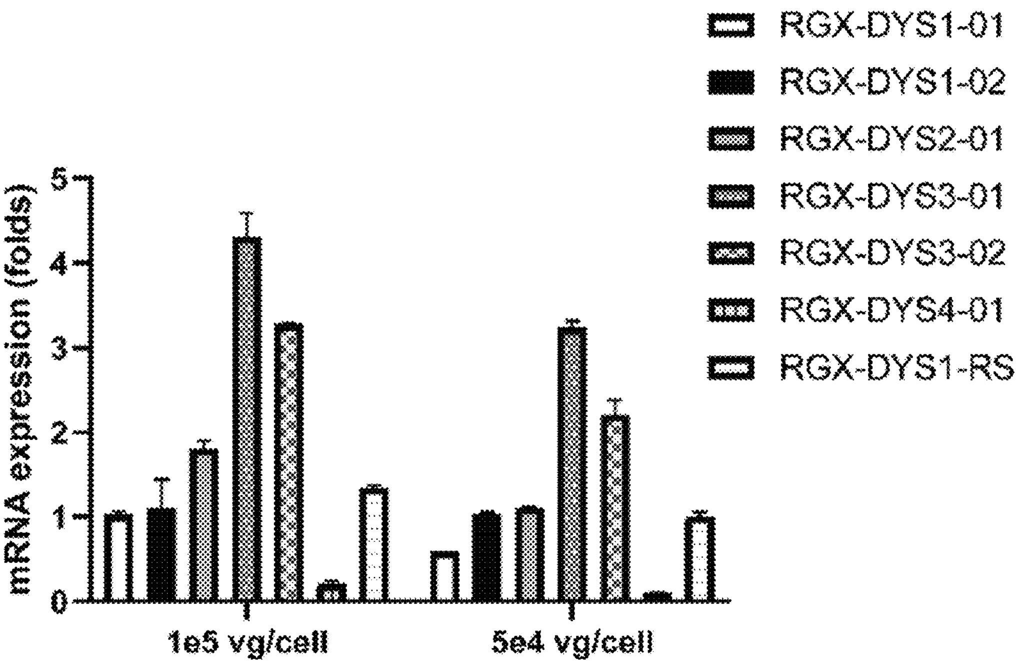

FIG. 7 provides microdystrophin data in mouse muscle cell line C2C12 cells for each vector from different production batches each using the same process (RGX-DYS1-01, RGX-DYS1-02, RGX-DYS2-01, RGX-DYS3-01, RGX-DYS3-02, RGX-DYS4-01, and RGX-DYS1-RS), as a measure of mRNA expression. Two different vector dosages were used to infect C2C12 cells (1e5 vg/cell and 5e4 vg/cell). mRNA expression level of each batch was calculated as the fold change (delta CT) in qPCR between primer/probe for microdystrophin and for endogenous control mouse GAPDH from the same cDNA sample. The graph shows fold increase and RGX-DYS1-RS was considered a 100% reference standard and set to 1.

Figure 8:
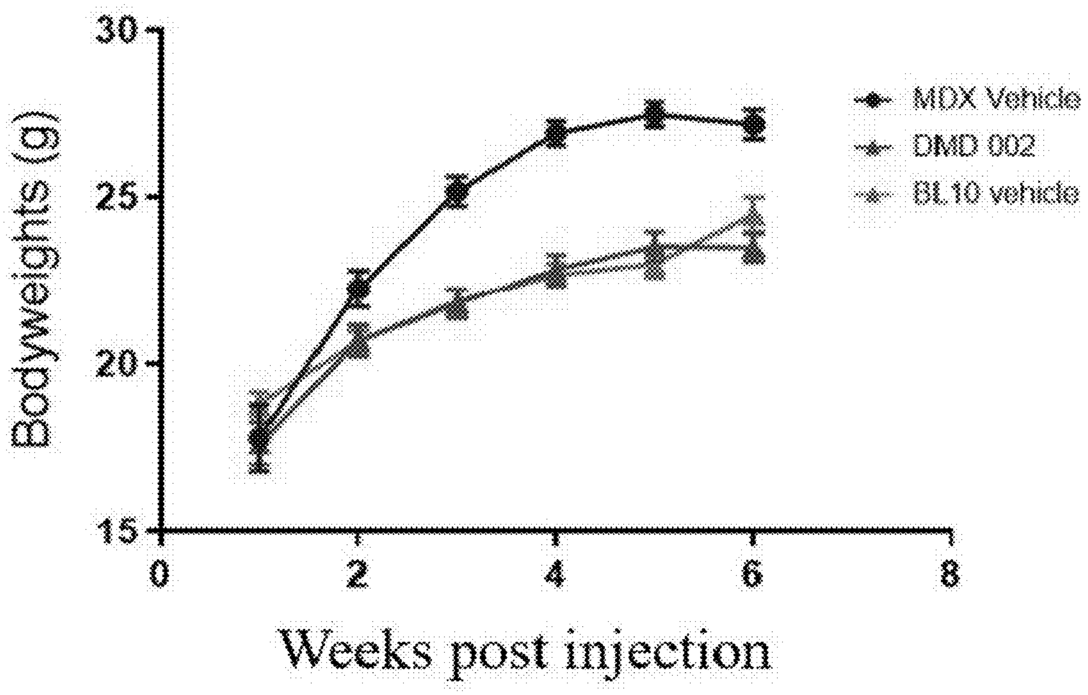

FIG. 8 shows weekly changes in body weight (g). Data are presented as mean±SEM. n=12 for mdx RGX-DYS1 group; n=13 for mdx vehicle group; n=14 for BL10 vehicle group.

Figure 9A:
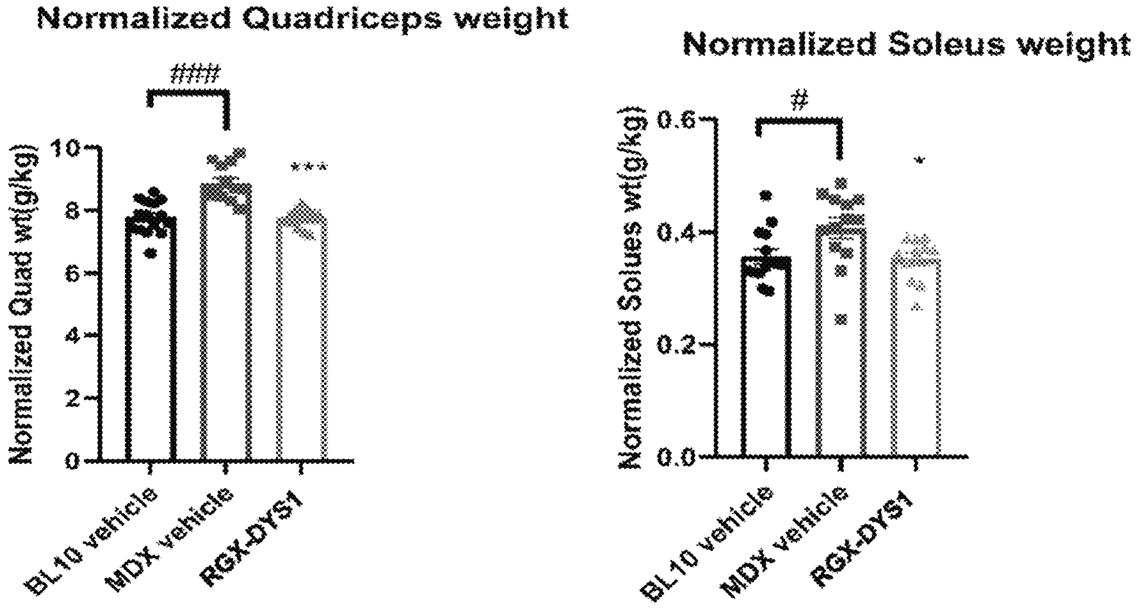
Figure 9B:
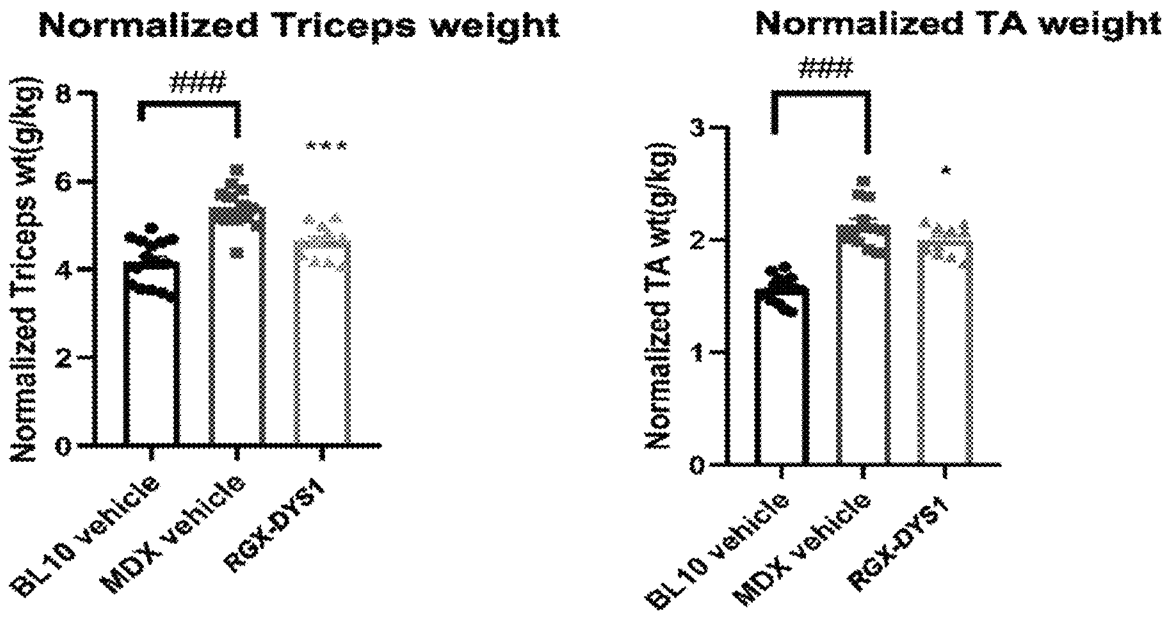

FIGS. 9A-B depicts mouse muscle and organ weight measurements (normalized to body weight, g/kg). Quadriceps and soleus weights are shown in FIG. 9A, and triceps and TA weights are shown in FIG. 9B. Data are presented as mean±SEM. n=12 for mdx RGX-DYS1 group; n=13 for mdx vehicle group; n=14 for BL10 vehicle group. ***P<0.001 (One-way ANOVA); ###P<0.001 (t-test).

Figure 10:
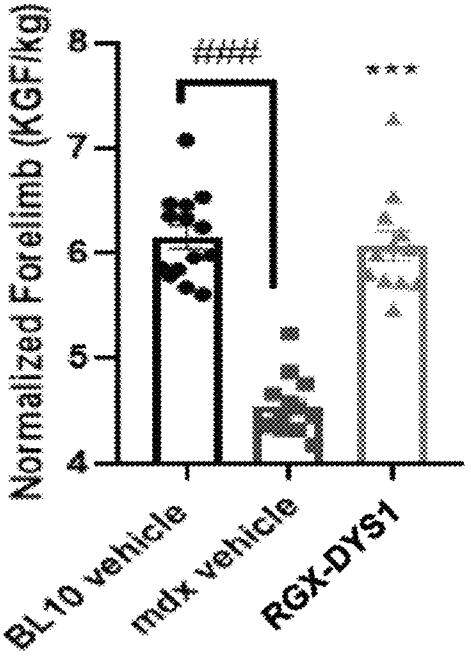

FIG. 10 depicts grip strength measurement (KGF/kg). *-One way ANOVA (***P<0.001); #-t-test (###p<0.001). The forearm muscle grip force was normalized for each mouse by muscle weight. n=12 for mdx RGX-DYS1 group; n=13 for mdx vehicle group; n=14 for BL10 vehicle group.

Figure 11:
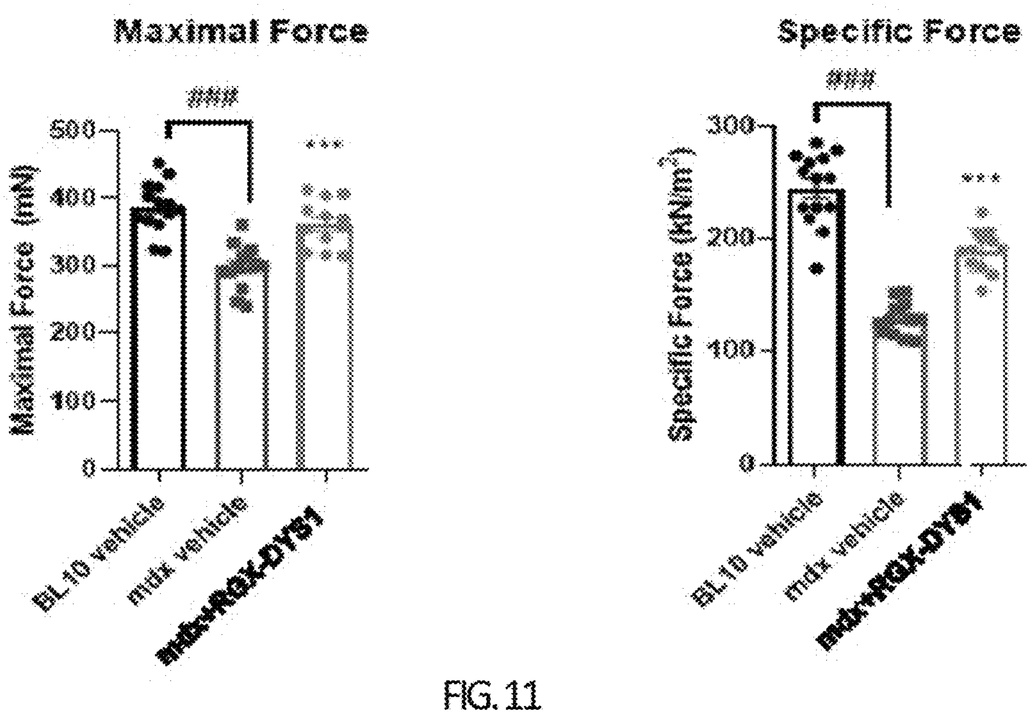

FIG. 11 illustrates in vitro muscle force contractile force analysis at week-6 post treatment revealed significant improvement of the muscle force in RGX-DYS1-treated mdx mice compared to mdx mice treated with vehicle. Maximal force (mN) and specific force (kN/m2) are shown. ***, p<0.001 by one-way ANOVA. ###, p<0.001 via t-test. n=12 of mdx RGX-DYS1 group; n=13 for mdx vehicle group; n=14 for BL10 vehicle group.

Figure 12:
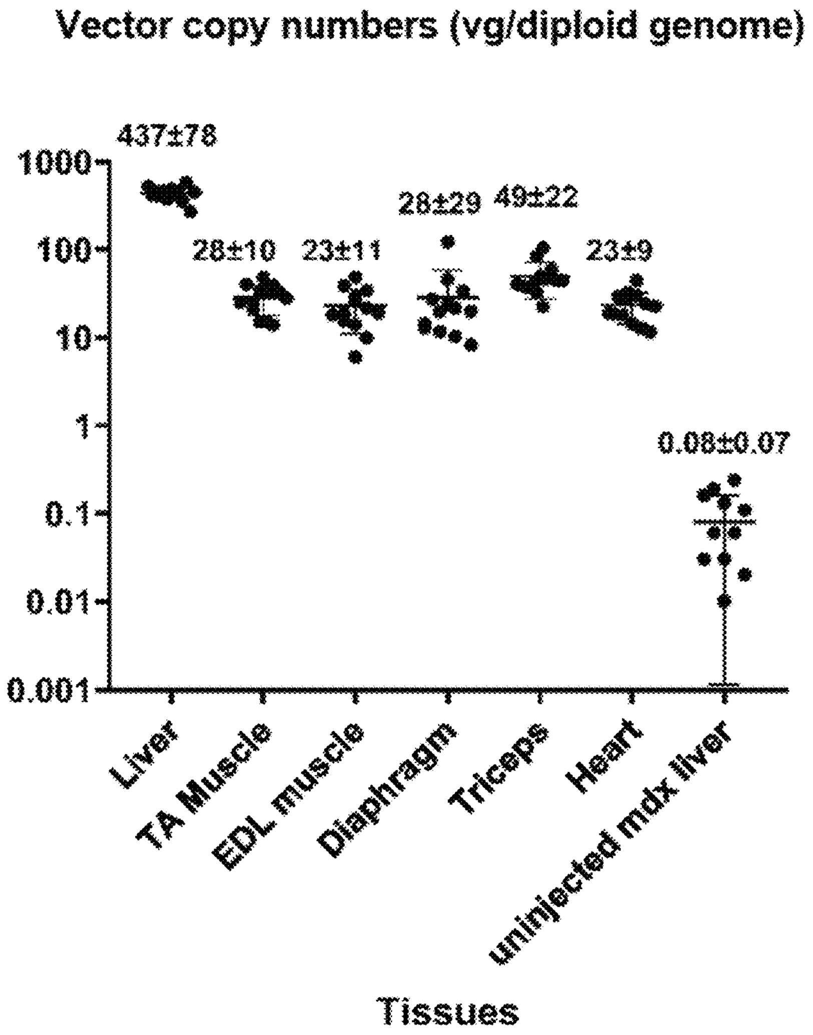

FIG. 12 Vector copy numbers (vg/diploid genome) in skeletal muscle, cardiac muscle, and liver by ddPCR method. The Naica Crystal Digital PCR system from Stilla Technologies was used. n=13 for each treated tissue. The numbers listed are average±Stdev. Vector copy number was calculated as 2× microdystrophin transgene copy number/endogenous control mouse glucagon copy number. The uninjected mdx liver samples (n=13) were used as negative control samples. TA, tibialis anterior muscle; EDL, extensor digitorum longus.

Figure 13:
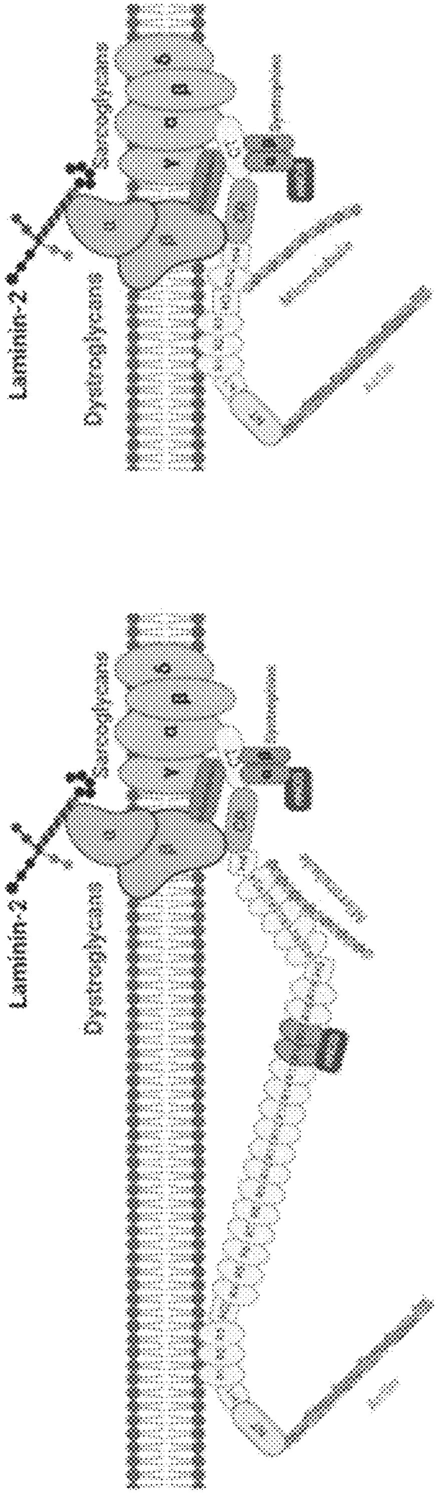

FIG. 13 Illustration of the sarcolemma showing interaction between a wild-type dystrophin or a microdystrophin containing dystrobrevin and α1- and β1-syntrophin binding sites, e.g. RGX-DYS1, and the dystrophin-associated protein complex (DAPC) with the actin cytoskeleton. It is envisioned that RGX-DYS1 having dystrobrevin, α1-syntrophin, and β1-syntrophin binding sites, will partly recruit and anchor nNOS to the sarcolemma through α1-syntrophin.

Figure 14:
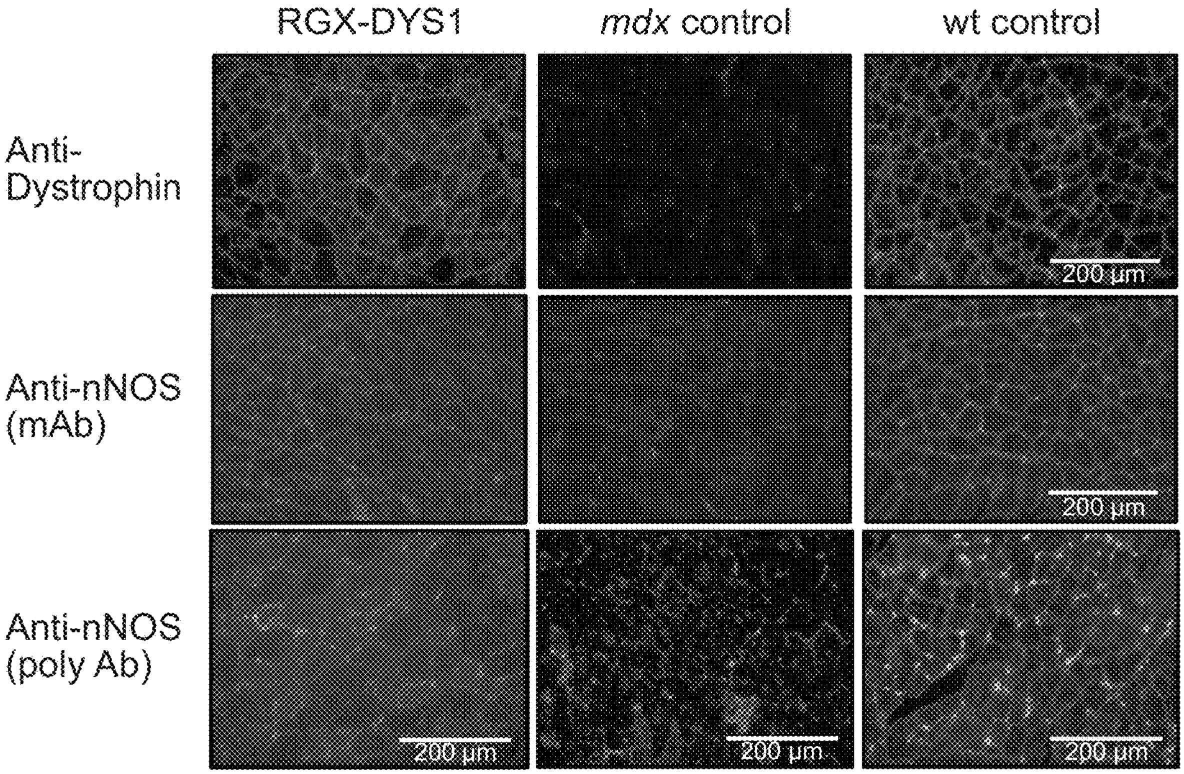
Figure 14:
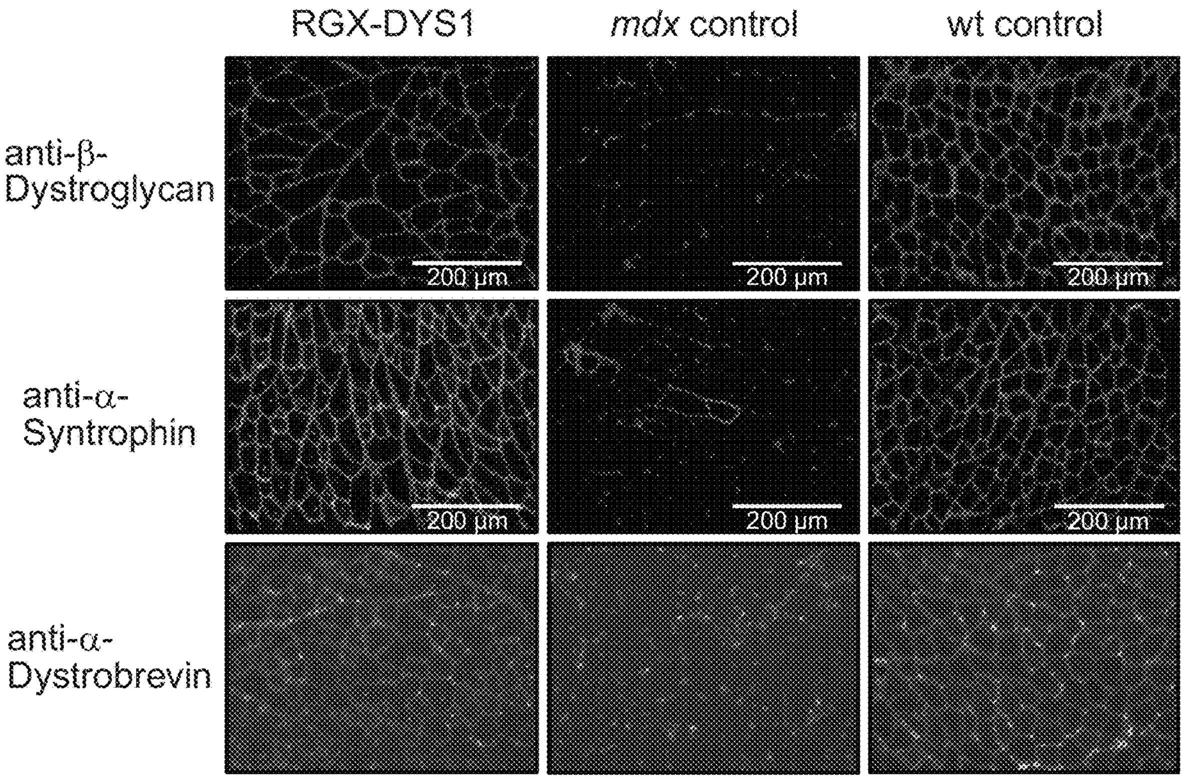

FIG. 14 Immunofluorescent staining on gastrocnemius muscle from mdx RGX-DYS1, mdx control, and WT control groups. Cryo-sections were stained with anti-α-dystrobrevin, anti-β-dystroglycan, anti-nNos, anti-dystrophin (anti-dys), and anti-α-syntrophin. The secondary antibody was labelled with CY3 and all sections were counterstained with DAPI before mounting.

Figure 15:
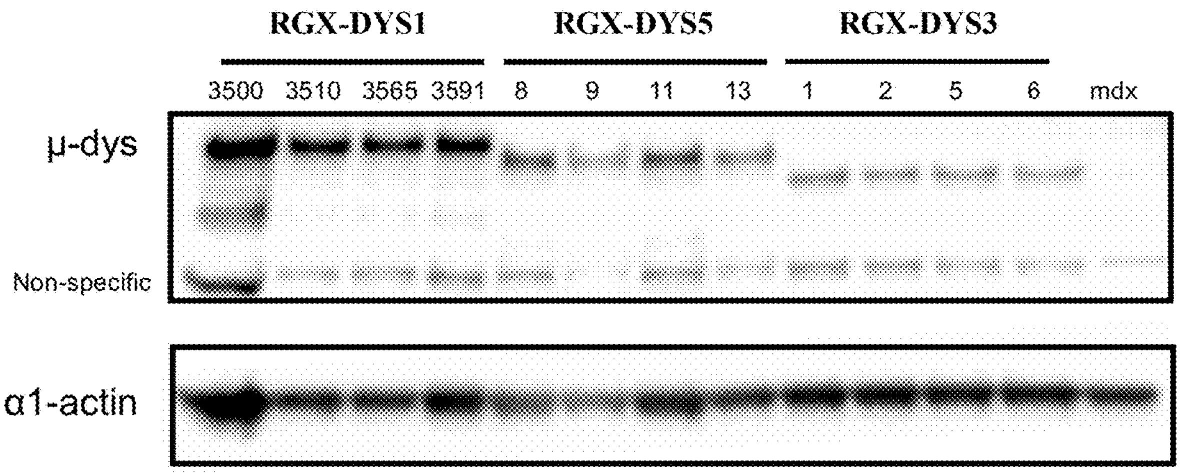

FIG. 15: Western blot against dystrophin extracted from AAV-μ-dystrophin vector-injected gastrocnemius muscle tissues. Lanes 1 through 4=protein samples from AAV8-RGX-DYS1-injected mdx mice, Lanes 5 through 8=protein samples from AAV8-RGX-DYS5 injected mdx mice, and Lanes 9 through 12=protein samples from AAV8-RGX-DYS3 injected mdx mice. α1-actin serves as the loading control in each lane. Mdx (Lane 13) indicated an un-injected mdx mice. For dystrophin blot, mouse anti-dystrophin monoclonal antibody was used (1:100 dilution). For anti-alpha1-actin blot, polyclonal antibody was used at a dilution factor of 1:10,000, and the secondary (anti-rabbit) antibody was used at 1:20,000.

Figures 16A, 16B:
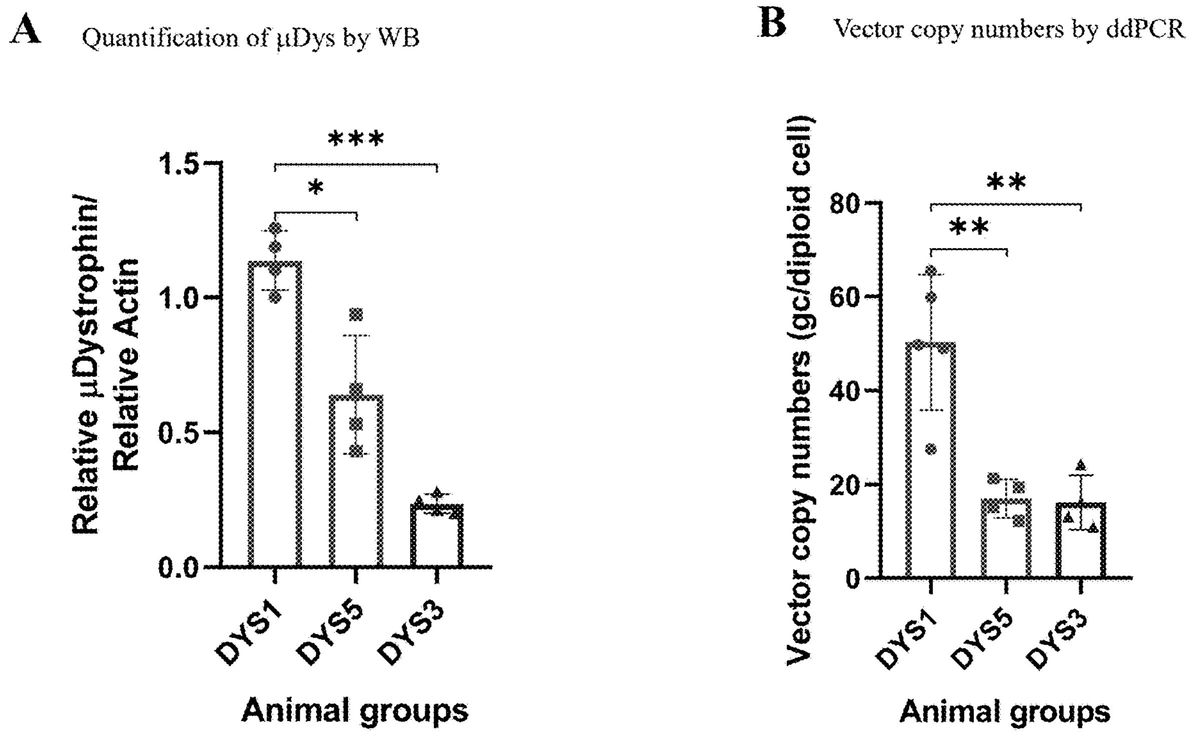
Figure 16C:
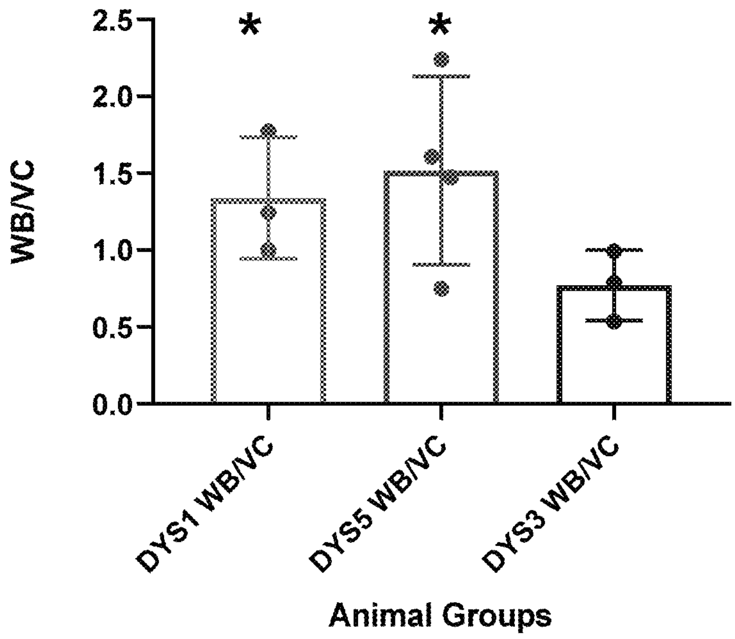

FIGS. 16A-C: Quantification of μ-dystrophin bands by western blot (Panel A), AAV-μ-Dys vector copy numbers by ddPCR (Panel B), and quantification of μ-dystrophin bands normalized by AAV-μ-Dys vector copy numbers (Panel C). * p<0.05;  P<0.01; *P<0001.

Figure 17A:
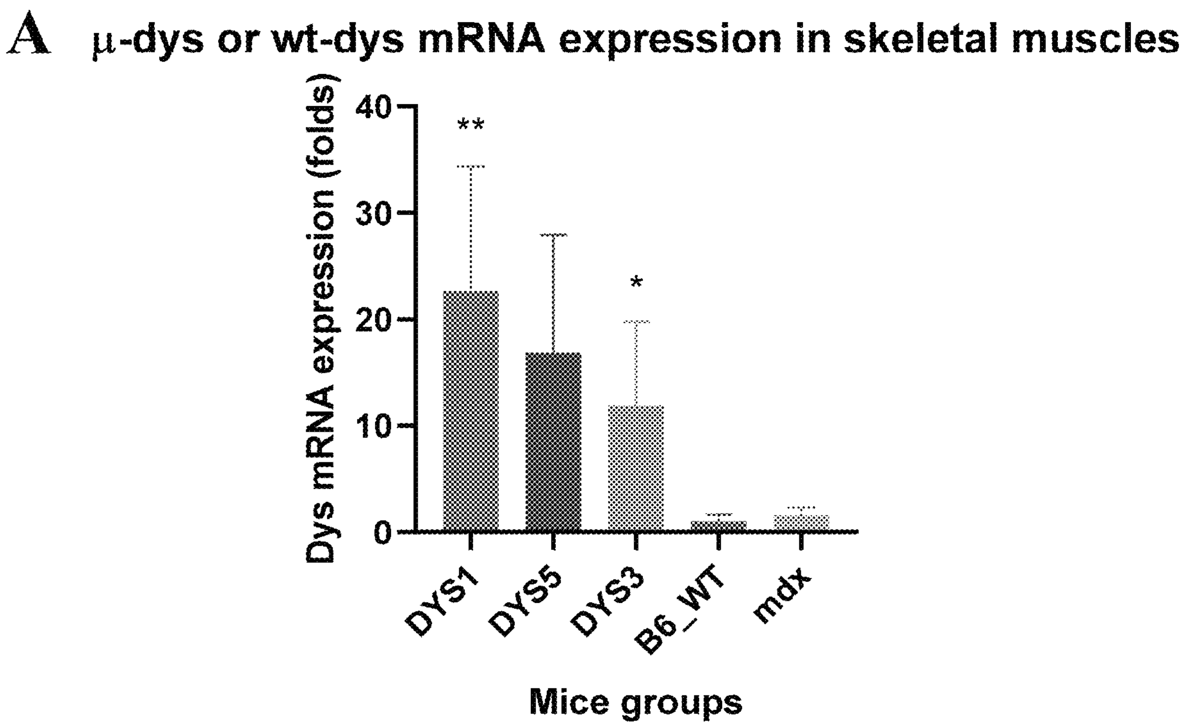
Figure 17B:
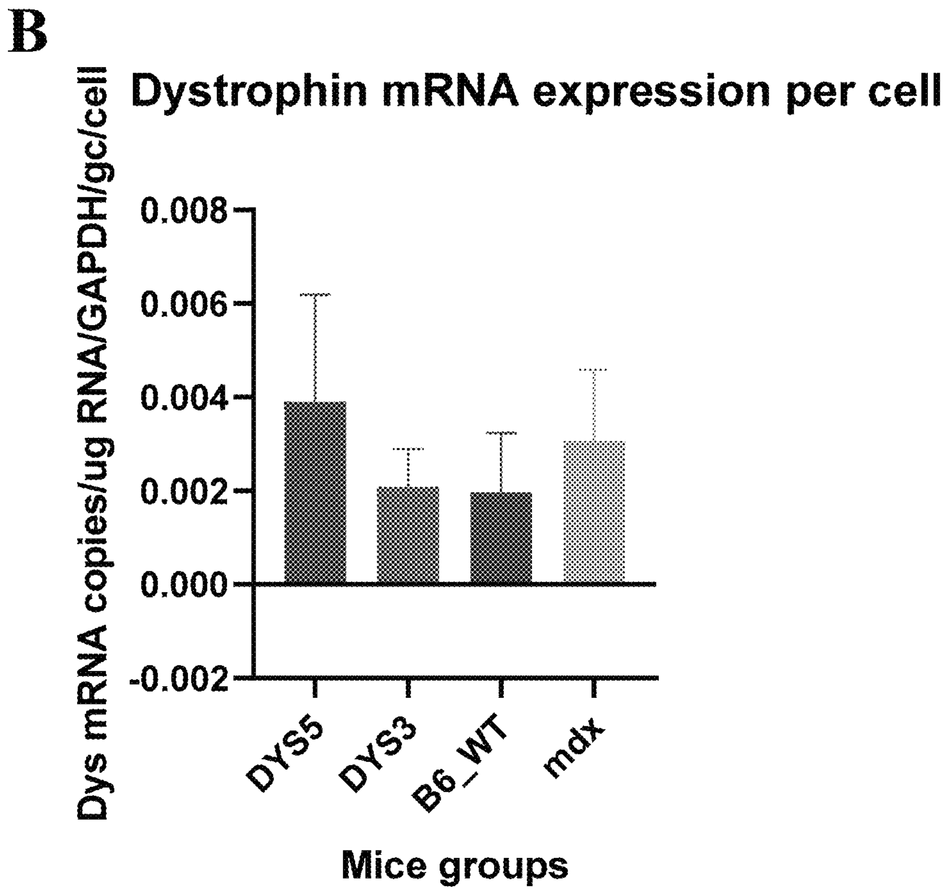

FIGS. 17A-B: mRNA expression of μ-dystrophin and wild-type (WT) dystrophin in skeletal muscles (gastrocnemius). Total RNA was extracted from the skeletal muscles and cDNA synthesized. The copies numbers of μ-dystrophin, WT-dystrophin, and endogenous control Glyceraldehyde 3-phosphate dehydrogenase (GAPDH) mRNA were measured using digital PCR (Naica Crystal Digital PCR system, Stilla technologies). A. Relative μ- or WT-dystrophin mRNA expression normalized by GAPDH. The ratio of WT-dystrophin to GAPDH in B6-WT skeletal muscle was considered as 1. B. Relative μ- or WT-dystrophin mRNA expression in a single cell. μ- or WT-dystrophin mRNA expression copy numbers were normalized by GAPDH and genome copy numbers per cell.

Figure 18:
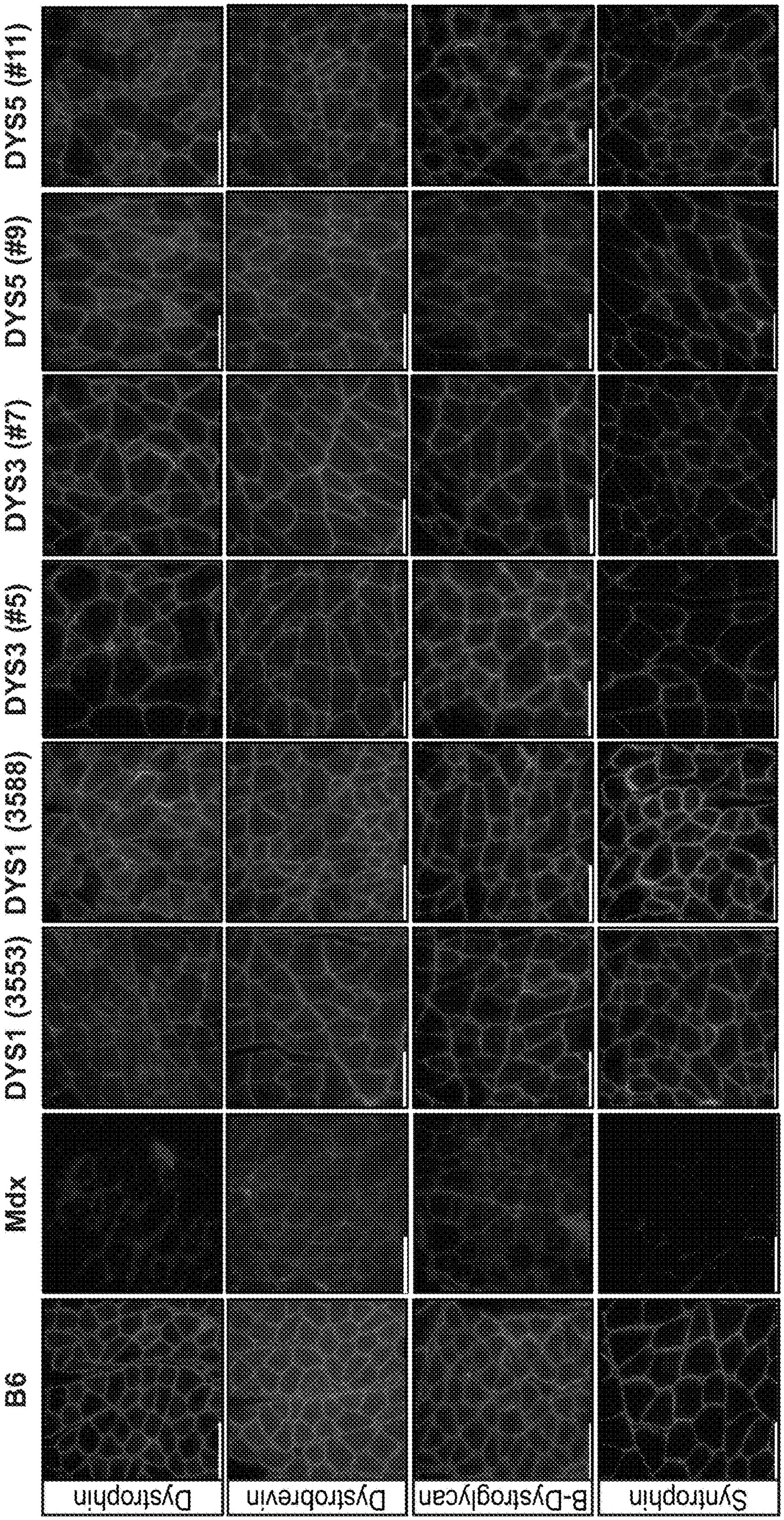

FIG. 18. Gastrocnemius muscle extracted from mdx mice, tissue sections prepared and immunofluorescently (IF) stained against dystrophin and dystrophin associated protein complexes including dystrobrevin, β-dystroglycan, and syntrophin. Mice were treated as described: Bl6 (untreated wild-type mice); RGX-DYS1 (mouse ID 3553, and mouse ID 3588); RGX-DYS3 (mouse ID 5, and mouse ID 7); and RGX-DYS5 (mouse ID 9, and mouse ID 11). Objective lens: 40×.

FIGS. 19A-E: Syntrophin expression in skeletal muscles. A. Gastrocnemius muscle extracted from mdx mice, tissue sections prepared and immunofluorescently (IF) stained against syntrophin. Mice were treated as described: Bl6 (untreated wild-type mice); RGX-DYS1 (mouse ID 3553, and mouse ID 3588); RGX-DYS3 (mouse ID 5, and mouse ID 7); and RGX-DYS5 (mouse ID 9, and mouse ID 11). Objective lens: 40×. B. Western blot against syntrophin from muscle tissue lysate. C. Quantification of western blot bands. *, $p<0.05$; ***, $p<0.0001$. D. Western blot against syntrophin from total muscle membrane protein. E. Quantification of western blot bands.

Figure 20A:
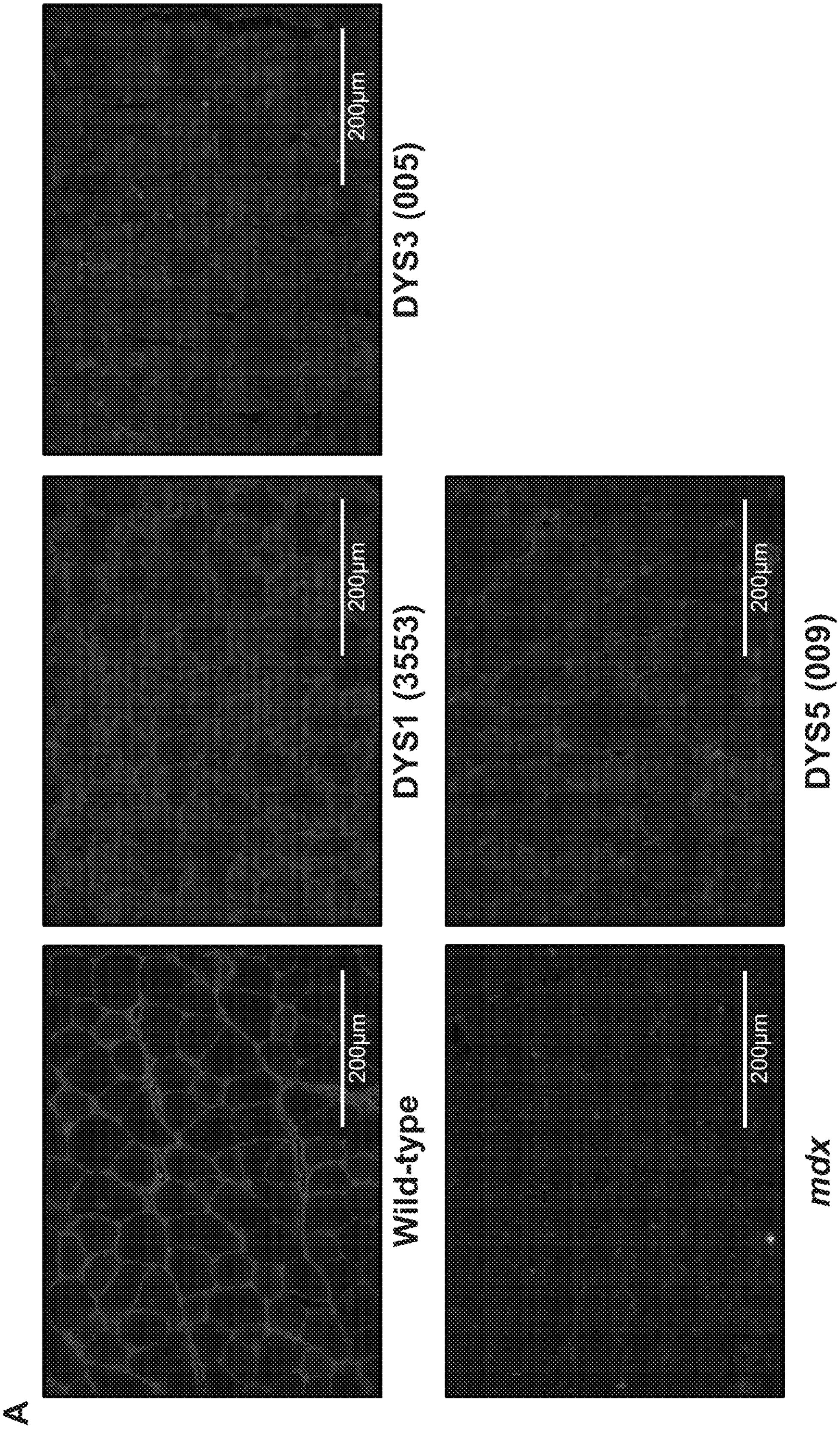
Figure 20B:
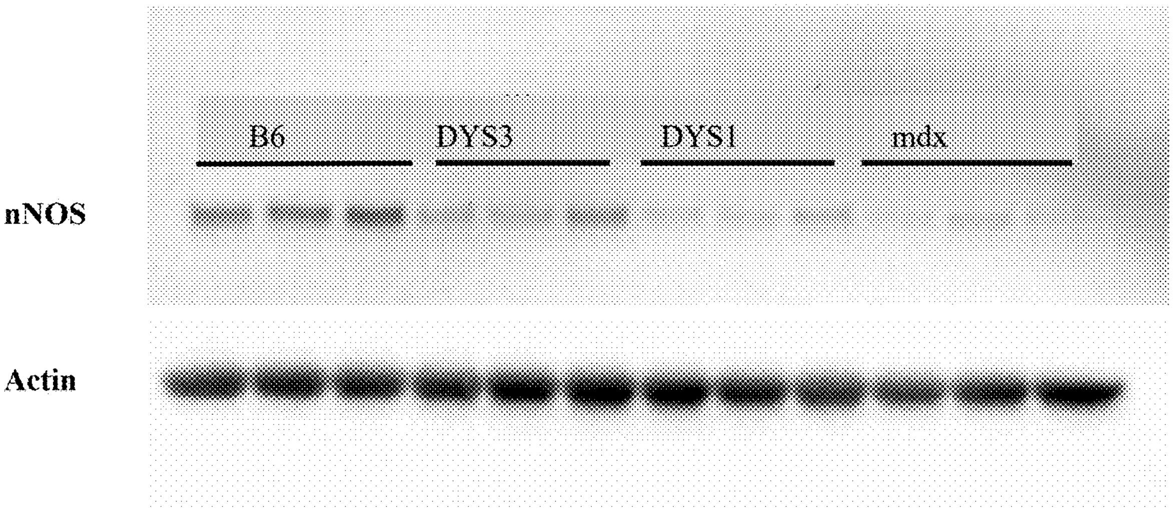
Figure 20C:
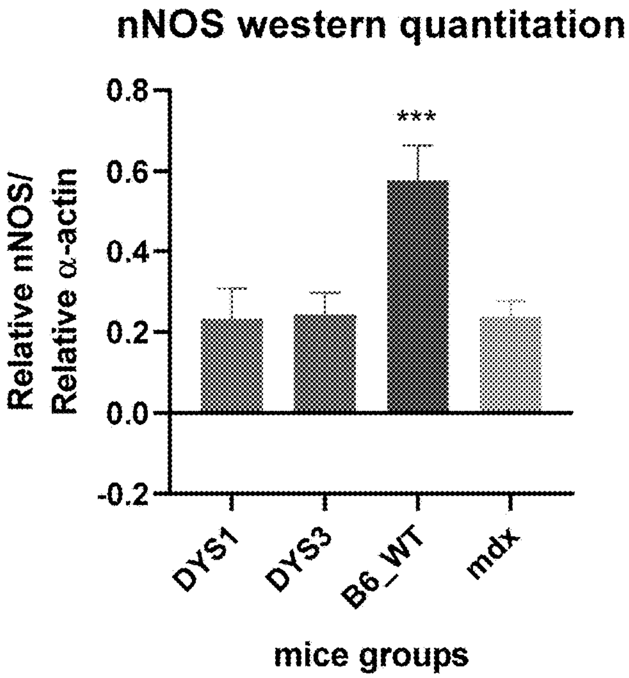

FIGS. 20A-C: nNOS expression in skeletal muscles. A. Immunofluorescent staining against nNOS. B. Western blot against nNOS. C. Quantification of western blot bands.

FIGS. 21A-E: Transduction of satellite cells and amelioration of cell regeneration by AAV vector encoding μ-dystrophin gene. A-B. RNAScope Images of RGX-DYS1-treated mdx mice (panel A) and untreated mdx mice (panel B) revealing co-expression of μ-dystrophin and pax7 satellite cells. The RNAscope multiplex fluorescent analysis of AAV transgene and Pax7 mRNA expression service was performed at Advanced Cell Diagnostics Inc (Newark, CA). C. Percentage of AAV-DMD transduced satellite cells. D. Total satellite cell counting in RNAscope images. E. Pax7 mRNA expression in skeletal muscles from different groups revealed by ddPCR. The primes and probe against μ-dystrophin was the same as previously described. The ratio of pax7 to GAPDH in B6-WT skeletal muscle was considered as 1. , $p<0.01$; *, $p<0.001$; ****, $p<0.0001$ as compared to the untreated mdx mice.

FIG. 22: Illustration of additional modified μ-dystrophin constructs. CR short: Cysteine-rich domain is 150 bp shorter than in wild-type dystrophin. R16/R17: dystrophin spectrin-like repeats 16 and 17.

Figures 23A, 23B:
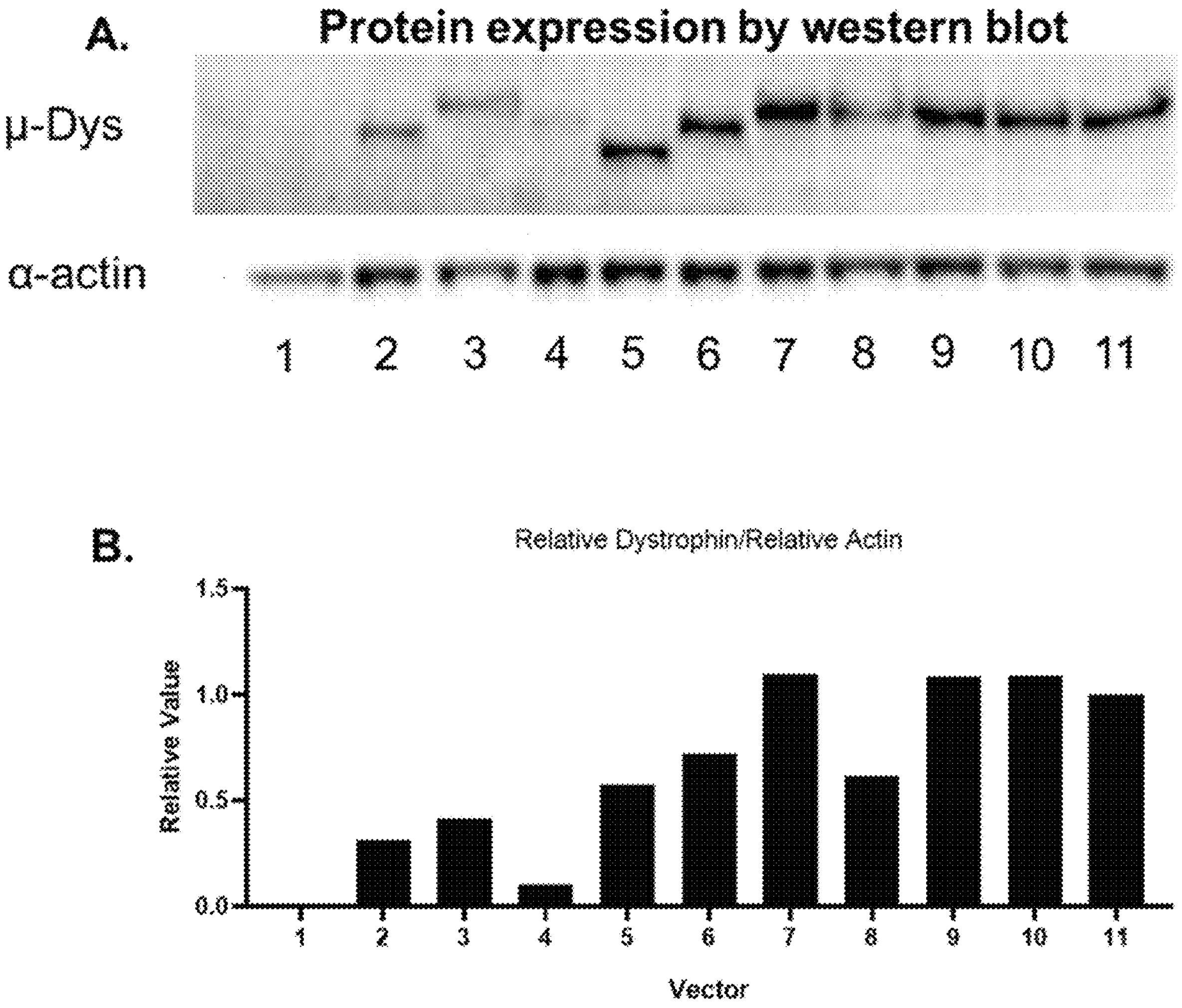
Figure 23C:
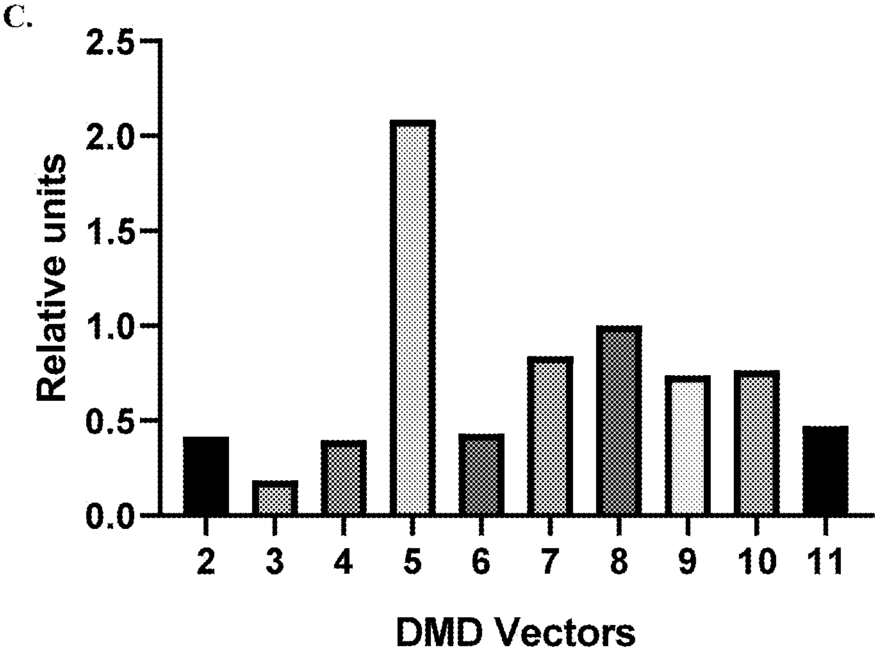

FIGS. 23A-C: In vitro infection of C2C12 myotubes with different versions of AAV8-μ-dystrophin constructs. C2C12 myoblast cells were induced in differentiation media, then infected with AAV vectors. The cells were harvested five days after infection for western blot or mRNA expression. 1: Negative control; 2: RGX-DYS8; 3: RGX-DYS7; 4: RGX-DYS6; 5: RGX-DYS3; 6: RGX-DYS5; 7: RGX-DYS1; 8: RGX-DYS1; 9: RGX-DYS1; 10: RGX-DYS1; 11: RGX-DYS1. A. Western blot analysis of μ-dystrophin expression from C2C12 cells. B. Quantification of western blot analysis. C. Detection of μ-dystrophin mRNA expression by ddPCR.

5. DETAILED DESCRIPTION

Provided are microdystrophin protein, for example, as shown in FIG. 1A and FIG. 22 and nucleic acid compositions and rAAV vectors encoding the same as well as pharmaceutical compositions and treatment methods related thereto.

5.1. Definitions

The term "AAV" or "adeno-associated virus" refers to a Dependoparvovirus within the Parvoviridae genus of viruses. The AAV can be an AAV derived from a naturally occurring "wild-type" virus, an AAV derived from a rAAV genome packaged into a capsid comprising capsid proteins encoded by a naturally occurring cap gene and/or from a rAAV genome packaged into a capsid comprising capsid proteins encoded by a non-naturally occurring capsid cap gene. An example of the latter includes a rAAV having a capsid protein having a modified sequence and/or a peptide insertion into the amino acid sequence of the naturally-occurring capsid.

The term "rAAV" refers to a "recombinant AAV." In some embodiments, a recombinant AAV has an AAV genome in which part or all of the rep and cap genes have been replaced with heterologous sequences.

The term "rep-cap helper plasmid" refers to a plasmid that provides the viral rep and cap gene function and aids the production of AAVs from rAAV genomes lacking functional rep and/or the cap gene sequences.

The term "cap gene" refers to the nucleic acid sequences that encode capsid proteins that form or help form the capsid coat of the virus. For AAV, the capsid protein may be VP1, VP2, or VP3.

The term "rep gene" refers to the nucleic acid sequences that encode the non-structural protein needed for replication and production of virus.

The terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

Amino acid residues as disclosed herein can be modified by conservative substitutions to maintain, or substantially maintain, overall polypeptide structure and/or function. As used herein, "conservative amino acid substitution" indicates that: hydrophobic amino acids (i.e., Ala, Cys, Gly, Pro, Met, Val, lie, and Leu) can be substituted with other hydrophobic amino acids; hydrophobic amino acids with bulky side chains (i.e., Phe, Tyr, and Trp) can be substituted with other hydrophobic amino acids with bulky side chains; amino acids with positively charged side chains (i.e., Arg, His, and Lys) can be substituted with other amino acids with positively charged side chains; amino acids with negatively charged side chains (i.e., Asp and Glu) can be substituted with other amino acids with negatively charged side chains; and amino acids with polar uncharged side chains (i.e., Ser, Thr, Asn, and Gln) can be substituted with other amino acids with polar uncharged side chains.

The terms “subject”, “host”, and “patient” are used interchangeably. A subject is preferably a mammal such as a non-primate (e.g., cows, pigs, horses, cats, dogs, rats etc.) or a primate (e.g., monkey and human), most preferably a human.

The term “therapeutically functional microdystrophin” means that the microdystrophin exhibits therapeutic efficacy in one or more of the assays for therapeutic utility described in Section 5.4 herein or in assessment of methods of treatment described in Section 5.5 herein.

The terms “subject”, “host”, and “patient” are used interchangeably. A subject is preferably a mammal such as a non-primate (e.g., cows, pigs, horses, cats, dogs, rats etc.) or a primate (e.g., monkey and human), most preferably a human.

The terms “therapeutic agent” refers to any agent which can be used in treating, managing, or ameliorating symptoms associated with a disease or disorder, where the disease or disorder is associated with a function to be provided by a transgene. A “therapeutically effective amount” refers to the amount of agent, (e.g., an amount of product expressed by the transgene) that provides at least one therapeutic benefit in the treatment or management of the target disease or disorder, when administered to a subject suffering therefrom. Further, a therapeutically effective amount with respect to an agent of the invention means that amount of agent alone, or when in combination with other therapies, that provides at least one therapeutic benefit in the treatment or management of the disease or disorder.

The term “prophylactic agent” refers to any agent which can be used in the prevention, reducing the likelihood of, delay, or slowing down of the progression of a disease or disorder, where the disease or disorder is associated with a function to be provided by a transgene. A “prophylactically effective amount” refers to the amount of the prophylactic agent (e.g., an amount of product expressed by the transgene) that provides at least one prophylactic benefit in the prevention or delay of the target disease or disorder, when administered to a subject predisposed thereto. A prophylactically effective amount also may refer to the amount of agent sufficient to prevent, reduce the likelihood of, or delay the occurrence of the target disease or disorder; or slow the progression of the target disease or disorder; the amount sufficient to delay or minimize the onset of the target disease or disorder; or the amount sufficient to prevent or delay the recurrence or spread thereof. A prophylactically effective amount also may refer to the amount of agent sufficient to prevent or delay the exacerbation of symptoms of a target disease or disorder. Further, a prophylactically effective amount with respect to a prophylactic agent of the invention means that amount of prophylactic agent alone, or when in combination with other agents, that provides at least one prophylactic benefit in the prevention or delay of the disease or disorder.

A prophylactic agent of the invention can be administered to a subject “pre-disposed” to a target disease or disorder. A subject that is “pre-disposed” to a disease or disorder is one that shows symptoms associated with the development of the disease or disorder, or that has a genetic makeup, environmental exposure, or other risk factor for such a disease or disorder, but where the symptoms are not yet at the level to be diagnosed as the disease or disorder. For example, a patient with a family history of a disease associated with a missing gene (to be provided by a transgene) may qualify as one predisposed thereto. Further, a patient with a dormant tumor that persists after removal of a primary tumor may qualify as one predisposed to recurrence of a tumor.

The term “CpG islands” means those distinctive regions of the genome that contain the dinucleotide CpG (e.g. C (cytosine) base followed immediately by a G (guanine) base (a CpG)) at high frequency, thus the G+C content of CpG islands is significantly higher than that of non-island DNA. CpG islands can be identified by analysis of nucleotide length, nucleotide composition, and frequency of CpG dinucleotides. CpG island content in any particular nucleotide sequence or genome may be measured using the following criteria: island size greater than 100, GC Percent greater than 50.0%, and ratio greater than 0.6 of observed number of CG dinucleotides to the expected number on the basis of the number of Gs and Cs in the segment (Obs/Exp greater than 0.6).

$$\text{Obs/Exp CpG=Number of CpG}*N/(\text{Number of } C*\text{Number of } G)$$

where N=length of sequence.

% Various software tools are available for such calculations, such as world-wide-web.urogene.org/cgi-bin/methprimer/methprimer.cgi, world-wide-web.cpgislands.usc.edu/, and world-wide-web.ebi.ac.uk/Tools/emboss/cpgplot/index.html world-wide-web.bioinformatics.org/sms2/cpg_islands.html. (See also Gardiner-Garden and Frommer, J Mol Biol. 1987 Jul. 20; 196 (2): 261-82; Li LC and Dahiya R. MethPrimer: designing primers for methylation PCRs. Bioinformatics. 2002 November; 18 (11): 1427-31.). In one embodiment the algorithm to identify CpG islands is found at urogene.org/cgi-bin/methprimer/methprimer.cgi.

5.2. Microdystrophin Transgenes

5.2.1 Microdystrophin

Embodiments described herein comprise a microdystrophin protein having from amino-terminus to the carboxy terminus: ABD-H1-R1-R2-R3-H3-R24-H4-CR (e.g., SEQ ID NO: 2) or ABD1-H1-R1-R2-R16-R17-R24-H4-CR (SEQ ID NO: 93), wherein ABD is an actin-binding domain of dystrophin, H1 is a hinge 1 region of dystrophin, R1 is a spectrin 1 region of dystrophin, R2 is a spectrin 2 region of dystrophin, R3 is a spectrin 3 region of dystrophin, H3 is a hinge 3 region of dystrophin, R16 is a spectrin 16 region of dystrophin, R17 is a spectrin 17 region of dystrophin, R24 is a spectrin 24 region of dystrophin, H4 is a hinge 4 region of dystrophin, CR is a cysteine-rich region of dystrophin.

As explained above, the microdystrophins in accordance with the present disclosure comprise ABD-H1-R1-R2-R3-R24-H4 or ABD-H1-R1-R2-R16-R17-R24-H4. The $NH_2$ terminus and a region in the rod domain of dystrophin bind directly to but do not cross-link cytoskeletal actin. The rod domain of wild type dystrophin is composed of 24 repeating units that are similar to the triple helical repeats of spectrin. This repeating unit accounts for the majority of the dystrophin protein and is thought to give the molecule a flexible rod-like structure similar to β-spectrin. These α-helical coiled-coil repeats are interrupted by four proline-rich hinge regions. At the end of the 24th repeat is the fourth hinge region that is immediately followed by the WW domain [Blake, D. et al, Function and Genetics of Dystrophin and Dystrophin-Related Proteins in Muscle. Physiol. Rev. 82: 291-329, 2002]. Microdystrophins disclosed herein do not include R4 to R23, or, alternatively, do not include R3 (or, in some embodiments R4) to R15 and R18 to R23 (that is, such that the microdystrophin includes R16 and R17, but may not, in certain embodiments, include R3), and only include 2 or 3 of the 4 hinge regions or portions thereof. Embodiments may contain dystrophin spectrin-like repeats 16 and 17 which are understood to anchor nNOS to the sarcolemma. In some embodiments, no new amino acid residues or linkers are introduced into the microdystrophin.

In some embodiments, microdystrophin comprises H3 (e.g, SEQ ID NOS: 1, 2, or 79). In embodiments, H3 can be a full endogenous H3 domain from N-terminal to C-terminal, e.g., SEQ ID NO: 11. Stated another way, some microdystrophin embodiments do not contain a fragment of the H3 domain but contain the entire H3 domain. In some embodiments, the C-terminal amino acid of the R3 domain is coupled directly (or covalently bonded to) the N-terminal amino acid of the H3 domain. In some embodiments, the C-terminal amino acid of the R3 domain coupled to the N-terminal amino acid of the H3 domain is Q. In some embodiments, the 5' amino acid of the H3 domain coupled to the R3 domain is Q.

In other embodiments, microdystrophin comprises H2 instead of H3. H2 can be the full endogenous H2 domain (SEQ ID NO: 19). Such microdystrophin protein embodiments have from amino-terminus to the carboxy terminus: ABD-H1-R1-R2-R3-H2-R24-H4-CR. In some embodiments, the C-terminal amino acid of the R3 domain coupled to the N-terminal amino acid of the hinge domain is Q. In other embodiments, the N-terminal amino acid of the H2 domain coupled to the R3 domain is P. In certain embodiments, the C-terminal amino acid of the R3 domain is directly coupled to the N-terminal amino acid of the hinge domain, wherein the N-terminal amino acid of the hinge domain is P or Q. In still other embodiments, the C-terminal amino acid of the R3 domain is directly coupled to the N-terminal amino acid of the H2 domain, wherein the N-terminal amino acid of the H2 domain is P.

Without being bound by any one theory, a full hinge domain may be appropriate in any microdystrophin construct in order to convey full activity upon the derived microdystrophin protein. Hinge segments of dystrophin have been recognized as being proline-rich in nature and may therefore confer flexibility to the protein product (Koenig and Kunkel, 265(6):4560-4566, 1990). Any deletion of a portion of the hinge, especially removal of one or more proline residues, may reduce its flexibility and therefore reduce its efficacy by hindering its interaction with other proteins in the DAP complex.

Microdystrophins disclosed herein comprise the wild-type dystrophin H4 sequence (which contains the WW domain) to and including the CR domain (which contains the ZZ domain, represented by a single underline (UniProtKB-P11532 aa 3307-3354) in SEQ ID NO: 15). The WW domain is a protein-binding module found in several signaling and regulatory molecules. The WW domain binds to proline-rich substrates in an analogous manner to the src homology-3 (SH3) domain. This region mediates the interaction between β-dystroglycan and dystrophin, since the cytoplasmic domain of β-dystroglycan is proline rich. The WW domain is in the Hinge 4 (H4 region). The CR domain contains two EF-hand motifs that are similar to those in α-actinin and that could bind intracellular $Ca^{2+}$. The ZZ domain contains a number of conserved cysteine residues that are predicted to form the coordination sites for divalent metal cations such as $Zn^{2+}$. The ZZ domain is similar to many types of zinc finger and is found both in nuclear and cytoplasmic proteins. The ZZ domain of dystrophin binds to calmodulin in a $Ca^{2+}$-dependent manner. Thus, the ZZ domain may represent a functional calmodulin-binding site and may have implications for calmodulin binding to other dystrophin-related proteins.

Certain embodiments comprise a truncated portion of the CR domain, which comprises the ZZ domain. For example, the microdystrophin protein comprises from amino-terminus to the carboxy terminus: ABD-H1-R1-R2-R3-H3-R24-H4-CR(short)-CT (e.g., SEQ ID NO: 91, see RGX-DYS6 in FIG. 22). In certain embodiments, the CR domain, for example, has an amino acid sequence of SEQ ID NO: 90.

To overcome the packaging limitation that is typical of AAV vectors, many of the microdystrophin genes developed for clinical use are lacking the CT domain. Several researchers have indicated that the DAPC does not even require the C-terminal domain in order to assemble or that the C-terminus is non-essential [Crawford, et al., J Cell Biol, 2000, 150(6):1399-1409; and Ramos, J. N, et al. *Molecular Therapy* 2019, 27(3):1-13]. The CT domain of dystrophin protein could nevertheless provide beneficial effects on cardiomyopathy. A special interaction between the CT domain of dystrophin and β-dystroglycan in cardiac muscle has been shown, where a direct molecular interaction exists at the plasma membrane interface, indicating a direct role for the CT domain in anchoring DAP complexes in the cardiomyocyte membrane [Stevenson, S., et al., Spatial relationship of the C-terminal domains of dystrophin and beta-dystroglycan in cardiac muscle support a direct molecular interaction at the plasma membrane interface. Circ Res, 1998. 82(1): p. 82-93]. Dystrophin genotype-cardiac phenotype corrections in a study of 274 Duchenne and Becker muscular dystrophy patients revealed the presence of N-terminal actin binding domain (ABD1) and CR domain plus CT domain had a decreased risk of cardiomyopathy, further pointing to a beneficial cardio-protective effect for the CT domain of dystrophin protein [Tandon, A., et al., Dystrophin genotype-cardiac phenotype correlations in Duchenne and Becker muscular dystrophies using cardiac magnetic resonance imaging. Am J Cardiol, 2015. 115(7): p. 967-71]. Additionally, overexpression of a microdystrophin gene containing helix 1 of the coiled-coil motif of the CT domain in skeletal muscle of mdx mice increased the recruitment α1-syntrophin and α-dystrobrevin, which are members of DAP complex, serving as modular adaptors for signaling proteins recruited to the sarcolemma membrane [Koo, T., et al., Delivery of AAV2/9-microdystrophin genes incorporating helix 1 of the coiled-coil motif in the C-terminal domain of dystrophin improves muscle pathology and restores the level of α1-syntrophin and α-dystrobrevin in skeletal muscles of mdx mice. Hum Gene Ther, 2011. 22(11): p. 1379-88]. Overexpression of the longer version of microdystrophin also improved the muscle resistance to lengthening contraction-induced muscle damage in the mdx mice as compared with the shorter version [Koo, T., et al. 2011, supra].

It has been shown that significantly reduced cardiac function persists in DMD patients. Treatments that restore neuronal nitric oxide synthase (nNOS) function are thought to be beneficial by improving cardiac function, as such leading to significant improvement of the systolic BP, fraction shortening and ejection fraction and in turn a reduction in cardiac fibrosis. Progression of cardiac fibrosis is indicated as patients first exhibit left ventricle (LV) dilation and hypertrophy, which progresses to a stage known as dilated cardiomyopathy (DCM).

The CT domain of dystrophin contains two polypeptide stretches that are predicted to form α-helical coiled coils similar to those in the rod domain (see H1 indicated by single underlining and H2 indicated by double underlining in SEQ ID 16 in Table 1 below). Each coiled coil has a conserved repeating heptad (a,b,c,d,e,f,g). similar to those found in leucine zippers where leucine predominates at the "d" position. This domain has been named the CC (coiled coil) domain. The CC region of dystrophin forms the binding site for dystrobrevin and may modulate the interaction between α1-syntrophin and other dystrophin-associated proteins.

Both syntrophin isoforms, α1-syntrophin and β1-syntrophin are thought to interact directly with dystrophin through more than one binding site in dystrophin exons 73 and 74 (Yang et al, JBC 270(10):4975-8 (1995)). α1- and 31-syntrophin bind separately to the dystrophin C-terminal domain, and the binding site for α1-syntrophin resides at least within the amino acid residues 3447 to 3481, while that for β1-syntrophin resides within the amino acid residues 3495 to 3535 (Table 1, SEQ ID NO: 16, italic). Alpha1-(α1-) syntrophin and alpha-syntrophin are used interchangeably throughout.

Helix 1 (see H1 indicated as single underlined sequence within SEQ ID NO: 16 in Table 1 below) of the coiled-coil motif in the C-terminal (CT) domain of the microdystrophin gene cassettes may be advantageous for cardiomyocyte protection, and otherwise stabilizing dystrophin-associated (glyco)protein (DAP) complexes (DAPCs). The DAPC may participate in important signaling roles as well as a structural role. Certainly, there have been indications of altered nitric oxide (NO) production, and possible alterations in other functions caused by the destabilization and loss of the complex.

Unexpectedly, certain microdystrophin constructs disclosed herein were found to bind to and recruit nNOS, as well as alpha-syntrophin, alpha-dystrobrevin and beta-dystroglycan. Binding to nNOS, in the context of a microdystrophin construct including a C-terminal domain of dystrophin binding to nNOS, means that the microdystrophin construct expressed in muscle tissue was determined by immunostaining with appropriate antibodies to identify each of alpha-syntrophin, alpha-dystrobrevin, and nNOS in or near the sarcolemma in a section of the transduced muscle tissue. See Example 5 and 7 in Sections 6.5 and 6.7, infra. In certain embodiments, the microdystrophin protein has a C-terminal domain that "increases binding" to α1-syntrophin, β-syntrophin and/or dystrobrevin compared to a comparable microdystrophin that does not contain the C-terminal domain (but has the same amino acid sequence otherwise, that is a "reference microdystrophin protein"), meaning that the DAPC is stabilized or anchored to the sarcolemma, to a greater extent than a reference microdystrophin that does not have the C-terminal domain (but has the same amino acid sequence otherwise as the microdystrophin), as determined by greater levels of one or more DAPC components in the muscle membrane by immunostaining of muscle sections or western blot analysis of muscle tissue lysates or muscle membrane preparations for one of more DAPC components, including al-syntrophin, β-syntrophin, α-dystrobrevin, β-dystroglycan or nNOS in mdx mouse muscle treated with the microdystrophin having the C-terminal domain, as compared to the mdx mouse muscle treated with the reference microdystrophin protein (having the same sequence and dystrophin components except not having the C-terminal domain) (see Sections 6.5 and 6.7 infra).

In some embodiments, the microdystrophin construct including a C-terminal domain of dystrophin comprises a syntrophin binding site and/or a dystrobrevin binding site in the C-terminal domain. In some embodiments, the C-terminal domain comprising an α1-syntrophin binding site is a truncated C-terminal domain. In certain embodiments, the amino acid sequence of the truncated C-terminal domain is SEQ ID NO: 83. In certain embodiments, the truncated C-terminal domain comprises the amino acid sequence MENSNGSYLNDSISPNESIDDEHLLIQHYCQSLNQ (al-syntrophin binding site) (SEQ ID NO: 84). In certain embodiments, the truncated C-terminal domain comprises an al-syntrophin binding site, wherein the binding site has amino acid sequence MENSNGSYLNDSISPNESIDDEHLLIQHYCQSLNQ (SEQ ID NO: 84) but does not have a j31-syntrophin or dystrobrevin binding site.

The microdystrophin constructs of the present disclosure may further prevent progressive ventricular fibrosis, as measured by the reduction in myocardial macrophage concentrations, the reduction of the expression of adhesion molecules, and/or normalized electrocardiogram (ECG) readouts, for example end systolic volume (left ventricle), end diastolic volume, stroke volume, ejection fraction, heart rate, or cardiac output, following administration of the microdystrophin constructs. End systolic volume and other cardiac readouts can also be measured using MRI (magnetic resonance tomography), cardiac CT (computed tomography) or SPECT (single photon emission computed tomography). Cardiac function improvements following administration of the microdystrophin constructs of the invention may also be tested in a DBA/2J-mdx mouse model.

Accordingly, embodiments described herein can further comprise all or a portion of the CT domain comprising the Helix 1 of the coiled-coil motif. For example, the microdystrophin protein comprises from amino-terminus to the carboxy terminus: ABD-H1-R1-R2-R3-H3-R24-H4-CR-CT (e.g., SEQ ID NO: 1, 79 or 91) or ABD-H1-R1-R2-R16-R17-R24-H4-CR-CT (e.g., SEQ ID NO: 92). In some embodiments, CT is at least a portion of a C-terminal domain of dystrophin comprising a α1-syntrophin binding site and/or a dystrobrevin binding site as illustrated in FIG. 14. In certain embodiments, the CT domain comprises an al-syntrophin binding site and does not have a 031-syntrophin or dystrobrevin binding site, for example it has an amino acid sequence of SEQ ID NO: 83, which function in part to recruit and anchor nNOS to the sarcolemma through α1-syntrophin. In some embodiments, the CT comprises the amino acid sequence of SEQ ID NO: 16 or 83.

Microdystrophin embodiments can further comprise linkers (L1, L2, L3, L4, L4.1 and/or L4.2) or portions thereof connected the domains as shown as follows: ABD1-L1-H1-L2-R1-R2-L3-R3-H3-L4-R24-H4-CR-CT (e.g., SEQ ID NO: 1, 79, or 91), ABD1-L1-H1-L2-R1-R2-L3-R3-H3-L4-R24-H4-CR (e.g., SEQ ID NO: 2), ABD1-L1-H1-L2-R1-R2-L3-R16-L4.1-R17-L4.2-R24-H4-CR (e.g., SEQ ID NO: 92), or ABD1-L1-H1-L2-R1-R2-L3-R16-L4.1-R17-L4.2-R24-H4-CR-CT (e.g., SEQ ID NO: 93). L1 can be an endogenous linker L1 (e.g., SEQ ID NO: 4) that can couple ABD1 to H1. L2 can be an endogenous linker L2 (e.g., SEQ ID NO: 6) that can couple H1 to R1. L3 can be an endogenous linker L3 (e.g., SEQ ID NO: 9) that can couple R2 to R3 or R16.

L4 can also be an endogenous linker that can couple H3 and R24. In some embodiments, L4 is 3 amino acids, e.g. TLE (SEQ ID NO: 12) that precede R24 in the native dystrophin sequence. In other embodiments, L4 can be the 4 amino acids that precede R24 in the native dystrophin sequence (SEQ ID NO: 17) or the 2 amino acids that precede R24 (SEQ ID NO: 18). In other embodiments, there is no linker, L4 or otherwise, in between H3 and R24. On the 5' end of H3, as mentioned above, no linker is present, but rather R3 is directly coupled to H3, or alternatively H2.

L4.1 can be an endogenous linker that can couple R16 and R17. In some embodiments, L4.1 is 2 amino acids, e.g. SV (SEQ ID NO: 110) that precede R17 in the native dystrophin sequence. In other embodiments, L4.2 can be an endogenous linker or part of an endogenous linker that can couple R17 and R24. In some embodiments, L4.2 is 4 amino acids, e.g. Q that follows R17 and TLE (SEQ ID NO: 12) that precede R24 (SEQ ID NO: 89).

The above described components of microdystrophin other domains not specifically described can have the amino acid sequences as provided in Table 1 below. The amino acid sequences for the domains provided herein correspond to the dystrophin isoform of UniProtKB-P11532 (DMD_HUMAN), which is herein incorporated by reference. Other embodiments can comprise the domains from naturally-occurring functional dystrophin isoforms known in the art, such as UniProtKB-A0A075B6G3 (A0A075B6G3_HUMAN), (incorporated by reference herein) wherein, for example, R24 has an R substituted for the Q at amino acid 3 of SEQ ID NO: 13.

TABLE 1

Microdystrophin segment amino acid sequences

| Structure | SEQ ID | Sequence |
|---|---|---|
| ABD1 | 3 | MLWWEEVEDCYEREDVQKKTFTKWVNAQFSKFGKQHIENL<br>FSDLQDGRRLLDLLEGLTGQKLPKEKGSTRVHALNNVNKA<br>LRVLQNNNVDLVNIGSTDIVDGNHKLTLGLIWNIILHWQV<br>KNVMKNIMAGLQQTNSEKILLSWVRQSTRNYPQVNVINFT<br>TSWSDGLALNALIHSHRPDLFDWNSVVCQQSATQRLEHAF<br>NIARYQLGIEKLLDPEDVDTTYPDKKSILMYITSLFQVLP |
| L1 | 4 | QQVSIEAIQEVE |
| H1 | 5 | MLPRPPKVTKEEHFQLHHQMHYSQQITVSLAQGYERTSSP<br>KPRFKSYAYTQAAYVTTSDPTRSPFPSQHLEAPED |
| L2 | 6 | KSFGSSLME |
| R1 | 7 | SEVNLDRYQTALEEVLSWLLSAEDTLQAQGEISNDVEVVK<br>DQFHTHEGYMMDLTAHQGRVGNILQLGSKLIGTGKLSEDE<br>ETEVQEQMNLLNSRWECLRVASMEKQSNLHR |
| R2 | 8 | VLMDLQNQKLKELNDWLTKTEERTRKMEEEPLGPDLEDLK<br>RQVQQHKVLQEDLEQEQVRVNSLTHMVVVVDESSGDHATA<br>ALEEQLKVLGDRWANICRWTEDRWVLLQD |
| L3 | 9 | IL |
| R3 | 10 | LKWQRLTEEQCLFSAWLSEKEDAVNKIHTTGFKDQNEMLS<br>SLQKLAVLKADLEKKKQSMGKLYSLKQDLLSTLKNKSVTQ<br>KTEAWLDNFARCWDNLVQKLEKSTAQISQ |
| H3 | 11 | QPDLAPGLTTIGASPTQTVTLVTQPVVTKETAISKLEMPS<br>SLMLEVP |
| L4 | 12 | TLE |
| R16 | 86 | EISYVPSTYLTEITHVSQALLEVEQLLNAPDLCAKDFEDL<br>FKQEESLKNIKDSLQQSSGRIDIIHSKKTAALQSATPVER<br>VKLQEALSQLDFQWEKVNKMYKDRQGRFDR |
| L4.1 | 110 | SV |
| R17 | 87 | EKWRRFHYDIKIFNQWLTEAEQFLRKTQIPENWEHAKYKW<br>YLKELQDGIGQRQTVVRTLNATGEEIIQQSSKTDASILQE<br>KLGSLNLRWQEVCKQLSDRKKRLEE |
| R16-R17 | 88 | EISYVPSTYLTEITHVSQALLEVEQLLNAPDLCAKDFEDL<br>FKQEESLKNIKDSLQQSSGRIDIIHSKKTAALQSATPVER<br>VKLQEALSQLDFQWEKVNKMYKDRQGRFDRSVEKWRRFHY<br>DIKIFNQWLTEAEQFLRKTQIPENWEHAKYKWYLKELQDG<br>IGORQTVVRTLNATGEEIIQQSSKTDASILQEKLGSLNLR<br>WQEVCKQLSDRKKRLEE<br>L4. 1 linker connecting R16 and R17 is underlined. |
| L4.2 | 89 | QTLE |
| R24 | 13 | RLQELQEATDELDLKLRQAEVIKGSWQPVGDLLIDSLQDH<br>LEKVKALRGEIAPLKENVSHVNDLARQLTTLGIQLSPYNL<br>STLEDLNTRWKLLQVAVEDRVRQLHE |
| H4 | 14 | AHRDFGPASQHELSTSVQGPWERAISPNKVPYYINHETQT<br>TCWDHPKMTELYQSLADLNNVRFSAYRTAMKL |

TABLE 1-continued

| Microdystrophin segment amino acid sequences | | |
|---|---|---|
| Structure | SEQ ID | Sequence |
| | | WW domain is represented by a single underline (UniProtKB-P11532 aa 3055-3088) |
| Cysteine-rich domain (CR) | 15 | RRLQKALCLDLLSLSAACDALDQHNLKQNDQPMDILQIIN<br>CLTTIYDRLEQEHNNLVNVPLCVDMCLNWLLNVYDTGRTG<br>RIRVLSFKTGIISLCKAHLEDKYRYLFKQVASSTGFCDQR<br>RLGLLLHDSIQIPROLGEVASFGGSNIEPSVRSCFQFANN<br>KPEIEAALFLDWMRLEPQSMVWLPVLHRVAAAETAKHQAK<br>CNICKECPIIGFRYRSLKHFNYDICQSCFFSGRVAKGHKM<br>HYPMVEYC<br>ZZ domain is represented by a single underline (UniProtKB-P11532 aa 3307-3354) |
| CR short | 90 | AKHQAKCNICKECPIIGFRYRSLKHFNYDICQSCFFSGRV<br>AKGHKMHYPMVEYC |
| C-terminal Domain (CT) | 16 | TPTTSGEDVRDFAKVLKNKFRTKRYFAKHPRMGYLPVQTV<br>LEGDNMETPVTLINFWPVDSAPASSPQLSHDDTHSRIEHY<br>ASRLAEMENSNGSYLNDSISPNESIDDEHLLIQHYCQSLN<br>QDSPLSQPRSPAQILISLES*EERGELERILADLEEENRNL*<br>*QAEYDRLKQQHEHKGLSPLPS*PPEMMPTSPQSPR<br>Coiled-coil motif H1 is represented by a single underline; motif H2 is represented by a double underline; dystrobrevin-binding side is in italics. |
| Minimal/ truncated C-terminal Domain (CT1.5) | 83 | TPTTSGEDVRDFAKVLKNKFRTKRYFAKHPRMGYLPVQTV<br>LEGDNMETPVTLINFWPVDSAPASSPQLSHDDTHSRIEHY<br>ASRLAE*MENSNGSYLNDSISPNESIDDEHLLIQHYCQSLN*<br>*Q*DSPLSQPRSPAQILISLES<br>α1-syntrophin-binding site is in italics. |
| L4 | 17 | ETLE |
| L4 | 18 | LE |
| H2 | 19 | PSLTQTTVMETVTTVTTREQILVKHAQEELPPPPPQKKRQ<br>ITVD |
| Minimal alpha-syntrophin binding site | 84 | MENSNGSYLNDSISPNESIDDEHLLIQHYCQSLNQ |

The present disclosure also contemplates variants of these sequences so long as the function of each domain and linker is substantially maintained and/or the therapeutic efficacy of microdystrophin comprising such variants is substantially maintained. Functional activity includes (1) binding to one of, a combination of, or all of actin, β-dystroglycan, α1-syntrophin, ax-dystrobrevin, and nNOS; (2) improved muscle function in an animal model (for example, in the mdx mouse model described herein) or in human subjects; and/or (3) cardioprotective or improvement in cardiac muscle function in animal models or human patients. In particular, microdystrophin can comprise ABD consisting of SEQ ID NO: 3 or an amino acid sequence with at least 80%, at least 85%, at least 90%, at least 95%, at least 96%, at least 97%, at least 98%, or at least 99% sequence identity to SEQ ID NO: 3; H1 consisting of SEQ ID NO: 5 or an amino acid sequence with at least 80%, at least 85%, at least 90%, at least 95%, at least 96%, at least 97%, at least 98%, or at least 99% sequence identity to SEQ ID NO: 5; R1 consisting of SEQ ID NO: 7 or an amino acid sequence with at least 80%, at least 85%, at least 90%, at least 95%, at least 96%, at least 97%, at least 98%, or at least 99% sequence identity to SEQ ID NO: 7; R2 consisting of SEQ ID NO: 8 or an amino acid sequence with at least 80%, at least 85%, at least 90%, at least 95%, at least 96%, at least 97%, at least 98%, or at least 99% sequence identity to SEQ ID NO: 8; H2 consisting of SEQ ID NO: 19 or an amino acid sequence with at least 80%, at least 85%, at least 90%, at least 95%, at least 96%, at least 97%, at least 98%, or at least 99% sequence identity to SEQ ID NO: 19; H3 consisting of SEQ ID NO: 11 or an amino acid sequence with at least 80%, at least 85%, at least 90%, at least 95%, at least 96%, at least 97%, at least 98%, or at least 99% sequence identity to SEQ ID NO: 11; R24 consisting of SEQ ID NO: 13 or an amino acid sequence with at least 80%, at least 85%, at least 90%, at least 95%, at least 96%, at least 97%, at least 98%, or at least 99% sequence identity to SEQ ID NO: 13; H4 consisting of SEQ ID NO: 14 or an amino acid sequence with at least 80%, at least 85%, at least 90%, at least 95%, at least 96%, at least 97%, at least 98%, or at least 99% sequence identity to SEQ ID NO: 14; CR consisting of SEQ ID NO: 15 or 90 or an amino acid sequence with at least 80%, at least 85%, at least 90%, at least 95%, at least 96%, at least 97%, at least 98%, or at least 99% sequence identity to SEQ ID NO: 15 or 90; CT consisting of SEQ ID NO: 16 or 83 or an amino acid sequence with at least 80%, at least 85%, at least 90%, at least 95%, at least 96%, at least 97%, at least 98%, or at least 99% sequence identity to SEQ ID NO: 16 or 83, or CT comprising SEQ ID NO: 84. An alternative embodiment is the same as the foregoing except that the H3 domain is replaced by the H2 domain that consists of SEQ ID NO: 19 or a sequence with at least 50%, at least 60%, at least 70%, at least 75%, at least 80%, at least 85%, at least 90%, at least 95%, at least 98% or at least 99% identity to SEQ ID NO: 19, likewise encoding a microdystrophin that has functional activity. In addition to the foregoing, microdystrophin can comprise linkers in the locations described above that comprise or consist of sequences as follows: L1 consisting of SEQ ID NO: 4 or an amino acid sequence with at least 80%, at least 85%, at least 90%, at least 95%, at least 98%, or at least 99% sequence identity to SEQ ID NO: 4; L2 consisting of SEQ ID NO: 6 or an amino acid sequence with at least 80%, at least 85%, at least 90%, at least 95%, at least 98%, or at least 99% sequence identity to SEQ ID NO: 6; L3 consisting of SEQ ID NO: 9 or an amino acid sequence with at least 50% identity to SEQ ID NO: 9 or a variant with conservative substitutions for both L3 residues; and L4 consisting of SEQ ID NO: 12, 17, or 18 or an amino acid sequence with at least 50%, at least 75% sequence identity to SEQ ID NO: 12, 17, or 18.

In particular embodiments, microdystrophin can comprise ABD consisting of SEQ ID NO: 3 or an amino acid sequence with at least 80%, at least 85%, at least 90%, at least 95%, at least 96%, at least 97%, at least 98%, or at least 99% sequence identity to SEQ ID NO: 3; H1 consisting of SEQ ID NO: 5 or an amino acid sequence with at least 80%, at least 85%, at least 90%, at least 95%, at least 96%, at least 97%, at least 98%, or at least 99% sequence identity to SEQ ID NO: 5; R1 consisting of SEQ ID NO: 7 or an amino acid sequence with at least 80%, at least 85%, at least 90%, at least 95%, at least 96%, at least 97%, at least 98%, or at least 99% sequence identity to SEQ ID NO: 7; R2 consisting of SEQ ID NO: 8 or an amino acid sequence with at least 80%, at least 85%, at least 90%, at least 95%, at least 96%, at least 97%, at least 98%, or at least 99% sequence identity to SEQ ID NO: 8; R16 consisting of SEQ ID NO: 86 or an amino acid sequence with at least 80%, at least 85%, at least 90%, at least 95%, at least 96%, at least 97%, at least 98%, or at least 99% sequence identity to SEQ ID NO: 86; R17 consisting of SEQ ID NO: 87 or an amino acid sequence with at least 80%, at least 85%, at least 90%, at least 95%, at least 96%, at least 97%, at least 98%, or at least 99% sequence identity to SEQ ID NO: 87; R24 consisting of SEQ ID NO: 13 or an amino acid sequence with at least 80%, at least 85%, at least 90%, at least 95%, at least 96%, at least 97%, at least 98%, or at least 99% sequence identity to SEQ ID NO: 13; H4 consisting of SEQ ID NO: 14 or an amino acid sequence with at least 80%, at least 85%, at least 90%, at least 95%, at least 96%, at least 97%, at least 98%, or at least 99% sequence identity to SEQ ID NO: 14; CR consisting of SEQ ID NO: 15 or 90 or an amino acid sequence with at least 80%, at least 85%, at least 90%, at least 95%, at least 96%, at least 97%, at least 98%, or at least 99% sequence identity to SEQ ID NO: 15 or 90; CT consisting of SEQ ID NO: 16 or 83 or an amino acid sequence with at least 80%, at least 85%, at least 90%, at least 95%, at least 96%, at least 97%, at least 98%, or at least 99% sequence identity to SEQ ID NO: 16 or 83, or CT comprising SEQ ID NO: 84. In addition to the foregoing, microdystrophin can comprise linkers in the locations described above that comprise or consist of sequences as follows: L1 consisting of SEQ ID NO: 4 or an amino acid sequence with at least 80%, at least 85%, at least 90%, at least 95%, at least 98%, or at least 99% sequence identity to SEQ ID NO: 4; L2 consisting of SEQ ID NO: 6 or an amino acid sequence with at least 80%, at least 85%, at least 90%, at least 95%, at least 98%, or at least 99% sequence identity to SEQ ID NO: 6; L3 consisting of SEQ ID NO: 9 or an amino acid sequence with at least 50% identity to SEQ ID NO: 9 or a variant with conservative substitutions for both L3 residues; L4.1 consisting of SEQ ID NO: 110 or an amino acid sequence with at least 50%, at least 75% sequence identity to SEQ ID NO: 110; and L4.2 consisting of SEQ ID NO: 89 or an amino acid sequence with at least 50%, at least 75% sequence identity to SEQ ID NO: 89.

Table 2 provides the amino acid sequences of the microdystrophin embodiments in accordance with the present disclosure. It is also contemplated that other embodiments are substituted variant of microdystrophin as defined by SEQ ID NOs: 1, 2, 79, 91, 92, or 93. For example, conservative substitutions can be made to SEQ ID NOs: 1, 2, 79, 91, 92, or 93 and substantially maintain its functional activity. In embodiments, microdystrophin may have at least 60%, at least 70%, at least 80%, at least 85%, at least 90%, at least 95%, at least 96%, at least 97%, at least 98%, or at least 99% sequence identity to the amino acid sequence of SEQ ID NOs: 1, 2, 79, 91, 92, or 93 and maintain functional microdystrophin activity, as determined, for example, by one or more of the in vitro assays or in vivo assays in animal models disclosed in Section 5.4, infra.

TABLE 2

Amino acid sequences of RGX-DYS proteins

| Structure | SEQ ID NO | Amino Acid Sequence |
| --- | --- | --- |
| DYS1,<br>DYS2,<br>and<br>DYS4 | 1 | MLWWEEVEDCYEREDVQKKTFTKWVNAQFSKFGKQHIENLFS<br>DLQDGRRLLDLLEGLTGQKLPKEKGSTRVHALNNVNKALRVL<br>QNNNVDLVNIGSTDIVDGNHKLTLGLIWNIILHWQVKNVMKN<br>IMAGLQQTNSEKILLSWVRQSTRNYPQVNVINFTTSWSDGLA<br>LNALIHSHRPDLFDWNSVVCQQSATORLEHAFNIARYQLGIE<br>KLLDPEDVDTTYPDKKSILMYITSLFQVLPQQVSIEAIQEVE<br>MLPRPPKVTKEEHFQLHHQMHYSQQITVSLAQGYERTSSPKP<br>RFKSYAYTQAAYVTTSDPTRSPFPSQHLEAPEDKSFGSSLME<br>SEVNLDRYQTALEEVLSWLLSAEDTLQAQGEISNDVEVVKDQ<br>FHTHEGYMMDLTAHQGRVGNILQLGSKLIGTGKLSEDEETEV<br>QEQMNLLNSRWECLRVASMEKQSNLHRVLMDLQNQKLKELND<br>WLTKTEERTRKMEEEPLGPDLEDLKRQVQQHKVLQEDLEQEQ<br>VRVNSLTHMVVVVDESSGDHATAALEEQLKVLGDRWANICRW<br>TEDRWVLLQDILLKWQRLTEEQCLFSAWLSEKEDAVNKIHTT<br>GFKDQNEMLSSLQKLAVLKADLEKKKQSMGKLYSLKQDLLST<br>LKNKSVTQKTEAWLDNFARCWDNLVQKLEKSTAQISQQPDLA |

TABLE 2-continued

Amino acid sequences of RGX-DYS proteins

| Structure | SEQ ID NO | Amino Acid Sequence |
|---|---|---|
| | | PGLTTIGASPTQTVTLVTQPVVTKETAISKLEMPSSLMLEVP<br>TLERLQELQEATDELDLKLRQAEVIKGSWQPVGDLLIDSLQD<br>HLEKVKALRGEIAPLKENVSHVNDLARQLTTLGIQLSPYNLS<br>TLEDLNTRWKLLQVAVEDRVRQLHEAHRDFGPASQHFLSTSV<br>QGPWERAISPNKVPYYINHETQTTCWDHPKMTELYQSLADLN<br>NVRFSAYRTAMKLRRLQKALCLDLLSLSAACDALDQHNLKQN<br>DQPMDILQIINCLTTIYDRLEQEHNNLVNVPLCVDMCLNWLL<br>NVYDTGRTGRIRVLSFKTGIISLCKAHLEDKYRYLFKQVASS<br>TGFCDQRRLGLLLHDSIQIPRQLGEVASFGGSNIEPSVRSCF<br>QFANNKPEIEAALFLDWMRLEPQSMVWLPVLHRVAAAETAKH<br>QAKCNICKECPIIGFRYRSLKHFNYDICQSCFFSGRVAKGHK<br>MHYPMVEYCTPTTSGEDVRDFAKVLKNKFRTKRYFAKHPRMG<br>YLPVQTVLEGDNMETPVTLINFWPVDSAPASSPQLSHDDTHS<br>RIEHYASRLAEMENSNGSYLNDSISPNESIDDEHLLIQHYCQ<br>SLNQDSPLSQPRSPAQILISLESEERGELERILADLEEENRN<br>LQAEYDRLKQQHEHKGLSPLPSPPEMMPTSPQSPR |
| DYS3 | 2 | MLWWEEVEDCYEREDVQKKTFTKWVNAQFSKFGKQHIENLFS<br>DLQDGRRLLDLLEGLTGQKLPKEKGSTRVHALNNVNKALRVL<br>QNNNVDLVNIGSTDIVDGNHKLTLGLIWNIILHWQVKNVMKN<br>IMAGLQQTNSEKILLSWVRQSTRNYPQVNVINFTTSWSDGLA<br>LNALIHSHRPDLFDWNSVVCQQSATQRLEHAFNIARYQLGIE<br>KLLDPEDVDTTYPDKKSILMYITSLFQVLPQQVSIEAIQEVE<br>MLPRPPKVTKEEHFQLHHQMHYSQQITVSLAQGYERTSSPKP<br>RFKSYAYTQAAYVTTSDPTRSPFPSQHLEAPEDKSFGSSLME<br>SEVNLDRYQTALEEVLSWLLSAEDTLQAQGEISNDVEVVKDQ<br>FHTHEGYMMDLTAHQGRVGNILQLGSKLIGTGKLSEDEETEV<br>QEQMNLLNSRWECLRVASMEKQSNLHRVLMDLQNQKLKELND<br>WLTKTEERTRKMEEEPLGPDLEDLKRQVQQHKVLQEDLEQEQ<br>VRVNSLTHMVVVVDESSGDHATAALEEQLKVLGDRWANICRW<br>TEDRWVLLQDILLKWQRLTEEQCLFSAWLSEKEDAVNKIHTT<br>GFKDQNEMLSSLQKLAVLKADLEKKKQSMGKLYSLKQDLLST<br>LKNKSVTQKTEAWLDNFARCWDNLVQKLEKSTAQISQQPDLA<br>PGLTTIGASPTQTVTLVTQPVVTKETAISKLEMPSSLMLEVP<br>TLERLQELQEATDELDLKLRQAEVIKGSWQPVGDLLIDSLQD<br>HLEKVKALRGEIAPLKENVSHVNDLARQLTTLGIQLSPYNLS<br>TLEDLNTRWKLLQVAVEDRVRQLHEAHRDFGPASQHFLSTSV<br>QGPWERAISPNKVPYYINHETQTTCWDHPKMTELYQSLADLN<br>NVRFSAYRTAMKLRRLOKALCLDLLSLSAACDALDQHNLKQN<br>DQPMDILQIINCLTTIYDRLEQEHNNLVNVPLCVDMCLNWLL<br>NVYDTGRTGRIRVLSFKTGIISLCKAHLEDKYRYLFKQVASS<br>TGFCDQRRLGLLLHDSIQIPRQLGEVASFGGSNIEPSVRSCF<br>QFANNKPEIEAALFLDWMRLEPQSMVWLPVLHRVAAAETAKH<br>QAKCNICKECPIIGFRYRSLKHFNYDICQSCFFSGRVAKGHK<br>MHYPMVEYCTPTTSGEDVRDFAKVLKNKFRTKRYFAKHPRMG<br>YLPVQTVLEGDNMET |
| DYS5 | 79 | MLWWEEVEDCYEREDVQKKTFTKWVNAQFSKFGKQHIENLFS<br>DLQDGRRLLDLLEGLTGQKLPKEKGSTRVHALNNVNKALRVL<br>QNNNVDLVNIGSTDIVDGNHKLTLGLIWNIILHWQVKNVMKN<br>IMAGLQQTNSEKILLSWVRQSTRNYPQVNVINFTTSWSDGLA<br>LNALIHSHRPDLFDWNSVVCQQSATQRLEHAFNIARYQLGIE<br>KLLDPEDVDTTYPDKKSILMYITSLFQVLPQQVSIEAIQEVE<br>MLPRPPKVTKEEHFQLHHQMHYSQQITVSLAQGYERTSSPKP<br>RFKSYAYTQAAYVTTSDPTRSPFPSQHLEAPEDKSFGSSLME<br>SEVNLDRYQTALEEVLSWLLSAEDTLQAQGEISNDVEVVKDQ<br>FHTHEGYMMDLTAHQGRVGNILQLGSKLIGTGKLSEDEETEV<br>QEQMNLLNSRWECLRVASMEKQSNLHRVLMDLQNQKLKELND<br>WLTKTEERTRKMEEEPLGPDLEDLKRQVQQHKVLQEDLEQEQ<br>VRVNSLTHMVVVVDESSGDHATAALEEQLKVLGDRWANICRW<br>TEDRWVLLQDILLKWQRLTEEQCLFSAWLSEKEDAVNKIHTT<br>GFKDQNEMLSSLQKLAVLKADLEKKKQSMGKLYSLKQDLLST<br>LKNKSVTQKTEAWLDNFARCWDNLVQKLEKSTAQISQQPDLA<br>PGLTTIGASPTQTVTLVTQPVVTKETAISKLEMPSSLMLEVP<br>TLERLQELQEATDELDLKLRQAEVIKGSWQPVGDLLIDSLQD<br>HLEKVKALRGEIAPLKENVSHVNDLARQLTTLGIQLSPYNLS<br>TLEDLNTRWKLLQVAVEDRVRQLHEAHRDFGPASQHFLSTSV<br>QGPWERAISPNKVPYYINHETQTTCWDHPKMTELYQSLADLN<br>NVRFSAYRTAMKLRRLOKALCLDLLSLSAACDALDQHNLKQN<br>DQPMDILQIINCLTTIYDRLEQEHNNLVNVPLCVDMCLNWLL<br>NVYDTGRTGRIRVLSFKTGIISLCKAHLEDKYRYLFKQVASS<br>TGFCDQRRLGLLLHDSIQIPRQLGEVASFGGSNIEPSVRSCF<br>QFANNKPEIEAALFLDWMRLEPQSMVWLPVLHRVAAAETAKH<br>QAKCNICKECPIIGFRYRSLKHFNYDICQSCFFSGRVAKGHK<br>MHYPMVEYCTPTTSGEDVRDFAKVLKNKFRTKRYFAKHPRMG<br>YLPVQTVLEGDNMETPVTLINFWPVDSAPASSPQLSHDDTHS |

TABLE 2-continued

Amino acid sequences of RGX-DYS proteins

| Structure | SEQ ID NO | Amino Acid Sequence |
| --- | --- | --- |
| | | RIEHYASRLAEMENSNGSYLNDSISPNESIDDEHLLIQHYCQ SLNQDSPLSQPRSPAQILISLES |
| DYS6 | 91 | MLWWEEVEDCYEREDVQKKTFTKWVNAQFSKFGKQHIENLFS DLQDGRRLLDLLEGLTGQKLPKEKGSTRVHALNNVNKALRVL QNNNVDLVNIGSTDIVDGNHKLTLGLIWNIILHWQVKNVMKN IMAGLQQTNSEKILLSWVRQSTRNYPQVNVINFTTSWSDGLA LNALIHSHRPDLFDWNSVVCQQSATQRLEHAFNIARYQLGIE KLLDPEDVDTTYPDKKSILMYITSLFQVLPQQVSIEAIQEVE MLPRPPKVTKEEHFQLHHQMHYSQQITVSLAQGYERTSSPKP RFKSYAYTQAAYVTTSDPTRSPFPSQHLEAPEDKSFGSSLME SEVNLDRYQTALEEVLSWLLSAEDTLQAQGEISNDVEVVKDQ FHTHEGYMMDLTAHQGRVGNILQLGSKLIGTGKLSEDEETEV QEQMNLLNSRWECLRVASMEKQSNLHRVLMDLQNQKLKELND WLTKTEERTRKMEEEPLGPDLEDLKRQVQQHKVLQEDLEQEQ VRVNSLTHMVVVVDESSGDHATAALEEQLKVLGDRWANICRW TEDRWVLLQDILLKWQRLTEEQCLFSAWLSEKEDAVNKIHTT GFKDQNEMLSSLQKLAVLKADLEKKKQSMGKLYSLKQDLLST LKNKSVTQKTEAWLDNFARCWDNLVQKLEKSTAQISQQPDLA PGLTTIGASPTQTVTLVTQPVVTKETAISKLEMPSSLMLEVP TLERLQELQEATDELDLKLRQAEVIKGSWQPVGDLLIDSLQD HLEKVKALRGEIAPLKENVSHVNDLARQLTTLGIQLSPYNLS TLEDLNTRWKLLQVAVEDRVRQLHEAHRDFGPASQHFLSTSV QGPWERAISPNKVPYYINHETQTTCWDHPKMTELYQSLADLN NVRFSAYRTAMKLRRLOKALCLDLLSLSAACDALDQHNLKQN DQPMDILQIINCLTTIYDRLEQEHNNLVNVPLCVDMCLNWLL NVYDTGRTGRIRVLSFKTGIISLCKAHLEDKYRYLFKQVASS TGFCDQRRLGLLLHDSIQIPRQLGEVASFGGAKHQAKCNICK ECPIIGFRYRSLKHFNYDICQSCFFSGRVAKGHKMHYPMVEY CTPTTSGEDVRDFAKVLKNKFRTKRYFAKHPRMGYLPVQTVL EGDNMETPVTLINFWPVDSAPASSPQLSHDDTHSRIEHYASR LAEMENSNGSYLNDSISPNESIDDEHLLIQHYCQSLNQDSPL SQPRSPAQILISLESEERGELERILADLEEENRNLQAEYDRL KQQHEHKGLSPLPSPPEMMPTSPQSPR |
| DYS7 | 92 | MLWWEEVEDCYEREDVQKKTFTKWVNAQFSKFGKQHIENLFS DLQDGRRLLDLLEGLTGQKLPKEKGSTRVHALNNVNKALRVL QNNNVDLVNIGSTDIVDGNHKLTLGLIWNIILHWQVKNVMKN IMAGLQQTNSEKILLSWVRQSTRNYPQVNVINFTTSWSDGLA LNALIHSHRPDLFDWNSVVCQQSATQRLEHAFNIARYQLGIE KLLDPEDVDTTYPDKKSILMYITSLFQVLPQQVSIEAIQEVE MLPRPPKVTKEEHFQLHHQMHYSQQITVSLAQGYERTSSPKP RFKSYAYTQAAYVTTSDPTRSPFPSQHLEAPEDKSFGSSLME SEVNLDRYQTALEEVLSWLLSAEDTLQAQGEISNDVEVVKDQ FHTHEGYMMDLTAHQGRVGNILQLGSKLIGTGKLSEDEETEV QEQMNLLNSRWECLRVASMEKQSNLHRVLMDLQNQKLKELND WLTKTEERTRKMEEEPLGPDLEDLKRQVQQHKVLQEDLEQEQ VRVNSLTHMVVVVDESSGDHATAALEEQLKVLGDRWANICRW TEDRWVLLQDILEISYVPSTYLTEITHVSQALLEVEQLLNAP DLCAKDFEDLFKQEESLKNIKDSLQQSSGRIDIIHSKKTAAL QSATPVERVKLQEALSQLDFQWEKVNKMYKDRQGRFDRSVEK WRRFHYDIKIFNOWLTEAEQFLRKTQIPENWEHAKYKWYLKE LQDGIGQRQTVVRTLNATGEEIIQQSSKTDASILQEKLGSLN LRWQEVCKQLSDRKKRLEEQTLERLQELQEATDELDLKLRQA EVIKGSWQPVGDLLIDSLQDHLEKVKALRGEIAPLKENVSHV NDLARQLTTLGIQLSPYNLSTLEDLNTRWKLLQVAVEDRVRQ LHEAHRDFGPASQHFLSTSVQGPWERAISPNKVPYYINHETQ TTCWDHPKMTELYQSLADLNNVRFSAYRTAMKLRRLQKALCL DLLSLSAACDALDOHNLKQNDQPMDILQIINCLTTIYDRLEQ EHNNLVNVPLCVDMCLNWLLNVYDTGRTGRIRVLSFKTGIIS LCKAHLEDKYRYLFKQVASSTGFCDQRRLGLLLHDSIQIPRQ LGEVASFGGSNIEPSVRSCFQFANNKPEIEAALFLDWMRLEP QSMVWLPVLHRVAAAETAKHQAKCNICKECPIIGFRYRSLKH FNYDICQSCFFSGRVAKGHKMHYPMVEYCTPTTSGEDVRDFA KVLKNKFRTKRYFAKHPRMGYLPVQTVLEGDNMETPVTLINF WPVDSAPASSPQLSHDDTHSRIEHYASRLAEMENSNGSYLND SISPNESIDDEHLLIQHYCQSLNQDSPLSQPRSPAQILISLE S |
| DSY8 | 93 | MLWWEEVEDCYEREDVQKKTFTKWVNAQFSKFGKQHIENLFS DLQDGRRLLDLLEGLTGQKLPKEKGSTRVHALNNVNKALRVL QNNNVDLVNIGSTDIVDGNHKLTLGLIWNIILHWQVKNVMKN IMAGLQQTNSEKILLSWVRQSTRNYPQVNVINFTTSWSDGLA LNALIHSHRPDLFDWNSVVCQQSATQRLEHAFNIARYQLGIE KLLDPEDVDTTYPDKKSILMYITSLFQVLPQQVSIEAIQEVE MLPRPPKVTKEEHFQLHHQMHYSQQITVSLAQGYERTSSPKP |

TABLE 2-continued

| Amino acid sequences of RGX-DYS proteins | | |
|---|---|---|
| Structure | SEQ ID NO | Amino Acid Sequence |
| | | RFKSYAYTQAAYVTTSDPTRSPFPSQHLEAPEDKSFGSSLME<br>SEVNLDRYQTALEEVLSWLLSAEDTLQAQGEISNDVEVVKDQ<br>FHTHEGYMMDLTAHQGRVGNILQLGSKLIGTGKLSEDEETEV<br>QEQMNLLNSRWECLRVASMEKQSNLHRVLMDLQNQKLKELND<br>WLTKTEERTRKMEEEPLGPDLEDLKRQVQQHKVLQEDLEQEQ<br>VRVNSLTHMVVVVDESSGDHATAALEEQLKVLGDRWANICRW<br>TEDRWVLLQDILEISYVPSTYLTEITHVSQALLEVEQLLNAP<br>DLCAKDFEDLFKQEESLKNIKDSLQQSSGRIDIIHSKKTAAL<br>QSATPVERVKLQEALSQLDFQWEKVNKMYKDRQGRFDRSVEK<br>WRRFHYDIKIFNQWLTEAEQFLRKTQIPENWEHAKYKWYLKE<br>LQDGIGQRQTVVRTLNATGEEIIQQSSKTDASILQEKLGSLN<br>LRWQEVCKQLSDRKKRLEEQTLERLQELQEATDELDLKLRQA<br>EVIKGSWQPVGDLLIDSLQDHLEKVKALRGEIAPLKENVSHV<br>NDLARQLTTLGIQLSPYNLSTLEDLNTRWKLLQVAVEDRVRQ<br>LHEAHRDFGPASQHFLSTSVQGPWERAISPNKVPYYINHETQ<br>TTCWDHPKMTELYQSLADLNNVRFSAYRTAMKLRRLQKALCL<br>DLLSLSAACDALDOHNLKQNDQPMDILQIINCLTTIYDRLEQ<br>EHNNLVNVPLCVDMCLNWLLNVYDTGRTGRIRVLSFKTGIIS<br>LCKAHLEDKYRYLFKQVASSTGFCDQRRLGLLLHDSIQIPRQ<br>LGEVASFGGSNIEPSVRSCFQFANNKPEIEAALFLDWMRLEP<br>QSMVWLPVLHRVAAAETAKHQAKCNICKECPIIGFRYRSLKH<br>FNYDICQSCFFSGRVAKGHKMHYPMVEYCTPTTSGEDVRDFA<br>KVLKNKFRTKRYFAKHPRMGYLPVQTVLEGDNMET |

5.2.2 Nucleic Acid Compositions Encoding Microdystrophin

Another aspect of the present disclosure are nucleic acids comprising a nucleotide sequence encoding a microdystrophin as described herein. Such nucleic acids comprise nucleotide sequences that encode the microdystrophin that has the domains arranged N-terminal to C-terminal as follows: ABD1-H1-R1-R2-R3-H3-R24-H4-CR-CT, ABD1-H1-R1-R2-R3-H3-R24-H4-CR, ABD1-H1-R1-R2-R16-R17-R24-H4-CR-CT, or ABD1-H1-R1-R2-R16-R17-R24-H4-CR. The nucleotide sequence can be any nucleotide sequence that encodes the domains. The nucleotide sequence may be codon optimized and/or depleted of CpG islands for expression in the appropriate context. In particular embodiments, the nucleotide sequences encode a microdystrophin having an amino acid sequence of SEQ ID NO: 1, 2, 79, 91, 92, or 93. The nucleotide sequence can be any sequence that encodes the microdystrophin, including the microdystrophin of SEQ ID NO: 1, SEQ ID NO: 2, SEQ ID NO: 79, SEQ ID NO: 91, SEQ ID NO: 92, or SEQ ID NO: 93, which nucleotide sequence may vary due to the degeneracy of the code. Tables 3 and 4 provide exemplary nucleotide sequences that encode the DMD domains. Table 3 provides the wild type DMD nucleotide sequence for the component and Table 4 provides the nucleotide sequence for the DMD component used in the constructs herein, including sequences that have been codon optimized and/or CpG depleted of CpG islands as follows:

TABLE 3

| Dystrophin segment nucleotide sequences | | |
|---|---|---|
| Structure | SEQ ID | Nucleic Acid Sequence |
| ABD1 | 22 | ATGCTTTGGTGGGAAGAAGTAGAGGACTGTTATGAAAGAGA<br>AGATGTTCAAAAGAAAACATTCACAAAATGGGTAAATGCAC<br>AATTTTCTAAGTTTGGGAAGCAGCATATTGAGAACCTCTTC<br>AGTGACCTACAGGATGGGAGGCGCCTCCTAGACCTCCTCGA<br>AGGCCTGACAGGGCAAAAACTGCCAAAAGAAAAAGGATCCA<br>CAAGAGTTCATGCCCTGAACAATGTCAACAAGGCACTGCGG<br>GTTTTGCAGAACAATAATGTTGATTTAGTGAATATTGGAAG<br>TACTGACATCGTAGATGGAAATCATAAACTGACTCTTGGTT<br>TGATTTGGAATATAATCCTCCACTGGCAGGTCAAAAATGTA<br>ATGAAAAATATCATGGCTGGATTGCAACAAACCAACAGTGA<br>AAAGATTCTCCTGAGCTGGGTCCGACAATCAACTCGTAATT<br>ATCCACAGGTTAATGTAATCAACTTCACCACCAGCTGGTCT<br>GATGGCCTGGCTTTGAATGCTCTCATCCATAGTCATAGGCC<br>AGACCTATTTGACTGGAATAGTGTGGTTTGCCAGCAGTCAG<br>CCACACAACGACTGGAACATGCATTCAACATCGCCAGATAT<br>CAATTAGGCATAGAGAAACTACTCGATCCTGAAGATGTTGA<br>TACCACCTATCCAGATAAGAAGTCCATCTTAATGTACATCA<br>CATCACTCTTCCAAGTTTTGCCT |
| L1 | 23 | CAACAAGTGAGCATTGAAGCCATCCAGGAAGTGGAA |
| H1 | 24 | ATGTTGCCAAGGCCACCTAAAGTGACTAAAGAAGAACATTT<br>TCAGTTACATCATCAAATGCACTATTCTCAACAGATCACGG<br>TCAGTCTAGCACAGGGATATGAGAGAACTTCTTCCCCTAAG<br>CCTCGATTCAAGAGCTATGCCTACACACAGGCTGCTTATGT |

TABLE 3-continued

| Dystrophin segment nucleotide sequences | | |
|---|---|---|
| Structure | SEQ ID | Nucleic Acid Sequence |
| | | CACCACCTCTGACCCTACACGGAGCCCATTTCCTTCACAGC ATTTGGAAGCTCCTGAAGAC |
| L2 | 25 | AAGTCATTTGGCAGTTCATTGATGGAG |
| R1 | 26 | AGTGAAGTAAACCTGGACCGTTATCAAACAGCTTTAGAAGA AGTATTATCGTGGCTTCTTTCTGCTGAGGACACATTGCAAG CACAAGGAGAGATTTCTAATGATGTGGAAGTGGTGAAAGAC CAGTTTCATACTCATGAGGGGTACATGATGGATTTGACAGC CCATCAGGGCCGGGTTGGTAATATTCTACAATTGGGAAGTA AGCTGATTGGAACAGGAAAATTATCAGAAGATGAAGAAACT GAAGTACAAGAGCAGATGAATCTCCTAAATTCAAGATGGGA ATGCCTCAGGGTAGCTAGCATGGAAAAACAAAGCAATTTAC ATAGA |
| R2 | 27 | GTTTTAATGGATCTCCAGAATCAGAAACTGAAAGAGTTGAA TGACTGGCTAACAAAAACAGAAGAAAGAACAAGGAAAATGG AGGAAGAGCCTCTTGGACCTGATCTTGAAGACCTAAAACGC CAAGTACAACAACATAAGGTGCTTCAAGAAGATCTAGAACA AGAACAAGTCAGGGTCAATTCTCTCACTCACATGGTGGTGG TAGTTGATGAATCTAGTGGAGATCACGCAACTGCTGCTTTG GAAGAACAACTTAAGGTATTGGGAGATCGATGGGCAAACAT CTGTAGATGGACAGAAGACCGCTGGGTTCTTTTACAAGAC |
| L3 | 28 | ATCCTT |
| R3 | 29 | CTCAAATGGCAACGTCTTACTGAAGAACAGTGCCTTTTTAG TGCATGGCTTTCAGAAAAAGAAGATGCAGTGAACAAGATTC ACACAACTGGCTTTAAAGATCAAAATGAAATGTTATCAAGT CTTCAAAAACTGGCCGTTTTAAAAGCGGATCTAGAAAAGAA AAAGCAATCCATGGGCAAACTGTATTCACTCAAACAAGATC TTCTTTCAACACTGAAGAATAAGTCAGTGACCCAGAAGACG GAAGCATGGCTGGATAACTTTGCCCGGTGTTGGGATAATTT AGTCCAAAAACTTGAAAAGAGTACAGCACAGATTTCACAG |
| R16 | 94 | gaaatttcttatgtgccttctacttatttgactgaaatcac tcatgtctcacaagccctattagaagtggaacaacttctca atgctcctgacctctgtgctaaggactttgaagatctcttt aagcaagaggagtctctgaagaatataaaagatagtctaca acaaagctcaggtcggattgacattattcatagcaagaaga cagcagcattgcaaagtgcaacgcctgtggaaagggtgaag ctacaggaagctctctcccagcttgatttccaatgggaaaa agttaacaaaatgtacaaggaccgacaagggcgatttgaca ga |
| L4.1 | 107 | TCTGTT |
| R17 | 95 | gagaaatggcggcgttttcattatgatataaagatatttaa tcagtggctaacagaagctgaacagtttctcagaaagacac aaattcctgagaattgggaacatgctaaatacaaatggtat cttaaggaactccaggatggcattgggcagcggcaaactgt tgtcagaacattgaatgcaactggggaagaaataattcagc aatcctcaaaaacagatgccagtattctacaggaaaaattg ggaagcctgaatctgcggtggcaggaggtctgcaaacagct gtcagacagaaaaaagaggctagaa |
| R16-R17 | 96 | gaaatttcttatgtgccttctacttatttgactgaaatcac tcatgtctcacaagccctattagaagtggaacaacttctca atgctcctgacctctgtgctaaggactttgaagatctcttt aagcaagaggagtctctgaagaatataaaagatagtctaca acaaagctcaggtcggattgacattattcatagcaagaaga cagcagcattgcaaagtgcaacgcctgtggaaagggtgaag ctacaggaagctctctcccagcttgatttccaatgggaaaa agttaacaaaatgtacaaggaccgacaagggcgatttgaca gaTCTGTTgagaaatggcggcgttttcattatgatataaag atatttaatcagtggctaacagaagctgaacagtttctcag aaagacacaaattcctgagaattgggaacatgctaaataca aatggtatcttaaggaactccaggatggcattgggcagcgg caaactgttgtcagaacattgaatgcaactggggaagaaat aattcagcaatcctcaaaaacagatgccagtattctacagg aaaaattgggaagcctgaatctgcggtggcaggaggtctgc aaacagctgtcagacagaaaaaagaggctagaa |
| L4.2 | 108 | CAAACCCTTGAA |

TABLE 3-continued

| Dystrophin segment nucleotide sequences | | |
|---|---|---|
| Structure | SEQ ID | Nucleic Acid Sequence |
| H3 | 30 | CAGCCTGACCTAGCTCCTGGACTGACCACTATTGGAGCCTC TCCTACTCAGACTGTTACTCTGGTGACACAACCTGTGGTTA CTAAGGAAACTGCCATCTCCAAACTAGAAATGCCATCTTCC TTGATGTTGGAGGTACCT |
| L4 | 31 | ACCCTTGAA |
| R24 | 32 | AGACTCCAACTTCAAGAGGCCACGGATGAGCTGGACCTCAA GCTGCGCCAAGCTGAGGTGATCAAGGGATCCTGGCAGCCCG TGGGCGATCTCCTCATTGACTCTCTCCAAGATCACCTCGAG AAAGTCAAGGCACTTCGAGGAGAAATTGCGCCTCTGAAAGA GAACGTGAGCCACGTCAATGACCTTGCTCGCCAGCTTACCA CTTTGGGCATTCAGCTCTCACCGTATAACCTCAGCACTCTG GAAGACCTGAACACCAGATGGAAGCTTCTGCAGGTGGCCGT CGAGGACCGAGTCAGGCAGCTGCATGAA |
| H4 | 33 | GCCCACAGGGACTTTGGTCCAGCATCTCAGCACTTTCTTTC CACGTCTGTCCAGGGTCCCTGGGAGAGAGCCATCTCGCCAA ACAAAGTGCCCTACTATATCAACCACGAGACTCAAACAACT TGCTGGGACCATCCCAAAATGACAGAGCTCTACCAGTCTTT AGCTGACCTGAATAATGTCAGATTCTCAGCTTATAGGACTG CCATGAAACTC |
| Cysteine-rich domain (CR) | 34 | CGAAGACTGCAGAAGGCCCTTTGCTTGGATCTCTTGAGCCT GTCAGCTGCATGTGATGCCTTGGACCAGCACAACCTCAAGC AAAATGACCAGCCCATGGATATCCTGCAGATTATTAATTGT TTGACCACTATTTATGACCGCCTGGAGCAAGAGCACAACAA TTTGGTCAACGTCCCTCTCTGCGTGGATATGTGTCTGAACT GGCTGCTGAATGTTTATGATACGGGACGAACAGGGAGGATC CGTGTCCTGTCTTTTAAAACTGGCATCATTTCCCTGTGTAA AGCACATTTGGAAGACAAGTACAGATACCTTTTCAAGCAAG TGGCAAGTTCAACAGGATTTTGTGACCAGCGCAGGCTGGGC CTCCTTCTGCATGATTCTATCCAAATTCCAAGACAGTTGGG TGAAGTTGCATCCTTTGGGGGCAGTAACATTGAGCCAAGTG TCCGGAGCTGCTTCCAATTTGCTAATAATAAGCCAGAGATC GAAGCGGCCCTCTTCCTAGACTGGATGAGACTGGAACCCCA GTCCATGGTGTGGCTGCCCGTCCTGCACAGAGTGGCTGCTG CAGAAACTGCCAAGCATCAGGCCAAATGTAACATCTGCAAA GAGTGTCCAATCATTGGATTCAGGTACAGGAGTCTAAAGCA CTTTAATTATGACATCTGCCAAAGCTGCTTTTTTTCTGGTC GAGTTGCAAAAGGCCATAAAATGCACTATCCCATGGTGGAA TATTGC |
| CR short | 109 | gccaagcatcaggccaaatgtaacatctgcaaagagtgtcc aatcattggattcaggtacaggagtctaaagcactttaatt atgacatctgccaaagctgctttttttctggtcgagttgca aaaggccataaaatgcactatcccatggtggaatattgc |
| C-terminal (CT) Domain | 35 | ACTCCGACTACATCAGGAGAAGATGTTCGAGACTTTGCCAA GGTACTAAAAAACAAATTTCGAACCAAAAGGTATTTTGCGA AGCATCCCCGAATGGGCTACCTGCCAGTGCAGACTGTCTTA GAGGGGGACAACATGGAAACTCCCGTTACTCTGATCAACTT CTGGCCAGTAGATTCTGCGCCTGCCTCGTCCCCTCAGCTTT CACACGATGATACTCATTCACGCATTGAACATTATGCTAGC AGGCTAGCAGAAATGGAAAACAGCAATGGATCTTATCTAAA TGATAGCATCTCTCCTAATGAGAGCATAGATGATGAACATT TGTTAATCCAGCATTACTGCCAAAGTTTGAACCAGGACTCC CCCCTGAGCCAGCCTCGTAGTCCTGCCCAGATCTTGATTTC CTTAGAGAGTGAGGAAAGAGGGGAGCTAGAGAGAATCCTAG CAGATCTTGAGGAAGAAAACAGGAATCTGCAAGCAGAATAT GACCGTCTAAAGCAGCAGCACGAACATAAAGGCCTGTCCCC ACTGCCGTCCCCTCCTGAAATGATGCCCACCTCTCCCCAGA GTCCCCGG |
| L4 | 36 | GAGACCCTTGAA |
| L4 | 37 | CTTGAA |
| H2 | 38 | CCATCACTAACACAGACAACTGTAATGGAAACAGTAACTAC GGTGACCACAAGGGAACAGATCCTGGTAAAGCATGCTCAAG AGGAACTTCCACCACCACCTCCCCAAAAGAAGAGGCAGATT ACTGTGGAT |

TABLE 4

| RGX-DYS segment nucleotide sequences | | |
|---|---|---|
| Structure | SEQ ID | Nucleic Acid Sequence |
| ABD | 57 | ATGCTTTGGTGGGAAGAGGTGGAAGATTGCTATGAGAGGG<br>AAGATGTGCAGAAGAAAACCTTCACCAAATGGGTCAATGC<br>CCAGTTCAGCAAGTTTGGCAAGCAGCACATTGAGAACCTG<br>TTCAGTGACCTGCAGGATGGCAGAAGGCTGCTGGATCTGC<br>TGGAAGGCCTGACAGGCCAGAAGCTGCCTAAAGAGAAGGG<br>CAGCACAAGAGTGCATGCCCTGAACAATGTGAACAAGGCC<br>CTGAGAGTGCTGCAGAACAACAATGTGGACCTGGTCAATA<br>TTGGCAGCACAGACATTGTGGATGGCAACCACAAGCTGAC<br>CCTGGGCCTGATCTGGAACATCATCCTGCACTGGCAAGTG<br>AAGAATGTGATGAAGAACATCATGGCTGGCCTGCAGCAGA<br>CCAACTCTGAGAAGATCCTGCTGAGCTGGGTCAGACAGAG<br>CACCAGAAACTACCCTCAAGTGAATGTGATCAACTTCACC<br>ACCTCTTGGAGTGATGGACTGGCCCTGAATGCCCTGATCC<br>ACAGCCACAGACCTGACCTGTTTGACTGGAACTCTGTTGT<br>GTGCCAGCAGTCTGCCACACAGAGACTGGAACATGCCTTC<br>AACATTGCCAGATACCAGCTGGGAATTGAGAAACTGCTGG<br>ACCCTGAGGATGTGGACACCACCTATCCTGACAAGAAATC<br>CATCCTCATGTACATCACCAGCCTGTTCCAGGTGCTGCCC |
| L1 | 58 | CAGCAAGTGTCCATTGAGGCCATTCAAGAGGTTGAG |
| H1 | 59 | ATGCTGCCCAGACCTCCTAAAGTGACCAAAGAGGAACACT<br>TCCAGCTGCACCACCAGATGCACTACTCTCAGCAGATCAC<br>AGTGTCTCTGGCCCAGGGATATGAGAGAACAAGCAGCCCC<br>AAGCCTAGGTTCAAGAGCTATGCCTACACACAGGCTGCCT<br>ATGTGACCACATCTGACCCCACAAGAAGCCCATTTCCAAG<br>CCAGCATCTGGAAGCCCCTGAGGAC |
| L2 | 60 | AAGAGCTTTGGCAGCAGCCTGATGGAA |
| R1 | 61 | TCTGAAGTGAACCTGGATAGATACCAGACAGCCCTGGAAG<br>AAGTGCTGTCCTGGCTGCTGTCTGCTGAGGATACACTGCA<br>GGCTCAGGGTGAAATCAGCAATGATGTGGAAGTGGTCAAG<br>GACCAGTTTCACACCCATGAGGGCTACATGATGGACCTGA<br>CAGCCCACCAGGGCAGAGTGGGAAATATCCTGCAGCTGGG<br>CTCCAAGCTGATTGGCACAGGCAAGCTGTCTGAGGATGAA<br>GAGACAGAGGTGCAAGAGCAGATGAACCTGCTGAACAGCA<br>GATGGGAGTGTCTGAGAGTGGCCAGCATGGAAAAGCAGAG<br>CAACCTGCACAGA |
| R2 | 62 | GTGCTCATGGACCTGCAGAATCAGAAACTGAAAGAACTGA<br>ATGACTGGCTGACCAAGACAGAAGAAAGGACTAGGAAGAT<br>GGAAGAGGAACCTCTGGGACCAGACCTGGAAGATCTGAAA<br>AGACAGGTGCAGCAGCATAAGGTGCTGCAAGAGGACCTTG<br>AGCAAGAGCAAGTCAGAGTGAACAGCCTGACACACATGGT<br>GGTGGTTGTGGATGAGTCCTCTGGGGATCATGCCACAGCT<br>GCTCTGGAAGAACAGCTGAAGGTGCTGGGAGACAGATGGG<br>CCAACATCTGTAGGTGGACAGAGGATAGATGGGTGCTGCT<br>CCAGGAC |
| L3 | 63 | ATTCTG |
| R3 | 64 | CTGAAGTGGCAGAGACTGACAGAGGAACAGTGCCTGTTTT<br>CTGCCTGGCTCTCTGAGAAAGAGGATGCTGTCAACAAGAT<br>CCATACCACAGGCTTCAAGGATCAGAATGAGATGCTCAGC<br>TCCCTGCAGAAACTGGCTGTGCTGAAGGCTGACCTGGAAA<br>AGAAAAAGCAGTCCATGGGCAAGCTCTACAGCCTGAAGCA<br>GGACCTGCTGTCTACCCTGAAGAACAAGTCTGTGACCCAG<br>AAAACTGAGGCCTGGCTGGACAACTTTGCTAGATGCTGGG<br>ACAACCTGGTGCAGAAGCTGGAAAAGTCTACAGCCCAGAT<br>CAGCCAG |
| H3 | 65 | CAACCTGATCTTGCCCCTGGCCTGACCACAATTGGAGCCT<br>CTCCAACACAGACTGTGACCCTGGTTACCCAGCCAGTGGT<br>CACCAAAGAGACAGCCATCAGCAAACTGGAAATGCCCAGC<br>TCTCTGATGCTGGAAGTCCCC |
| L4 | 66 | ACACTGGAA |
| R16 | 97 | GAGATCAGCTATGTGCCCAGCACCTACCTGACAGAGATCA<br>CCCATGTGTCTCAGGCCCTGCTGGAAGTGGAACAGCTGCT<br>GAATGCCCCTGACCTGTGTGCCAAGGACTTTGAGGACCTG<br>TTCAAGCAAGAGGAAAGCCTGAAGAACATCAAGGACAGCC<br>TGCAGCAGTCCTCTGGCAGAATTGACATCATCCACAGCAA<br>GAAAACAGCTGCCCTGCAGTCTGCCACACCTGTGGAAAGA<br>GTGAAGCTGCAAGAGGCCCTGAGCCAGCTGGACTTCCAGT |

TABLE 4-continued

RGX-DYS segment nucleotide sequences

| Structure | SEQ ID | Nucleic Acid Sequence |
|---|---|---|
| | | GGGAGAAAGTGAACAAGATGTACAAGGACAGGCAGGGCAG ATTTGATAGA |
| L4.1 | 125 | AGTGTG |
| R17 | 98 | GAAAAGTGGAGAAGGTTCCACTATGACATCAAGATCTTCA ACCAGTGGCTGACAGAGGCTGAGCAGTTCCTGAGAAAGAC ACAGATCCCTGAGAACTGGGAGCATGCCAAGTACAAGTGG TATCTGAAAGAACTGCAGGATGGCATTGGCCAGAGACAGA CAGTTGTCAGAACCCTGAATGCCACAGGGGAAGAGATCAT CCAGCAGAGCAGCAAGACAGATGCCAGCATCCTGCAAGAG AAGCTGGGCAGCCTGAACCTGAGATGGCAAGAAGTGTGCA AGCAGCTGTCTGACAGAAAGAAGAGGCTGGAAGAA |
| R16-R17 | 99 | GAGATCAGCTATGTGCCCAGCACCTACCTGACAGAGATCA CCCATGTGTCTCAGGCCCTGCTGGAAGTGGAACAGCTGCT GAATGCCCCTGACCTGTGTGCCAAGGACTTTGAGGACCTG TTCAAGCAAGAGGAAAGCCTGAAGAACATCAAGGACAGCC TGCAGCAGTCCTCTGGCAGAATTGACATCATCCACAGCAA GAAAACAGCTGCCCTGCAGTCTGCCACACCTGTGGAAAGA GTGAAGCTGCAAGAGGCCCTGAGCCAGCTGGACTTCCAGT GGGAGAAAGTGAACAAGATGTACAAGGACAGGCAGGGCAG ATTTGATAGAAGTGTGGAAAAGTGGAGAAGGTTCCACTAT GACATCAAGATCTTCAACCAGTGGCTGACAGAGGCTGAGC AGTTCCTGAGAAAGACACAGATCCCTGAGAACTGGGAGCA TGCCAAGTACAAGTGGTATCTGAAAGAACTGCAGGATGGC ATTGGCCAGAGACAGACAGTTGTCAGAACCCTGAATGCCA CAGGGGAAGAGATCATCCAGCAGAGCAGCAAGACAGATGC CAGCATCCTGCAAGAGAAGCTGGGCAGCCTGAACCTGAGA TGGCAAGAAGTGTGCAAGCAGCTGTCTGACAGAAAGAAGA GGCTGGAAGAA |
| L4.2 | 126 | CAGACACTGGAA |
| R24 | 67 | AGGCTGCAAGAACTTCAAGAGGCCACAGATGAGCTGGACC TGAAGCTGAGACAGGCTGAAGTGATCAAAGGCAGCTGGCA GCCAGTTGGGGACCTGCTCATTGATAGCCTGCAGGACCAT CTGGAAAAAGTGAAAGCCCTGAGGGGAGAGATTGCCCCTC TGAAAGAAAATGTGTCCCATGTGAATGACCTGGCCAGACA GCTGACCACACTGGGAATCCAGCTGAGCCCCTACAACCTG AGCACCCTTGAGGACCTGAACACCAGGTGGAAGCTCCTCC AGGTGGCAGTGGAAGATAGAGTCAGGCAGCTGCATGAG |
| H4 | 68 | GCCCACAGAGATTTTGGACCAGCCAGCCAGCACTTTCTGT CTACCTCTGTGCAAGGCCCCTGGGAGAGAGCTATCTCTCC TAACAAGGTGCCCTACTACATCAACCATGAGACACAGACC ACCTGTTGGGATCACCCCAAGATGACAGAGCTGTACCAGA GTCTGGCAGACCTCAACAATGTCAGATTCAGTGCCTACAG GACTGCCATGAAGCTC |
| Cysteine-rich domain (CR) | 69 | AGAAGGCTCCAGAAAGCTCTGTGCCTGGACCTGCTTTCCC TGAGTGCAGCTTGTGATGCCCTGGACCAGCACAATCTGAA GCAGAATGACCAGCCTATGGACATCCTCCAGATCATCAAC TGCCTCACCACCATCTATGATAGGCTGGAACAAGAGCACA ACAATCTGGTCAATGTGCCCCTGTGTGTGGACATGTGCCT GAATTGGCTGCTGAATGTGTATGACACAGGCAGAACAGGC AGGATCAGAGTCCTGTCCTTCAAGACAGGCATCATCTCCC TGTGCAAAGCCCACTTGGAGGACAAGTACAGATACCTGTT CAAGCAAGTGGCCTCCAGCACAGGCTTTTGTGACCAGAGA AGGCTGGGCCTGCTCCTGCATGACAGCATTCAGATCCCTA GACAGCTGGGAGAAGTGGCTTCCTTTGGAGGCAGCAATAT TGAGCCATCAGTCAGGTCCTGTTTTCAGTTTGCCAACAAC AAGCCTGAGATTGAGGCTGCCCTGTTCCTGGACTGGATGA GACTTGAGCCTCAGAGCATGGTCTGGCTGCCTGTGCTTCA TAGAGTGGCTGCTGCTGAGACTGCCAAGCACCAGGCCAAG TGCAACATCTGCAAAGAGTGCCCCATCATTGGCTTCAGAT ACAGATCCCTGAAGCACTTCAACTATGATATCTGCCAGAG CTGCTTCTTTAGTGGCAGGGTTGCCAAGGGCCACAAAATG CACTACCCCATGGTGGAATACTGC |
| CR short (DYS6) | 100 | GCCAAGCACCAGGCCAAGTGCAACATCTGCAAAGAGTGCC CCATCATTGGCTTCAGATACAGATCCCTGAAGCACTTCAA CTATGATATCTGCCAGAGCTGCTTCTTTAGTGGCAGGGTT GCCAAGGGCCACAAAATGCACTACCCCATGGTGGAATACT GC |

TABLE 4-continued

RGX-DYS segment nucleotide sequences

| Structure | SEQ ID | Nucleic Acid Sequence |
|---|---|---|
| C-terminal (CT) Domain (DYS1, DYS2, DYS4, DYS6) | 70 | ACCCCAACAACCTCTGGGGAAGATGTTAGAGACTTTGCCA AGGTGCTGAAAAACAAGTTCAGGACCAAGAGATACTTTGC TAAGCACCCCAGAATGGGCTACCTGCCTGTCCAGACAGTG CTTGAGGGTGACAACATGGAAACCCCTGTGACACTGATCA ATTTCTGGCCAGTGGACTCTGCCCCTGCCTCAAGTCCACA GCTGTCCCATGATGACACCCACAGCAGAATTGAGCACTAT GCCTCCAGACTGGCAGAGATGGAAAACAGCAATGGCAGCT ACCTGAATGATAGCATCAGCCCCAATGAGAGCATTGATGA TGAGCATCTGCTGATCCAGCACTACTGTCAGTCCCTGAAC CAGGACTCTCCACTGAGCCAGCCTAGAAGCCCTGCTCAGA TCCTGATCAGCCTTGAGTCTGAGGAAAGGGGAGAGCTGGA AAGAATCCTGGCAGATCTTGAGGAAGAGAACAGAAACCTG CAGGCAGAGTATGACAGGCTCAAACAGCAGCATGAGCACA AGGGACTGAGCCCTCTGCCTTCTCCTCCTGAAATGATGCC CACCTCTCCACAGTCTCCAAGGTGATGA (stop codons underlined) |
| Minimal C-terminal (CT1.5) Domain (DYS5, DYS7) | 80 | ACCCCAACAACCTCTGGGGAAGATGTTAGAGACTTTGCCA AGGTGCTGAAAAACAAGTTCAGGACCAAGAGATACTTTGC TAAGCACCCCAGAATGGGCTACCTGCCTGTCCAGACAGTG CTTGAGGGTGACAACATGGAAACCCCTGTGACACTGATCA ATTTCTGGCCAGTGGACTCTGCCCCTGCCTCAAGTCCACA GCTGTCCCATGATGACACCCACAGCAGAATTGAGCACTAT GCCTCCAGACTGGCAGAGATGGAAAACAGCAATGGCAGCT ACCTGAATGATAGCATCAGCCCCAATGAGAGCATTGATGA TGAGCATCTGCTGATCCAGCACTACTGTCAGTCCCTGAAC CAGGACTCTCCACTGAGCCAGCCTAGAAGCCCTGCTCAGA TCCTGATCAGCCTTGAGTCTTGATGA (stop codons underlined) |
| L4 | 71 | GAAACACTGGAA or GAGACACTGGAA |
| L4 | 72 | CTGGAA |

In some embodiments, such compositions comprise a nucleic acid sequence encoding ABD1 that consists of SEQ ID NO: 22 or a sequence with at least 75%, at least 80%, at least 85%, at least 90%, at least 95%, at least 98% or at least 99% identity to SEQ ID NO: 22; a nucleic acid sequence encoding H1 that consists of SEQ ID NO: 24 or a sequence with at least 75%, at least 80%, at least 85%, at least 90%, at least 95%, at least 98% or at least 99% identity to SEQ ID NO: 24; a nucleic acid sequence encoding R1 that consists of SEQ ID NO: 26 or a sequence with at least 75%, at least 80%, at least 85%, at least 90%, at least 95%, at least 98% or at least 99% identity to SEQ ID NO: 26; a nucleic acid sequence encoding R2 that consists of SEQ ID NO: 27 or a sequence with at least 75%, at least 80%, at least 85%, at least 90%, at least 95%, at least 98% or at least 99% identity to SEQ ID NO: 27; a nucleic acid sequence encoding R3 that consists of SEQ ID NO: 29 or a sequence with at least 75%, at least 80%, at least 85%, at least 90%, at least 95%, at least 98% or at least 99% identity to SEQ ID NO: 29; a nucleic acid sequence encoding H3 that consists of SEQ ID NO: 30 or a sequence with at least 75%, at least 80%, at least 85%, at least 90%, at least 95%, at least 98% or at least 99% identity to SEQ ID NO: 30; a nucleic acid sequence encoding R24 that consists of SEQ ID NO: 32 or a sequence with at least 75%, at least 80%, at least 85%, at least 90%, at least 95%, at least 98% or at least 99% identity to SEQ ID NO: 32; a nucleic acid sequence encoding H4 that consists of SEQ ID NO: 33 or a sequence with at least 75%, at least 80%, at least 85%, at least 90%, at least 95%, at least 98%, or at least 99% identity to SEQ ID NO: 33; a nucleic acid sequence encoding CR that consists of SEQ ID NO: 34 or 109 or a sequence with at least 75%, at least 80%, at least 85%, at least 90%, at least 95%, at least 98% or at least 99% identity to SEQ ID NO: 34 or 109; and/or a nucleic acid sequence encoding CT that consists of SEQ ID NO: 35 or a sequence with at least 75%, at least 80%, at least 85%, at least 90%, at least 95%, at least 98% or at least 99% identity to SEQ ID NO: 35, encoding a microdystrophin that has functional activity. An alternative embodiment is the same as the foregoing except that the H3 nucleic acid sequence is replaced by a nucleic acid encoding H2 that consists of SEQ ID NO: 38 or a sequence with at least 50%, at least 60%, at least 70%, at least 75%, at least 80%, at least 85%, at least 90%, at least 95%, at least 98% or at least 99% identity to SEQ ID NO: 38, likewise encoding a microdystrophin that has functional activity.

In some embodiments, such compositions comprise a nucleic acid sequence encoding ABD1 that consists of SEQ ID NO: 22 or a sequence with at least 75%, at least 80%, at least 85%, at least 90%, at least 95%, at least 98% or at least 99% identity to SEQ ID NO: 22 and encodes for the ABD1 domain of SEQ ID NO: 3; a nucleic acid sequence encoding H1 that consists of SEQ ID NO: 24 or a sequence with at least 75%, at least 80%, at least 85%, at least 90%, at least 95%, at least 98% or at least 99% identity to SEQ ID NO: 24 and encodes for the H1 domain of SEQ ID NO: 5; a nucleic acid sequence encoding R1 that consists of SEQ ID NO: 26 or a sequence with at least 75%, at least 80%, at least 85%, at least 90%, at least 95%, at least 98% or at least 99% identity to SEQ ID NO: 26 and encodes for the R1 domain of SEQ ID NO: 7; a nucleic acid sequence encoding R2 that consists of SEQ ID NO: 27 or a sequence with at least 75%, at least 80%, at least 85%, at least 90%, at least 95%, at least 98% or at least 99% identity to SEQ ID NO: 27 and encodes for the R2 domain of SEQ ID NO: 8; a nucleic acid sequence encoding R3 that consists of SEQ ID NO: 29 or a sequence with at least 75%, at least 80%, at least 85%, at least 90%, at least 95%, at least 98% or at least 99% identity to SEQ ID NO: 29 and encodes for the R3 domain of SEQ ID NO: 10; a nucleic acid sequence encoding H3 that consists of SEQ ID NO: 30 or a sequence with at least 75%, at least 80%, at least 85%, at least 90%, at least 95%, at least 98% or at least 99% identity to SEQ ID NO: 30 and encodes for the H3 domain of SEQ ID NO: 11; a nucleic acid sequence encoding R24 that consists of SEQ ID NO: 32 or a sequence with at least 75%, at least 80%, at least 85%, at least 90%, at least 95%, at least 98% or at least 99% identity to SEQ ID NO: 32 and encodes for the R24 domain of SEQ ID NO: 13; a nucleic acid sequence encoding H4 that consists of SEQ ID NO: 33 or a sequence with at least 75%, at least 80%, at least 85%, at least 90%, at least 95%, at least 98%, or at least 99% identity to SEQ ID NO: 33 and encodes for the H4 domain of SEQ ID NO: 14; a nucleic acid sequence encoding CR that consists of SEQ ID NO: 34 or 109 or a sequence with at least 75%, at least 80%, at least 85%, at least 90%, at least 95%, at least 98% or at least 99% identity to SEQ ID NO: 34 or 109 and encodes for the CR domain of SEQ ID NO: 15 or 90; and/or a nucleic acid sequence encoding CT that consists of SEQ ID NO: 35 or 80 or a sequence with at least 75%, at least 80%, at least 85%, at least 90%, at least 95%, at least 98% or at least 99% identity to SEQ ID NO: 35 or 80 and encodes for the CT domain of SEQ ID NO: 16 or 83. An alternative embodiment is the same as the foregoing except that the H3 nucleic acid sequence is replaced by a nucleic acid encoding H2 that consists of SEQ ID NO: 38 or a sequence with at least 75%, at least 80%, at least 85%, at least 90%, at least 95%, at least 98% or at least 99% identity to SEQ ID NO: 38 and encodes the H2 domain of SEQ ID NO: 19.

In addition to the foregoing, the nucleic acid compositions can optionally comprise nucleotide sequences encoding linkers in the locations described above that comprise or consist of sequences as follows: a nucleic acid sequence encoding L1 consisting of SEQ ID NO: 23 or a sequence with at least 80%, at least 85%, at least 90%, at least 95%, at least 98%, or at least 99% sequence identity to SEQ ID NO: 23 (e.g. encoding the L1 domain of SEQ ID NO: 4); a nucleic acid sequence encoding L2 consisting of SEQ ID NO: 25 or sequence with at least 80%, at least 85%, at least 90%, at least 95%, at least 98%, or at least 99% sequence identity to SEQ ID NO: 25 (e.g. encoding the L2 domain of SEQ ID NO: 6); a nucleic acid sequence encoding L3 consisting of SEQ ID NO: 28 or a sequence with at least 50% identity to SEQ ID NO: 28, encoding the L3 domain of SEQ ID NO: 9 or a variant with conservative substitutions for both L3 residues; and a nucleic acid sequence encoding L4 consisting of SEQ ID NO: 31, 36, or 37 or a sequence with at least 50%, at least 75% sequence identity to SEQ ID NO: 31, 36, or 37 (e.g. encoding the L4 domain of SEQ ID NO: 12, 17, or 18 or a variant with conservative substitutions for any of the L4 residues).

In some embodiments, such compositions comprise a nucleic acid sequence encoding ABD1 that consists of SEQ ID NO: 22 or a sequence with at least 75%, at least 80%, at least 85%, at least 90%, at least 95%, at least 98% or at least 99% identity to SEQ ID NO: 22; a nucleic acid sequence encoding H1 that consists of SEQ ID NO: 24 or a sequence with at least 75%, at least 80%, at least 85%, at least 90%, at least 95%, at least 98% or at least 99% identity to SEQ ID NO: 24; a nucleic acid sequence encoding R1 that consists of SEQ ID NO: 26 or a sequence with at least 75%, at least 80%, at least 85%, at least 90%, at least 95%, at least 98% or at least 99% identity to SEQ ID NO: 26; a nucleic acid sequence encoding R2 that consists of SEQ ID NO: 27 or a sequence with at least 75%, at least 80%, at least 85%, at least 90%, at least 95%, at least 98% or at least 99% identity to SEQ ID NO: 27; a nucleic acid sequence encoding R16 that consists of SEQ ID NO: 94 or a sequence with at least 75%, at least 80%, at least 85%, at least 90%, at least 95%, at least 98% or at least 99% identity to SEQ ID NO: 94; a nucleic acid sequence encoding R17 that consists of SEQ ID NO: 95 or a sequence with at least 75%, at least 80%, at least 85%, at least 90%, at least 95%, at least 98% or at least 99% identity to SEQ ID NO: 95; a nucleic acid sequence encoding R24 that consists of SEQ ID NO: 32 or a sequence with at least 75%, at least 80%, at least 85%, at least 90%, at least 95%, at least 98% or at least 99% identity to SEQ ID NO: 32; a nucleic acid sequence encoding H4 that consists of SEQ ID NO: 33 or a sequence with at least 75%, at least 80%, at least 85%, at least 90%, at least 95%, at least 98%, or at least 99% identity to SEQ ID NO: 33; a nucleic acid sequence encoding CR that consists of SEQ ID NO: 34 or 109 or a sequence with at least 75%, at least 80%, at least 85%, at least 90%, at least 95%, at least 98% or at least 99% identity to SEQ ID NO: 34 or 109; and/or a nucleic acid sequence encoding CT that consists of SEQ ID NO: 35 or a sequence with at least 75%, at least 80%, at least 85%, at least 90%, at least 95%, at least 98% or at least 99% identity to SEQ ID NO: 35, encoding a microdystrophin that has functional activity. An alternative embodiment is the same as the foregoing except that the H3 nucleic acid sequence is replaced by a nucleic acid encoding H2 that consists of SEQ ID NO: 38 or a sequence with at least 50%, at least 60%, at least 70%, at least 75%, at least 80%, at least 85%, at least 90%, at least 95%, at least 98% or at least 99% identity to SEQ ID NO: 38, likewise encoding a microdystrophin that has functional activity.

In some embodiments, such compositions comprise a nucleic acid sequence encoding ABD1 that consists of SEQ ID NO: 22 or a sequence with at least 75%, at least 80%, at least 85%, at least 90%, at least 95%, at least 98% or at least 99% identity to SEQ ID NO: 22 and encodes for the ABD1 domain of SEQ ID NO: 3; a nucleic acid sequence encoding H1 that consists of SEQ ID NO: 24 or a sequence with at least 75%, at least 80%, at least 85%, at least 90%, at least 95%, at least 98% or at least 99% identity to SEQ ID NO: 24 and encodes for the H1 domain of SEQ ID NO: 5; a nucleic acid sequence encoding R1 that consists of SEQ ID NO: 26 or a sequence with at least 75%, at least 80%, at least 85%, at least 90%, at least 95%, at least 98% or at least 99% identity to SEQ ID NO: 26 and encodes for the R1 domain of SEQ ID NO: 7; a nucleic acid sequence encoding R2 that consists of SEQ ID NO: 27 or a sequence with at least 75%, at least 80%, at least 85%, at least 90%, at least 95%, at least 98% or at least 99% identity to SEQ ID NO: 27 and encodes for the R2 domain of SEQ ID NO: 8; a nucleic acid sequence encoding R16 that consists of SEQ ID NO: 94 or a sequence with at least 75%, at least 80%, at least 85%, at least 90%, at least 95%, at least 98% or at least 99% identity to SEQ ID NO: 94 and encodes for the R16 domain of SEQ ID NO: 86; a nucleic acid sequence encoding R17 that consists of SEQ ID NO: 95 or a sequence with at least 75%, at least 80%, at least 85%, at least 90%, at least 95%, at least 98% or at least 99% identity to SEQ ID NO: 95 and encodes for the R17 domain of SEQ ID NO: 87; a nucleic acid sequence encoding R24 that consists of SEQ ID NO: 32 or a sequence with at least 75%, at least 80%, at least 85%, at least 90%, at least 95%, at least 98% or at least 99% identity to SEQ ID NO: 32 and encodes for the R24 domain of SEQ ID NO: 13; a nucleic acid sequence encoding H4 that consists of SEQ ID NO: 33 or a sequence with at least 75%, at least 80%, at least 85%, at least 90%, at least 95%, at least 98%, or at least 99% identity to SEQ ID NO: 33 and encodes for the H4 domain of SEQ ID NO: 14; a nucleic acid sequence encoding CR that consists of SEQ ID NO: 34 or 109 or a sequence with at least 75%, at least 80%, at least 85%, at least 90%, at least 95%, at least 98% or at least 99% identity to SEQ ID NO: 34 or 109 and encodes for the CR domain of SEQ ID NO: 15 or 90; and/or a nucleic acid sequence encoding CT that consists of SEQ ID NO: 35 or 80 or a sequence with at least 75%, at least 80%, at least 85%, at least 90%, at least 95%, at least 98% or at least 99% identity to SEQ ID NO: 35 or 80 and encodes for the CT domain of SEQ ID NO: 16 or 83. An alternative embodiment is the same as the foregoing except that the H3 nucleic acid sequence is replaced by a nucleic acid encoding H2 that consists of SEQ ID NO: 38 or a sequence with at least 75%, at least 80%, at least 85%, at least 90%, at least 95%, at least 98% or at least 99% identity to SEQ ID NO: 38 and encodes the H2 domain of SEQ ID NO: 19.

In addition to the foregoing, the nucleic acid compositions can optionally comprise nucleotide sequences encoding linkers in the locations described above that comprise or consist of sequences as follows: a nucleic acid sequence encoding L1 consisting of SEQ ID NO: 23 or a sequence with at least 80%, at least 85%, at least 90%, at least 95%, at least 98%, or at least 99% sequence identity to SEQ ID NO: 23 (e.g. encoding the L1 domain of SEQ ID NO: 4); a nucleic acid sequence encoding L2 consisting of SEQ ID NO: 25 or sequence with at least 80%, at least 85%, at least 90%, at least 95%, at least 98%, or at least 99% sequence identity to SEQ ID NO: 25 (e.g. encoding the L2 domain of SEQ ID NO: 6); a nucleic acid sequence encoding L3 consisting of SEQ ID NO: 28 or a sequence with at least 50% identity to SEQ ID NO: 28, encoding the L3 domain of SEQ ID NO: 9 or a variant with conservative substitutions for both L3 residues; a nucleic acid sequence encoding L4.1 consisting of SEQ ID NO: 125 or a sequence with at least 50%, at least 75% sequence identity to SEQ ID NO: 125 (e.g. encoding the L4.1 domain of SEQ ID NO: 110 or a variant with conservative substitutions for any of the L4.1 residues); and a nucleic acid sequence encoding L4.2 consisting of SEQ ID NO: 126 or a sequence with at least 50%, at least 75% sequence identity to SEQ ID NO: 126 (e.g. encoding the L4.2 domain of SEQ ID NO: 89 or a variant with conservative substitutions for any of the L4.2 residues).

In various embodiments, the nucleic acid comprises a nucleotide sequence encoding the microdystrophin having the amino acid sequence of SEQ ID NO: 1, SEQ ID NO:2, SEQ ID NO: 79, SEQ ID NO: 91, SEQ ID NO: 92, or SEQ ID NO: 93. In embodiments, the nucleic acid comprises a nucleotide sequence which is SEQ ID NO: 20, SEQ ID NO: 21, SEQ ID NO: 81, SEQ ID NO: 101, SEQ ID NO: 102, or SEQ ID NO: 103 (encoding the microdystrophins of SEQ ID NO: 1, SEQ ID NO:2, SEQ ID NO: 79, SEQ ID NO: 91, SEQ ID NO: 92, and SEQ ID NO: 93, respectively). In various embodiments, the nucleotide sequence encoding a microdystrophin may have at least 50%, at least 60%, at least 70%, at least 75%, at least 80%, at least 85%, at least 90%, at least 95%, at least 98% or at least 99% sequence identity to the nucleotide sequence of SEQ ID NO: 20, 21, 83, 101, 102, or 103 (Table 5) or the reverse complement thereof and encode a therapeutically effective microdystrophin.

TABLE 5

RGX-DYS Construct nucleotide sequences

| Structure | SEQ ID | Nucleic Acid Sequence |
| --- | --- | --- |
| DYS1, DYS2, and DYS4 | 20 | ATGCTTTGGTGGGAAGAGGTGGAAGATTGCTATGAGAGGGAA GATGTGCAGAAGAAAACCTTCACCAAATGGGTCAATGCCCAG TTCAGCAAGTTTGGCAAGCAGCACATTGAGAACCTGTTCAGT GACCTGCAGGATGGCAGAAGGCTGCTGGATCTGCTGGAAGGC CTGACAGGCCAGAAGCTGCCTAAAGAGAAGGGCAGCACAAGA GTGCATGCCCTGAACAATGTGAACAAGGCCCTGAGAGTGCTG CAGAACAACAATGTGGACCTGGTCAATATTGGCAGCACAGAC ATTGTGGATGGCAACCACAAGCTGACCCTGGGCCTGATCTGG AACATCATCCTGCACTGGCAAGTGAAGAATGTGATGAAGAAC ATCATGGCTGGCCTGCAGCAGACCAACTCTGAGAAGATCCTG CTGAGCTGGGTCAGACAGAGCACCAGAAACTACCCTCAAGTG AATGTGATCAACTTCACCACCTCTTGGAGTGATGGACTGGCC CTGAATGCCCTGATCCACAGCCACAGACCTGACCTGTTTGAC TGGAACTCTGTTGTGTGCCAGCAGTCTGCCACACAGAGACTG GAACATGCCTTCAACATTGCCAGATACCAGCTGGGAATTGAG AAACTGCTGGACCCTGAGGATGTGGACACCACCTATCCTGAC AAGAAATCCATCCTCATGTACATCACCAGCCTGTTCCAGGTG CTGCCCCAGCAAGTGTCCATTGAGGCCATTCAAGAGGTTGAG ATGCTGCCCAGACCTCCTAAAGTGACCAAAGAGGAACACTTC CAGCTGCACCACCAGATGCACTACTCTCAGCAGATCACAGTG TCTCTGGCCCAGGGATATGAGAGAACAAGCAGCCCCAAGCCT AGGTTCAAGAGCTATGCCTACACACAGGCTGCCTATGTGACC ACATCTGACCCCACAAGAAGCCCATTTCCAAGCCAGCATCTG GAAGCCCCTGAGGACAAGAGCTTTGGCAGCAGCCTGATGGAA TCTGAAGTGAACCTGGATAGATACCAGACAGCCCTGGAAGAA GTGCTGTCCTGGCTGCTGTCTGCTGAGGATACACTGCAGGCT CAGGGTGAAATCAGCAATGATGTGGAAGTGGTCAAGGACCAG TTTCACACCCATGAGGGCTACATGATGGACCTGACAGCCCAC CAGGGCAGAGTGGGAAATATCCTGCAGCTGGGCTCCAAGCTG ATTGGCACAGGCAAGCTGTCTGAGGATGAAGAGACAGAGGTG CAAGAGCAGATGAACCTGCTGAACAGCAGATGGGAGTGTCTG AGAGTGGCCAGCATGGAAAAGCAGAGCAACCTGCACAGAGTG CTCATGGACCTGCAGAATCAGAAACTGAAAGAACTGAATGAC TGGCTGACCAAGACAGAAGAAAGGACTAGGAAGATGGAAGAG GAACCTCTGGGACCAGACCTGGAAGATCTGAAAAGACAGGTG |

TABLE 5-continued

RGX-DYS Construct nucleotide sequences

| Structure | SEQ ID | Nucleic Acid Sequence |
|---|---|---|
| | | CAGCAGCATAAGGTGCTGCAAGAGGACCTTGAGCAAGAGCAA<br>GTCAGAGTGAACAGCCTGACACACATGGTGGTGGTTGTGGAT<br>GAGTCCTCTGGGGATCATGCCACAGCTGCTCTGGAAGAACAG<br>CTGAAGGTGCTGGGAGACAGATGGGCCAACATCTGTAGGTGG<br>ACAGAGGATAGATGGGTGCTGCTCCAGGACATTCTGCTGAAG<br>TGGCAGAGACTGACAGAGGAACAGTGCCTGTTTTCTGCCTGG<br>CTCTCTGAGAAAGAGGATGCTGTCAACAAGATCCATACCACA<br>GGCTTCAAGGATCAGAATGAGATGCTCAGCTCCCTGCAGAAA<br>CTGGCTGTGCTGAAGGCTGACCTGGAAAAGAAAAAGCAGTCC<br>ATGGGCAAGCTCTACAGCCTGAAGCAGGACCTGCTGTCTACC<br>CTGAAGAACAAGTCTGTGACCCAGAAAACTGAGGCCTGGCTG<br>GACAACTTTGCTAGATGCTGGGACAACCTGGTGCAGAAGCTG<br>GAAAAGTCTACAGCCCAGATCAGCCAGCAACCTGATCTTGCC<br>CCTGGCCTGACCACAATTGGAGCCTCTCCAACACAGACTGTG<br>ACCCTGGTTACCCAGCCAGTGGTCACCAAAGAGACAGCCATC<br>AGCAAACTGGAAATGCCCAGCTCTCTGATGCTGGAAGTCCCC<br>ACACTGGAAAGGCTGCAAGAACTTCAAGAGGCCACAGATGAG<br>CTGGACCTGAAGCTGAGACAGGCTGAAGTGATCAAAGGCAGC<br>TGGCAGCCAGTTGGGGACCTGCTCATTGATAGCCTGCAGGAC<br>CATCTGGAAAAAGTGAAAGCCCTGAGGGGAGAGATTGCCCCT<br>CTGAAAGAAAATGTGTCCCATGTGAATGACCTGGCCAGACAG<br>CTGACCACACTGGGAATCCAGCTGAGCCCCTACAACCTGAGC<br>ACCCTTGAGGACCTGAACACCAGGTGGAAGCTCCTCCAGGTG<br>GCAGTGGAAGATAGAGTCAGGCAGCTGCATGAGGCCCACAGA<br>GATTTTGGACCAGCCAGCCAGCACTTTCTGTCTACCTCTGTG<br>CAAGGCCCCTGGGAGAGAGCTATCTCTCCTAACAAGGTGCCC<br>TACTACATCAACCATGAGACACAGACCACCTGTTGGGATCAC<br>CCCAAGATGACAGAGCTGTACCAGAGTCTGGCAGACCTCAAC<br>AATGTCAGATTCAGTGCCTACAGGACTGCCATGAAGCTCAGA<br>AGGCTCCAGAAAGCTCTGTGCCTGGACCTGCTTTCCCTGAGT<br>GCAGCTTGTGATGCCCTGGACCAGCACAATCTGAAGCAGAAT<br>GACCAGCCTATGGACATCCTCCAGATCATCAACTGCCTCACC<br>ACCATCTATGATAGGCTGGAACAAGAGCACAACAATCTGGTC<br>AATGTGCCCCTGTGTGTGGACATGTGCCTGAATTGGCTGCTG<br>AATGTGTATGACACAGGCAGAACAGGCAGGATCAGAGTCCTG<br>TCCTTCAAGACAGGCATCATCTCCCTGTGCAAAGCCCACTTG<br>GAGGACAAGTACAGATACCTGTTCAAGCAAGTGGCCTCCAGC<br>ACAGGCTTTTGTGACCAGAGAAGGCTGGGCCTGCTCCTGCAT<br>GACAGCATTCAGATCCCTAGACAGCTGGGAGAAGTGGCTTCC<br>TTTGGAGGCAGCAATATTGAGCCATCAGTCAGGTCCTGTTTT<br>CAGTTTGCCAACAACAAGCCTGAGATTGAGGCTGCCCTGTTC<br>CTGGACTGGATGAGACTTGAGCCTCAGAGCATGGTCTGGCTG<br>CCTGTGCTTCATAGAGTGGCTGCTGCTGAGACTGCCAAGCAC<br>CAGGCCAAGTGCAACATCTGCAAAGAGTGCCCCATCATTGGC<br>TTCAGATACAGATCCCTGAAGCACTTCAACTATGATATCTGC<br>CAGAGCTGCTTCTTTAGTGGCAGGGTTGCCAAGGGCCACAAA<br>ATGCACTACCCCATGGTGGAATACTGCACCCCAACAACCTCT<br>GGGGAAGATGTTAGAGACTTTGCCAAGGTGCTGAAAAACAAG<br>TTCAGGACCAAGAGATACTTTGCTAAGCACCCCAGAATGGGC<br>TACCTGCCTGTCCAGACAGTGCTTGAGGGTGACAACATGGAA<br>ACCCCTGTGACACTGATCAATTTCTGGCCAGTGGACTCTGCC<br>CCTGCCTCAAGTCCACAGCTGTCCCATGATGACACCCACAGC<br>AGAATTGAGCACTATGCCTCCAGACTGGCAGAGATGGAAAAC<br>AGCAATGGCAGCTACCTGAATGATAGCATCAGCCCCAATGAG<br>AGCATTGATGATGAGCATCTGCTGATCCAGCACTACTGTCAG<br>TCCCTGAACCAGGACTCTCCACTGAGCCAGCCTAGAAGCCCT<br>GCTCAGATCCTGATCAGCCTTGAGTCTGAGGAAAGGGGAGAG<br>CTGGAAAGAATCCTGGCAGATCTTGAGGAAGAGAACAGAAAC<br>CTGCAGGCAGAGTATGACAGGCTCAAACAGCAGCATGAGCAC<br>AAGGGACTGAGCCCTCTGCCTTCTCCTCCTGAAATGATGCCC<br>ACCTCTCCACAGTCTCCAAGGTGATGA |
| DYS3 | 21 | ATGCTTTGGTGGGAAGAGGTGGAAGATTGCTATGAGAGGGAA<br>GATGTGCAGAAGAAAACCTTCACCAAATGGGTCAATGCCCAG<br>TTCAGCAAGTTTGGCAAGCAGCACATTGAGAACCTGTTCAGT<br>GACCTGCAGGATGGCAGAAGGCTGCTGGATCTGCTGGAAGGC<br>CTGACAGGCCAGAAGCTGCCTAAAGAGAAGGGCAGCACAAGA<br>GTGCATGCCCTGAACAATGTGAACAAGGCCCTGAGAGTGCTG<br>CAGAACAACAATGTGGACCTGGTCAATATTGGCAGCACAGAC<br>ATTGTGGATGGCAACCACAAGCTGACCCTGGGCCTGATCTGG<br>AACATCATCCTGCACTGGCAAGTGAAGAATGTGATGAAGAAC<br>ATCATGGCTGGCCTGCAGCAGACCAACTCTGAGAAGATCCTG<br>CTGAGCTGGGTCAGACAGAGCACCAGAAACTACCCTCAAGTG<br>AATGTGATCAACTTCACCACCTCTTGGAGTGATGGACTGGCC<br>CTGAATGCCCTGATCCACAGCCACAGACCTGACCTGTTTGAC<br>TGGAACTCTGTTGTGTGCCAGCAGTCTGCCACACAGAGACTG |

TABLE 5-continued

RGX-DYS Construct nucleotide sequences

| Structure | SEQ ID | Nucleic Acid Sequence |
|---|---|---|
| | | GAACATGCCTTCAACATTGCCAGATACCAGCTGGGAATTGAG<br>AAACTGCTGGACCCTGAGGATGTGGACACCACCTATCCTGAC<br>AAGAAATCCATCCTCATGTACATCACCAGCCTGTTCCAGGTG<br>CTGCCCCAGCAAGTGTCCATTGAGGCCATTCAAGAGGTTGAG<br>ATGCTGCCCAGACCTCCTAAAGTGACCAAAGAGGAACACTTC<br>CAGCTGCACCACCAGATGCACTACTCTCAGCAGATCACAGTG<br>TCTCTGGCCCAGGGATATGAGAGAACAAGCAGCCCCAAGCCT<br>AGGTTCAAGAGCTATGCCTACACACAGGCTGCCTATGTGACC<br>ACATCTGACCCCACAAGAAGCCCATTTCCAAGCCAGCATCTG<br>GAAGCCCCTGAGGACAAGAGCTTTGGCAGCAGCCTGATGGAA<br>TCTGAAGTGAACCTGGATAGATACCAGACAGCCCTGGAAGAA<br>GTGCTGTCCTGGCTGCTGTCTGCTGAGGATACACTGCAGGCT<br>CAGGGTGAAATCAGCAATGATGTGGAAGTGGTCAAGGACCAG<br>TTTCACACCCATGAGGGCTACATGATGGACCTGACAGCCCAC<br>CAGGGCAGAGTGGGAAATATCCTGCAGCTGGGCTCCAAGCTG<br>ATTGGCACAGGCAAGCTGTCTGAGGATGAAGAGACAGAGGTG<br>CAAGAGCAGATGAACCTGCTGAACAGCAGATGGGAGTGTCTG<br>AGAGTGGCCAGCATGGAAAAGCAGAGCAACCTGCACAGAGTG<br>CTCATGGACCTGCAGAATCAGAAACTGAAAGAACTGAATGAC<br>TGGCTGACCAAGACAGAAGAAAGGACTAGGAAGATGGAAGAG<br>GAACCTCTGGGACCAGACCTGGAAGATCTGAAAAGACAGGTG<br>CAGCAGCATAAGGTGCTGCAAGAGGACCTTGAGCAAGAGCAA<br>GTCAGAGTGAACAGCCTGACACACATGGTGGTGGTTGTGGAT<br>GAGTCCTCTGGGGATCATGCCACAGCTGCTCTGGAAGAACAG<br>CTGAAGGTGCTGGGAGACAGATGGGCCAACATCTGTAGGTGG<br>ACAGAGGATAGATGGGTGCTGCTCCAGGACATTCTGCTGAAG<br>TGGCAGAGACTGACAGAGGAACAGTGCCTGTTTTCTGCCTGG<br>CTCTCTGAGAAAGAGGATGCTGTCAACAAGATCCATACCACA<br>GGCTTCAAGGATCAGAATGAGATGCTCAGCTCCCTGCAGAAA<br>CTGGCTGTGCTGAAGGCTGACCTGGAAAAGAAAAAGCAGTCC<br>ATGGGCAAGCTCTACAGCCTGAAGCAGGACCTGCTGTCTACC<br>CTGAAGAACAAGTCTGTGACCCAGAAAACTGAGGCCTGGCTG<br>GACAACTTTGCTAGATGCTGGGACAACCTGGTGCAGAAGCTG<br>GAAAAGTCTACAGCCCAGATCAGCCAGCAACCTGATCTTGCC<br>CCTGGCCTGACCACAATTGGAGCCTCTCCAACACAGACTGTG<br>ACCCTGGTTACCCAGCCAGTGGTCACCAAAGAGACAGCCATC<br>AGCAAACTGGAAATGCCCAGCTCTCTGATGCTGGAAGTCCCC<br>ACACTGGAAAGGCTGCAAGAACTTCAAGAGGCCACAGATGAG<br>CTGGACCTGAAGCTGAGACAGGCTGAAGTGATCAAAGGCAGC<br>TGGCAGCCAGTTGGGGACCTGCTCATTGATAGCCTGCAGGAC<br>CATCTGGAAAAAGTGAAAGCCCTGAGGGGAGAGATTGCCCCT<br>CTGAAAGAAAATGTGTCCCATGTGAATGACCTGGCCAGACAG<br>CTGACCACACTGGGAATCCAGCTGAGCCCCTACAACCTGAGC<br>ACCCTTGAGGACCTGAACACCAGGTGGAAGCTCCTCCAGGTG<br>GCAGTGGAAGATAGAGTCAGGCAGCTGCATGAGGCCCACAGA<br>GATTTTGGACCAGCCAGCCAGCACTTTCTGTCTACCTCTGTG<br>CAAGGCCCCTGGGAGAGAGCTATCTCTCCTAACAAGGTGCCC<br>TACTACATCAACCATGAGACACAGACCACCTGTTGGGATCAC<br>CCCAAGATGACAGAGCTGTACCAGAGTCTGGCAGACCTCAAC<br>AATGTCAGATTCAGTGCCTACAGGACTGCCATGAAGCTCAGA<br>AGGCTCCAGAAAGCTCTGTGCCTGGACCTGCTTTCCCTGAGT<br>GCAGCTTGTGATGCCCTGGACCAGCACAATCTGAAGCAGAAT<br>GACCAGCCTATGGACATCCTCCAGATCATCAACTGCCTCACC<br>ACCATCTATGATAGGCTGGAACAAGAGCACAACAATCTGGTC<br>AATGTGCCCCTGTGTGTGGACATGTGCCTGAATTGGCTGCTG<br>AATGTGTATGACACAGGCAGAACAGGCAGGATCAGAGTCCTG<br>TCCTTCAAGACAGGCATCATCTCCCTGTGCAAAGCCCACTTG<br>GAGGACAAGTACAGATACCTGTTCAAGCAAGTGGCCTCCAGC<br>ACAGGCTTTTGTGACCAGAGAAGGCT |
| DYS5 | 81 | GGGCCTGCTCCTGCATGACAGCATTCAGATCCCTAGACAGCT<br>GGGAGAAGTGGCTTCCTTTGGAGGCAGCAATATTGAGCCATC<br>AGTCAGGTCCTGTTTTCAGTTTGCCAACAACAAGCCTGAGAT<br>TGAGGCTGCCCTGTTCCTGGACTGGATGAGACTTGAGCCTCA<br>GAGCATGGTCTGGCTGCCTGTGCTTCATAGAGTGGCTGCTGC<br>TGAGACTGCCAAGCACCAGGCCAAGTGCAACATCTGCAAAGA<br>GTGCCCCATCATTGGCTTCAGATACAGATCCCTGAAGCACTT<br>CAACTATGATATCTGCCAGAGCTGCTTCTTTAGTGGCAGGGT<br>TGCCAAGGGCCACAAAATGCACTACCCCATGGTGGAATACTG<br>CACCCCAACAACCTCTGGGGAAGATGTTAGAGACTTTGCCAA<br>GGTGCTGAAAAACAAGTTCAGGACCAAGAGATACTTTGCTAA<br>GCACCCCAGAATGGGCTACCTGCCTGTCCAGACAGTGCTTGA<br>GGGTGACAACATGGAAACCATGCTTTGGTGGGAAGAGGTGGA<br>AGATTGCTATGAGAGGGAAGATGTGCAGAAGAAAACCTTCAC<br>CAAATGGGTCAATGCCCAGTTCAGCAAGTTTGGCAAGCAGCA<br>CATTGAGAACCTGTTCAGTGACCTGCAGGATGGCAGAAGGCT |

TABLE 5-continued

| RGX-DYS Construct nucleotide sequences | | |
|---|---|---|
| Structure | SEQ ID | Nucleic Acid Sequence |
| | | GCTGGATCTGCTGGAAGGCCTGACAGGCCAGAAGCTGCCTAA |
| | | AGAGAAGGGCAGCACAAGAGTGCATGCCCTGAACAATGTGAA |
| | | CAAGGCCCTGAGAGTGCTGCAGAACAACAATGTGGACCTGGT |
| | | CAATATTGGCAGCACAGACATTGTGGATGGCAACCACAAGCT |
| | | GACCCTGGGCCTGATCTGGAACATCATCCTGCACTGGCAAGT |
| | | GAAGAATGTGATGAAGAACATCATGGCTGGCCTGCAGCAGAC |
| | | CAACTCTGAGAAGATCCTGCTGAGCTGGGTCAGACAGAGCAC |
| | | CAGAAACTACCCTCAAGTGAATGTGATCAACTTCACCACCTC |
| | | TTGGAGTGATGGACTGGCCCTGAATGCCCTGATCCACAGCCA |
| | | CAGACCTGACCTGTTTGACTGGAACTCTGTTGTGTGCCAGCA |
| | | GTCTGCCACACAGAGACTGGAACATGCCTTCAACATTGCCAG |
| | | ATACCAGCTGGGAATTGAGAAACTGCTGGACCCTGAGGATGT |
| | | GGACACCACCTATCCTGACAAGAAATCCATCCTCATGTACAT |
| | | CACCAGCCTGTTCCAGGTGCTGCCCCAGCAAGTGTCCATTGA |
| | | GGCCATTCAAGAGGTTGAGATGCTGCCCAGACCTCCTAAAGT |
| | | GACCAAAGAGGAACACTTCCAGCTGCACCACCAGATGCACTA |
| | | CTCTCAGCAGATCACAGTGTCTCTGGCCCAGGGATATGAGAG |
| | | AACAAGCAGCCCCAAGCCTAGGTTCAAGAGCTATGCCTACAC |
| | | ACAGGCTGCCTATGTGACCACATCTGACCCCACAAGAAGCCC |
| | | ATTTCCAAGCCAGCATCTGGAAGCCCCTGAGGACAAGAGCTT |
| | | TGGCAGCAGCCTGATGGAATCTGAAGTGAACCTGGATAGATA |
| | | CCAGACAGCCCTGGAAGAAGTGCTGTCCTGGCTGCTGTCTGC |
| | | TGAGGATACACTGCAGGCTCAGGGTGAAATCAGCAATGATGT |
| | | GGAAGTGGTCAAGGACCAGTTTCACACCCATGAGGGCTACAT |
| | | GATGGACCTGACAGCCCACCAGGGCAGAGTGGGAAATATCCT |
| | | GCAGCTGGGCTCCAAGCTGATTGGCACAGGCAAGCTGTCTGA |
| | | GGATGAAGAGACAGAGGTGCAAGAGCAGATGAACCTGCTGAA |
| | | CAGCAGATGGGAGTGTCTGAGAGTGGCCAGCATGGAAAAGCA |
| | | GAGCAACCTGCACAGAGTGCTCATGGACCTGCAGAATCAGAA |
| | | ACTGAAAGAACTGAATGACTGGCTGACCAAGACAGAAGAAAG |
| | | GACTAGGAAGATGGAAGAGGAACCTCTGGGACCAGACCTGGA |
| | | AGATCTGAAAAGACAGGTGCAGCAGCATAAGGTGCTGCAAGA |
| | | GGACCTTGAGCAAGAGCAAGTCAGAGTGAACAGCCTGACACA |
| | | CATGGTGGTGGTTGTGGATGAGTCCTCTGGGGATCATGCCAC |
| | | AGCTGCTCTGGAAGAACAGCTGAAGGTGCTGGGAGACAGATG |
| | | GGCCAACATCTGTAGGTGGACAGAGGATAGATGGGTGCTGCT |
| | | CCAGGACATTCTGCTGAAGTGGCAGAGACTGACAGAGGAACA |
| | | GTGCCTGTTTTCTGCCTGGCTCTCTGAGAAAGAGGATGCTGT |
| | | CAACAAGATCCATACCACAGGCTTCAAGGATCAGAATGAGAT |
| | | GCTCAGCTCCCTGCAGAAACTGGCTGTGCTGAAGGCTGACCT |
| | | GGAAAAGAAAAAGCAGTCCATGGGCAAGCTCTACAGCCTGAA |
| | | GCAGGACCTGCTGTCTACCCTGAAGAACAAGTCTGTGACCCA |
| | | GAAAACTGAGGCCTGGCTGGACAACTTTGCTAGATGCTGGGA |
| | | CAACCTGGTGCAGAAGCTGGAAAAGTCTACAGCCCAGATCAG |
| | | CCAGCAACCTGATCTTGCCCCTGGCCTGACCACAATTGGAGC |
| | | CTCTCCAACACAGACTGTGACCCTGGTTACCCAGCCAGTGGT |
| | | CACCAAAGAGACAGCCATCAGCAAACTGGAAATGCCCAGCTC |
| | | TCTGATGCTGGAAGTCCCCACACTGGAAAGGCTGCAAGAACT |
| | | TCAAGAGGCCACAGATGAGCTGGACCTGAAGCTGAGACAGGC |
| | | TGAAGTGATCAAAGGCAGCTGGCAGCCAGTTGGGGACCTGCT |
| | | CATTGATAGCCTGCAGGACCATCTGGAAAAAGTGAAAGCCCT |
| | | GAGGGGAGAGATTGCCCCTCTGAAAGAAAATGTGTCCCATGT |
| | | GAATGACCTGGCCAGACAGCTGACCACACTGGGAATCCAGCT |
| | | GAGCCCCTACAACCTGAGCACCCTTGAGGACCTGAACACCAG |
| | | GTGGAAGCTCCTCCAGGTGGCAGTGGAAGATAGAGTCAGGCA |
| | | GCTGCATGAGGCCCACAGAGATTTTGGACCAGCCAGCCAGCA |
| | | CTTTCTGTCTACCTCTGTGCAAGGCCCCTGGGAGAGAGCTAT |
| | | CTCTCCTAACAAGGTGCCCTACTACATCAACCATGAGACACA |
| | | GACCACCTGTTGGGATCACCCCAAGATGACAGAGCTGTACCA |
| | | GAGTCTGGCAGACCTCAACAATGTCAGATTCAGTGCCTACAG |
| | | GACTGCCATGAAGCTCAGAAGGCTCCAGAAAGCTCTGTGCCT |
| | | GGACCTGCTTTCCCTGAGTGCAGCTTGTGATGCCCTGGACCA |
| | | GCACAATCTGAAGCAGAATGACCAGCCTATGGACATCCTCCA |
| | | GATCATCAACTGCCTCACCACCATCTATGATAGGCTGGAACA |
| | | AGAGCACAACAATCTGGTCAATGTGCCCCTGTGTGTGGACAT |
| | | GTGCCTGAATTGGCTGCTGAATGTGTATGACACAGGCAGAAC |
| | | AGGCAGGATCAGAGTCCTGTCCTTCAAGACAGGCATCATCTC |
| | | CCTGTGCAAAGCCCACTTGGAGGACAAGTACAGATACCTGTT |
| | | CAAGCAAGTGGCCTCCAGCACAGGCTTTTGTGACCAGAGAAG |
| | | GCTGGGCCTGCTCCTGCATGACAGCATTCAGATCCCTAGACA |
| | | GCTGGGAGAAGTGGCTTCCTTTGGAGGCAGCAATATTGAGCC |
| | | ATCAGTCAGGTCCTGTTTTCAGTTTGCCAACAACAAGCCTGA |
| | | GATTGAGGCTGCCCTGTTCCTGGACTGGATGAGACTTGAGCC |
| | | TCAGAGCATGGTCTGGCTGCCTGTGCTTCATAGAGTGGCTGC |
| | | TGCTGAGACTGCCAAGCACCAGGCCAAGTGCAACATCTGCAA |
| | | AGAGTGCCCCATCATTGGCTTCAGATACAGATCCCTGAAGCA |

TABLE 5-continued

RGX-DYS Construct nucleotide sequences

| Structure | SEQ ID | Nucleic Acid Sequence |
|---|---|---|
| | | CTTCAACTATGATATCTGCCAGAGCTGCTTCTTTAGTGGCAG |
| | | GGTTGCCAAGGGCCACAAAATGCACTACCCCATGGTGGAATA |
| | | CTGCACCCCAACAACCTCTGGGGAAGATGTTAGAGACTTTGC |
| | | CAAGGTGCTGAAAAACAAGTTCAGGACCAAGAGATACTTTGC |
| | | TAAGCACCCCAGAATGGGCTACCTGCCTGTCCAGACAGTGCT |
| | | TGAGGGTGACAACATGGAAACCCCTGTGACACTGATCAATTT |
| | | CTGGCCAGTGGACTCTGCCCCTGCCTCAAGTCCACAGCTGTC |
| | | CCATGATGACACCCACAGCAGAATTGAGCACTATGCCTCCAG |
| | | ACTGGCAGAGATGGAAAACAGCAATGGCAGCTACCTGAATGA |
| | | TAGCATCAGCCCCAATGAGAGCATTGATGATGAGCATCTGCT |
| | | GATCCAGCACTACTGTCAGTCCCTGAACCAGGACTCTCCACT |
| | | GAGCCAGCCTAGAAGCCCTGCTCAGATCCTGATCAGCCTTGA |
| | | GTCTTGATGA |
| RGX-DYS6 | 101 | ATGCTTTGGTGGGAAGAGGTGGAAGATTGCTATGAGAGGGAA |
| (coding | | GATGTGCAGAAGAAAACCTTCACCAAATGGGTCAATGCCCAG |
| sequence | | TTCAGCAAGTTTGGCAAGCAGCACATTGAGAACCTGTTCAGT |
| 3867 bp) | | GACCTGCAGGATGGCAGAAGGCTGCTGGATCTGCTGGAAGGC |
| | | CTGACAGGCCAGAAGCTGCCTAAAGAGAAGGGCAGCACAAGA |
| | | GTGCATGCCCTGAACAATGTGAACAAGGCCCTGAGAGTGCTG |
| | | CAGAACAACAATGTGGACCTGGTCAATATTGGCAGCACAGAC |
| | | ATTGTGGATGGCAACCACAAGCTGACCCTGGGCCTGATCTGG |
| | | AACATCATCCTGCACTGGCAAGTGAAGAATGTGATGAAGAAC |
| | | ATCATGGCTGGCCTGCAGCAGACCAACTCTGAGAAGATCCTG |
| | | CTGAGCTGGGTCAGACAGAGCACCAGAAACTACCCTCAAGTG |
| | | AATGTGATCAACTTCACCACCTCTTGGAGTGATGGACTGGCC |
| | | CTGAATGCCCTGATCCACAGCCACAGACCTGACCTGTTTGAC |
| | | TGGAACTCTGTTGTGTGCCAGCAGTCTGCCACACAGAGACTG |
| | | GAACATGCCTTCAACATTGCCAGATACCAGCTGGGAATTGAG |
| | | AAACTGCTGGACCCTGAGGATGTGGACACCACCTATCCTGAC |
| | | AAGAAATCCATCCTCATGTACATCACCAGCCTGTTCCAGGTG |
| | | CTGCCCCAGCAAGTGTCCATTGAGGCCATTCAAGAGGTTGAG |
| | | ATGCTGCCCAGACCTCCTAAAGTGACCAAAGAGGAACACTTC |
| | | CAGCTGCACCACCAGATGCACTACTCTCAGCAGATCACAGTG |
| | | TCTCTGGCCCAGGGATATGAGAGAACAAGCAGCCCCAAGCCT |
| | | AGGTTCAAGAGCTATGCCTACACACAGGCTGCCTATGTGACC |
| | | ACATCTGACCCCACAAGAAGCCCATTTCCAAGCCAGCATCTG |
| | | GAAGCCCCTGAGGACAAGAGCTTTGGCAGCAGCCTGATGGAA |
| | | TCTGAAGTGAACCTGGATAGATACCAGACAGCCCTGGAAGAA |
| | | GTGCTGTCCTGGCTGCTGTCTGCTGAGGATACACTGCAGGCT |
| | | CAGGGTGAAATCAGCAATGATGTGGAAGTGGTCAAGGACCAG |
| | | TTTCACACCCATGAGGGCTACATGATGGACCTGACAGCCCAC |
| | | CAGGGCAGAGTGGGAAATATCCTGCAGCTGGGCTCCAAGCTG |
| | | ATTGGCACAGGCAAGCTGTCTGAGGATGAAGAGACAGAGGTG |
| | | CAAGAGCAGATGAACCTGCTGAACAGCAGATGGGAGTGTCTG |
| | | AGAGTGGCCAGCATGGAAAAGCAGAGCAACCTGCACAGAGTG |
| | | CTCATGGACCTGCAGAATCAGAAACTGAAAGAACTGAATGAC |
| | | TGGCTGACCAAGACAGAAGAAAGGACTAGGAAGATGGAAGAG |
| | | GAACCTCTGGGACCAGACCTGGAAGATCTGAAAAGACAGGTG |
| | | CAGCAGCATAAGGTGCTGCAAGAGGACCTTGAGCAAGAGCAA |
| | | GTCAGAGTGAACAGCCTGACACACATGGTGGTGGTTGTGGAT |
| | | GAGTCCTCTGGGGATCATGCCACAGCTGCTCTGGAAGAACAG |
| | | CTGAAGGTGCTGGGAGACAGATGGGCCAACATCTGTAGGTGG |
| | | ACAGAGGATAGATGGGTGCTGCTCCAGGACATTCTGCTGAAG |
| | | TGGCAGAGACTGACAGAGGAACAGTGCCTGTTTTCTGCCTGG |
| | | CTCTCTGAGAAAGAGGATGCTGTCAACAAGATCCATACCACA |
| | | GGCTTCAAGGATCAGAATGAGATGCTCAGCTCCCTGCAGAAA |
| | | CTGGCTGTGCTGAAGGCTGACCTGGAAAAGAAAAAGCAGTCC |
| | | ATGGGCAAGCTCTACAGCCTGAAGCAGGACCTGCTGTCTACC |
| | | CTGAAGAACAAGTCTGTGACCCAGAAAACTGAGGCCTGGCTG |
| | | GACAACTTTGCTAGATGCTGGGACAACCTGGTGCAGAAGCTG |
| | | GAAAAGTCTACAGCCCAGATCAGCCAGCAACCTGATCTTGCC |
| | | CCTGGCCTGACCACAATTGGAGCCTCTCCAACACAGACTGTG |
| | | ACCCTGGTTACCCAGCCAGTGGTCACCAAAGAGACAGCCATC |
| | | AGCAAACTGGAAATGCCCAGCTCTCTGATGCTGGAAGTCCCC |
| | | ACACTGGAAAGGCTGCAAGAACTTCAAGAGGCCACAGATGAG |
| | | CTGGACCTGAAGCTGAGACAGGCTGAAGTGATCAAAGGCAGC |
| | | TGGCAGCCAGTTGGGGACCTGCTCATTGATAGCCTGCAGGAC |
| | | CATCTGGAAAAAGTGAAAGCCCTGAGGGGAGAGATTGCCCCT |
| | | CTGAAAGAAAATGTGTCCCATGTGAATGACCTGGCCAGACAG |
| | | CTGACCACACTGGGAATCCAGCTGAGCCCCTACAACCTGAGC |
| | | ACCCTTGAGGACCTGAACACCAGGTGGAAGCTCCTCCAGGTG |
| | | GCAGTGGAAGATAGAGTCAGGCAGCTGCATGAGGCCCACAGA |
| | | GATTTTGGACCAGCCAGCCAGCACTTTCTGTCTACCTCTGTG |
| | | CAAGGCCCCTGGGAGAGAGCTATCTCTCCTAACAAGGTGCCC |
| | | TACTACATCAACCATGAGACACAGACCACCTGTTGGGATCAC |

TABLE 5-continued

RGX-DYS Construct nucleotide sequences

| Structure | SEQ ID | Nucleic Acid Sequence |
|---|---|---|
| | | CCCAAGATGACAGAGCTGTACCAGAGTCTGGCAGACCTCAAC<br>AATGTCAGATTCAGTGCCTACAGGACTGCCATGAAGCTCAGA<br>AGGCTCCAGAAAGCTCTGTGCCTGGACCTGCTTTCCCTGAGT<br>GCAGCTTGTGATGCCCTGGACCAGCACAATCTGAAGCAGAAT<br>GACCAGCCTATGGACATCCTCCAGATCATCAACTGCCTCACC<br>ACCATCTATGATAGGCTGGAACAAGAGCACAACAATCTGGTC<br>AATGTGCCCCTGTGTGTGGACATGTGCCTGAATTGGCTGCTG<br>AATGTGTATGACACAGGCAGAACAGGCAGGATCAGAGTCCTG<br>TCCTTCAAGACAGGCATCATCTCCCTGTGCAAAGCCCACTTG<br>GAGGACAAGTACAGATACCTGTTCAAGCAAGTGGCCTCCAGC<br>ACAGGCTTTTGTGACCAGAGAAGGCTGGGCCTGCTCCTGCAT<br>GACAGCATTCAGATCCCTAGACAGCTGGGAGAAGTGGCTTCC<br>TTTGGAGGCGCCAAGCACCAGGCCAAGTGCAACATCTGCAAA<br>GAGTGCCCCATCATTGGCTTCAGATACAGATCCCTGAAGCAC<br>TTCAACTATGATATCTGCCAGAGCTGCTTCTTTAGTGGCAGG<br>GTTGCCAAGGGCCACAAAATGCACTACCCCATGGTGGAATAC<br>TGCACCCCAACAACCTCTGGGGAAGATGTTAGAGACTTTGCC<br>AAGGTGCTGAAAAACAAGTTCAGGACCAAGAGATACTTTGCT<br>AAGCACCCCAGAATGGGCTACCTGCCTGTCCAGACAGTGCTT<br>GAGGGTGACAACATGGAAACCCCTGTGACACTGATCAATTTC<br>TGGCCAGTGGACTCTGCCCCTGCCTCAAGTCCACAGCTGTCC<br>CATGATGACACCCACAGCAGAATTGAGCACTATGCCTCCAGA<br>CTGGCAGAGATGGAAAACAGCAATGGCAGCTACCTGAATGAT<br>AGCATCAGCCCCAATGAGAGCATTGATGATGAGCATCTGCTG<br>ATCCAGCACTACTGTCAGTCCCTGAACCAGGACTCTCCACTG<br>AGCCAGCCTAGAAGCCCTGCTCAGATCCTGATCAGCCTTGAG<br>TCTGAGGAAAGGGGAGAGCTGGAAAGAATCCTGGCAGATCTT<br>GAGGAAGAGAACAGAAACCTGCAGGCAGAGTATGACAGGCTC<br>AAACAGCAGCATGAGCACAAGGGACTGAGCCCTCTGCCTTCT<br>CCTCCTGAAATGATGCCCACCTCTCCACAGTCTCCAAGGTGA<br>TGA Stop codons underlined |
| RGX-DYS7 (coding sequence 4041 bp) | 102 | ATGCTTTGGTGGGAAGAGGTGGAAGATTGCTATGAGAGGGAA<br>GATGTGCAGAAGAAAACCTTCACCAAATGGGTCAATGCCCAG<br>TTCAGCAAGTTTGGCAAGCAGCACATTGAGAACCTGTTCAGT<br>GACCTGCAGGATGGCAGAAGGCTGCTGGATCTGCTGGAAGGC<br>CTGACAGGCCAGAAGCTGCCTAAAGAGAAGGGCAGCACAAGA<br>GTGCATGCCCTGAACAATGTGAACAAGGCCCTGAGAGTGCTG<br>CAGAACAACAATGTGGACCTGGTCAATATTGGCAGCACAGAC<br>ATTGTGGATGGCAACCACAAGCTGACCCTGGGCCTGATCTGG<br>AACATCATCCTGCACTGGCAAGTGAAGAATGTGATGAAGAAC<br>ATCATGGCTGGCCTGCAGCAGACCAACTCTGAGAAGATCCTG<br>CTGAGCTGGGTCAGACAGAGCACCAGAAACTACCCTCAAGTG<br>AATGTGATCAACTTCACCACCTCTTGGAGTGATGGACTGGCC<br>CTGAATGCCCTGATCCACAGCCACAGACCTGACCTGTTTGAC<br>TGGAACTCTGTTGTGTGCCAGCAGTCTGCCACACAGAGACTG<br>GAACATGCCTTCAACATTGCCAGATACCAGCTGGGAATTGAG<br>AAACTGCTGGACCCTGAGGATGTGGACACCACCTATCCTGAC<br>AAGAAATCCATCCTCATGTACATCACCAGCCTGTTCCAGGTG<br>CTGCCCCAGCAAGTGTCCATTGAGGCCATTCAAGAGGTTGAG<br>ATGCTGCCCAGACCTCCTAAAGTGACCAAAGAGGAACACTTC<br>CAGCTGCACCACCAGATGCACTACTCTCAGCAGATCACAGTG<br>TCTCTGGCCCAGGGATATGAGAGAACAAGCAGCCCCAAGCCT<br>AGGTTCAAGAGCTATGCCTACACACAGGCTGCCTATGTGACC<br>ACATCTGACCCCACAAGAAGCCCATTTCCAAGCCAGCATCTG<br>GAAGCCCCTGAGGACAAGAGCTTTGGCAGCAGCCTGATGGAA<br>TCTGAAGTGAACCTGGATAGATACCAGACAGCCCTGGAAGAA<br>GTGCTGTCCTGGCTGCTGTCTGCTGAGGATACACTGCAGGCT<br>CAGGGTGAAATCAGCAATGATGTGGAAGTGGTCAAGGACCAG<br>TTTCACACCCATGAGGGCTACATGATGGACCTGACAGCCCAC<br>CAGGGCAGAGTGGGAAATATCCTGCAGCTGGGCTCCAAGCTG<br>ATTGGCACAGGCAAGCTGTCTGAGGATGAAGAGACAGAGGTG<br>CAAGAGCAGATGAACCTGCTGAACAGCAGATGGGAGTGTCTG<br>AGAGTGGCCAGCATGGAAAAGCAGAGCAACCTGCACAGAGTG<br>CTCATGGACCTGCAGAATCAGAAACTGAAAGAACTGAATGAC<br>TGGCTGACCAAGACAGAAGAAAGGACTAGGAAGATGGAAGAG<br>GAACCTCTGGGACCAGACCTGGAAGATCTGAAAAGACAGGTG<br>CAGCAGCATAAGGTGCTGCAAGAGGACCTTGAGCAAGAGCAA<br>GTCAGAGTGAACAGCCTGACACACATGGTGGTGGTTGTGGAT<br>GAGTCCTCTGGGGATCATGCCACAGCTGCTCTGGAAGAACAG<br>CTGAAGGTGCTGGGAGACAGATGGGCCAACATCTGTAGGTGG<br>ACAGAGGATAGATGGGTGCTGCTCCAGGACATTCTGGAGATC<br>AGCTATGTGCCCAGCACCTACCTGACAGAGATCACCCATGTG<br>TCTCAGGCCCTGCTGGAAGTGGAACAGCTGCTGAATGCCCCT<br>GACCTGTGTGCCAAGGACTTTGAGGACCTGTTCAAGCAAGAG<br>GAAAGCCTGAAGAACATCAAGGACAGCCTGCAGCAGTCCTCT |

TABLE 5-continued

| RGX-DYS Construct nucleotide sequences | | |
|---|---|---|
| Structure | SEQ ID | Nucleic Acid Sequence |
| | | GGCAGAATTGACATCATCCACAGCAAGAAAACAGCTGCCCTG<br>CAGTCTGCCACACCTGTGGAAAGAGTGAAGCTGCAAGAGGCC<br>CTGAGCCAGCTGGACTTCCAGTGGGAGAAAGTGAACAAGATG<br>TACAAGGACAGGCAGGGCAGATTTGATAGAAGTGTGGAAAAG<br>TGGAGAAGGTTCCACTATGACATCAAGATCTTCAACCAGTGG<br>CTGACAGAGGCTGAGCAGTTCCTGAGAAAGACACAGATCCCT<br>GAGAACTGGGAGCATGCCAAGTACAAGTGGTATCTGAAAGAA<br>CTGCAGGATGGCATTGGCCAGAGACAGACAGTTGTCAGAACC<br>CTGAATGCCACAGGGGAAGAGATCATCCAGCAGAGCAGCAAG<br>ACAGATGCCAGCATCCTGCAAGAGAAGCTGGGCAGCCTGAAC<br>CTGAGATGGCAAGAAGTGTGCAAGCAGCTGTCTGACAGAAAG<br>AAGAGGCTGGAAGAACAGACACTGGAAAGGCTGCAAGAACTT<br>CAAGAGGCCACAGATGAGCTGGACCTGAAGCTGAGACAGGCT<br>GAAGTGATCAAAGGCAGCTGGCAGCCAGTTGGGGACCTGCTC<br>ATTGATAGCCTGCAGGACCATCTGGAAAAAGTGAAAGCCCTG<br>AGGGGAGAGATTGCCCCTCTGAAAGAAAATGTGTCCCATGTG<br>AATGACCTGGCCAGACAGCTGACCACACTGGGAATCCAGCTG<br>AGCCCCTACAACCTGAGCACCCTTGAGGACCTGAACACCAGG<br>TGGAAGCTCCTCCAGGTGGCAGTGGAAGATAGAGTCAGGCAG<br>CTGCATGAGGCCCACAGAGATTTTGGACCAGCCAGCCAGCAC<br>TTTCTGTCTACCTCTGTGCAAGGCCCCTGGGAGAGAGCTATC<br>TCTCCTAACAAGGTGCCCTACTACATCAACCATGAGACACAG<br>ACCACCTGTTGGGATCACCCCAAGATGACAGAGCTGTACCAG<br>AGTCTGGCAGACCTCAACAATGTCAGATTCAGTGCCTACAGG<br>ACTGCCATGAAGCTCAGAAGGCTCCAGAAAGCTCTGTGCCTG<br>GACCTGCTTTCCCTGAGTGCAGCTTGTGATGCCCTGGACCAG<br>CACAATCTGAAGCAGAATGACCAGCCTATGGACATCCTCCAG<br>ATCATCAACTGCCTCACCACCATCTATGATAGGCTGGAACAA<br>GAGCACAACAATCTGGTCAATGTGCCCCTGTGTGTGGACATG<br>TGCCTGAATTGGCTGCTGAATGTGTATGACACAGGCAGAACA<br>GGCAGGATCAGAGTCCTGTCCTTCAAGACAGGCATCATCTCC<br>CTGTGCAAAGCCCACTTGGAGGACAAGTACAGATACCTGTTC<br>AAGCAAGTGGCCTCCAGCACAGGCTTTTGTGACCAGAGAAGG<br>CTGGGCCTGCTCCTGCATGACAGCATTCAGATCCCTAGACAG<br>CTGGGAGAAGTGGCTTCCTTTGGAGGCAGCAATATTGAGCCA<br>TCAGTCAGGTCCTGTTTTCAGTTTGCCAACAACAAGCCTGAG<br>ATTGAGGCTGCCCTGTTCCTGGACTGGATGAGACTTGAGCCT<br>CAGAGCATGGTCTGGCTGCCTGTGCTTCATAGAGTGGCTGCT<br>GCTGAGACTGCCAAGCACCAGGCCAAGTGCAACATCTGCAAA<br>GAGTGCCCCATCATTGGCTTCAGATACAGATCCCTGAAGCAC<br>TTCAACTATGATATCTGCCAGAGCTGCTTCTTTAGTGGCAGG<br>GTTGCCAAGGGCCACAAAATGCACTACCCCATGGTGGAATAC<br>TGCACCCCAACAACCTCTGGGGAAGATGTTAGAGACTTTGCC<br>AAGGTGCTGAAAAACAAGTTCAGGACCAAGAGATACTTTGCT<br>AAGCACCCCAGAATGGGCTACCTGCCTGTCCAGACAGTGCTT<br>GAGGGTGACAACATGGAAACCCCTGTGACACTGATCAATTTC<br>TGGCCAGTGGACTCTGCCCCTGCCTCAAGTCCACAGCTGTCC<br>CATGATGACACCCACAGCAGAATTGAGCACTATGCCTCCAGA<br>CTGGCAGAGATGGAAAACAGCAATGGCAGCTACCTGAATGAT<br>AGCATCAGCCCCAATGAGAGCATTGATGATGAGCATCTGCTG<br>ATCCAGCACTACTGTCAGTCCCTGAACCAGGACTCTCCACTG<br>AGCCAGCCTAGAAGCCCTGCTCAGATCCTGATCAGCCTTGAG<br>TCTTGATGA Stop codons underlined |
| RGX-DYS8<br>(coding<br>sequence<br>3765 bp) | 103 | ATGCTTTGGTGGGAAGAGGTGGAAGATTGCTATGAGAGGGAA<br>GATGTGCAGAAGAAAACCTTCACCAAATGGGTCAATGCCCAG<br>TTCAGCAAGTTTGGCAAGCAGCACATTGAGAACCTGTTCAGT<br>GACCTGCAGGATGGCAGAAGGCTGCTGGATCTGCTGGAAGGC<br>CTGACAGGCCAGAAGCTGCCTAAAGAGAAGGGCAGCACAAGA<br>GTGCATGCCCTGAACAATGTGAACAAGGCCCTGAGAGTGCTG<br>CAGAACAACAATGTGGACCTGGTCAATATTGGCAGCACAGAC<br>ATTGTGGATGGCAACCACAAGCTGACCCTGGGCCTGATCTGG<br>AACATCATCCTGCACTGGCAAGTGAAGAATGTGATGAAGAAC<br>ATCATGGCTGGCCTGCAGCAGACCAACTCTGAGAAGATCCTG<br>CTGAGCTGGGTCAGACAGAGCACCAGAAACTACCCTCAAGTG<br>AATGTGATCAACTTCACCACCTCTTGGAGTGATGGACTGGCC<br>CTGAATGCCCTGATCCACAGCCACAGACCTGACCTGTTTGAC<br>TGGAACTCTGTTGTGTGCCAGCAGTCTGCCACACAGAGACTG<br>GAACATGCCTTCAACATTGCCAGATACCAGCTGGGAATTGAG<br>AAACTGCTGGACCCTGAGGATGTGGACACCACCTATCCTGAC<br>AAGAAATCCATCCTCATGTACATCACCAGCCTGTTCCAGGTG<br>CTGCCCCAGCAAGTGTCCATTGAGGCCATTCAAGAGGTTGAG<br>ATGCTGCCCAGACCTCCTAAAGTGACCAAAGAGGAACACTTC<br>CAGCTGCACCACCAGATGCACTACTCTCAGCAGATCACAGTG<br>TCTCTGGCCCAGGGATATGAGAGAACAAGCAGCCCCAAGCCT<br>AGGTTCAAGAGCTATGCCTACACACAGGCTGCCTATGTGACC |

TABLE 5-continued

RGX-DYS Construct nucleotide sequences

| Structure | SEQ ID | Nucleic Acid Sequence |
|---|---|---|
| | | ACATCTGACCCCACAAGAAGCCCATTTCCAAGCCAGCATCTG<br>GAAGCCCCTGAGGACAAGAGCTTTGGCAGCAGCCTGATGGAA<br>TCTGAAGTGAACCTGGATAGATACCAGACAGCCCTGGAAGAA<br>GTGCTGTCCTGGCTGCTGTCTGCTGAGGATACACTGCAGGCT<br>CAGGGTGAAATCAGCAATGATGTGGAAGTGGTCAAGGACCAG<br>TTTCACACCCATGAGGGCTACATGATGGACCTGACAGCCCAC<br>CAGGGCAGAGTGGGAAATATCCTGCAGCTGGGCTCCAAGCTG<br>ATTGGCACAGGCAAGCTGTCTGAGGATGAAGAGACAGAGGTG<br>CAAGAGCAGATGAACCTGCTGAACAGCAGATGGGAGTGTCTG<br>AGAGTGGCCAGCATGGAAAAGCAGAGCAACCTGCACAGAGTG<br>CTCATGGACCTGCAGAATCAGAAACTGAAAGAACTGAATGAC<br>TGGCTGACCAAGACAGAAGAAAGGACTAGGAAGATGGAAGAG<br>GAACCTCTGGGACCAGACCTGGAAGATCTGAAAAGACAGGTG<br>CAGCAGCATAAGGTGCTGCAAGAGGACCTTGAGCAAGAGCAA<br>GTCAGAGTGAACAGCCTGACACACATGGTGGTGGTTGTGGAT<br>GAGTCCTCTGGGGATCATGCCACAGCTGCTCTGGAAGAACAG<br>CTGAAGGTGCTGGGAGACAGATGGGCCAACATCTGTAGGTGG<br>ACAGAGGATAGATGGGTGCTGCTCCAGGACATTCTGGAGATC<br>AGCTATGTGCCCAGCACCTACCTGACAGAGATCACCCATGTG<br>TCTCAGGCCCTGCTGGAAGTGGAACAGCTGCTGAATGCCCCT<br>GACCTGTGTGCCAAGGACTTTGAGGACCTGTTCAAGCAAGAG<br>GAAAGCCTGAAGAACATCAAGGACAGCCTGCAGCAGTCCTCT<br>GGCAGAATTGACATCATCCACAGCAAGAAAACAGCTGCCCTG<br>CAGTCTGCCACACCTGTGGAAAGAGTGAAGCTGCAAGAGGCC<br>CTGAGCCAGCTGGACTTCCAGTGGGAGAAAGTGAACAAGATG<br>TACAAGGACAGGCAGGGCAGATTTGATAGAAGTGTGGAAAAG<br>TGGAGAAGGTTCCACTATGACATCAAGATCTTCAACCAGTGG<br>CTGACAGAGGCTGAGCAGTTCCTGAGAAAGACACAGATCCCT<br>GAGAACTGGGAGCATGCCAAGTACAAGTGGTATCTGAAAGAA<br>CTGCAGGATGGCATTGGCCAGAGACAGACAGTTGTCAGAACC<br>CTGAATGCCACAGGGGAAGAGATCATCCAGCAGAGCAGCAAG<br>ACAGATGCCAGCATCCTGCAAGAGAAGCTGGGCAGCCTGAAC<br>CTGAGATGGCAAGAAGTGTGCAAGCAGCTGTCTGACAGAAAG<br>AAGAGGCTGGAAGAACAGACACTGGAAAGGCTGCAAGAACTT<br>CAAGAGGCCACAGATGAGCTGGACCTGAAGCTGAGACAGGCT<br>GAAGTGATCAAAGGCAGCTGGCAGCCAGTTGGGGACCTGCTC<br>ATTGATAGCCTGCAGGACCATCTGGAAAAAGTGAAAGCCCTG<br>AGGGGAGAGATTGCCCCTCTGAAAGAAAATGTGTCCCATGTG<br>AATGACCTGGCCAGACAGCTGACCACACTGGGAATCCAGCTG<br>AGCCCCTACAACCTGAGCACCCTTGAGGACCTGAACACCAGG<br>TGGAAGCTCCTCCAGGTGGCAGTGGAAGATAGAGTCAGGCAG<br>CTGCATGAGGCCCACAGAGATTTTGGACCAGCCAGCCAGCAC<br>TTTCTGTCTACCTCTGTGCAAGGCCCCTGGGAGAGAGCTATC<br>TCTCCTAACAAGGTGCCCTACTACATCAACCATGAGACACAG<br>ACCACCTGTTGGGATCACCCCAAGATGACAGAGCTGTACCAG<br>AGTCTGGCAGACCTCAACAATGTCAGATTCAGTGCCTACAGG<br>ACTGCCATGAAGCTCAGAAGGCTCCAGAAAGCTCTGTGCCTG<br>GACCTGCTTTCCCTGAGTGCAGCTTGTGATGCCCTGGACCAG<br>CACAATCTGAAGCAGAATGACCAGCCTATGGACATCCTCCAG<br>ATCATCAACTGCCTCACCACCATCTATGATAGGCTGGAACAA<br>GAGCACAACAATCTGGTCAATGTGCCCCTGTGTGTGGACATG<br>TGCCTGAATTGGCTGCTGAATGTGTATGACACAGGCAGAACA<br>GGCAGGATCAGAGTCCTGTCCTTCAAGACAGGCATCATCTCC<br>CTGTGCAAAGCCCACTTGGAGGACAAGTACAGATACCTGTTC<br>AAGCAAGTGGCCTCCAGCACAGGCTTTTGTGACCAGAGAAGG<br>CTGGGCCTGCTCCTGCATGACAGCATTCAGATCCCTAGACAG<br>CTGGGAGAAGTGGCTTCCTTTGGAGGCAGCAATATTGAGCCA<br>TCAGTCAGGTCCTGTTTTCAGTTTGCCAACAACAAGCCTGAG<br>ATTGAGGCTGCCCTGTTCCTGGACTGGATGAGACTTGAGCCT<br>CAGAGCATGGTCTGGCTGCCTGTGCTTCATAGAGTGGCTGCT<br>GCTGAGACTGCCAAGCACCAGGCCAAGTGCAACATCTGCAAA<br>GAGTGCCCCATCATTGGCTTCAGATACAGATCCCTGAAGCAC<br>TTCAACTATGATATCTGCCAGAGCTGCTTCTTTAGTGGCAGG<br>GTTGCCAAGGGCCACAAAATGCACTACCCCATGGTGGAATAC<br>TGCACCCCAACAACCTCTGGGGAAGATGTTAGAGACTTTGCC<br>AAGGTGCTGAAAAACAAGTTCAGGACCAAGAGATACTTTGCT<br>AAGCACCCCAGAATGGGCTACCTGCCTGTCCAGACAGTGCTT<br>GAGGGTGACAACATGGAAACCTGATGA Stop codons<br>underlined |

5.2.2.1 Codon Optimization and CpG Depletion

In one aspect the nucleotide sequence encoding the micro-dystrophin cassette is modified by codon optimization and CpG dinucleotide and CpG island depletion. Immune response against microdystrophin transgene is a concern for human clinical application, as evidenced in the first Duchenne Muscular Dystrophy (DMD) gene therapy clinical trials and in several adeno-associated vial (AAV)-minidystrophin gene therapy in canine models [Mendell, J. R., et al., Dystrophin immunity in Duchenne's muscular dystrophy. *N Engl J Med,* 2010. 363(15): p. 1429-37; and Kornegay, J. N., et al., Widespread muscle expression of an AAV9 human mini-dystrophin vector after intravenous injection in neonatal dystrophin-deficient dogs. *Mol Ther,* 2010. 18(8): p. 1501-8].

AAV-directed immune responses can be inhibited by reducing the number of CpG di-nucleotides in the AAV genome [Faust, S. M., et al., CpG-depleted adeno-associated virus vectors evade immune detection. *J Clin Invest,* 2013. 123(7): p. 2994-3001]. Depleting the transgene sequence of CpG motifs may diminish the role of TLR9 in activation of innate immunity upon recognition of the transgene as non-self, and thus provide stable and prolonged transgene expression. [See also Wang, D., P. W. L. Tai, and G. Gao, Adeno-associated virus vector as a platform for gene therapy delivery. *Nat Rev Drug Discov,* 2019. 18(5): p. 358-378; and Rabinowitz, J., Y. K. Chan, and R. J. Samulski, Adeno-associated Virus (AAV) versus Immune Response. *Viruses,* 2019. 11(2)]. In embodiments, the microdystrophin cassette is human codon-optimized with CpG depletion. Codon-optimized and CpG depleted nucleotide sequences may be designed by any method known in the art, including for example, by Thermo Fisher Scientific GeneArt Gene Synthesis tools utilizing GeneOptimizer (Waltham, MA USA)). Nucleotide sequences SEQ ID NOs: 20, 21, 57-72, 80, 81, and 101-103 described herein represent codon-optimized and CpG depleted sequences.

Provided are microdystrophin transgenes that have reduced numbers of CpG dinucleotide sequences and, as a result, have reduced number of CpG islands. In certain embodiments, the microdystrophin nucleotide sequence has fewer than two (2) CpG islands, or one (1) CpG island or zero (0) CpG islands. In embodiments, provided are micro-dystrophin transgenes having fewer than 2, or 1 CpG islands, or 0 CpG islands that have reduced immunogenicity, as measured by anti-drug antibody titer compared to a microdystrophin transgene having more than 2 CpG islands. In certain embodiments, the microdystrophin nucleotide sequence consisting essentially of SEQ ID NO: 20, 21, 81, 101, 102 or 103 has zero (0) CpG islands. In other embodiments, the microdystrophin transgene nucleotide sequence consisting essentially of a microdystrophin gene operably linked to a promoter, wherein the microdystrophin consists of SEQ ID NO: 20, 21, 81, 101, 102 or 103, has less than two (2) CpG islands. In still other embodiments, the microdystrophin transgene nucleotide sequence consisting essentially of a microdystrophin gene operably linked to a promoter, wherein the microdystrophin consists of SEQ ID NO: 20, 21, 81, 101, 102 or 103, has one (1) CpG island.

5.3. Gene Cassettes and Regulatory Elements

Another aspect of the present invention relates to nucleic acid expression cassettes comprising regulatory elements designed to confer or enhance expression of the microdystrophins. The invention further involves engineering regulatory elements, including promoter elements, and optionally enhancer elements and/or introns, to enhance or facilitate expression of the transgene. In some embodiments, the rAAV vector also includes such regulatory control elements known to one skilled in the art to influence the expression of the RNA and/or protein products encoded by nucleic acids (transgenes) within target cells of the subject. Regulatory control elements and may be tissue-specific, that is, active (or substantially more active or significantly more active) only in the target cell/tissue.

5.3.1 Promoters 5.3.1.1 Tissue-Specific Promoters

In specific embodiments, the expression cassette of an AAV vector comprises a regulatory sequence, such as a promoter, operably linked to the transgene that allows for expression in target tissues. The promoter may be a constitutive promoter, for example, the CB7 promoter. Additional promoters include: cytomegalovirus (CMV) promoter, Rous sarcoma virus (RSV) promoter, MMT promoter, EF-1 alpha promoter (SEQ ID NO: 118), UB6 promoter, chicken beta-actin promoter, CAG promoter (SEQ ID NO: 116), RPE65 promoter, opsin promoter, the TBG (Thyroxine-binding Globulin) promoter, the APOA2 promoter, SERPINA1 (hAAT) promoter, or MIR122 promoter. In some embodiments, particularly where it may be desirable to turn off transgene expression, an inducible promoter is used, e.g., hypoxia-inducible or rapamycin-inducible promoter.

In certain embodiments, the promoter is a muscle-specific promoter. The phrase "muscle-specific", "muscle-selective" or "muscle-directed" refers to nucleic acid elements that have adapted their activity in muscle cells or tissue due to the interaction of such elements with the intracellular environment of the muscle cells. Such muscle cells may include myocytes, myotubes, cardiomyocytes, and the like. Specialized forms of myocytes with distinct properties such as cardiac, skeletal, and smooth muscle cells are included. Various therapeutics may benefit from muscle-specific expression of a transgene. In particular, gene therapies that treat various forms of muscular dystrophy delivered to and enabling high transduction efficiency in muscle cells have the added benefit of directing expression of the transgene in the cells where the transgene is most needed. Cardiac tissue will also benefit from muscle-directed expression of the transgene. Muscle-specific promoters may be operably linked to the transgenes of the invention. In some embodiments, the muscle-specific promoter is selected from an SPc5-12 promoter, a muscle creatine kinase myosin light chain (MLC) promoter, a myosin heavy chain (MHC) promoter, a desmin promoter (SEQ ID NO: 119), a MHCK7 promoter (SEQ ID NO: 120), a CK6 promoter, a CK8 promoter (SEQ ID NO: 115), a MCK promoter (or a truncated form thereof) (SEQ ID NO: 121), an alpha actin promoter, an beta actin promoter, an gamma actin promoter, an E-syn promoter, a cardiac troponin C promoter, a troponin I promoter, a myoD gene family promoter, or a muscle-selective promoter residing within intron 1 of the ocular form of Pitx3.

Synthetic promoter c5-12 (Li, X. et al. Nature Biotechnology Vol. 17, pp. 241-245, MARCH 1999), known as the SPc5-12 promoter, has been shown to have cell type restricted expression, specifically muscle-cell specific expression. At less than 350 bp in length, the SPc5-12 promoter is smaller in length than most endogenous promoters, which can be advantageous when the length of the nucleic acid encoding the therapeutic protein is relatively long. In embodiments, provided are gene therapy cassettes with an SPc5-12 promoter (SEQ ID NO: 39).

In order to further reduce the length of a vector, regulatory elements can be a reduced or shortened version (referred to herein as a "minimal promoter") of any one of the promoters described herein. A minimal promoter comprises at least the transcriptionally active domain of the full-length version and is therefore still capable of driving expression. For example, in some embodiments, an AAV vector can comprise the transcriptionally active domain of a muscle-specific promoter, e.g., a minimal SPc5-12 promoter (e.g., SEQ ID NO: 40), operably linked to a therapeutic protein transgene. In embodiments, the therapeutic protein is microdystrophin as described herein. A minimal promoter of the present disclosure may or may not contain the portion of the promoter sequence that contributes to regulating expression in a tissue-specific manner.

Accordingly, in embodiments, provided are gene therapy cassettes with an SPc5-12 promoter (SEQ ID NO: 39). In embodiments, provided are gene therapy cassettes with minimal promoters that direct expression of the microdystrophin in muscle cells. One such promoter is a minimal SPc5-12 promoter of SEQ ID NO: 40. Sequences of these promoters are provided in Table 6.

TABLE 6

Promoter sequences

| Promoter | SEQ ID | Nucleic Acid Sequence |
|---|---|---|
| SPc5-12 | 39 | GGCCGTCCGCCCTCGGCACCATCCTCACGACACCCAAA<br>TATGGCGACGGGTGAGGAATGGTGGGGAGTTATTTTTA<br>GAGCGGTGAGGAAGGTGGGCAGGCAGCAGGTGTTGGCG<br>CTCTAAAAATAACTCCCGGGAGTTATTTTTAGAGCGGA<br>GGAATGGTGGACACCCAAATATGGCGACGGTTCCTCAC<br>CCGTCGCCATATTTGGGTGTCCGCCCTCGGCCGGGGCC<br>GCATTCCTGGGGGCCGGGCGGTGCTCCCGCCCGCCTCG<br>ATAAAAGGCTCCGGGGCCGGCGGCGGCCCACGAGCTAC<br>CCGGAGGAGCGGGAGGCGCCAAGC |
| minSPc5-12 | 40 | GAATGGTGGACACCCAAATATGGCGACGGTTCCTCACC<br>CGTCGCCATATTTGGGTGTCCGCCCTCGGCCGGGGCCG<br>CATTCCTGGGGGCCGGGCGGTGCTCCCGCCCGCCTCGA<br>TAAAAGGCTCCGGGGCCGGCGGCGGCCCACGAGCTACC<br>CGGAGGAGCGGGAGGCGCCAAG |
| CK8 | 115 | ccactacgggtttaggctgcccatgtaaggaggcaagg<br>cctggggacacccgagatgcctggttataattaaccca<br>gacatgtggctgccccccccccccccaacacctgctgc<br>ctctaaaaataaccctgtccctggtggatcccactacg<br>ggtttaggctgcccatgtaaggaggcaaggcctgggga<br>cacccgagatgcctggttataattaacccagacatgtg<br>getgccccccccccccccaacacctgctgcctctaaaa<br>ataaccctgtccctggtggatcccactacgggtttagg<br>ctgcccatgtaaggaggcaaggcctggggacacccgag<br>atgcctggttataattaacccagacatgtggctgcccc<br>ccccccccccaacacctgctgcctctaaaaataaccct<br>gtccctggtggatcccctgcatgcgaagatcttcgaac<br>aaggctgtgggggactgagggcaggctgtaacaggctt<br>attactgttccatgttcccggcgaagggccagctgtcc<br>cccgccagctagactcagcacttagtttaggaaccagt<br>gagcaagtcagcccttggggcagcccatacaaggccat<br>acggtgcccgggcaacgagctgaaagctcatctgctct<br>caggggcccctccctggggacagcccctcctggctagt<br>cacaccctgtaggctcctctatataacccaggggcaca<br>ggggctgccctcattctaccaccacctccacagcacag<br>acagacactcaggagccagccagcgtcga |
| CAG | 116 | gacattgattattgactagttattaatagtaatcaatt<br>acggggtcattagttcatagcccatatatggagttccg<br>cgttacataacttacggtaaatggcccgcctggctgac<br>cgcccaacgacccccgcccattgacgtcaataatgacg<br>tatgttoccatagtaacgccaatagggactttccattg<br>acgtcaatgggtggagtatttacggtaaactgcccact<br>tggcagtacatcaagtgtatcatatgccaagtacgccc<br>cctattgacgtcaatgacggtaaatggcccgcctggca |

TABLE 6-continued

Promoter sequences

| Promoter | SEQ ID | Nucleic Acid Sequence |
|---|---|---|
| | | ttatgcccagtacatgaccttatgggactttcctactt<br>ggcagtacatctacgtattagtcatcgctattaccatg<br>gtcgaggtgagccccacgttctgcttcactctccccat<br>ctcccccccctccccacccccaatttgtatttattta<br>ttttttaattattttgtgcagcgatgggggcggggggg<br>ccaatcagagcggcgcgctccgaaagtttccttttatg<br>gcgaggcggcggcggcggcggccctataaaaagcgaag<br>cgcgcggcgggcgggagtcgctgcgcgctgccttcgcc<br>ccgtgccccgctccgccgccgcctcgcgccgcccgccc<br>cggctctgactgaccgcgttactcccacaggtgagcgg<br>gcgggacggcccttctcctccgggctgtaattagcgct<br>tggtttaatgacggcttgtttcttttctgtggctgcgt<br>gaaagccttgaggggctccgggagggccctttgtgcgg<br>ggggagcggctcgggggggtgcgtgcgtgtgtgtgtgcg<br>tggggagcgccgcgtgcggctccgcgctgcccggcggc<br>tgtgagcgctgcgggcgcggcgcggggctttgtgcgct<br>ccgcagtgtgcgcgaggggagcgcggccgggggcggtg<br>ccccgcggtgcggggggggctgcgaggggaacaaaggc<br>tgcgtgcggggtgtgtgcgtgggggggtgagcaggggg<br>tgtgggcgcgtcggtcgggctgcaaccccccctgcacc<br>cccctccccgagttgctgagcacggcccggcttcgggt<br>gcggggctccgtacggggcgtggcgcggggctcgccgt<br>gggcggggccgcctcgggccggggagggctcgggggag<br>gggcgcggcggcccccggagcgccggcggctgtcgagg<br>cgcggcgagccgcagccattgccttttatggtaatcgt<br>gcgagagggcgcagggacttcctttgtcccaaatctgt<br>gcggagccgaaatctgggaggcgccgccgcaccccctc<br>tagcgggcgcggggcgaagcggtgcggcgccggcagga<br>cgccgtccccttctccctctccagcctcggggctgtcc<br>gcctctgctaaccatgttcatgccttcttctttttcct<br>acagctcctgggcaacgtgctggttattgtgctgtctc<br>atcattttggcaaag |
| mU1a | 117 | atggaggcggtactatgtagatgagaattcaggagcaa<br>actgggaaaagcaactgcttccaaatatttgtgatttt<br>tacagtgtagttttggaaaaactcttagcctaccaatt<br>cttctaagtgttttaaaatgtgggagccagtacacatg<br>aagttatagagtgttttaatgaggcttaaatatttacc<br>gtaactatgaaatgctacgcatatcatgctgttcaggc<br>tccgtggccacgcaactcatact |
| EF-1□ | 118 | gggcagagcgcacatcgcccacagtccccgagaagttg<br>gggggaggggtcggcaattgaacgggtgcctagagaag<br>gtggcgcggggtaaactgggaaagtgatgtcgtgtact<br>ggctccgcctttttcccgagggtgggggagaaccgtat<br>ataagtgcagtagtcgccgtgaacgttctttttcgcaa<br>cgggtttgccgccagaacacag |
| Human desmin | 119 | ctgcagacatgcttgctgcctgccctggcgtgccctgg<br>cgaggcttgccgtcacaggacccccgctggctgactca<br>ggggcgcaggctcttgcgggggagctggcctcccgccc<br>ccacggccacgggccctttcctggcaggacagcgggat<br>cttgcagctgtcaggggaggggatgacgggggactgat<br>gtcaggaggggatacaaatagtgccgaacaaggaccgg<br>attagatctacc |
| MHCK7 | 120 | aagcttgcat gtctaagcta gacccttcag<br>attaaaaata actgaggtaa gggcctgggt<br>aggggaggtg gtgtgagacg ctcctgtctc<br>tcctctatct gcccateggc cctttgggga<br>ggaggaatgt goccaaggac taaaaaaagg<br>ccatggagcc agaggggcga gggcaacaga<br>cctttcatgg gcaaaccttg gggccctgct<br>gtctagcatg ccccactacg ggtctaggct<br>gcccatgtaa ggaggcaagg cctggggaca<br>cccgagatgc ctggttataa ttaacccaga<br>catgtggctg cccccccccc cccaacacct<br>getgcctcta aaaataaccc tgtccctggt<br>ggatcccctg catgcgaaga tottcgaaca<br>aggctgtggg ggactgaggg caggctgtaa<br>caggettggg ggccagggct tatacgtgcc<br>tgggactccc aaagtattac tgttccatgt<br>tcccggcgaa gggccagctg tcccccgcca<br>gctagactca gcacttagtt taggaaccag<br>tgagcaagtc agcccttggg gcagcccata |

TABLE 6-continued

| Promoter sequences | | |
|---|---|---|
| Promoter | SEQ ID | Nucleic Acid Sequence |
| | | caaggccatg gggctgggca agctgcacgc<br>ctgggtccgg ggtgggcacg gtgcccgggc<br>aacgagctga aagctcatct gctctcaggg<br>gcccctccct ggggacagcc cctcctggct<br>agtcacaccc tgtaggctcc tctatataac<br>ccaggggcac aggggctgcc ctcattctac<br>caccacctcc acagcacaga cagacactca<br>ggagcagcca gc |
| Truncated MCK | 121 | ccactacggg tctaggctgc ccatgtaagg<br>aggcaaggcc tggggacacc cgagatgcct<br>ggttataatt aaccccaaca cctgctgccc<br>cccccccccc aacacctgct gectgagcct<br>gagcggttac ccccaccccgg tgcctgggtc<br>ttaggctctg tacaccatgg aggagaagct<br>cgctctaaaa ataaccctgt ccctggtgga<br>tccactacgg gtctatgctg cccatgtaag<br>gaggcaaggc ctggggacac ccgagatgcc<br>tggttataat taaccccaac acctgctgcc<br>cccccccccc caacacctgc tgcctgagcc<br>tgagcggtta ccccaccccg gtgcctgggt<br>cttaggetct gtacaccatg gaggagaagc<br>togctctaaa aataaccctg tccctggtgg<br>accactacgg gtctaggctg cccatgtaag<br>gaggcaaggc ctggggacac ccgagatgcc<br>togttataat taaccccaac acctgctgcc<br>cccccccccc aacacctgct gectgagcct<br>gagcggttac cccaccccgg tgcctgggtc<br>ttaggctctg tacaccatgg aggagaagct<br>cgctctaaaa ataaccctgt ccctggtcct<br>ccctggggac agcccctect ggctagtcac<br>accctgtagg ctcctctata taacccaggg<br>gcacaggggc tgcccccggg tcac |

In certain embodiments, the promoter is a CNS-specific promoter. For example, an expression cassette can comprise a promoter selected from a promoter isolated from the genes of neuron specific enolase (NSE), any neuronal promoter such as the promoter of Dopamine-1 receptor or Dopamine-2 receptor, the synapsin promoter, CB7 promoter (a chicken β-actin promoter and CMV enhancer), RSV promoter, GFAP promoter (glial fibrillary acidic protein), MBP promoter (myelin basic protein), MMT promoter, EF-1α, U86 promoter, RPE65 promoter or opsin promoter, an inducible promoter, for example, a hypoxia-inducible promoter, and a drug inducible promoter, such as a promoter induced by rapamycin and related agents.

In still other embodiments, expression cassettes can comprise multiple promoters which may be placed in tandem in the expression cassette comprising a microdystrophin transgene. As such, tandem or hybrid promoters may be employed in order to enhance expression and/or direct expression to multiple tissue types, (see, e.g. PCT International Publication No. WO2019154939A1, published Aug. 15, 2019, incorporated herein by reference) and, in particular, LMTP6, LMTP13, LMTP14, LMTP15, LMTP18, LMTP19, or LMTP20 as disclosed in PCT International Application No. PCT/US2020/043578, filed Jul. 24, 2020, hereby incorporated by reference).

5.3.2 Introns

Another aspect of the present disclosure relates to an AAV vector comprising an intron within the regulatory cassette. Example 2 demonstrates that the VH4 intron 5' of the microdystrophin coding sequence enhances proper splicing and, thus, microdystrophin expression. Accordingly, in some embodiments, an intron is coupled to the 5' end of a sequence encoding a microdystrophin protein, e.g., ABD-H1-R1-R2-R3-H3-R24-H4-CR, ABD-H1-R1-R2-R3-H3-R24-H4-CR-CT, ABD-H1-R1-R2-R16-R17-R24-H4-CR, or ABD-H1-R1-R2-R16-R17-R24-H4-CR-CT. In particular, the intron can be linked to the actin-binding domain. In other embodiments, the intron is less than 100 nucleotides in length.

In embodiments, the intron is a VH4 intron. The VH4 intron nucleic acid can comprise SEQ ID NO: 41 as shown in Table 7 below.

TABLE 7

| Nucleotide sequences for different introns | | |
|---|---|---|
| Structure | SEQ ID | Sequence |
| VH4 intron | 41 | GTGAGTATCTCAGGGATCCAGACATGGGGATA<br>TGGGAGGTGCCTCTGATCCCAGGGCTCACTGT<br>GGGTCTCTCTGTTCACAG |
| Chimeric intron | 75 | GTAAGTATCAAGGTTACAAGACAGGTTTAAGG<br>AGACCAATAGAAACTGGGCTTGTCGAGACAGA<br>GAAGACTCTTGCGTTTCTGATAGGCACCTATT<br>GGTCTTACTGACATCCACTTTGCCTTTCTCTC<br>CACAG |
| SV40 intron | 76 | GTAAGTTTAGTCTTTTTGTCTTTTATTTCAGG<br>TCCCGGATCCGGTGGTGGTGCAAATCAAAGAA<br>CTGCTCCTCAGTGGATGTTGCCTTTACTTCTA<br>G |

In other embodiments, the intron is a chimeric intron derived from human β-globin and Ig heavy chain (also known as β-globin splice donor/immunoglobulin heavy chain splice acceptor intron, or β-globin/IgG chimeric intron) (Table 7, SEQ ID NO: 75). Other introns well known to the skilled person may be employed, such as the chicken β-actin intron, minute virus of mice (MVM) intron, human factor IX intron (e.g., FIX truncated intron 1), β-globin splice donor/immunoglobulin heavy chain splice acceptor intron, adenovirus splice donor/immunoglobulin splice acceptor intron, SV40 late splice donor/splice acceptor (19S/16S) intron (Table 7, SEQ ID NO: 76).

5.3.3 Other Regulatory Elements 5.3.3.1 polyA

Another aspect of the present disclosure relates to expression cassettes comprising a polyadenylation (polyA) site downstream of the coding region of the microdystrophin transgene. Any polyA site that signals termination of transcription and directs the synthesis of a polyA tail is suitable for use in AAV vectors of the present disclosure. Exemplary polyA signals are derived from, but not limited to, the following: the SV40 late gene, the rabbit 3-globin gene, the bovine growth hormone (BPH) gene, the human growth hormone (hGH) gene, and the synthetic polyA (SPA) site. In one embodiment, the polyA signal comprises SEQ ID NO: 42 as shown in Table 8.

TABLE 8

| Nucleotide sequence of the poly A signal | | |
|---|---|---|
| Structure | SEQ ID | Sequence |
| polyA | 42 | AGGCCTAATAAAGAGCTCAGATGCATCG<br>ATCAGAGTGTGTTGGTTTTTTG |

5.3.4 Viral Vectors

The microdystrophin transgene in accordance with the present disclosure can be included in an AAV vector for gene therapy administration to a human subject. In some embodiments, recombinant AAV (rAAV) vectors can comprise an AAV viral capsid and a viral or artificial genome comprising an expression cassette flanked by AAV inverted terminal repeats (ITRs) wherein the expression cassette comprises a microdystrophin transgene, operably linked to one or more regulatory sequences that control expression of the transgene in human muscle or CNS cells to express and deliver the microdystrophin. The provided methods are suitable for use in the production of any isolated recombinant AAV particles for delivery of a microdystrophins described herein, in the production of a composition comprising any isolated recombinant AAV particles encoding a microdystrophin, or in the method for treating a disease or disorder amenable for treatment with a microdystrophin in a subject in need thereof comprising the administration of any isolated recombinant AAV particles encoding a microdystrophin described herein. As such, the rAAV can be of any serotype, variant, modification, hybrid, or derivative thereof, known in the art, or any combination thereof (collectively referred to as "serotype"). In particular embodiments, the AAV serotype has a tropism for muscle tissue. In other embodiments, the AAV serotype has a tropism for the CNS. In other embodiments, the AAV serotype has a tropism for both muscle tissue and the CNS. And, in other embodiments, the AAV serotype has a tropism for the liver, in which case the liver cells transduced with the AAV form a depot of microdystrophin secreting cells, secretin the microdystrophin into the circulation.

In some embodiments, rAAV particles have a capsid protein from an AAV serotype selected from AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV.PHP.eB, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, rAAV.Anc80L65, AAV.7m8, AAV.PHP.B, AAV.PHP.eB, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16, or a derivative, modification, or pseudotype thereof.

For example, a population of rAAV particles can comprise two or more serotypes, e.g., comprising two or more of AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV.PHP.eB, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other rAAV particles, or combinations of two or more thereof.)

In some embodiments, rAAV particles comprise the capsid of Anc80 or Anc80L65, as described in Zinn et al., 2015, Cell Rep. 12(6): 1056-1068, which is incorporated by reference in its entirety. In certain embodiments, the rAAV particles comprise the capsid with one of the following amino acid insertions: LGETTRP or LALGETTRP, as described in U.S. Pat. Nos. 9,193,956; 9,458,517; and 9,587,282 and US patent application publication no. 2016/0376323, each of which is incorporated herein by reference in its entirety. In some embodiments, rAAV particles comprise the capsid of AAV.7m8, as described in U.S. Pat. Nos. 9,193,956; 9,458,517; and 9,587,282 and US patent application publication no. 2016/0376323, each of which is incorporated herein by reference in its entirety. In some embodiments, rAAV particles comprise any AAV capsid disclosed in U.S. Pat. No. 9,585,971, such as AAVPHP.B. In some embodiments, rAAV particles comprise any AAV capsid disclosed in U.S. Pat. No. 9,840,719 and WO 2015/013313, such as AAV.Rh74 and RHM4-1, each of which is incorporated herein by reference in its entirety. In some embodiments, rAAV particles comprise any AAV capsid disclosed in WO 2014/172669, such as AAV rh.74, which is incorporated herein by reference in its entirety. In some embodiments, rAAV particles comprise the capsid of AAV2/5, as described in Georgiadis et al., 2016, Gene Therapy 23: 857-862 and Georgiadis et al., 2018, Gene Therapy 25: 450, each of which is incorporated by reference in its entirety. In some embodiments, rAAV particles comprise any AAV capsid disclosed in WO 2017/070491, such as AAV2tYF, which is incorporated herein by reference in its entirety. In some embodiments, rAAV particles comprise the capsids of AAVLK03 or AAV3B, as described in Puzzo et al., 2017, Sci. Transl. Med. 29(9): 418, which is incorporated by reference in its entirety. In some embodiments, rAAV particles comprise any AAV capsid disclosed in U.S. Pat. Nos. 8,628,966; 8,927,514; 9,923,120 and WO 2016/049230, such as HSC1, HSC2, HSC3, HSC4, HSC5, HSC6, HSC7, HSC8, HSC9, HSC10, HSC11, HSC12, HSC13, HSC14, HSC15, or HSC16, each of which is incorporated by reference in its entirety.

In some embodiments, rAAV particles comprise an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024;

2017/0051257; and International Patent Application Nos. PCT/US2015/034799; PCT/EP2015/053335.

In some embodiments, rAAV particles have a capsid protein disclosed in Intl. Appl. Publ. No. WO 2003/052051 (see, e.g., SEQ ID NO: 2 of '051), WO 2005/033321 (see, e.g., SEQ ID NOs: 123 and 88 of '321), WO 03/042397 (see, e.g., SEQ ID NOs: 2, 81, 85, and 97 of '397), WO 2006/068888 (see, e.g., SEQ ID NOs: 1 and 3-6 of '888), WO 2006/110689, (see, e.g., SEQ ID NOs: 5-38 of '689) WO2009/104964 (see, e.g., SEQ ID NOs: 1-5, 7, 9, 20, 22, 24 and 31 of '964), WO 2010/127097 (see, e.g., SEQ ID NOs: 5-38 of '097), and WO 2015/191508 (see, e.g., SEQ ID NOs: 80-294 of '508), and U.S. Appl. Publ. No. 20150023924 (see, e.g., SEQ ID NOs: 1, 5-10 of '924), the contents of each of which is herein incorporated by reference in its entirety. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in Intl. Appl. Publ. No. WO 2003/052051 (see, e.g., SEQ ID NO: 2 of '051), WO 2005/033321 (see, e.g., SEQ ID NOs: 123 and 88 of '321), WO 03/042397 (see, e.g., SEQ ID NOs: 2, 81, 85, and 97 of '397), WO 2006/068888 (see, e.g., SEQ ID NOs: 1 and 3-6 of '888), WO 2006/110689 (see, e.g., SEQ ID NOs: 5-38 of '689) WO2009/104964 (see, e.g., SEQ ID NOs: 1-5, 7, 9, 20, 22, 24 and 31 of 964), WO 2010/127097 (see, e.g., SEQ ID NOs: 5-38 of '097), and WO 2015/191508 (see, e.g., SEQ ID NOs: 80-294 of '508), and U.S. Appl. Publ. No. 20150023924 (see, e.g., SEQ ID NOs: 1, 5-10 of '924).

Nucleic acid sequences of AAV based viral vectors and methods of making recombinant AAV and AAV capsids are taught, for example, in U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; International Patent Application Nos. PCT/US2015/034799; PCT/EP2015/053335; WO 2003/052051, WO 2005/033321, WO 03/042397, WO 2006/068888, WO 2006/110689, WO2009/104964, WO 2010/127097, and WO 2015/191508, and U.S. Appl. Publ. No. 20150023924.

In additional embodiments, rAAV particles comprise a pseudotyped AAV capsid. In some embodiments, the pseudotyped AAV capsids are rAAV2/8 or rAAV2/9 pseudotyped AAV capsids. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In certain embodiments, a single-stranded AAV (ssAAV) can be used. In certain embodiments, a self-complementary vector, e.g., scAAV, can be used (see, e.g., Wu, 2007, Human Gene Therapy, 18(2):171-82, McCarty et al, 2001, Gene Therapy, Vol. 8, Number 16, Pages 1248-1254; and U.S. Pat. Nos. 6,596,535; 7,125,717; and 7,456,683, each of which is incorporated herein by reference in its entirety).

In some embodiments, rAAV particles comprise a capsid protein from an AAV capsid serotype selected from AAV8 or AAV9. In some embodiments, the rAAV particles comprise a capsid protein from an AAV capsid serotype selected from the group consisting of AAV7, AAV8, AAV9, AAV.rh8, AAV.rh10, AAV.rh20, AAV.rh39, AAV.Rh74, AAV.RHM4-1, AAV.hu31, AAV.hu32, AAV.hu37, AAV.PHP.B, AAV.PHP.eB, and AAV.7m8. In some embodiments, the rAAV particles comprise a capsid protein with high sequence homology to AAV8 or AAV9 such as, AAV.rh10, AAV.rh20, AAV.rh39, AAV.Rh74, AAV.RHM4-1, AAV.hu31, AAV.hu32, and AAV.hu37. In some embodiments, the rAAV particles have an AAV capsid serotype of AAV1 or a derivative, modification, or pseudotype thereof. In some embodiments, the rAAV particles have an AAV capsid serotype of AAV4 or a derivative, modification, or pseudotype thereof. In some embodiments, the rAAV particles have an AAV capsid serotype of AAV5 or a derivative, modification, or pseudotype thereof. In some embodiments, the rAAV particles have an AAV capsid serotype of AAV8 or a derivative, modification, or pseudotype thereof. In some embodiments, the rAAV particles have an AAV capsid serotype of AAV9 or a derivative, modification, or pseudotype thereof.

In some embodiments, rAAV particles comprise a capsid protein that is a derivative, modification, or pseudotype of AAV8 or AAV9 capsid protein. In some embodiments, rAAV particles comprise a capsid protein that has an AAV8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV8 capsid protein. In some embodiments, rAAV particles comprise a capsid protein that is a derivative, modification, or pseudotype of AAV9 capsid protein. In some embodiments, rAAV particles comprise a capsid protein that has an AAV8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV9 capsid protein.

In some embodiments, the rAAV particles comprise a capsid protein that has at least 80% or more identity, e.g., 85%, 85%, 87%, 88%, 89%, 90%, 91%, 92%, 93%, 94%, 95%, 96%, 97%, 98%, 99%, 99.5%, etc., i.e. up to 100% identity, to the VP1, VP2 and/or VP3 sequence of AAV7, AAV8, AAV9, AAV.rh8, AAV.rh10, AAV.rh20, AAV.rh39, AAV.Rh74, AAV.RHM4-1, AAV.hu31, AAV.hu32, AAV.hu37, AAV.PHP.B, AAV.PHP.eB, or AAV.7m8 capsid protein. In some embodiments, the rAAV particles comprise a capsid protein that has at least 80% or more identity, e.g., 85%, 85%, 87%, 88%, 89%, 90%, 91%, 92%, 93%, 94%, 95%, 96%, 97%, 98%, 99%, 99.5%, etc., i.e. up to 100% identity, to the VP1, VP2 and/or VP3 sequence of an AAV capsid protein with high sequence homology to AAV8 or AAV9 such as, AAV.rh10, AAV.rh20, AAV.rh39, AAV.Rh74, AAV.RHM4-1, AAV.hu31, AAV.hu32, and AAV.hu37.

In additional embodiments, rAAV particles comprise a mosaic capsid. Mosaic AAV particles are composed of a mixture of viral capsid proteins from different serotypes of AAV. In some embodiments, rAAV particles comprise a mosaic capsid containing capsid proteins of a serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV.PHP.eB, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

In some embodiments, rAAV particles comprise a mosaic capsid containing capsid proteins of a serotype selected from AAV1, AAV2, AAV5, AAV6, AAV7, AAV8, AAV9, AAV10, AAVrh.8, and AAVrh.10.

In additional embodiments, rAAV particles comprise a pseudotyped rAAV particle. In some embodiments, the pseudotyped rAAV particle comprises (a) a nucleic acid vector comprising AAV ITRs and (b) a capsid comprised of capsid proteins derived from AAVx (e.g., AAV1, AAV3, AAV4, AAV5, AAV6, AAV7, AAV8, AAV9, AAV10 AAV11, AAV12, AAV13, AAV14, AAV15 and AAV16). In additional embodiments, rAAV particles comprise a pseudotyped rAAV particle comprised of a capsid protein of an AAV serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu31, AAV.hu32, AAV.hu37, AAV.Anc80, AAV.Anc80L65, AAV.7m8, AAV.PHP.B, AAV.PHP.eB, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In additional embodiments, rAAV particles comprise a pseudotyped rAAV particle containing AAV8 capsid protein. In additional embodiments, rAAV particles comprise a pseudotyped rAAV particle is comprised of AAV9 capsid protein. In some embodiments, the pseudotyped rAAV8 or rAAV9 particles are rAAV2/8 or rAAV2/9 pseudotyped particles. Methods for producing and using pseudotypedrAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, rAAV particles comprise a capsid containing a capsid protein chimeric of two or more AAV capsid serotypes. In further embodiments, the capsid protein is a chimeric of 2 or more AAV capsid proteins from AAV serotypes selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV.PHP.eB, AAV2.5, AAV2tYF, AAV3B, rAAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In further embodiments, the capsid protein is a chimeric of 2 or more AAV capsid proteins from AAV serotypes selected from AAV1, AAV2, AAV5, AAV6, AAV7, AAV8, AAV9, AAV10, AAVrh.8, and AAVrh.10.

In some embodiments, the rAAV particles comprise an AAV capsid protein chimeric of AAV8 capsid protein and one or more AAV capsid proteins from an AAV serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV.PHP.eB, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise an AAV capsid protein chimeric of AAV8 capsid protein and one or more AAV capsid proteins from an AAV serotype selected from AAV1, AAV2, AAV5, AAV6, AAV7, AAV9, AAV10, AAVrh.8, and AAVrh.10.

In some embodiments, the rAAV particles comprise an AAV capsid protein chimeric of AAV9 capsid protein the capsid protein of one or more AAV capsid serotypes selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV.PHP.eB, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

In some embodiments, the rAAV particles comprise an AAV capsid protein chimeric ofAAV9 capsidprotein the capsidprotein ofone or more AAV capsid serotypes selected from AAV1, AAV2, AAV3, AAV4, AAV5, AA6, AAV7, AAV8, AAV9, AAVrh.8, and AAVrh.10.

In some embodiments the rAAV particles comprises a Clade A, B, E, or F AAV capsid protein. In some embodiments, the rAAV particles comprises a Clade F AAV capsid protein. In some embodiments the rAAV particles comprises a Clade E AAV capsid protein.

Table 9 below provides examples of amino acid sequences for an AAV8, AAV9, AAV.rh74, AAV.hu3l, AAV.hu32, and AAV.hu37 capsid proteins and the nucleic acid sequence of AAV2 5'- and 3' TRs.

TABLE 9

| Structure | SEQ ID | Sequence |
|---|---|---|
| 5'-ITR | 73 | cgcgcgctcgctcgctcactgaggccgcccgggcaaagcccgggcgtcgggcga cctttggtcgcccggcctcagtgagcgagcgagcgcgcagagagggagtggcca actccatcactaggggttcct<br>Rep protein binding site (rps) is underlined. |
| 3'-ITR | 74 | aggaacccctagtgatggagttggccactccctctctgcgcgctcgctcgctca ctgaggccgggcgaccaaaggtcgcccgacgcccgggctttgcccgggggct cagtgagcgagcgagcgcgcag<br>Rep protein binding site (rps) is underlined. |
| AAV8 Capsid | 77 | MAADGYLPDW LEDNLSEGIR EWWALKPGAP KPKANQQKQD DGRGLVLPGY KYLGPFNGLD KGEPVNAADA AALEHDKAYD QQLQAGDNPY LRYNHADAEF QERLQEDTSF GGNLGRAVFQ AKKRVLEPLG LVEEGAKTAP GKKRPVEPSP QRSPDSSTGI GKKGQQPARK RLNFGQTGDS ESVPDPQPLG EPPAAPSGVG PNTMAAGGGA PMADNNEGAD GVGSSSGNWH CDSTWLGDRV ITTSTRTWAL |

TABLE 9-continued

| Structure | SEQ ID | Sequence |
|---|---|---|
| | | PTYNNHLYKQ ISNGTSGGAT NDNTYFGYST PWGYFDFNRF HCHFSPRDWQ |
| | | RLINNNWGFR PKRLSFKLFN IQVKEVTQNE GTKTIANNLT STIQVFTDSE |
| | | YQLPYVLGSA HQGCLPPFPA DVFMIPQYGY LTLNNGSQAV GRSSFYCLEY |
| | | FPSQMLRTGN NFQFTYTFED VPFHSSYAHS QSLDRLMNPL IDQYLYYLSR |
| | | TOTTGGTANT QTLGFSQGGP NTMANQAKNW LPGPCYRQQR VSTTTGQNNN |
| | | SNFAWTAGTK YHLNGRNSLA NPGIAMATHK DDEERFFPSN GILIFGKQNA |
| | | ARDNADYSDV MLTSEEEIKT TNPVATEEYG IVADNLQQQN TAPQIGTVNS |
| | | QGALPGMVWQ NRDVYLQGPI WAKIPHTDGN FHPSPLMGGF GLKHPPPQIL |
| | | IKNTPVPADP PTTFNQSKLN SFITQYSTGQ VSVEIEWELQ KENSKRWNPE |
| | | IQYTSNYYKS TSVDFAVNTE GVYSEPRPIG TRYLTRNL |
| AAV9 | 78 | MAADGYLPDW LEDNLSEGIR EWWALKPGAP QPKANQQHQD NARGLVLPGY |
| Capsid | | KYLGPGNGLD KGEPVNAADA AALEHDKAYD QQLKAGDNPY LKYNHADAEF |
| | | QERLKEDTSF GGNLGRAVFQ AKKRLLEPLG LVEEAAKTAP GKKRPVEQSP |
| | | QEPDSSAGIG KSGAQPAKKR LNFGQTGDTE SVPDPQPIGE PPAAPSGVGS |
| | | LTMASGGGAP VADNNEGADG VGSSSGNWHC DSQWLGDRVI TTSTRTWALP |
| | | TYNNHLYKQI SNSTSGGSSN DNAYFGYSTP WGYFDFNRFH CHFSPRDWQR |
| | | LINNNWGFRP KRLNFKLFNI QVKEVTDNNG VKTIANNLTS TVQVFTDSDY |
| | | QLPYVLGSAH EGCLPPFPAD VFMIPQYGYL TLNDGSQAVG RSSFYCLEYF |
| | | PSQMLRTGNN FQFSYEFENV PFHSSYAHSQ SLDRLMNPLI DQYLYYLSKT |
| | | INGSGQNQQT LKFSVAGPSN MAVQGRNYIP GPSYRQQRVS TTVTQNNNSE |
| | | FAWPGASSWA LNGRNSLMNP GPAMASHKEG EDRFFPLSGS LIFGKQGTGR |
| | | DNVDADKVMI TNEEEIKTTN PVATESYGQV ATNHQSAQAQ AQTGWVQNQG |
| | | ILPGMVWQDR DVYLQGPIWA KIPHTDGNFH PSPLMGGFGM KHPPPQILIK |
| | | NTPVPADPPT AFNKDKLNSF ITQYSTGQVS VEIEWELQKE NSKRWNPEIQ |
| | | YTSNYYKSNN VEFAVNTEGV YSEPRPIGTR YLTRNL |
| hu.37 | 112 | MAADGYLPDW LEDNLSEGIR EWWDLKPGAP KPKANQQKQD DGRGLVLPGY |
| Capsid | | KYLGPFNGLD KGEPVNAADA AALEHDKAYD QQLKAGDNPY LRYNHADAEF |
| | | QERLQEDTSF GGNLGRAVFQ AKKRVLEPLG LVEEAAKTAP GKKRPVEPSP |
| | | QRSPDSSTGI GKKGQQPAKK RLNFGQTGDS ESVPDPQPIG EPPAGPSGLG |
| | | SGTMAAGGGA PMADNNEGAD GVGSSSGNWH CDSTWLGDRV ITTSTRTWAL |
| | | PTYNNHLYKQ ISNGTSGGST NDNTYFGYST PWGYFDFNRF HCHFSPRDWQ |
| | | RLINNNWGFR PKRLSFKLFN IQVKEVTQNE GTKTIANNLT STIQVFTDSE |
| | | YQLPYVLGSA HQGCLPPFPA DVFMIPQYGY LTLNNGSQAV GRSSFYCLEY |
| | | FPSQMLRTGN NFEFSYTFED VPFHSSYAHS QSLDRLMNPL IDQYLYYLSR |
| | | TQSTGGTQGT QQLLFSQAGP ANMSAQAKNW LPGPCYRQQR VSTTLSQNNN |
| | | SNFAWTGATK YHLNGRDSLV NPGVAMATHK DDEERFFPSS GVLMFGKQGA |
| | | GRDNVDYSSV MLTSEEEIKT TNPVATEQYG VVADNLQQTN TGPIVGNVNS |
| | | QGALPGMVWQ NRDVYLQGPI WAKIPHTDGN FHPSPLMGGF GLKHPPPQIL |
| | | IKNTPVPADP PTTFSQAKLA SFITQYSTGQ VSVEIEWELQ KENSKRWNPE |
| | | IQYTSNYYKS TNVDFAVNTE GTYSEPRPIG TRYLTRNL |
| hu.31 | 113 | MAADGYLPDW LEDTLSEGIR QWWKLKPGPP PPKPAERHKD DSRGLVLPGY |
| Capsid | | KYLGPGNGLD KGEPVNAADA AALEHDKAYD QQLKAGDNPY LKYNHADAEF |
| | | QERLKEDTSF GGNLGRAVFQ AKKRLLEPLG LVEEAAKTAP GKKRPVEQSP |
| | | QEPDSSAGIG KSGSQPAKKK LNFGQTGDTE SVPDPQPIGE PPAAPSGVGS |
| | | LTMASGGGAP VADNNEGADG VGSSSGNWHC DSQWLGDRVI TTSTRTWALP |
| | | TYNNHLYKQI SNSTSGGSSN DNAYFGYSTP WGYFDFNRFH CHFSPRDWQR |
| | | LINNNWGFRP KRLNFKLFNI QVKEVTDNNG VKTIANNLTS TVQVFTDSDY |
| | | QLPYVLGSAH EGCLPPFPAD VFMIPQYGYL TLNDGGQAVG RSSFYCLEYF |
| | | PSQMLKTGNN FQFSYEFENV PFHSSYAHSQ SLDKLMNPL1 DQYLYYLSKT |
| | | IN3SGQNQQT LKFSVAGPSN MAVQGRNYIP GPSYRQQRVS TTVTQNNNSE |
| | | FAWPGASSWA LNGRNSLMNP GPAMASHKEG EDRFFPLSGS LIFGKQGTGR |
| | | DNVDADKVMI TNEEEIKTTN PVATESYGQV ATNHQSAQAQ AQTGWVQNQG |
| | | ILPGMVWQDR DVYLQGPIWA KIPHTDGNFH PSPLMGGFGM KHPPPQILIK |
| | | NTPVPADPPT AFNKDKLNSF ITQYSTGQVS VEIEWELQKE NSKRWNPEIQ |
| | | YTSNYYKSNN VEFAVSTEGV YSEPRPIGTR YLTRNL |
| hu.32 | 114 | MAADGYLPDW LEDTLSEGIR QWWKLKPGPP PPKPAERHKD DSRGLVLPGY |
| Capsid | | KYLGPGNGLD KGEPVNAADA AALEHDKAYD QQLKAGDNPY LKYNHADAEF |
| | | QERLKEDTSF GGNLGRAVFQ AKKRLLEPLG LVEEAAKTAP GKKRPVEQSP |
| | | QEPDSSAGIG KSGSQPAKKK LNFGQTGDTE SVPDPGQPIG EPPAAPSGVG |
| | | SLTMASGGGA PVADNNEGAD GVGSSSGNWH CDSQWLGDRV ITTSTRTWAL |
| | | PTYNNHLYKQ ISNSTSGGSS NDNAYFGYST PWGYFDFNRF HCHFSPRDWQ |
| | | RLINNNWGFR PKRLNFKLFN IQVKEVTDNN GVKTIANNLT STVQVFTDSD |
| | | YQLPYVLGSA HEGCLPPFPA DVFMIPQYGY LTLNDGSQAV GRSSFYCLEY |
| | | FPSQMLRTGN NFQFSYEFEN VPFHSSYAHS QSLDRLMNPL IDQYLYYLSK |
| | | TINGSGQNQQ TLKFSVAGPS NMAVQGRNYI PGPSYRQQRV STTVTQNNNS |
| | | EFAWPGASSW ALNGRNSLMN PGPAMASHKE GEDRFFPLSG SLIFGKQGTG |
| | | RDNVDADKVM ITNEEEIKTT NPVATESYGQ VATNHQSAQA QAQTGWVQNQ |
| | | GILPGMVWQD RDVYLQGPIW AKIPHTDGNF HPSPLMGGFG MKHPPPQILI |
| | | KNTPVPADPP TAFNKDKLNS FITQYSTGQV SVEIEWELQK ENSKRWNPEI |
| | | QYTSNYYKSN NVEFAVNTEG VYSEPRPIGT RYLTRNL |
| Rh.74 | 127 | MAADGYLPD WLEDNLSEG IREWWDLKP GAPKPKANQ QKQDNGRGL |
| version 1 | | VLPGYKYLG PFNGLDKGE PVNAADAAA LEHDKAYDQ QLQAGDNPY |

TABLE 9-continued

| Structure | SEQ ID | Sequence |
|---|---|---|
| | | LRYNHADAE FQERLQEDT SFGGNLGRA VFQAKKRVL EPLGLVESP<br>VKTAPGKKR PVEPSPQRS PDSSTGIGK KGQQPAKKR LNFGQTGDS<br>ESVPDPQPI GEPPAGPSG LGSGTMAAG GGAPMADNN EGADGVGSS<br>SGNWHCDST WLGDRVITT STRTWALPT YNNHLYKQI SNGTSGGST<br>NDNTYFGYS TPWGYFDFN RFHCHFSPR DWQRLINNN WGFRPKRLN<br>FKLFNIQVK EVTQNEGTK TIANNLTST IQVFTDSEY QLPYVLGSA<br>HQGCLPPFP ADVFMIPQY GYLTLNNGS QAVGRSSFY CLEYFPSQM<br>LRTGNNFEF SYNFEDVPF HSSYAHSQS LDRLMNPLI DQYLYYLSR<br>TQSTGGTAG TQQLLFSQA GPNNMSAQA KNWLPGPCY RQQRVSTTL<br>3QNNNSNFA WTGATKYHL NGRDSLVNP GVAMATHKD DEERFFPSS<br>GVLMFGKQG AGKDNVDYS SVMLTSEEE IKTTNPVAT EQYGvvADN<br>LQQQNAAPI VGAVNSQGA LPGMVWQNR DVYLQGPIW AKIPHTDGN<br>FHPSPLMGG FGLKHPPPQ ILIKNTPVP ADPPTTFNQ AKLASFITQ<br>YSTGQVSVE IEWELQKEN SKRWNPEIQ YTSNYYKST NVDFAVNTE<br>GTYSEPRPI GTRYLTRNL |
| Rh.74 version 2 | 85 | MAADGYLPD WLEDNLSEG IREWWDLKP GAPKPKANQ QKQDNGRGL<br>VLPGYKYLG PFNGLDKGE PVNAADAAA LEHDKAYDQ QLQAGDNPY<br>LRYNHADAE FQFRLQFDT SFGGNTGRA VFQAKKRVT FPLGTVFSP<br>VKTAPGKKR PVEPSPQRS PDSSTGIGK KGQQPAKKR LNFGQTGDS<br>ESVPDPQPI GEPPAAPSG VGPNTMAAG GGAPMADNN EGADGVGSS<br>3CNWHCDST WLCDRVITT STRTWALPT YNNHLYKQI SNCTSCCST<br>NDNTYFGYS TPWGYFDFN RFHCHFSPR DWQRLINNN WGFRPKRLN<br>FKLFNIQVK EVTQNEGTK TIANNLTST IQVFTDSEY QLPYVLGSA<br>HQGCLPPFP ADVFMIPQY GYLTLNNGS QAVGRSSFY CLEYFPSQM<br>LRTGNNFEF SYNFEDVPF HSSYAHSQS LDRLMNPLI DQYLYYLSR<br>TQSTGGTAG TQQLLFSQA GPNNMSAQA KNWLPGPCY RQQRVSTTL<br>3QNNNSNFA WTGATKYHL NGRDSLVNP GVAMATHKD DEERFFPSS<br>GVLMFGKQG AGKDNVDYS SVMLTSEEE IKTTNPVAT EQYGVVADN<br>LQQQNAAPI VGAVNSQGA LPGMVWQNR DVYLQGPIW AKIPHTDGN<br>FHPSPLMGG FGLKHPPPQ ILIKNTPVP ADPPTTFNQ AKLASFITQ<br>YSTGQVSVE IEWELQKEN SKRWNPEIQ YTSNYYKST NVDFAVNTE<br>GTYSEPRPI GTRYLTRNL |

The provided methods are suitable for use in the production of recombinant AAV encoding a transgene. In certain embodiments, the transgene is a microdystrophin as described herein. In some embodiments, the rAAV genome comprises a vector comprising the following components: (1) AAV inverted terminal repeats that flank an expression cassette; (2) regulatory control elements, such as a) promoter/enhancers, b) a poly A signal, and c) optionally an intron; and (3) nucleic acid sequences coding for the described transgene. In a specific embodiment, the constructs described herein comprise the following components: (1) AAV2 or AAV8 inverted terminal repeats (ITRs) that flank the expression cassette; (2) control elements, which include a muscle-specific SPc5.12 promoter and a small poly A signal; and (3) transgene providing (e.g., coding for) a nucleic acid encoding microdystrophin as described herein. In a specific embodiment, the constructs described herein comprise the following components: (1) AAV2 or AAV8 ITRs that flank the expression cassette; (2) control elements, which include a) the muscle-specific SPc5.12 promoter, b) a small poly A signal; and (3) microdystrophin cassette, which includes from the N-terminus to the C-terminus, ABD1-H1-R1-R2-R3-H3-R24-H4-CR, ABD1-H1-R1-R2-R3-H3-R24-H4-CR-CT, ABD-H1-R1-R2-R16-R17-R24-H4-CR, or ABD-H1-R1-R2-R16-R17-R24-H4-CR-CT. In a specific embodiment, the constructs described herein comprise the following components: (1) AAV2 or AAV8 ITRs that flank the expression cassette; (2) control elements, which include a) a CNS promoter, b) a small poly A signal; and (3) microdystrophin cassette, which includes from the N-terminus to the C-terminus, ABD1-H1-R1-R2-R3-H3-R24-H4-CR, ABD1-H1-R1-R2-R3-H3-R24-H4-CR-CT, ABD-H1-R1-R2-R16-R17-R24-H4-CR, or ABD-H1-R1-R2-R16-R17-R24-H4-CR-CT. In a specific embodiment, the constructs described herein comprise the following components: (1) AAV2 or AAV8 ITRs that flank the expression cassette; (2) control elements, which include a) the muscle-specific SPc5.12 promoter, b) an intron (e.g., VH4) and c) a small poly A signal; and (3) microdystrophin cassette, which includes from the N-terminus to the C-terminus ABD1-H1-R1-R2-R3-H3-R24-H4-CR, ABD1-H1-R1-R2-R3-H3-R24-H4-CR-CT, ABD-H1-R1-R2-R16-R17-R24-H4-CR, or ABD-H1-R1-R2-R16-R17-R24-H4-CR-CT, ABD1 being directly coupled to VH4. In a specific embodiment, the constructs described herein comprise the following components: (1) AAV2 or AAV8 ITRs that flank the expression cassette; (2) control elements, which include a) a CNS promoter, b) an intron (e.g., VH4) and c) a small poly A signal; and (3) microdystrophin cassette, which includes from the N-terminus to the C-terminus ABD1-H1-R1-R2-R3-H3-R24-H4-CR, ABD1-H1-R1-R2-R3-H3-R24-H4-CR-CT, ABD-H1-R1-R2-R16-R17-R24-H4-CR, or ABD-H1-R1-R2-R16-R17-R24-H4-CR-CT, ABD1 being directly coupled to VH4. In a specific embodiment, the constructs described herein comprise the following components: (1) AAV2 or AAV8 ITRs that flank the expression cassette; (2) control elements, which include a) a minimal SPc promoter for muscle-specific transgene expression, b) optionally, a human immunoglobin heavy chain variable region intron (e.g., VH4) and c) a small poly A signal; and (3) microdystrophin cassette, which includes from the N-terminus to the C-terminus ABD1-H1-R1-R2-R3-H3-R24-H4-CR, ABD1-H1-R1-R2-R3-H3-R24-H4-CR-CT, ABD-H1-R1-R2-R16-R17-R24-H4-CR, or ABD-H1-R1-R2-R16-R17-R24-H4-CR-CT. In a specific embodiment, the constructs described herein comprise the following components: (1) AAV2 or AAV8 ITRs that flank the expression cassette; (2) control elements, which include a) the muscle-specific SPc5.12 promoter or a CNS promoter, b) an intron (e.g., VH4) and c) a small poly A signal; and (3) microdystrophin cassette, which includes from the N-terminus to the C-terminus ABD1-H1-R1-R2-R3-H2-R24-H4-CR, ABD1-H1-R1-R2-R3-H2-R24-H4-CR-CT, ABD-H1-R1-R2-R16-R17-R24-H4-CR, or ABD-H1-R1-R2-R16-R17-R24-H4-CR-CT, ABD1 being directly coupled to VH4. In some embodiments, constructs described herein comprising AAV ITRs flanking a microdystrophin expression cassette, which includes from the N-terminus to the C-terminus ABD1-H1-R1-R2-R3-H2-R24-H4-CR, ABD1-H1-R1-R2-R3-H2-R24-H4-CR-CT, ABD-H1-R1-R2-R16-R17-R24-H4-CR, or ABD-H1-R1-R2-R16-R17-R24-H4-CR-CT can be between 4000 nt and 5000 nt in length. In some embodiments, such constructs are less than 4900 nt, 4800 nt, 4700 nt, 4600 nt, 4500 nt, 4400 nt, or 4300 nt in length.

Some nucleic acid embodiments of the present disclosure comprise rAAV vectors encoding microdystrophin comprising or consisting of a nucleotide sequence of SEQ ID NO: 53, 54, 55, 56, or 82 provided in Table 10 below. In various embodiments, an rAAV vector comprising a nucleotide sequence that has at least 50%, at least 60%, at least 70%, at least 75%, at least 80%, at least 85%, at least 90%, at least 95%, at least 98% or at least 99% sequence identity to the nucleotide sequence of SEQ ID NO: 53, 54, 55, 56, 82 or the reverse complement thereof and encodes a rAAV vector suitable for expression of a therapeutically effective microdystrophin in muscle cells.

TABLE 10

RGX-DYS cassette nucleotide sequences

| Structure | SEQ ID | Nucleic Acid Sequence |
|---|---|---|
| RGX-DYS1<br>(full cassette<br>SPc5-12 to<br>poly A<br>including<br>intervening<br>seqs)<br>4734 bp<br>ITRs shown in<br>lower case | 53 | ctgcgcgctcgctcgctcactgaggccgcccgggcaaagc<br>ccgggcgtcgggcgacctttggtcgcccggcctcagtgag<br>cgagcgagcgcgcagagagggagtggccaactccatcact<br>aggggttcctCATATGcagggtaatggggatcctCTAGAG<br>GCCGTCCGCCCTCGGCACCATCCTCACGACACCCAAATAT<br>GGCGACGGGTGAGGAATGGTGGGGAGTTATTTTTAGAGCG<br>GTGAGGAAGGTGGGCAGGCAGCAGGTGTTGGCGCTCTAAA<br>AATAACTCCCGGGAGTTATTTTTAGAGCGGAGGAATGGTG<br>GACACCCAAATATGGCGACGGTTCCTCACCCGTCGCCATA<br>TTTGGGTGTCCGCCCTCGGCCGGGGCCGCATTCCTGGGGG<br>CCGGGCGGTGCTCCCGCCCGCCTCGATAAAAGGCTCCGGG<br>GCCGGCGGCGGCCCACGAGCTACCCGGAGGAGCGGGAGGC<br>GCCAAGCGgAATTCGCCACCATGCTTTGGTGGGAAGAGGT<br>GGAAGATTGCTATGAGAGGGAAGATGTGCAGAAGAAAACC<br>TTCACCAAATGGGTCAATGCCCAGTTCAGCAAGTTTGGCA<br>AGCAGCACATTGAGAACCTGTTCAGTGACCTGCAGGATGG<br>CAGAAGGCTGCTGGATCTGCTGGAAGGCCTGACAGGCCAG<br>AAGCTGCCTAAAGAGAAGGGCAGCACAAGAGTGCATGCCC<br>TGAACAATGTGAACAAGGCCCTGAGAGTGCTGCAGAACAA<br>CAATGTGGACCTGGTCAATATTGGCAGCACAGACATTGTG<br>GATGGCAACCACAAGCTGACCCTGGGCCTGATCTGGAACA<br>TCATCCTGCACTGGCAAGTGAAGAATGTGATGAAGAACAT<br>CATGGCTGGCCTGCAGCAGACCAACTCTGAGAAGATCCTG<br>CTGAGCTGGGTCAGACAGAGCACCAGAAACTACCCTCAAG<br>TGAATGTGATCAACTTCACCACCTCTTGGAGTGATGGACT<br>GGCCCTGAATGCCCTGATCCACAGCCACAGACCTGACCTG<br>TTTGACTGGAACTCTGTTGTGTGCCAGCAGTCTGCCACAC<br>AGAGACTGGAACATGCCTTCAACATTGCCAGATACCAGCT<br>GGGAATTGAGAAACTGCTGGACCCTGAGGATGTGGACACC<br>ACCTATCCTGACAAGAAATCCATCCTCATGTACATCACCA<br>GCCTGTTCCAGGTGCTGCCCCAGCAAGTGTCCATTGAGGC<br>CATTCAAGAGGTTGAGATGCTGCCCAGACCTCCTAAAGTG<br>ACCAAAGAGGAACACTTCCAGCTGCACCACCAGATGCACT<br>ACTCTCAGCAGATCACAGTGTCTCTGGCCCAGGGATATGA<br>GAGAACAAGCAGCCCCAAGCCTAGGTTCAAGAGCTATGCC<br>TACACACAGGCTGCCTATGTGACCACATCTGACCCCACAA<br>GAAGCCCATTTCCAAGCCAGCATCTGGAAGCCCCTGAGGA<br>CAAGAGCTTTGGCAGCAGCCTGATGGAATCTGAAGTGAAC<br>CTGGATAGATACCAGACAGCCCTGGAAGAAGTGCTGTCCT<br>GGCTGCTGTCTGCTGAGGATACACTGCAGGCTCAGGGTGA<br>AATCAGCAATGATGTGGAAGTGGTCAAGGACCAGTTTCAC<br>ACCCATGAGGGCTACATGATGGACCTGACAGCCCACCAGG<br>GCAGAGTGGGAAATATCCTGCAGCTGGGCTCCAAGCTGAT<br>TGGCACAGGCAAGCTGTCTGAGGATGAAGAGACAGAGGTG<br>CAAGAGCAGATGAACCTGCTGAACAGCAGATGGGAGTGTC<br>TGAGAGTGGCCAGCATGGAAAAGCAGAGCAACCTGCACAG<br>AGTGCTCATGGACCTGCAGAATCAGAAACTGAAAGAACTG<br>AATGACTGGCTGACCAAGACAGAAGAAAGGACTAGGAAGA<br>TGGAAGAGGAACCTCTGGGACCAGACCTGGAAGATCTGAA<br>AAGACAGGTGCAGCAGCATAAGGTGCTGCAAGAGGACCTT<br>GAGCAAGAGCAAGTCAGAGTGAACAGCCTGACACACATGG<br>TGGTGGTTGTGGATGAGTCCTCTGGGGATCATGCCACAGC<br>TGCTCTGGAAGAACAGCTGAAGGTGCTGGGAGACAGATGG<br>GCCAACATCTGTAGGTGGACAGAGGATAGATGGGTGCTGC<br>TCCAGGACATTCTGCTGAAGTGGCAGAGACTGACAGAGGA<br>ACAGTGCCTGTTTTCTGCCTGGCTCTCTGAGAAAGAGGAT<br>GCTGTCAACAAGATCCATACCACAGGCTTCAAGGATCAGA<br>ATGAGATGCTCAGCTCCCTGCAGAAACTGGCTGTGCTGAA |

TABLE 10-continued

RGX-DYS cassette nucleotide sequences

| Structure | SEQ ID | Nucleic Acid Sequence |
|---|---|---|
| | | GGCTGACCTGGAAAAGAAAAAGCAGTCCATGGGCAAGCTC<br>TACAGCCTGAAGCAGGACCTGCTGTCTACCCTGAAGAACA<br>AGTCTGTGACCCAGAAAACTGAGGCCTGGCTGGACAACTT<br>TGCTAGATGCTGGGACAACCTGGTGCAGAAGCTGGAAAAG<br>TCTACAGCCCAGATCAGCCAGCAACCTGATCTTGCCCCTG<br>GCCTGACCACAATTGGAGCCTCTCCAACACAGACTGTGAC<br>CCTGGTTACCCAGCCAGTGGTCACCAAAGAGACAGCCATC<br>AGCAAACTGGAAATGCCCAGCTCTCTGATGCTGGAAGTCC<br>CCACACTGGAAAGGCTGCAAGAACTTCAAGAGGCCACAGA<br>TGAGCTGGACCTGAAGCTGAGACAGGCTGAAGTGATCAAA<br>GGCAGCTGGCAGCCAGTTGGGGACCTGCTCATTGATAGCC<br>TGCAGGACCATCTGGAAAAAGTGAAAGCCCTGAGGGGAGA<br>GATTGCCCCTCTGAAAGAAAATGTGTCCCATGTGAATGAC<br>CTGGCCAGACAGCTGACCACACTGGGAATCCAGCTGAGCC<br>CCTACAACCTGAGCACCCTTGAGGACCTGAACACCAGGTG<br>GAAGCTCCTCCAGGTGGCAGTGGAAGATAGAGTCAGGCAG<br>CTGCATGAGGCCCACAGAGATTTTGGACCAGCCAGCCAGC<br>ACTTTCTGTCTACCTCTGTGCAAGGCCCCTGGGAGAGAGC<br>TATCTCTCCTAACAAGGTGCCCTACTACATCAACCATGAG<br>ACACAGACCACCTGTTGGGATCACCCCAAGATGACAGAGC<br>TGTACCAGAGTCTGGCAGACCTCAACAATGTCAGATTCAG<br>TGCCTACAGGACTGCCATGAAGCTCAGAAGGCTCCAGAAA<br>GCTCTGTGCCTGGACCTGCTTTCCCTGAGTGCAGCTTGTG<br>ATGCCCTGGACCAGCACAATCTGAAGCAGAATGACCAGCC<br>TATGGACATCCTCCAGATCATCAACTGCCTCACCACCATC<br>TATGATAGGCTGGAACAAGAGCACAACAATCTGGTCAATG<br>TGCCCCTGTGTGTGGACATGTGCCTGAATTGGCTGCTGAA<br>TGTGTATGACACAGGCAGAACAGGCAGGATCAGAGTCCTG<br>TCCTTCAAGACAGGCATCATCTCCCTGTGCAAAGCCCACT<br>TGGAGGACAAGTACAGATACCTGTTCAAGCAAGTGGCCTC<br>CAGCACAGGCTTTTGTGACCAGAGAAGGCTGGGCCTGCTC<br>CTGCATGACAGCATTCAGATCCCTAGACAGCTGGGAGAAG<br>TGGCTTCCTTTGGAGGCAGCAATATTGAGCCATCAGTCAG<br>GTCCTGTTTTCAGTTTGCCAACAACAAGCCTGAGATTGAG<br>GCTGCCCTGTTCCTGGACTGGATGAGACTTGAGCCTCAGA<br>GCATGGTCTGGCTGCCTGTGCTTCATAGAGTGGCTGCTGC<br>TGAGACTGCCAAGCACCAGGCCAAGTGCAACATCTGCAAA<br>GAGTGCCCCATCATTGGCTTCAGATACAGATCCCTGAAGC<br>ACTTCAACTATGATATCTGCCAGAGCTGCTTCTTTAGTGG<br>CAGGGTTGCCAAGGGCCACAAAATGCACTACCCCATGGTG<br>GAATACTGCACCCCAACAACCTCTGGGGAAGATGTTAGAG<br>ACTTTGCCAAGGTGCTGAAAAACAAGTTCAGGACCAAGAG<br>ATACTTTGCTAAGCACCCCAGAATGGGCTACCTGCCTGTC<br>CAGACAGTGCTTGAGGGTGACAACATGGAAACCCCTGTGA<br>CACTGATCAATTTCTGGCCAGTGGACTCTGCCCCTGCCTC<br>AAGTCCACAGCTGTCCCATGATGACACCCACAGCAGAATT<br>GAGCACTATGCCTCCAGACTGGCAGAGATGGAAAACAGCA<br>ATGGCAGCTACCTGAATGATAGCATCAGCCCCAATGAGAG<br>CATTGATGATGAGCATCTGCTGATCCAGCACTACTGTCAG<br>TCCCTGAACCAGGACTCTCCACTGAGCCAGCCTAGAAGCC<br>CTGCTCAGATCCTGATCAGCCTTGAGTCTGAGGAAAGGGG<br>AGAGCTGGAAAGAATCCTGGCAGATCTTGAGGAAGAGAAC<br>AGAAACCTGCAGGCAGAGTATGACAGGCTCAAACAGCAGC<br>ATGAGCACAAGGGACTGAGCCCTCTGCCTTCTCCTCCTGA<br>AATGATGCCCACCTCTCCACAGTCTCCAAGGTGATGACTC<br>GAGAGGCCTAATAAAGAGCTCAGATGCATCGATCAGAGTG<br>TGTTGGTTTTTTGTGTGCCAGGGTAATGGGCTAGCTGCGG<br>CCGCaggaacccctagtgatggagttggccactccctctc<br>tgcgcgctcgctcgctcactgaggccgggcgaccaaaggt<br>cgcccgacgcccgggctttgcccgggcggcctcagtgagc<br>gagcgagcgcgcag |
| RGX-DYS2<br>(full cassette<br>SPc5-12 to<br>poly A<br>including<br>intervening<br>seqs)<br>4814 bp<br>ITRs shown in<br>lower case | 54 | ctgcgcgctcgctcgctcactgaggccgcccgggcaaagc<br>ccgggcgtcgggcgacctttggtcgcccggcctcagtgag<br>cgagcgagcgcgcagagagggagtggccaactccatcact<br>aggggttcctCATATGcagggtaatggggatcctCTAGAG<br>GCCGTCCGCCCTCGGCACCATCCTCACGACACCCAAATAT<br>GGCGACGGGTGAGGAATGGTGGGGAGTTATTTTTAGAGCG<br>GTGAGGAAGGTGGGCAGGCAGCAGGTGTTGGCGCTCTAAA<br>AATAACTCCCGGGAGTTATTTTTAGAGCGGAGGAATGGTG<br>GACACCCAAATATGGCGACGGTTCCTCACCCGTCGCCATA<br>TTTGGGTGTCCGCCCTCGGCCGGGGCCGCATTCCTGGGGG<br>CCGGGCGGTGCTCCCGCCCGCCTCGATAAAAGGCTCCGGG<br>GCCGGCGGCGGCCCACGAGCTACCCGGAGGAGCGGGAGGC<br>GCCAAGGTGAGTATCTCAGGGATCCAGACATGGGGATATG<br>GGAGGTGCCTCTGATCCCAGGGCTCACTGTGGGTCTCTCT |

TABLE 10-continued

RGX-DYS cassette nucleotide sequences

| Structure | SEQ ID | Nucleic Acid Sequence |
|---|---|---|
| | | GTTCACAGGAATTCGCCACCATGCTTTGGTGGGAAGAGGT |
| | | GGAAGATTGCTATGAGAGGGAAGATGTGCAGAAGAAAACC |
| | | TTCACCAAATGGGTCAATGCCCAGTTCAGCAAGTTTGGCA |
| | | AGCAGCACATTGAGAACCTGTTCAGTGACCTGCAGGATGG |
| | | CAGAAGGCTGCTGGATCTGCTGGAAGGCCTGACAGGCCAG |
| | | AAGCTGCCTAAAGAGAAGGGCAGCACAAGAGTGCATGCCC |
| | | TGAACAATGTGAACAAGGCCCTGAGAGTGCTGCAGAACAA |
| | | CAATGTGGACCTGGTCAATATTGGCAGCACAGACATTGTG |
| | | GATGGCAACCACAAGCTGACCCTGGGCCTGATCTGGAACA |
| | | TCATCCTGCACTGGCAAGTGAAGAATGTGATGAAGAACAT |
| | | CATGGCTGGCCTGCAGCAGACCAACTCTGAGAAGATCCTG |
| | | CTGAGCTGGGTCAGACAGAGCACCAGAAACTACCCTCAAG |
| | | TGAATGTGATCAACTTCACCACCTCTTGGAGTGATGGACT |
| | | GGCCCTGAATGCCCTGATCCACAGCCACAGACCTGACCTG |
| | | TTTGACTGGAACTCTGTTGTGTGCCAGCAGTCTGCCACAC |
| | | AGAGACTGGAACATGCCTTCAACATTGCCAGATACCAGCT |
| | | GGGAATTGAGAAACTGCTGGACCCTGAGGATGTGGACACC |
| | | ACCTATCCTGACAAGAAATCCATCCTCATGTACATCACCA |
| | | GCCTGTTCCAGGTGCTGCCCCAGCAAGTGTCCATTGAGGC |
| | | CATTCAAGAGGTTGAGATGCTGCCCAGACCTCCTAAAGTG |
| | | ACCAAAGAGGAACACTTCCAGCTGCACCACCAGATGCACT |
| | | ACTCTCAGCAGATCACAGTGTCTCTGGCCCAGGGATATGA |
| | | GAGAACAAGCAGCCCCAAGCCTAGGTTCAAGAGCTATGCC |
| | | TACACACAGGCTGCCTATGTGACCACATCTGACCCCACAA |
| | | GAAGCCCATTTCCAAGCCAGCATCTGGAAGCCCCTGAGGA |
| | | CAAGAGCTTTGGCAGCAGCCTGATGGAATCTGAAGTGAAC |
| | | CTGGATAGATACCAGACAGCCCTGGAAGAAGTGCTGTCCT |
| | | GGCTGCTGTCTGCTGAGGATACACTGCAGGCTCAGGGTGA |
| | | AATCAGCAATGATGTGGAAGTGGTCAAGGACCAGTTTCAC |
| | | ACCCATGAGGGCTACATGATGGACCTGACAGCCCACCAGG |
| | | GCAGAGTGGGAAATATCCTGCAGCTGGGCTCCAAGCTGAT |
| | | TGGCACAGGCAAGCTGTCTGAGGATGAAGAGACAGAGGTG |
| | | CAAGAGCAGATGAACCTGCTGAACAGCAGATGGGAGTGTC |
| | | TGAGAGTGGCCAGCATGGAAAAGCAGAGCAACCTGCACAG |
| | | AGTGCTCATGGACCTGCAGAATCAGAAACTGAAAGAACTG |
| | | AATGACTGGCTGACCAAGACAGAAGAAAGGACTAGGAAGA |
| | | TGGAAGAGGAACCTCTGGGACCAGACCTGGAAGATCTGAA |
| | | AAGACAGGTGCAGCAGCATAAGGTGCTGCAAGAGGACCTT |
| | | GAGCAAGAGCAAGTCAGAGTGAACAGCCTGACACACATGG |
| | | TGGTGGTTGTGGATGAGTCCTCTGGGGATCATGCCACAGC |
| | | TGCTCTGGAAGAACAGCTGAAGGTGCTGGGAGACAGATGG |
| | | GCCAACATCTGTAGGTGGACAGAGGATAGATGGGTGCTGC |
| | | TCCAGGACATTCTGCTGAAGTGGCAGAGACTGACAGAGGA |
| | | ACAGTGCCTGTTTTCTGCCTGGCTCTCTGAGAAAGAGGAT |
| | | GCTGTCAACAAGATCCATACCACAGGCTTCAAGGATCAGA |
| | | ATGAGATGCTCAGCTCCCTGCAGAAACTGGCTGTGCTGAA |
| | | GGCTGACCTGGAAAAGAAAAAGCAGTCCATGGGCAAGCTC |
| | | TACAGCCTGAAGCAGGACCTGCTGTCTACCCTGAAGAACA |
| | | AGTCTGTGACCCAGAAAACTGAGGCCTGGCTGGACAACTT |
| | | TGCTAGATGCTGGGACAACCTGGTGCAGAAGCTGGAAAAG |
| | | TCTACAGCCCAGATCAGCCAGCAACCTGATCTTGCCCCTG |
| | | GCCTGACCACAATTGGAGCCTCTCCAACACAGACTGTGAC |
| | | CCTGGTTACCCAGCCAGTGGTCACCAAAGAGACAGCCATC |
| | | AGCAAACTGGAAATGCCCAGCTCTCTGATGCTGGAAGTCC |
| | | CCACACTGGAAAGGCTGCAAGAACTTCAAGAGGCCACAGA |
| | | TGAGCTGGACCTGAAGCTGAGACAGGCTGAAGTGATCAAA |
| | | GGCAGCTGGCAGCCAGTTGGGGACCTGCTCATTGATAGCC |
| | | TGCAGGACCATCTGGAAAAAGTGAAAGCCCTGAGGGGAGA |
| | | GATTGCCCCTCTGAAAGAAAATGTGTCCCATGTGAATGAC |
| | | CTGGCCAGACAGCTGACCACACTGGGAATCCAGCTGAGCC |
| | | CCTACAACCTGAGCACCCTTGAGGACCTGAACACCAGGTG |
| | | GAAGCTCCTCCAGGTGGCAGTGGAAGATAGAGTCAGGCAG |
| | | CTGCATGAGGCCCACAGAGATTTTGGACCAGCCAGCCAGC |
| | | ACTTTCTGTCTACCTCTGTGCAAGGCCCCTGGGAGAGAGC |
| | | TATCTCTCCTAACAAGGTGCCCTACTACATCAACCATGAG |
| | | ACACAGACCACCTGTTGGGATCACCCCAAGATGACAGAGC |
| | | TGTACCAGAGTCTGGCAGACCTCAACAATGTCAGATTCAG |
| | | TGCCTACAGGACTGCCATGAAGCTCAGAAGGCTCCAGAAA |
| | | GCTCTGTGCCTGGACCTGCTTTCCCTGAGTGCAGCTTGTG |
| | | ATGCCCTGGACCAGCACAATCTGAAGCAGAATGACCAGCC |
| | | TATGGACATCCTCCAGATCATCAACTGCCTCACCACCATC |
| | | TATGATAGGCTGGAACAAGAGCACAACAATCTGGTCAATG |
| | | TGCCCCTGTGTGTGGACATGTGCCTGAATTGGCTGCTGAA |
| | | TGTGTATGACACAGGCAGAACAGGCAGGATCAGAGTCCTG |
| | | TCCTTCAAGACAGGCATCATCTCCCTGTGCAAAGCCCACT |
| | | TGGAGGACAAGTACAGATACCTGTTCAAGCAAGTGGCCTC |

TABLE 10-continued

RGX-DYS cassette nucleotide sequences

| Structure | SEQ ID | Nucleic Acid Sequence |
|---|---|---|
| | | CAGCACAGGCTTTTGTGACCAGAGAAGGCTGGGCCTGCTC<br>CTGCATGACAGCATTCAGATCCCTAGACAGCTGGGAGAAG<br>TGGCTTCCTTTGGAGGCAGCAATATTGAGCCATCAGTCAG<br>GTCCTGTTTTCAGTTTGCCAACAACAAGCCTGAGATTGAG<br>GCTGCCCTGTTCCTGGACTGGATGAGACTTGAGCCTCAGA<br>GCATGGTCTGGCTGCCTGTGCTTCATAGAGTGGCTGCTGC<br>TGAGACTGCCAAGCACCAGGCCAAGTGCAACATCTGCAAA<br>GAGTGCCCCATCATTGGCTTCAGATACAGATCCCTGAAGC<br>ACTTCAACTATGATATCTGCCAGAGCTGCTTCTTTAGTGG<br>CAGGGTTGCCAAGGGCCACAAAATGCACTACCCCATGGTG<br>GAATACTGCACCCCAACAACCTCTGGGGAAGATGTTAGAG<br>ACTTTGCCAAGGTGCTGAAAAACAAGTTCAGGACCAAGAG<br>ATACTTTGCTAAGCACCCCAGAATGGGCTACCTGCCTGTC<br>CAGACAGTGCTTGAGGGTGACAACATGGAAACCCCTGTGA<br>CACTGATCAATTTCTGGCCAGTGGACTCTGCCCCTGCCTC<br>AAGTCCACAGCTGTCCCATGATGACACCCACAGCAGAATT<br>GAGCACTATGCCTCCAGACTGGCAGAGATGGAAAACAGCA<br>ATGGCAGCTACCTGAATGATAGCATCAGCCCCAATGAGAG<br>CATTGATGATGAGCATCTGCTGATCCAGCACTACTGTCAG<br>TCCCTGAACCAGGACTCTCCACTGAGCCAGCCTAGAAGCC<br>CTGCTCAGATCCTGATCAGCCTTGAGTCTGAGGAAAGGGG<br>AGAGCTGGAAAGAATCCTGGCAGATCTTGAGGAAGAGAAC<br>AGAAACCTGCAGGCAGAGTATGACAGGCTCAAACAGCAGC<br>ATGAGCACAAGGGACTGAGCCCTCTGCCTTCTCCTCCTGA<br>AATGATGCCCACCTCTCCACAGTCTCCAAGGTGATGACTC<br>GAGAGGCCTAATAAAGAGCTCAGATGCATCGATCAGAGTG<br>TGTTGGTTTTTTGTGTGCCAGGGTAATGGGCTAGCTGCGG<br>CCGCaggaacccctagtgatggagttggccactccctctc<br>tgcgcgctcgctcgctcactgaggccgggcgaccaaaggt<br>cgcccgacgcccgggctttgcccgggcggcctcagtgagc<br>gagcgagcgcgcag |
| RGX-DYS3 (full cassette SPc5-12 to poly A including intervening seqs) 4364 bp) ITRs shown in lower case | 55 | ctgcgcgctcgctcgctcactgaggccgcccgggcaaagc<br>ccgggcgtcgggcgacctttggtcgcccggcctcagtgag<br>cgagcgagcgcgcagagagggagtggccaactccatcact<br>aggggttcctCATATGcagggtaatggggatcctCTAGAG<br>GCCGTCCGCCCTCGGCACCATCCTCACGACACCCAAATAT<br>GGCGACGGGTGAGGAATGGTGGGGAGTTATTTTTAGAGCG<br>GTGAGGAAGGTGGGCAGGCAGCAGGTGTTGGCGCTCTAAA<br>AATAACTCCCGGGAGTTATTTTTAGAGCGGAGGAATGGTG<br>GACACCCAAATATGGCGACGGTTCCTCACCCGTCGCCATA<br>TTTGGGTGTCCGCCCTCGGCCGGGGCCGCATTCCTGGGGG<br>CCGGGCGGTGCTCCCGCCCGCCTCGATAAAAGGCTCCGGG<br>GCCGGCGGCGGCCCACGAGCTACCCGGAGGAGCGGGAGGC<br>GCCAAGGTGAGTATCTCAGGGATCCAGACATGGGGATATG<br>GGAGGTGCCTCTGATCCCAGGGCTCACTGTGGGTCTCTCT<br>GTTCACAGGAATTCGCCACCATGCTTTGGTGGGAAGAGGT<br>GGAAGATTGCTATGAGAGGGAAGATGTGCAGAAGAAAACC<br>TTCACCAAATGGGTCAATGCCCAGTTCAGCAAGTTTGGCA<br>AGCAGCACATTGAGAACCTGTTCAGTGACCTGCAGGATGG<br>CAGAAGGCTGCTGGATCTGCTGGAAGGCCTGACAGGCCAG<br>AAGCTGCCTAAAGAGAAGGGCAGCACAAGAGTGCATGCCC<br>TGAACAATGTGAACAAGGCCCTGAGAGTGCTGCAGAACAA<br>CAATGTGGACCTGGTCAATATTGGCAGCACAGACATTGTG<br>GATGGCAACCACAAGCTGACCCTGGGCCTGATCTGGAACA<br>TCATCCTGCACTGGCAAGTGAAGAATGTGATGAAGAACAT<br>CATGGCTGGCCTGCAGCAGACCAACTCTGAGAAGATCCTG<br>CTGAGCTGGGTCAGACAGAGCACCAGAAACTACCCTCAAG<br>TGAATGTGATCAACTTCACCACCTCTTGGAGTGATGGACT<br>GGCCCTGAATGCCCTGATCCACAGCCACAGACCTGACCTG<br>TTTGACTGGAACTCTGTTGTGTGCCAGCAGTCTGCCACAC<br>AGAGACTGGAACATGCCTTCAACATTGCCAGATACCAGCT<br>GGGAATTGAGAAACTGCTGGACCCTGAGGATGTGGACACC<br>ACCTATCCTGACAAGAAATCCATCCTCATGTACATCACCA<br>GCCTGTTCCAGGTGCTGCCCCAGCAAGTGTCCATTGAGGC<br>CATTCAAGAGGTTGAGATGCTGCCCAGACCTCCTAAAGTG<br>ACCAAAGAGGAACACTTCCAGCTGCACCACCAGATGCACT<br>ACTCTCAGCAGATCACAGTGTCTCTGGCCCAGGGATATGA<br>GAGAACAAGCAGCCCCAAGCCTAGGTTCAAGAGCTATGCC<br>TACACACAGGCTGCCTATGTGACCACATCTGACCCCACAA<br>GAAGCCCATTTCCAAGCCAGCATCTGGAAGCCCCTGAGGA<br>CAAGAGCTTTGGCAGCAGCCTGATGGAATCTGAAGTGAAC<br>CTGGATAGATACCAGACAGCCCTGGAAGAAGTGCTGTCCT<br>GGCTGCTGTCTGCTGAGGATACACTGCAGGCTCAGGGTGA<br>AATCAGCAATGATGTGGAAGTGGTCAAGGACCAGTTTCAC<br>ACCCATGAGGGCTACATGATGGACCTGACAGCCCACCAGG |

TABLE 10-continued

RGX-DYS cassette nucleotide sequences

| Structure | SEQ ID | Nucleic Acid Sequence |
|---|---|---|
| | | GCAGAGTGGGAAATATCCTGCAGCTGGGCTCCAAGCTGAT<br>TGGCACAGGCAAGCTGTCTGAGGATGAAGAGACAGAGGTG<br>CAAGAGCAGATGAACCTGCTGAACAGCAGATGGGAGTGTC<br>TGAGAGTGGCCAGCATGGAAAAGCAGAGCAACCTGCACAG<br>AGTGCTCATGGACCTGCAGAATCAGAAACTGAAAGAACTG<br>AATGACTGGCTGACCAAGACAGAAGAAAGGACTAGGAAGA<br>TGGAAGAGGAACCTCTGGGACCAGACCTGGAAGATCTGAA<br>AAGACAGGTGCAGCAGCATAAGGTGCTGCAAGAGGACCTT<br>GAGCAAGAGCAAGTCAGAGTGAACAGCCTGACACACATGG<br>TGGTGGTTGTGGATGAGTCCTCTGGGGATCATGCCACAGC<br>TGCTCTGGAAGAACAGCTGAAGGTGCTGGGAGACAGATGG<br>GCCAACATCTGTAGGTGGACAGAGGATAGATGGGTGCTGC<br>TCCAGGACATTCTGCTGAAGTGGCAGAGACTGACAGAGGA<br>ACAGTGCCTGTTTTCTGCCTGGCTCTCTGAGAAAGAGGAT<br>GCTGTCAACAAGATCCATACCACAGGCTTCAAGGATCAGA<br>ATGAGATGCTCAGCTCCCTGCAGAAACTGGCTGTGCTGAA<br>GGCTGACCTGGAAAAGAAAAAGCAGTCCATGGGCAAGCTC<br>TACAGCCTGAAGCAGGACCTGCTGTCTACCCTGAAGAACA<br>AGTCTGTGACCCAGAAAACTGAGGCCTGGCTGGACAACTT<br>TGCTAGATGCTGGGACAACCTGGTGCAGAAGCTGGAAAAG<br>TCTACAGCCCAGATCAGCCAGCAACCTGATCTTGCCCCTG<br>GCCTGACCACAATTGGAGCCTCTCCAACACAGACTGTGAC<br>CCTGGTTACCCAGCCAGTGGTCACCAAAGAGACAGCCATC<br>AGCAAACTGGAAATGCCCAGCTCTCTGATGCTGGAAGTCC<br>CCACACTGGAAAGGCTGCAAGAACTTCAAGAGGCCACAGA<br>TGAGCTGGACCTGAAGCTGAGACAGGCTGAAGTGATCAAA<br>GGCAGCTGGCAGCCAGTTGGGGACCTGCTCATTGATAGCC<br>TGCAGGACCATCTGGAAAAAGTGAAAGCCCTGAGGGGAGA<br>GATTGCCCCTCTGAAAGAAAATGTGTCCCATGTGAATGAC<br>CTGGCCAGACAGCTGACCACACTGGGAATCCAGCTGAGCC<br>CCTACAACCTGAGCACCCTTGAGGACCTGAACACCAGGTG<br>GAAGCTCCTCCAGGTGGCAGTGGAAGATAGAGTCAGGCAG<br>CTGCATGAGGCCCACAGAGATTTTGGACCAGCCAGCCAGC<br>ACTTTCTGTCTACCTCTGTGCAAGGCCCCTGGGAGAGAGC<br>TATCTCTCCTAACAAGGTGCCCTACTACATCAACCATGAG<br>ACACAGACCACCTGTTGGGATCACCCCAAGATGACAGAGC<br>TGTACCAGAGTCTGGCAGACCTCAACAATGTCAGATTCAG<br>TGCCTACAGGACTGCCATGAAGCTCAGAAGGCTCCAGAAA<br>GCTCTGTGCCTGGACCTGCTTTCCCTGAGTGCAGCTTGTG<br>ATGCCCTGGACCAGCACAATCTGAAGCAGAATGACCAGCC<br>TATGGACATCCTCCAGATCATCAACTGCCTCACCACCATC<br>TATGATAGGCTGGAACAAGAGCACAACAATCTGGTCAATG<br>TGCCCCTGTGTGTGGACATGTGCCTGAATTGGCTGCTGAA<br>TGTGTATGACACAGGCAGAACAGGCAGGATCAGAGTCCTG<br>TCCTTCAAGACAGGCATCATCTCCCTGTGCAAAGCCCACT<br>TGGAGGACAAGTACAGATACCTGTTCAAGCAAGTGGCCTC<br>CAGCACAGGCTTTTGTGACCAGAGAAGGCTGGGCCTGCTC<br>CTGCATGACAGCATTCAGATCCCTAGACAGCTGGGAGAAG<br>TGGCTTCCTTTGGAGGCAGCAATATTGAGCCATCAGTCAG<br>GTCCTGTTTTCAGTTTGCCAACAACAAGCCTGAGATTGAG<br>GCTGCCCTGTTCCTGGACTGGATGAGACTTGAGCCTCAGA<br>GCATGGTCTGGCTGCCTGTGCTTCATAGAGTGGCTGCTGC<br>TGAGACTGCCAAGCACCAGGCCAAGTGCAACATCTGCAAA<br>GAGTGCCCCATCATTGGCTTCAGATACAGATCCCTGAAGC<br>ACTTCAACTATGATATCTGCCAGAGCTGCTTCTTTAGTGG<br>CAGGGTTGCCAAGGGCCACAAAATGCACTACCCCATGGTG<br>GAATACTGCACCCCAACAACCTCTGGGGAAGATGTTAGAG<br>ACTTTGCCAAGGTGCTGAAAAACAAGTTCAGGACCAAGAG<br>ATACTTTGCTAAGCACCCCAGAATGGGCTACCTGCCTGTC<br>CAGACAGTGCTTGAGGGTGACAACATGGAAACCTGATGAG<br>TCGACAGGCCTAATAAAGAGCTCAGATGCATCGATCAGAG<br>TGTGTTGGTTTTTTGTGTGGCTAGCTGCGGCCGCaggaac<br>ccctagtgatggagttggccactccctctctgcgcgctcg<br>ctcgctcactgaggccgggcgaccaaaggtcgcccgacgc<br>ccgggctttgcccgggcggcctcagtgagcgagcgagcgc<br>gcag |
| RGX-DYS4<br>(full cassette<br>mini-SPc5-12 to<br>polyA including<br>intervening<br>seqs)<br>4661 bp<br>ITRs shown in<br>lower case | 56 | ctgcgcgctcgctcgctcactgaggccgcccgggcaaagc<br>ccgggcgtcgggcgacctttggtcgcccggcctcagtgag<br>cgagcgagcgcgcagagagggagtggccaactccatcact<br>aggggttcctCATATGcagggtaatggggatcctCTAGAG<br>AATGGTGGACACCCAAATATGGCGACGGTTCCTCACCCGT<br>CGCCATATTTGGGTGTCCGCCCTCGGCCGGGGCCGCATTC<br>CTGGGGGCCGGGCGGTGCTCCCGCCCGCCTCGATAAAAGG<br>CTCCGGGGCCGGCGGCGGCCCACGAGCTACCCGGAGGAGC<br>GGGAGGCGCCAAGGTGAGTATCTCAGGGATCCAGACATGG |

TABLE 10-continued

RGX-DYS cassette nucleotide sequences

| Structure | SEQ ID | Nucleic Acid Sequence |
|---|---|---|
| | | GGATATGGGAGGTGCCTCTGATCCCAGGGCTCACTGTGGG |
| | | TCTCTCTGTTCACAGGAATTCGCCACCATGCTTTGGTGGG |
| | | AAGAGGTGGAAGATTGCTATGAGAGGGAAGATGTGCAGAA |
| | | GAAAACCTTCACCAAATGGGTCAATGCCCAGTTCAGCAAG |
| | | TTTGGCAAGCAGCACATTGAGAACCTGTTCAGTGACCTGC |
| | | AGGATGGCAGAAGGCTGCTGGATCTGCTGGAAGGCCTGAC |
| | | AGGCCAGAAGCTGCCTAAAGAGAAGGGCAGCACAAGAGTG |
| | | CATGCCCTGAACAATGTGAACAAGGCCCTGAGAGTGCTGC |
| | | AGAACAACAATGTGGACCTGGTCAATATTGGCAGCACAGA |
| | | CATTGTGGATGGCAACCACAAGCTGACCCTGGGCCTGATC |
| | | TGGAACATCATCCTGCACTGGCAAGTGAAGAATGTGATGA |
| | | AGAACATCATGGCTGGCCTGCAGCAGACCAACTCTGAGAA |
| | | GATCCTGCTGAGCTGGGTCAGACAGAGCACCAGAAACTAC |
| | | CCTCAAGTGAATGTGATCAACTTCACCACCTCTTGGAGTG |
| | | ATGGACTGGCCCTGAATGCCCTGATCCACAGCCACAGACC |
| | | TGACCTGTTTGACTGGAACTCTGTTGTGTGCCAGCAGTCT |
| | | GCCACACAGAGACTGGAACATGCCTTCAACATTGCCAGAT |
| | | ACCAGCTGGGAATTGAGAAACTGCTGGACCCTGAGGATGT |
| | | GGACACCACCTATCCTGACAAGAAATCCATCCTCATGTAC |
| | | ATCACCAGCCTGTTCCAGGTGCTGCCCCAGCAAGTGTCCA |
| | | TTGAGGCCATTCAAGAGGTTGAGATGCTGCCCAGACCTCC |
| | | TAAAGTGACCAAAGAGGAACACTTCCAGCTGCACCACCAG |
| | | ATGCACTACTCTCAGCAGATCACAGTGTCTCTGGCCCAGG |
| | | GATATGAGAGAACAAGCAGCCCCAAGCCTAGGTTCAAGAG |
| | | CTATGCCTACACACAGGCTGCCTATGTGACCACATCTGAC |
| | | CCCACAAGAAGCCCATTTCCAAGCCAGCATCTGGAAGCCC |
| | | CTGAGGACAAGAGCTTTGGCAGCAGCCTGATGGAATCTGA |
| | | AGTGAACCTGGATAGATACCAGACAGCCCTGGAAGAAGTG |
| | | CTGTCCTGGCTGCTGTCTGCTGAGGATACACTGCAGGCTC |
| | | AGGGTGAAATCAGCAATGATGTGGAAGTGGTCAAGGACCA |
| | | GTTTCACACCCATGAGGGCTACATGATGGACCTGACAGCC |
| | | CACCAGGGCAGAGTGGGAAATATCCTGCAGCTGGGCTCCA |
| | | AGCTGATTGGCACAGGCAAGCTGTCTGAGGATGAAGAGAC |
| | | AGAGGTGCAAGAGCAGATGAACCTGCTGAACAGCAGATGG |
| | | GAGTGTCTGAGAGTGGCCAGCATGGAAAAGCAGAGCAACC |
| | | TGCACAGAGTGCTCATGGACCTGCAGAATCAGAAACTGAA |
| | | AGAACTGAATGACTGGCTGACCAAGACAGAAGAAAGGACT |
| | | AGGAAGATGGAAGAGGAACCTCTGGGACCAGACCTGGAAG |
| | | ATCTGAAAAGACAGGTGCAGCAGCATAAGGTGCTGCAAGA |
| | | GGACCTTGAGCAAGAGCAAGTCAGAGTGAACAGCCTGACA |
| | | CACATGGTGGTGGTTGTGGATGAGTCCTCTGGGGATCATG |
| | | CCACAGCTGCTCTGGAAGAACAGCTGAAGGTGCTGGGAGA |
| | | CAGATGGGCCAACATCTGTAGGTGGACAGAGGATAGATGG |
| | | GTGCTGCTCCAGGACATTCTGCTGAAGTGGCAGAGACTGA |
| | | CAGAGGAACAGTGCCTGTTTTCTGCCTGGCTCTCTGAGAA |
| | | AGAGGATGCTGTCAACAAGATCCATACCACAGGCTTCAAG |
| | | GATCAGAATGAGATGCTCAGCTCCCTGCAGAAACTGGCTG |
| | | TGCTGAAGGCTGACCTGGAAAAGAAAAAGCAGTCCATGGG |
| | | CAAGCTCTACAGCCTGAAGCAGGACCTGCTGTCTACCCTG |
| | | AAGAACAAGTCTGTGACCCAGAAAACTGAGGCCTGGCTGG |
| | | ACAACTTTGCTAGATGCTGGGACAACCTGGTGCAGAAGCT |
| | | GGAAAAGTCTACAGCCCAGATCAGCCAGCAACCTGATCTT |
| | | GCCCCTGGCCTGACCACAATTGGAGCCTCTCCAACACAGA |
| | | CTGTGACCCTGGTTACCCAGCCAGTGGTCACCAAAGAGAC |
| | | AGCCATCAGCAAACTGGAAATGCCCAGCTCTCTGATGCTG |
| | | GAAGTCCCCACACTGGAAAGGCTGCAAGAACTTCAAGAGG |
| | | CCACAGATGAGCTGGACCTGAAGCTGAGACAGGCTGAAGT |
| | | GATCAAAGGCAGCTGGCAGCCAGTTGGGGACCTGCTCATT |
| | | GATAGCCTGCAGGACCATCTGGAAAAAGTGAAAGCCCTGA |
| | | GGGGAGAGATTGCCCCTCTGAAAGAAAATGTGTCCCATGT |
| | | GAATGACCTGGCCAGACAGCTGACCACACTGGGAATCCAG |
| | | CTGAGCCCCTACAACCTGAGCACCCTTGAGGACCTGAACA |
| | | CCAGGTGGAAGCTCCTCCAGGTGGCAGTGGAAGATAGAGT |
| | | CAGGCAGCTGCATGAGGCCCACAGAGATTTTGGACCAGCC |
| | | AGCCAGCACTTTCTGTCTACCTCTGTGCAAGGCCCCTGGG |
| | | AGAGAGCTATCTCTCCTAACAAGGTGCCCTACTACATCAA |
| | | CCATGAGACACAGACCACCTGTTGGGATCACCCCAAGATG |
| | | ACAGAGCTGTACCAGAGTCTGGCAGACCTCAACAATGTCA |
| | | GATTCAGTGCCTACAGGACTGCCATGAAGCTCAGAAGGCT |
| | | CCAGAAAGCTCTGTGCCTGGACCTGCTTTCCCTGAGTGCA |
| | | GCTTGTGATGCCCTGGACCAGCACAATCTGAAGCAGAATG |
| | | ACCAGCCTATGGACATCCTCCAGATCATCAACTGCCTCAC |
| | | CACCATCTATGATAGGCTGGAACAAGAGCACAACAATCTG |
| | | GTCAATGTGCCCCTGTGTGTGGACATGTGCCTGAATTGGC |
| | | TGCTGAATGTGTATGACACAGGCAGAACAGGCAGGATCAG |
| | | AGTCCTGTCCTTCAAGACAGGCATCATCTCCCTGTGCAAA |

TABLE 10-continued

RGX-DYS cassette nucleotide sequences

| Structure | SEQ ID | Nucleic Acid Sequence |
| --- | --- | --- |
| | | GCCCACTTGGAGGACAAGTACAGATACCTGTTCAAGCAAG<br>TGGCCTCCAGCACAGGCTTTTGTGACCAGAGAAGGCTGGG<br>CCTGCTCCTGCATGACAGCATTCAGATCCCTAGACAGCTG<br>GGAGAAGTGGCTTCCTTTGGAGGCAGCAATATTGAGCCAT<br>CAGTCAGGTCCTGTTTTCAGTTTGCCAACAACAAGCCTGA<br>GATTGAGGCTGCCCTGTTCCTGGACTGGATGAGACTTGAG<br>CCTCAGAGCATGGTCTGGCTGCCTGTGCTTCATAGAGTGG<br>CTGCTGCTGAGACTGCCAAGCACCAGGCCAAGTGCAACAT<br>CTGCAAAGAGTGCCCCATCATTGGCTTCAGATACAGATCC<br>CTGAAGCACTTCAACTATGATATCTGCCAGAGCTGCTTCT<br>TTAGTGGCAGGGTTGCCAAGGGCCACAAAATGCACTACCC<br>CATGGTGGAATACTGCACCCCAACAACCTCTGGGGAAGAT<br>GTTAGAGACTTTGCCAAGGTGCTGAAAAACAAGTTCAGGA<br>CCAAGAGATACTTTGCTAAGCACCCCAGAATGGGCTACCT<br>GCCTGTCCAGACAGTGCTTGAGGGTGACAACATGGAAACC<br>CCTGTGACACTGATCAATTTCTGGCCAGTGGACTCTGCCC<br>CTGCCTCAAGTCCACAGCTGTCCCATGATGACACCCACAG<br>CAGAATTGAGCACTATGCCTCCAGACTGGCAGAGATGGAA<br>AACAGCAATGGCAGCTACCTGAATGATAGCATCAGCCCCA<br>ATGAGAGCATTGATGATGAGCATCTGCTGATCCAGCACTA<br>CTGTCAGTCCCTGAACCAGGACTCTCCACTGAGCCAGCCT<br>AGAAGCCCTGCTCAGATCCTGATCAGCCTTGAGTCTGAGG<br>AAAGGGGAGAGCTGGAAAGAATCCTGGCAGATCTTGAGGA<br>AGAGAACAGAAACCTGCAGGCAGAGTATGACAGGCTCAAA<br>CAGCAGCATGAGCACAAGGGACTGAGCCCTCTGCCTTCTC<br>CTCCTGAAATGATGCCCACCTCTCCACAGTCTCCAAGGTG<br>ATGACTCGAGAGGCCTAATAAAGAGCTCAGATGCATCGAT<br>CAGAGTGTGTTGGTTTTTTGTGTGCCAGGGTAATGGGCTA<br>GCTGCGGCCGCaggaacccctagtgatggagttggccact<br>ccctctctgcgcgctcgctcgctcactgaggccgggcgac<br>caaaggtcgcccgacgcccgggctttgcccgggcggcctc<br>agtgagcgagcgagcgcgcag |
| RGX-DYS5<br>(full cassette<br>SPc5-12 to<br>poly A<br>including<br>intervening<br>seqs)<br>4560 bp<br>ITRs shown in<br>lower case | 82 | ctgcgcgctcgctcgctcactgaggccgcccgggcaaagc<br>ccgggcgtcgggcgacctttggtcgcccggcctcagtgag<br>cgagcgagcgcgcagagagggagtggccaactccatcact<br>aggggttcctCATATGcagggtaatggggatcctCTAGAG<br>GCCGTCCGCCCTCGGCACCATCCTCACGACACCCAAATAT<br>GGCGACGGGTGAGGAATGGTGGGGAGTTATTTTTAGAGCG<br>GTGAGGAAGGTGGGCAGGCAGCAGGTGTTGGCGCTCTAAA<br>AATAACTCCCGGGAGTTATTTTTAGAGCGGAGGAATGGTG<br>GACACCCAAATATGGCGACGGTTCCTCACCCGTCGCCATA<br>TTTGGGTGTCCGCCCTCGGCCGGGGCCGCATTCCTGGGGG<br>CCGGGCGGTGCTCCCGCCCGCCTCGATAAAAGGCTCCGGG<br>GCCGGCGGCGGCCCACGAGCTACCCGGAGGAGCGGGAGGC<br>GCCAAGCGGAATTCGCCACCATGCTTTGGTGGGAAGAGGT<br>GGAAGATTGCTATGAGAGGGAAGATGTGCAGAAGAAAACC<br>TTCACCAAATGGGTCAATGCCCAGTTCAGCAAGTTTGGCA<br>AGCAGCACATTGAGAACCTGTTCAGTGACCTGCAGGATGG<br>CAGAAGGCTGCTGGATCTGCTGGAAGGCCTGACAGGCCAG<br>AAGCTGCCTAAAGAGAAGGGCAGCACAAGAGTGCATGCCC<br>TGAACAATGTGAACAAGGCCCTGAGAGTGCTGCAGAACAA<br>CAATGTGGACCTGGTCAATATTGGCAGCACAGACATTGTG<br>GATGGCAACCACAAGCTGACCCTGGGCCTGATCTGGAACA<br>TCATCCTGCACTGGCAAGTGAAGAATGTGATGAAGAACAT<br>CATGGCTGGCCTGCAGCAGACCAACTCTGAGAAGATCCTG<br>CTGAGCTGGGTCAGACAGAGCACCAGAAACTACCCTCAAG<br>TGAATGTGATCAACTTCACCACCTCTTGGAGTGATGGACT<br>GGCCCTGAATGCCCTGATCCACAGCCACAGACCTGACCTG<br>TTTGACTGGAACTCTGTTGTGTGCCAGCAGTCTGCCACAC<br>AGAGACTGGAACATGCCTTCAACATTGCCAGATACCAGCT<br>GGGAATTGAGAAACTGCTGGACCCTGAGGATGTGGACACC<br>ACCTATCCTGACAAGAAATCCATCCTCATGTACATCACCA<br>GCCTGTTCCAGGTGCTGCCCCAGCAAGTGTCCATTGAGGC<br>CATTCAAGAGGTTGAGATGCTGCCCAGACCTCCTAAAGTG<br>ACCAAAGAGGAACACTTCCAGCTGCACCACCAGATGCACT<br>ACTCTCAGCAGATCACAGTGTCTCTGGCCCAGGGATATGA<br>GAGAACAAGCAGCCCCAAGCCTAGGTTCAAGAGCTATGCC<br>TACACACAGGCTGCCTATGTGACCACATCTGACCCCACAA<br>GAAGCCCATTTCCAAGCCAGCATCTGGAAGCCCCTGAGGA<br>CAAGAGCTTTGGCAGCAGCCTGATGGAATCTGAAGTGAAC<br>CTGGATAGATACCAGACAGCCCTGGAAGAAGTGCTGTCCT<br>GGCTGCTGTCTGCTGAGGATACACTGCAGGCTCAGGGTGA<br>AATCAGCAATGATGTGGAAGTGGTCAAGGACCAGTTTCAC<br>ACCCATGAGGGCTACATGATGGACCTGACAGCCCACCAGG<br>GCAGAGTGGGAAATATCCTGCAGCTGGGCTCCAAGCTGAT |

TABLE 10-continued

RGX-DYS cassette nucleotide sequences

| Structure | SEQ ID | Nucleic Acid Sequence |
|---|---|---|
| | | TGGCACAGGCAAGCTGTCTGAGGATGAAGAGACAGAGGTG |
| | | CAAGAGCAGATGAACCTGCTGAACAGCAGATGGGAGTGTC |
| | | TGAGAGTGGCCAGCATGGAAAAGCAGAGCAACCTGCACAG |
| | | AGTGCTCATGGACCTGCAGAATCAGAAACTGAAAGAACTG |
| | | AATGACTGGCTGACCAAGACAGAAGAAAGGACTAGGAAGA |
| | | TGGAAGAGGAACCTCTGGGACCAGACCTGGAAGATCTGAA |
| | | AAGACAGGTGCAGCAGCATAAGGTGCTGCAAGAGGACCTT |
| | | GAGCAAGAGCAAGTCAGAGTGAACAGCCTGACACACATGG |
| | | TGGTGGTTGTGGATGAGTCCTCTGGGGATCATGCCACAGC |
| | | TGCTCTGGAAGAACAGCTGAAGGTGCTGGGAGACAGATGG |
| | | GCCAACATCTGTAGGTGGACAGAGGATAGATGGGTGCTGC |
| | | TCCAGGACATTCTGCTGAAGTGGCAGAGACTGACAGAGGA |
| | | ACAGTGCCTGTTTTCTGCCTGGCTCTCTGAGAAAGAGGAT |
| | | GCTGTCAACAAGATCCATACCACAGGCTTCAAGGATCAGA |
| | | ATGAGATGCTCAGCTCCCTGCAGAAACTGGCTGTGCTGAA |
| | | GGCTGACCTGGAAAAGAAAAAGCAGTCCATGGGCAAGCTC |
| | | TACAGCCTGAAGCAGGACCTGCTGTCTACCCTGAAGAACA |
| | | AGTCTGTGACCCAGAAAACTGAGGCCTGGCTGGACAACTT |
| | | TGCTAGATGCTGGGACAACCTGGTGCAGAAGCTGGAAAAG |
| | | TCTACAGCCCAGATCAGCCAGCAACCTGATCTTGCCCCTG |
| | | GCCTGACCACAATTGGAGCCTCTCCAACACAGACTGTGAC |
| | | CCTGGTTACCCAGCCAGTGGTCACCAAAGAGACAGCCATC |
| | | AGCAAACTGGAAATGCCCAGCTCTCTGATGCTGGAAGTCC |
| | | CCACACTGGAAAGGCTGCAAGAACTTCAAGAGGCCACAGA |
| | | TGAGCTGGACCTGAAGCTGAGACAGGCTGAAGTGATCAAA |
| | | GGCAGCTGGCAGCCAGTTGGGGACCTGCTCATTGATAGCC |
| | | TGCAGGACCATCTGGAAAAAGTGAAAGCCCTGAGGGGAGA |
| | | GATTGCCCCTCTGAAAGAAAATGTGTCCCATGTGAATGAC |
| | | CTGGCCAGACAGCTGACCACACTGGGAATCCAGCTGAGCC |
| | | CCTACAACCTGAGCACCCTTGAGGACCTGAACACCAGGTG |
| | | GAAGCTCCTCCAGGTGGCAGTGGAAGATAGAGTCAGGCAG |
| | | CTGCATGAGGCCCACAGAGATTTTGGACCAGCCAGCCAGC |
| | | ACTTTCTGTCTACCTCTGTGCAAGGCCCCTGGGAGAGAGC |
| | | TATCTCTCCTAACAAGGTGCCCTACTACATCAACCATGAG |
| | | ACACAGACCACCTGTTGGGATCACCCCAAGATGACAGAGC |
| | | TGTACCAGAGTCTGGCAGACCTCAACAATGTCAGATTCAG |
| | | TGCCTACAGGACTGCCATGAAGCTCAGAAGGCTCCAGAAA |
| | | GCTCTGTGCCTGGACCTGCTTTCCCTGAGTGCAGCTTGTG |
| | | ATGCCCTGGACCAGCACAATCTGAAGCAGAATGACCAGCC |
| | | TATGGACATCCTCCAGATCATCAACTGCCTCACCACCATC |
| | | TATGATAGGCTGGAACAAGAGCACAACAATCTGGTCAATG |
| | | TGCCCCTGTGTGTGGACATGTGCCTGAATTGGCTGCTGAA |
| | | TGTGTATGACACAGGCAGAACAGGCAGGATCAGAGTCCTG |
| | | TCCTTCAAGACAGGCATCATCTCCCTGTGCAAAGCCCACT |
| | | TGGAGGACAAGTACAGATACCTGTTCAAGCAAGTGGCCTC |
| | | CAGCACAGGCTTTTGTGACCAGAGAAGGCTGGGCCTGCTC |
| | | CTGCATGACAGCATTCAGATCCCTAGACAGCTGGGAGAAG |
| | | TGGCTTCCTTTGGAGGCAGCAATATTGAGCCATCAGTCAG |
| | | GTCCTGTTTTCAGTTTGCCAACAACAAGCCTGAGATTGAG |
| | | GCTGCCCTGTTCCTGGACTGGATGAGACTTGAGCCTCAGA |
| | | GCATGGTCTGGCTGCCTGTGCTTCATAGAGTGGCTGCTGC |
| | | TGAGACTGCCAAGCACCAGGCCAAGTGCAACATCTGCAAA |
| | | GAGTGCCCCATCATTGGCTTCAGATACAGATCCCTGAAGC |
| | | ACTTCAACTATGATATCTGCCAGAGCTGCTTCTTTAGTGG |
| | | CAGGGTTGCCAAGGGCCACAAAATGCACTACCCCATGGTG |
| | | GAATACTGCACCCCAACAACCTCTGGGGAAGATGTTAGAG |
| | | ACTTTGCCAAGGTGCTGAAAAACAAGTTCAGGACCAAGAG |
| | | ATACTTTGCTAAGCACCCCAGAATGGGCTACCTGCCTGTC |
| | | CAGACAGTGCTTGAGGGTGACAACATGGAAACCCCTGTGA |
| | | CACTGATCAATTTCTGGCCAGTGGACTCTGCCCCTGCCTC |
| | | AAGTCCACAGCTGTCCCATGATGACACCCACAGCAGAATT |
| | | GAGCACTATGCCTCCAGACTGGCAGAGATGGAAAACAGCA |
| | | ATGGCAGCTACCTGAATGATAGCATCAGCCCCAATGAGAG |
| | | CATTGATGATGAGCATCTGCTGATCCAGCACTACTGTCAG |
| | | TCCCTGAACCAGGACTCTCCACTGAGCCAGCCTAGAAGCC |
| | | CTGCTCAGATCCTGATCAGCCTTGAGTCTTGATGAGTCGA |
| | | CAGGCCTAATAAAGAGCTCAGATGCATCGATCAGAGTGTG |
| | | TTGGTTTTTTGTGTGGCTAGCTGCGGCCGCaggaacccct |
| | | agtgatggagttggccactccctctctgcgcgctcgctcg |
| | | ctcactgaggccgggcgaccaaaggtcgcccgacgcccgg |
| | | gctttgcccgggcggcctcagtgagcgagcgagcgcgcag |
| RGX-DYS6 | 104 | ctgcgcgctcgctcgctcactgaggccgcccgggcaaagc |
| (full cassette | | ccgggcgtcgggcgacctttggtcgcccggcctcagtgag |
| including | | cgagcgagcgcgcagagagggagtggccaactccatcact |
| flanking ITRs, | | aggggttcctCATATGCAGGGTAATGGGGATCCTCTAGAG |

TABLE 10-continued

RGX-DYS cassette nucleotide sequences

| Structure | SEQ ID | Nucleic Acid Sequence |
|---|---|---|
| Spc5-12 | | GCCGTCCGCCCTCGGCACCATCCTCACGACACCCAAATAT |
| promoter to | | GGCGACGGGTGAGGAATGGTGGGGAGTTATTTTTAGAGCG |
| poly A and | | GTGAGGAAGGTGGGCAGGCAGCAGGTGTTGGCGCTCTAAA |
| intervening | | AATAACTCCCGGGAGTTATTTTTAGAGCGGAGGAATGGTG |
| seqs) | | GACACCCAAATATGGCGACGGTTCCTCACCCGTCGCCATA |
| 4584 bp | | TTTGGGTGTCCGCCCTCGGCCGGGGCCGCATTCCTGGGGG |
| ITRs shown in | | CCGGGCGGTGCTCCCGCCCGCCTCGATAAAAGGCTCCGGG |
| lower case | | GCCGGCGGCGGCCCACGAGCTACCCGGAGGAGCGGGAGGC |
| | | GCCAAGCGgAATTCGCCACCATGCTTTGGTGGGAAGAGGT |
| | | GGAAGATTGCTATGAGAGGGAAGATGTGCAGAAGAAAACC |
| | | TTCACCAAATGGGTCAATGCCCAGTTCAGCAAGTTTGGCA |
| | | AGCAGCACATTGAGAACCTGTTCAGTGACCTGCAGGATGG |
| | | CAGAAGGCTGCTGGATCTGCTGGAAGGCCTGACAGGCCAG |
| | | AAGCTGCCTAAAGAGAAGGGCAGCACAAGAGTGCATGCCC |
| | | TGAACAATGTGAACAAGGCCCTGAGAGTGCTGCAGAACAA |
| | | CAATGTGGACCTGGTCAATATTGGCAGCACAGACATTGTG |
| | | GATGGCAACCACAAGCTGACCCTGGGCCTGATCTGGAACA |
| | | TCATCCTGCACTGGCAAGTGAAGAATGTGATGAAGAACAT |
| | | CATGGCTGGCCTGCAGCAGACCAACTCTGAGAAGATCCTG |
| | | CTGAGCTGGGTCAGACAGAGCACCAGAAACTACCCTCAAG |
| | | TGAATGTGATCAACTTCACCACCTCTTGGAGTGATGGACT |
| | | GGCCCTGAATGCCCTGATCCACAGCCACAGACCTGACCTG |
| | | TTTGACTGGAACTCTGTTGTGTGCCAGCAGTCTGCCACAC |
| | | AGAGACTGGAACATGCCTTCAACATTGCCAGATACCAGCT |
| | | GGGAATTGAGAAACTGCTGGACCCTGAGGATGTGGACACC |
| | | ACCTATCCTGACAAGAAATCCATCCTCATGTACATCACCA |
| | | GCCTGTTCCAGGTGCTGCCCCAGCAAGTGTCCATTGAGGC |
| | | CATTCAAGAGGTTGAGATGCTGCCCAGACCTCCTAAAGTG |
| | | ACCAAAGAGGAACACTTCCAGCTGCACCACCAGATGCACT |
| | | ACTCTCAGCAGATCACAGTGTCTCTGGCCCAGGGATATGA |
| | | GAGAACAAGCAGCCCCAAGCCTAGGTTCAAGAGCTATGCC |
| | | TACACACAGGCTGCCTATGTGACCACATCTGACCCCACAA |
| | | GAAGCCCATTTCCAAGCCAGCATCTGGAAGCCCCTGAGGA |
| | | CAAGAGCTTTGGCAGCAGCCTGATGGAATCTGAAGTGAAC |
| | | CTGGATAGATACCAGACAGCCCTGGAAGAAGTGCTGTCCT |
| | | GGCTGCTGTCTGCTGAGGATACACTGCAGGCTCAGGGTGA |
| | | AATCAGCAATGATGTGGAAGTGGTCAAGGACCAGTTTCAC |
| | | ACCCATGAGGGCTACATGATGGACCTGACAGCCCACCAGG |
| | | GCAGAGTGGGAAATATCCTGCAGCTGGGCTCCAAGCTGAT |
| | | TGGCACAGGCAAGCTGTCTGAGGATGAAGAGACAGAGGTG |
| | | CAAGAGCAGATGAACCTGCTGAACAGCAGATGGGAGTGTC |
| | | TGAGAGTGGCCAGCATGGAAAAGCAGAGCAACCTGCACAG |
| | | AGTGCTCATGGACCTGCAGAATCAGAAACTGAAAGAACTG |
| | | AATGACTGGCTGACCAAGACAGAAGAAAGGACTAGGAAGA |
| | | TGGAAGAGGAACCTCTGGGACCAGACCTGGAAGATCTGAA |
| | | AAGACAGGTGCAGCAGCATAAGGTGCTGCAAGAGGACCTT |
| | | GAGCAAGAGCAAGTCAGAGTGAACAGCCTGACACACATGG |
| | | TGGTGGTTGTGGATGAGTCCTCTGGGGATCATGCCACAGC |
| | | TGCTCTGGAAGAACAGCTGAAGGTGCTGGGAGACAGATGG |
| | | GCCAACATCTGTAGGTGGACAGAGGATAGATGGGTGCTGC |
| | | TCCAGGACATTCTGCTGAAGTGGCAGAGACTGACAGAGGA |
| | | ACAGTGCCTGTTTTCTGCCTGGCTCTCTGAGAAAGAGGAT |
| | | GCTGTCAACAAGATCCATACCACAGGCTTCAAGGATCAGA |
| | | ATGAGATGCTCAGCTCCCTGCAGAAACTGGCTGTGCTGAA |
| | | GGCTGACCTGGAAAAGAAAAAGCAGTCCATGGGCAAGCTC |
| | | TACAGCCTGAAGCAGGACCTGCTGTCTACCCTGAAGAACA |
| | | AGTCTGTGACCCAGAAAACTGAGGCCTGGCTGGACAACTT |
| | | TGCTAGATGCTGGGACAACCTGGTGCAGAAGCTGGAAAAG |
| | | TCTACAGCCCAGATCAGCCAGCAACCTGATCTTGCCCCTG |
| | | GCCTGACCACAATTGGAGCCTCTCCAACACAGACTGTGAC |
| | | CCTGGTTACCCAGCCAGTGGTCACCAAAGAGACAGCCATC |
| | | AGCAAACTGGAAATGCCCAGCTCTCTGATGCTGGAAGTCC |
| | | CCACACTGGAAAGGCTGCAAGAACTTCAAGAGGCCACAGA |
| | | TGAGCTGGACCTGAAGCTGAGACAGGCTGAAGTGATCAAA |
| | | GGCAGCTGGCAGCCAGTTGGGGACCTGCTCATTGATAGCC |
| | | TGCAGGACCATCTGGAAAAAGTGAAAGCCCTGAGGGGAGA |
| | | GATTGCCCCTCTGAAAGAAAATGTGTCCCATGTGAATGAC |
| | | CTGGCCAGACAGCTGACCACACTGGGAATCCAGCTGAGCC |
| | | CCTACAACCTGAGCACCCTTGAGGACCTGAACACCAGGTG |
| | | GAAGCTCCTCCAGGTGGCAGTGGAAGATAGAGTCAGGCAG |
| | | CTGCATGAGGCCCACAGAGATTTTGGACCAGCCAGCCAGC |
| | | ACTTTCTGTCTACCTCTGTGCAAGGCCCCTGGGAGAGAGC |
| | | TATCTCTCCTAACAAGGTGCCCTACTACATCAACCATGAG |
| | | ACACAGACCACCTGTTGGGATCACCCCAAGATGACAGAGC |
| | | TGTACCAGAGTCTGGCAGACCTCAACAATGTCAGATTCAG |
| | | TGCCTACAGGACTGCCATGAAGCTCAGAAGGCTCCAGAAA |

TABLE 10-continued

RGX-DYS cassette nucleotide sequences

| Structure | SEQ ID | Nucleic Acid Sequence |
|---|---|---|
| | | GCTCTGTGCCTGGACCTGCTTTCCCTGAGTGCAGCTTGTG<br>ATGCCCTGGACCAGCACAATCTGAAGCAGAATGACCAGCC<br>TATGGACATCCTCCAGATCATCAACTGCCTCACCACCATC<br>TATGATAGGCTGGAACAAGAGCACAACAATCTGGTCAATG<br>TGCCCCTGTGTGTGGACATGTGCCTGAATTGGCTGCTGAA<br>TGTGTATGACACAGGCAGAACAGGCAGGATCAGAGTCCTG<br>TCCTTCAAGACAGGCATCATCTCCCTGTGCAAAGCCCACT<br>TGGAGGACAAGTACAGATACCTGTTCAAGCAAGTGGCCTC<br>CAGCACAGGCTTTTGTGACCAGAGAAGGCTGGGCCTGCTC<br>CTGCATGACAGCATTCAGATCCCTAGACAGCTGGGAGAAG<br>TGGCTTCCTTTGGAGGCGCCAAGCACCAGGCCAAGTGCAA<br>CATCTGCAAAGAGTGCCCCATCATTGGCTTCAGATACAGA<br>TCCCTGAAGCACTTCAACTATGATATCTGCCAGAGCTGCT<br>TCTTTAGTGGCAGGGTTGCCAAGGGCCACAAAATGCACTA<br>CCCCATGGTGGAATACTGCACCCCAACAACCTCTGGGGAA<br>GATGTTAGAGACTTTGCCAAGGTGCTGAAAAACAAGTTCA<br>GGACCAAGAGATACTTTGCTAAGCACCCCAGAATGGGCTA<br>CCTGCCTGTCCAGACAGTGCTTGAGGGTGACAACATGGAA<br>ACCCCTGTGACACTGATCAATTTCTGGCCAGTGGACTCTG<br>CCCCTGCCTCAAGTCCACAGCTGTCCCATGATGACACCCA<br>CAGCAGAATTGAGCACTATGCCTCCAGACTGGCAGAGATG<br>GAAAACAGCAATGGCAGCTACCTGAATGATAGCATCAGCC<br>CCAATGAGAGCATTGATGATGAGCATCTGCTGATCCAGCA<br>CTACTGTCAGTCCCTGAACCAGGACTCTCCACTGAGCCAG<br>CCTAGAAGCCCTGCTCAGATCCTGATCAGCCTTGAGTCTG<br>AGGAAAGGGGAGAGCTGGAAAGAATCCTGGCAGATCTTGA<br>GGAAGAGAACAGAAACCTGCAGGCAGAGTATGACAGGCTC<br>AAACAGCAGCATGAGCACAAGGGACTGAGCCCTCTGCCTT<br>CTCCTCCTGAAATGATGCCCACCTCTCCACAGTCTCCAAG<br>GTGATGACTCGAGAGGCCTAATAAAGAGCTCAGATGCATC<br>GATCAGAGTGTGTTGGTTTTTTGTGTGCCAGGGTAATGGG<br>CTAGCTGCGGCCGCaggaacccctagtgatggagttggcc<br>actccctctctgcgcgctcgctcgctcactgaggccgggc<br>gaccaaaggtcgcccgacgcccgggctttgcccgggcggc<br>ctcagtgagcgagcgagcgcgcag |
| RGX-DYS7<br>(full cassette<br>including<br>flanking ITRs,<br>Spc5-12<br>promoter to<br>poly A and<br>intervening<br>seqs)<br>4746 bp<br>ITRs shown in<br>lower case | 105 | ctgcgcgctcgctcgctcactgaggccgcccgggcaaagc<br>ccgggcgtcgggcgacctttggtcgcccggcctcagtgag<br>cgagcgagcgcgcagagagggagtggccaactccatcact<br>aggggttcctCATATGCAGGGTAATGGGGATCCTCTAGAG<br>GCCGTCCGCCCTCGGCACCATCCTCACGACACCCAAATAT<br>GGCGACGGGTGAGGAATGGTGGGGAGTTATTTTTAGAGCG<br>GTGAGGAAGGTGGGCAGGCAGCAGGTGTTGGCGCTCTAAA<br>AATAACTCCCGGGAGTTATTTTTAGAGCGGAGGAATGGTG<br>GACACCCAAATATGGCGACGGTTCCTCACCCGTCGCCATA<br>TTTGGGTGTCCGCCCTCGGCCGGGGCCGCATTCCTGGGGG<br>CCGGGCGGTGCTCCCGCCCGCCTCGATAAAAGGCTCCGGG<br>GCCGGCGGCGGCCCACGAGCTACCCGGAGGAGCGGGAGGC<br>GCCAAGCGgAATTCGCCACCATGCTTTGGTGGGAAGAGGT<br>GGAAGATTGCTATGAGAGGGAAGATGTGCAGAAGAAAACC<br>TTCACCAAATGGGTCAATGCCCAGTTCAGCAAGTTTGGCA<br>AGCAGCACATTGAGAACCTGTTCAGTGACCTGCAGGATGG<br>CAGAAGGCTGCTGGATCTGCTGGAAGGCCTGACAGGCCAG<br>AAGCTGCCTAAAGAGAAGGGCAGCACAAGAGTGCATGCCC<br>TGAACAATGTGAACAAGGCCCTGAGAGTGCTGCAGAACAA<br>CAATGTGGACCTGGTCAATATTGGCAGCACAGACATTGTG<br>GATGGCAACCACAAGCTGACCCTGGGCCTGATCTGGAACA<br>TCATCCTGCACTGGCAAGTGAAGAATGTGATGAAGAACAT<br>CATGGCTGGCCTGCAGCAGACCAACTCTGAGAAGATCCTG<br>CTGAGCTGGGTCAGACAGAGCACCAGAAACTACCCTCAAG<br>TGAATGTGATCAACTTCACCACCTCTTGGAGTGATGGACT<br>GGCCCTGAATGCCCTGATCCACAGCCACAGACCTGACCTG<br>TTTGACTGGAACTCTGTTGTGTGCCAGCAGTCTGCCACAC<br>AGAGACTGGAACATGCCTTCAACATTGCCAGATACCAGCT<br>GGGAATTGAGAAACTGCTGGACCCTGAGGATGTGGACACC<br>ACCTATCCTGACAAGAAATCCATCCTCATGTACATCACCA<br>GCCTGTTCCAGGTGCTGCCCCAGCAAGTGTCCATTGAGGC<br>CATTCAAGAGGTTGAGATGCTGCCCAGACCTCCTAAAGTG<br>ACCAAAGAGGAACACTTCCAGCTGCACCACCAGATGCACT<br>ACTCTCAGCAGATCACAGTGTCTCTGGCCCAGGGATATGA<br>GAGAACAAGCAGCCCCAAGCCTAGGTTCAAGAGCTATGCC<br>TACACACAGGCTGCCTATGTGACCACATCTGACCCCACAA<br>GAAGCCCATTTCCAAGCCAGCATCTGGAAGCCCCTGAGGA<br>CAAGAGCTTTGGCAGCAGCCTGATGGAATCTGAAGTGAAC<br>CTGGATAGATACCAGACAGCCCTGGAAGAAGTGCTGTCCT<br>GGCTGCTGTCTGCTGAGGATACACTGCAGGCTCAGGGTGA |

TABLE 10-continued

RGX-DYS cassette nucleotide sequences

| Structure | SEQ ID | Nucleic Acid Sequence |
| --- | --- | --- |
| | | AATCAGCAATGATGTGGAAGTGGTCAAGGACCAGTTTCAC |
| | | ACCCATGAGGGCTACATGATGGACCTGACAGCCCACCAGG |
| | | GCAGAGTGGGAAATATCCTGCAGCTGGGCTCCAAGCTGAT |
| | | TGGCACAGGCAAGCTGTCTGAGGATGAAGAGACAGAGGTG |
| | | CAAGAGCAGATGAACCTGCTGAACAGCAGATGGGAGTGTC |
| | | TGAGAGTGGCCAGCATGGAAAAGCAGAGCAACCTGCACAG |
| | | AGTGCTCATGGACCTGCAGAATCAGAAACTGAAAGAACTG |
| | | AATGACTGGCTGACCAAGACAGAAGAAAGGACTAGGAAGA |
| | | TGGAAGAGGAACCTCTGGGACCAGACCTGGAAGATCTGAA |
| | | AAGACAGGTGCAGCAGCATAAGGTGCTGCAAGAGGACCTT |
| | | GAGCAAGAGCAAGTCAGAGTGAACAGCCTGACACACATGG |
| | | TGGTGGTTGTGGATGAGTCCTCTGGGGATCATGCCACAGC |
| | | TGCTCTGGAAGAACAGCTGAAGGTGCTGGGAGACAGATGG |
| | | GCCAACATCTGTAGGTGGACAGAGGATAGATGGGTGCTGC |
| | | TCCAGGACATTCTGGAGATCAGCTATGTGCCCAGCACCTA |
| | | CCTGACAGAGATCACCCATGTGTCTCAGGCCCTGCTGGAA |
| | | GTGGAACAGCTGCTGAATGCCCCTGACCTGTGTGCCAAGG |
| | | ACTTTGAGGACCTGTTCAAGCAAGAGGAAAGCCTGAAGAA |
| | | CATCAAGGACAGCCTGCAGCAGTCCTCTGGCAGAATTGAC |
| | | ATCATCCACAGCAAGAAAACAGCTGCCCTGCAGTCTGCCA |
| | | CACCTGTGGAAAGAGTGAAGCTGCAAGAGGCCCTGAGCCA |
| | | GCTGGACTTCCAGTGGGAGAAAGTGAACAAGATGTACAAG |
| | | GACAGGCAGGGCAGATTTGATAGAAGTGTGGAAAAGTGGA |
| | | GAAGGTTCCACTATGACATCAAGATCTTCAACCAGTGGCT |
| | | GACAGAGGCTGAGCAGTTCCTGAGAAAGACACAGATCCCT |
| | | GAGAACTGGGAGCATGCCAAGTACAAGTGGTATCTGAAAG |
| | | AACTGCAGGATGGCATTGGCCAGAGACAGACAGTTGTCAG |
| | | AACCCTGAATGCCACAGGGGAAGAGATCATCCAGCAGAGC |
| | | AGCAAGACAGATGCCAGCATCCTGCAAGAGAAGCTGGGCA |
| | | GCCTGAACCTGAGATGGCAAGAAGTGTGCAAGCAGCTGTC |
| | | TGACAGAAAGAAGAGGCTGGAAGAACAGACACTGGAAAGG |
| | | CTGCAAGAACTTCAAGAGGCCACAGATGAGCTGGACCTGA |
| | | AGCTGAGACAGGCTGAAGTGATCAAAGGCAGCTGGCAGCC |
| | | AGTTGGGGACCTGCTCATTGATAGCCTGCAGGACCATCTG |
| | | GAAAAAGTGAAAGCCCTGAGGGGAGAGATTGCCCCTCTGA |
| | | AAGAAAATGTGTCCCATGTGAATGACCTGGCCAGACAGCT |
| | | GACCACACTGGGAATCCAGCTGAGCCCCTACAACCTGAGC |
| | | ACCCTTGAGGACCTGAACACCAGGTGGAAGCTCCTCCAGG |
| | | TGGCAGTGGAAGATAGAGTCAGGCAGCTGCATGAGGCCCA |
| | | CAGAGATTTTGGACCAGCCAGCCAGCACTTTCTGTCTACC |
| | | TCTGTGCAAGGCCCCTGGGAGAGAGCTATCTCTCCTAACA |
| | | AGGTGCCCTACTACATCAACCATGAGACACAGACCACCTG |
| | | TTGGGATCACCCCAAGATGACAGAGCTGTACCAGAGTCTG |
| | | GCAGACCTCAACAATGTCAGATTCAGTGCCTACAGGACTG |
| | | CCATGAAGCTCAGAAGGCTCCAGAAAGCTCTGTGCCTGGA |
| | | CCTGCTTTCCCTGAGTGCAGCTTGTGATGCCCTGGACCAG |
| | | CACAATCTGAAGCAGAATGACCAGCCTATGGACATCCTCC |
| | | AGATCATCAACTGCCTCACCACCATCTATGATAGGCTGGA |
| | | ACAAGAGCACAACAATCTGGTCAATGTGCCCCTGTGTGTG |
| | | GACATGTGCCTGAATTGGCTGCTGAATGTGTATGACACAG |
| | | GCAGAACAGGCAGGATCAGAGTCCTGTCCTTCAAGACAGG |
| | | CATCATCTCCCTGTGCAAAGCCCACTTGGAGGACAAGTAC |
| | | AGATACCTGTTCAAGCAAGTGGCCTCCAGCACAGGCTTTT |
| | | GTGACCAGAGAAGGCTGGGCCTGCTCCTGCATGACAGCAT |
| | | TCAGATCCCTAGACAGCTGGGAGAAGTGGCTTCCTTTGGA |
| | | GGCAGCAATATTGAGCCATCAGTCAGGTCCTGTTTTCAGT |
| | | TTGCCAACAACAAGCCTGAGATTGAGGCTGCCCTGTTCCT |
| | | GGACTGGATGAGACTTGAGCCTCAGAGCATGGTCTGGCTG |
| | | CCTGTGCTTCATAGAGTGGCTGCTGCTGAGACTGCCAAGC |
| | | ACCAGGCCAAGTGCAACATCTGCAAAGAGTGCCCCATCAT |
| | | TGGCTTCAGATACAGATCCCTGAAGCACTTCAACTATGAT |
| | | ATCTGCCAGAGCTGCTTCTTTAGTGGCAGGGTTGCCAAGG |
| | | GCCACAAAATGCACTACCCCATGGTGGAATACTGCACCCC |
| | | AACAACCTCTGGGGAAGATGTTAGAGACTTTGCCAAGGTG |
| | | CTGAAAAACAAGTTCAGGACCAAGAGATACTTTGCTAAGC |
| | | ACCCCAGAATGGGCTACCTGCCTGTCCAGACAGTGCTTGA |
| | | GGGTGACAACATGGAAACCCCTGTGACACTGATCAATTTC |
| | | TGGCCAGTGGACTCTGCCCCTGCCTCAAGTCCACAGCTGT |
| | | CCCATGATGACACCCACAGCAGAATTGAGCACTATGCCTC |
| | | CAGACTGGCAGAGATGGAAAACAGCAATGGCAGCTACCTG |
| | | AATGATAGCATCAGCCCCAATGAGAGCATTGATGATGAGC |
| | | ATCTGCTGATCCAGCACTACTGTCAGTCCCTGAACCAGGA |
| | | CTCTCCACTGAGCCAGCCTAGAAGCCCTGCTCAGATCCTG |
| | | ATCAGCCTTGAGTCTTGATGAGTCGACAGGCCTAATAAAG |
| | | AGCTCAGATGCATCGATCAGAGTGTGTTGGTTTTTTGTGT |
| | | GGCTAGCTGCGGCCGCaggaacccctagtgatggagttgg |

TABLE 10-continued

RGX-DYS cassette nucleotide sequences

| Structure | SEQ ID | Nucleic Acid Sequence |
|---|---|---|
| | | ccactccctctctgcgcgctcgctcgctcactgaggccgg<br>gcgaccaaaggtcgcccgacgcccgggctttgcccgggcg<br>gcctcagtgagcgagcgagcgcgcag |
| RGX-DYS8<br>(full cassette<br>including<br>flanking ITRs,<br>Spc5-12<br>promoter to<br>poly A and<br>intervening<br>seqs)<br>4470 bp<br>ITRs shown in<br>lower case | 106 | ctgcgcgctcgctcgctcactgaggccgcccgggcaaagc<br>ccgggcgtcgggcgacctttggtcgcccggcctcagtgag<br>cgagcgagcgcgcagagagggagtggccaactccatcact<br>aggggttcctCATATGCAGGGTAATGGGGATCCTCTAGAG<br>GCCGTCCGCCCTCGGCACCATCCTCACGACACCCAAATAT<br>GGCGACGGGTGAGGAATGGTGGGGAGTTATTTTTAGAGCG<br>GTGAGGAAGGTGGGCAGGCAGCAGGTGTTGGCGCTCTAAA<br>AATAACTCCCGGGAGTTATTTTTAGAGCGGAGGAATGGTG<br>GACACCCAAATATGGCGACGGTTCCTCACCCGTCGCCATA<br>TTTGGGTGTCCGCCCTCGGCCGGGGCCGCATTCCTGGGGG<br>CCGGGCGGTGCTCCCGCCCGCCTCGATAAAAGGCTCCGGG<br>GCCGGCGGCGGCCCACGAGCTACCCGGAGGAGCGGGAGGC<br>GCCAAGCGgAATTCGCCACCATGCTTTGGTGGGAAGAGGT<br>GGAAGATTGCTATGAGAGGGAAGATGTGCAGAAGAAAACC<br>TTCACCAAATGGGTCAATGCCCAGTTCAGCAAGTTTGGCA<br>AGCAGCACATTGAGAACCTGTTCAGTGACCTGCAGGATGG<br>CAGAAGGCTGCTGGATCTGCTGGAAGGCCTGACAGGCCAG<br>AAGCTGCCTAAAGAGAAGGGCAGCACAAGAGTGCATGCCC<br>TGAACAATGTGAACAAGGCCCTGAGAGTGCTGCAGAACAA<br>CAATGTGGACCTGGTCAATATTGGCAGCACAGACATTGTG<br>GATGGCAACCACAAGCTGACCCTGGGCCTGATCTGGAACA<br>TCATCCTGCACTGGCAAGTGAAGAATGTGATGAAGAACAT<br>CATGGCTGGCCTGCAGCAGACCAACTCTGAGAAGATCCTG<br>CTGAGCTGGGTCAGACAGAGCACCAGAAACTACCCTCAAG<br>TGAATGTGATCAACTTCACCACCTCTTGGAGTGATGGACT<br>GGCCCTGAATGCCCTGATCCACAGCCACAGACCTGACCTG<br>TTTGACTGGAACTCTGTTGTGTGCCAGCAGTCTGCCACAC<br>AGAGACTGGAACATGCCTTCAACATTGCCAGATACCAGCT<br>GGGAATTGAGAAACTGCTGGACCCTGAGGATGTGGACACC<br>ACCTATCCTGACAAGAAATCCATCCTCATGTACATCACCA<br>GCCTGTTCCAGGTGCTGCCCCAGCAAGTGTCCATTGAGGC<br>CATTCAAGAGGTTGAGATGCTGCCCAGACCTCCTAAAGTG<br>ACCAAAGAGGAACACTTCCAGCTGCACCACCAGATGCACT<br>ACTCTCAGCAGATCACAGTGTCTCTGGCCCAGGGATATGA<br>GAGAACAAGCAGCCCCAAGCCTAGGTTCAAGAGCTATGCC<br>TACACACAGGCTGCCTATGTGACCACATCTGACCCCACAA<br>GAAGCCCATTTCCAAGCCAGCATCTGGAAGCCCCTGAGGA<br>CAAGAGCTTTGGCAGCAGCCTGATGGAATCTGAAGTGAAC<br>CTGGATAGATACCAGACAGCCCTGGAAGAAGTGCTGTCCT<br>GGCTGCTGTCTGCTGAGGATACACTGCAGGCTCAGGGTGA<br>AATCAGCAATGATGTGGAAGTGGTCAAGGACCAGTTTCAC<br>ACCCATGAGGGCTACATGATGGACCTGACAGCCCACCAGG<br>GCAGAGTGGGAAATATCCTGCAGCTGGGCTCCAAGCTGAT<br>TGGCACAGGCAAGCTGTCTGAGGATGAAGAGACAGAGGTG<br>CAAGAGCAGATGAACCTGCTGAACAGCAGATGGGAGTGTC<br>TGAGAGTGGCCAGCATGGAAAAGCAGAGCAACCTGCACAG<br>AGTGCTCATGGACCTGCAGAATCAGAAACTGAAAGAACTG<br>AATGACTGGCTGACCAAGACAGAAGAAAGGACTAGGAAGA<br>TGGAAGAGGAACCTCTGGGACCAGACCTGGAAGATCTGAA<br>AAGACAGGTGCAGCAGCATAAGGTGCTGCAAGAGGACCTT<br>GAGCAAGAGCAAGTCAGAGTGAACAGCCTGACACACATGG<br>TGGTGGTTGTGGATGAGTCCTCTGGGGATCATGCCACAGC<br>TGCTCTGGAAGAACAGCTGAAGGTGCTGGGAGACAGATGG<br>GCCAACATCTGTAGGTGGACAGAGGATAGATGGGTGCTGC<br>TCCAGGACATTCTGGAGATCAGCTATGTGCCCAGCACCTA<br>CCTGACAGAGATCACCCATGTGTCTCAGGCCCTGCTGGAA<br>GTGGAACAGCTGCTGAATGCCCCTGACCTGTGTGCCAAGG<br>ACTTTGAGGACCTGTTCAAGCAAGAGGAAAGCCTGAAGAA<br>CATCAAGGACAGCCTGCAGCAGTCCTCTGGCAGAATTGAC<br>ATCATCCACAGCAAGAAAACAGCTGCCCTGCAGTCTGCCA<br>CACCTGTGGAAAGAGTGAAGCTGCAAGAGGCCCTGAGCCA<br>GCTGGACTTCCAGTGGGAGAAAGTGAACAAGATGTACAAG<br>GACAGGCAGGGCAGATTTGATAGAAGTGTGGAAAAGTGGA<br>GAAGGTTCCACTATGACATCAAGATCTTCAACCAGTGGCT<br>GACAGAGGCTGAGCAGTTCCTGAGAAAGACACAGATCCCT<br>GAGAACTGGGAGCATGCCAAGTACAAGTGGTATCTGAAAG<br>AACTGCAGGATGGCATTGGCCAGAGACAGACAGTTGTCAG<br>AACCCTGAATGCCACAGGGGAAGAGATCATCCAGCAGAGC<br>AGCAAGACAGATGCCAGCATCCTGCAAGAGAAGCTGGGCA<br>GCCTGAACCTGAGATGGCAAGAAGTGTGCAAGCAGCTGTC<br>TGACAGAAAGAAGAGGCTGGAAGAACAGACACTGGAAAGG<br>CTGCAAGAACTTCAAGAGGCCACAGATGAGCTGGACCTGA |

TABLE 10-continued

RGX-DYS cassette nucleotide sequences

| Structure | SEQ ID | Nucleic Acid Sequence |
|---|---|---|
| | | AGCTGAGACAGGCTGAAGTGATCAAAGGCAGCTGGCAGCC<br>AGTTGGGGACCTGCTCATTGATAGCCTGCAGGACCATCTG<br>GAAAAAGTGAAAGCCCTGAGGGGAGAGATTGCCCCTCTGA<br>AAGAAAATGTGTCCCATGTGAATGACCTGGCCAGACAGCT<br>GACCACACTGGGAATCCAGCTGAGCCCCTACAACCTGAGC<br>ACCCTTGAGGACCTGAACACCAGGTGGAAGCTCCTCCAGG<br>TGGCAGTGGAAGATAGAGTCAGGCAGCTGCATGAGGCCCA<br>CAGAGATTTTGGACCAGCCAGCCAGCACTTTCTGTCTACC<br>TCTGTGCAAGGCCCCTGGGAGAGAGCTATCTCTCCTAACA<br>AGGTGCCCTACTACATCAACCATGAGACACAGACCACCTG<br>TTGGGATCACCCCAAGATGACAGAGCTGTACCAGAGTCTG<br>GCAGACCTCAACAATGTCAGATTCAGTGCCTACAGGACTG<br>CCATGAAGCTCAGAAGGCTCCAGAAAGCTCTGTGCCTGGA<br>CCTGCTTTCCCTGAGTGCAGCTTGTGATGCCCTGGACCAG<br>CACAATCTGAAGCAGAATGACCAGCCTATGGACATCCTCC<br>AGATCATCAACTGCCTCACCACCATCTATGATAGGCTGGA<br>ACAAGAGCACAACAATCTGGTCAATGTGCCCCTGTGTGTG<br>GACATGTGCCTGAATTGGCTGCTGAATGTGTATGACACAG<br>GCAGAACAGGCAGGATCAGAGTCCTGTCCTTCAAGACAGG<br>CATCATCTCCCTGTGCAAAGCCCACTTGGAGGACAAGTAC<br>AGATACCTGTTCAAGCAAGTGGCCTCCAGCACAGGCTTTT<br>GTGACCAGAGAAGGCTGGGCCTGCTCCTGCATGACAGCAT<br>TCAGATCCCTAGACAGCTGGGAGAAGTGGCTTCCTTTGGA<br>GGCAGCAATATTGAGCCATCAGTCAGGTCCTGTTTTCAGT<br>TTGCCAACAACAAGCCTGAGATTGAGGCTGCCCTGTTCCT<br>GGACTGGATGAGACTTGAGCCTCAGAGCATGGTCTGGCTG<br>CCTGTGCTTCATAGAGTGGCTGCTGCTGAGACTGCCAAGC<br>ACCAGGCCAAGTGCAACATCTGCAAAGAGTGCCCCATCAT<br>TGGCTTCAGATACAGATCCCTGAAGCACTTCAACTATGAT<br>ATCTGCCAGAGCTGCTTCTTTAGTGGCAGGGTTGCCAAGG<br>GCCACAAAATGCACTACCCCATGGTGGAATACTGCACCCC<br>AACAACCTCTGGGGAAGATGTTAGAGACTTTGCCAAGGTG<br>CTGAAAAACAAGTTCAGGACCAAGAGATACTTTGCTAAGC<br>ACCCCAGAATGGGCTACCTGCCTGTCCAGACAGTGCTTGA<br>GGGTGACAACATGGAAACCTGATGAGTCGACAGGCCTAAT<br>AAAGAGCTCAGATGCATCGATCAGAGTGTGTTGGTTTTTT<br>GTGTGGCTAGCTGCGGCCGCaggaacccctagtgatggag<br>ttggccactccctctctgcgcgctcgctcgctcactgagg<br>ccgggcgaccaaaggtcgcccgacgcccgggctttgcccg<br>ggcggcctcagtgagcgagcgagcgcgcag |

5.3.5 Methods of Making rAAV Particles

Another aspect of the present invention involves making molecules disclosed herein. In some embodiments, a molecule according to the invention is made by providing a nucleotide comprising the nucleic acid sequence encoding any of the capsid protein molecules herein; and using a packaging cell system to prepare corresponding rAAV particles with capsid coats made up of the capsid protein. Such capsid proteins are described in Section 5.3.4, supra. In some embodiments, the nucleic acid sequence encodes a sequence having at least 60%, 70%, 80%, 85%, 90%, or 95%, preferably 96%, 97%, 98%, 99% or 99.9%, identity to the sequence of a capsid protein molecule described herein and retains (or substantially retains) biological function of the capsid protein and the inserted peptide from a heterologous protein or domain thereof. In some embodiments, the nucleic acid encodes a sequence having at least 60%, 70%, 80%, 85%, 90%, or 95%, preferably 96%, 97%, 98%, 99% or 99.9%, identity to the sequence of the AAV8 capsid protein, while retaining (or substantially retaining) biological function of the AAV8 capsid protein and the inserted peptide.

The capsid protein, coat, and rAAV particles may be produced by techniques known in the art. In some embodiments, the viral genome comprises at least one inverted terminal repeat to allow packaging into a vector. In some embodiments, the viral genome further comprises a cap gene and/or a rep gene for expression and splicing of the cap gene. In embodiments, the cap and rep genes are provided by a packaging cell and not present in the viral genome.

In some embodiments, the nucleic acid encoding the engineered capsid protein is cloned into an AAV Rep-Cap plasmid in place of the existing capsid gene. When introduced together into host cells, this plasmid helps package an rAAV genome into the engineered capsid protein as the capsid coat. Packaging cells can be any cell type possessing the genes necessary to promote AAV genome replication, capsid assembly, and packaging.

Numerous cell culture-based systems are known in the art for production of rAAV particles, any of which can be used to practice a method disclosed herein. The cell culture-based systems include transfection, stable cell line production, and infectious hybrid virus production systems which include, but are not limited to, adenovirus-AAV hybrids, herpesvirus-AAV hybrids and baculovirus-AAV hybrids. rAAV production cultures for the production of rAAV virus particles require: (1) suitable host cells, including, for example, human-derived cell lines, mammalian cell lines, or insect-derived cell lines; (2) suitable helper virus function, provided by wild type or mutant adenovirus (such as temperature-sensitive adenovirus), herpes virus, baculovirus, or a plasmid construct providing helper functions; (3) AAV rep and cap genes and gene products; (4) a transgene (such as a therapeutic transgene) flanked by AAV ITR sequences and optionally regulatory elements; and (5) suitable media and media components (nutrients) to support cell growth/survival and rAAV production.

Nonlimiting examples of host cells include: A549, WEHI, 10T1/2, BHK, MDCK, COS1, COS7, BSC 1, BSC 40, BMT 10, VERO, W138, HeLa, HEK293 and their derivatives (HEK293T cells, HEK293F cells), Saos, C2C12, L, HT1080, HepG2, primary fibroblast, hepatocyte, myoblast cells, CHO cells or CHO-derived cells, or insect-derived cell lines such as SF-9 (e.g. in the case of baculovirus production systems). For a review, see Aponte-Ubillus et al., 2018, Appl. Microbiol. Biotechnol. 102:1045-1054, which is incorporated by reference herein in its entirety for manufacturing techniques.

In one aspect, provided herein is a method of producing rAAV particles, comprising (a) providing a cell culture comprising an insect cell; (b) introducing into the cell one or more baculovirus vectors encoding at least one of: i. an rAAV genome to be packaged, ii. an AAV rep protein sufficient for packaging, and iii. an AAV cap protein sufficient for packaging; (c) adding to the cell culture sufficient nutrients and maintaining the cell culture under conditions that allow production of the rAAV particles. In some embodiments, the method comprises using a first baculovirus vector encoding the rep and cap genes and a second baculovirus vector encoding the rAAV genome. In some embodiments, the method comprises using a baculovirus encoding the rAAV genome and an insect cell expressing the rep and cap genes. In some embodiments, the method comprises using a baculovirus vector encoding the rep and cap genes and the rAAV genome. In some embodiments, the insect cell is an Sf-9 cell. In some embodiments, the insect cell is an Sf-9 cell comprising one or more stably integrated heterologous polynucleotide encoding the rep and cap genes.

In some embodiments, a method disclosed herein uses a baculovirus production system. In some embodiments the baculovirus production system uses a first baculovirus encoding the rep and cap genes and a second baculovirus encoding the rAAV genome. In some embodiments the baculovirus production system uses a baculovirus encoding the rAAV genome and a host cell expressing the rep and cap genes. In some embodiments the baculovirus production system uses a baculovirus encoding the rep and cap genes and the rAAV genome. In some embodiments, the baculovirus production system uses insect cells, such as Sf-9 cells.

A skilled artisan is aware of the numerous methods by which AAV rep and cap genes, AAV helper genes (e.g., adenovirus E1a gene, E1b gene, E4 gene, E2a gene, and VA gene), and rAAV genomes (comprising one or more genes of interest flanked by inverted terminal repeats (ITRs)) can be introduced into cells to produce or package rAAV. The phrase "adenovirus helper functions" refers to a number of viral helper genes expressed in a cell (as RNA or protein) such that the AAV grows efficiently in the cell. The skilled artisan understands that helper viruses, including adenovirus and herpes simplex virus (HSV), promote AAV replication and certain genes have been identified that provide the essential functions, e.g. the helper may induce changes to the cellular environment that facilitate such AAV gene expression and replication. In some embodiments of a method disclosed herein, AAV rep and cap genes, helper genes, and rAAV genomes are introduced into cells by transfection of one or more plasmid vectors encoding the AAV rep and cap genes, helper genes, and rAAV genome. In some embodiments of a method disclosed herein, AAV rep and cap genes, helper genes, and rAAV genomes can be introduced into cells by transduction with viral vectors, for example, rHSV vectors encoding the AAV rep and cap genes, helper genes, and rAAV genome. In some embodiments of a method disclosed herein, one or more of AAV rep and cap genes, helper genes, and rAAV genomes are introduced into the cells by transduction with an rHSV vector. In some embodiments, the rHSV vector encodes the AAV rep and cap genes. In some embodiments, the rHSV vector encodes the helper genes. In some embodiments, the rHSV vector encodes the rAAV genome. In some embodiments, the rHSV vector encodes the AAV rep and cap genes. In some embodiments, the rHSV vector encodes the helper genes and the rAAV genome. In some embodiments, the rHSV vector encodes the helper genes and the AAV rep and cap genes.

In one aspect, provided herein is a method of producing rAAV particles, comprising (a) providing a cell culture comprising a host cell; (b) introducing into the cell one or more rHSV vectors encoding at least one of: i. an rAAV genome to be packaged, ii. helper functions necessary for packaging the rAAV particles, iii. an AAV rep protein sufficient for packaging, and iv. an AAV cap protein sufficient for packaging; (c) adding to the cell culture sufficient nutrients and maintaining the cell culture under conditions that allow production of the rAAV particles. In some embodiments, the rHSV vector encodes the AAV rep and cap genes. In some embodiments, the rHSV vector encodes helper functions. In some embodiments, the rHSV vector comprises one or more endogenous genes that encode helper functions. In some embodiments, the rHSV vector comprises one or more heterogeneous genes that encode helper functions. In some embodiments, the rHSV vector encodes the rAAV genome. In some embodiments, the rHSV vector encodes the AAV rep and cap genes. In some embodiments, the rHSV vector encodes helper functions and the rAAV genome. In some embodiments, the rHSV vector encodes helper functions and the AAV rep and cap genes. In some embodiments, the cell comprises one or more stably integrated heterologous polynucleotide encoding the rep and cap genes.

In one aspect, provided herein is a method of producing rAAV particles, comprising (a) providing a cell culture comprising a mammalian cell; (b) introducing into the cell one or more polynucleotides encoding at least one of: i. an rAAV genome to be packaged, ii. helper functions necessary for packaging the rAAV particles, iii. an AAV rep protein sufficient for packaging, and iv. an AAV cap protein sufficient for packaging; (c) adding to the cell culture sufficient nutrients and maintaining the cell culture under conditions that allow production of the rAAV particles. In some embodiments, the helper functions are encoded by adenovirus genes. In some embodiments, the mammalian cell comprises one or more stably integrated heterologous polynucleotide encoding the rep and cap genes.

Molecular biology techniques to develop plasmid or viral vectors encoding the AAV rep and cap genes, helper genes, and/or rAAV genome are commonly known in the art. In some embodiments, AAV rep and cap genes are encoded by one plasmid vector. In some embodiments, AAV helper genes (e.g., adenovirus E1a gene, E1b gene, E4 gene, E2a gene, and VA gene) are encoded by one plasmid vector. In some embodiments, the E1a gene or E1b gene is stably expressed by the host cell, and the remaining AAV helper genes are introduced into the cell by transfection by one viral vector. In some embodiments, the E1a gene and E1b gene are stably expressed by the host cell, and the E4 gene, E2a gene, and VA gene are introduced into the cell by transfection by one plasmid vector. In some embodiments, one or more helper genes are stably expressed by the host cell, and one or more helper genes are introduced into the cell by transfection by one plasmid vector. In some embodiments, the helper genes are stably expressed by the host cell. In some embodiments, AAV rep and cap genes are encoded by one viral vector. In some embodiments, AAV helper genes (e.g., adenovirus Ela gene, E1b gene, E4 gene, E2a gene, and VA gene) are encoded by one viral vector. In some embodiments, the E1a gene or E1b gene is stably expressed by the host cell, and the remaining AAV helper genes are introduced into the cell by transfection by one viral vector. In some embodiments, the E1a gene and E1b gene are stably expressed by the host cell, and the E4 gene, E2a gene, and VA gene are introduced into the cell by transfection by one viral vector. In some embodiments, one or more helper genes are stably expressed by the host cell, and one or more helper genes are introduced into the cell by transfection by one viral vector. In some embodiments, the AAV rep and cap genes, the adenovirus helper functions necessary for packaging, and the rAAV genome to be packaged are introduced to the cells by transfection with one or more polynucleotides, e.g., vectors. In some embodiments, a method disclosed herein comprises transfecting the cells with a mixture of three polynucleotides: one encoding the cap and rep genes, one encoding adenovirus helper functions necessary for packaging (e.g., adenovirus E1a gene, E1b gene, E4 gene, E2a gene, and VA gene), and one encoding the rAAV genome to be packaged. In some embodiments, the AAV cap gene is an AAV8 or AAV9 cap gene. In some embodiments, the AAV cap gene is an AAV.rh8, AAV.rh10, AAV.rh20, AAV.rh39, AAV.Rh74, AAV.RHM4-1, AAV.hu37, AAV.PHB, or AAV.7m8 cap gene. In some embodiments, the AAV cap gene encodes a capsid protein with high sequence homology to AAV8 or AAV9 such as, AAV.rh10, AAV.rh20, AAV.rh39, AAV.Rh74, AAV.RHM4-1, and AAV.hu37. In some embodiments, the vector encoding the rAAV genome to be packaged comprises a gene of interest flanked by AAV ITRs. In some embodiments, the AAV ITRs are from AAV1, AAV2, AAV3, AAV4, AAV5, AAV6, AAV7, AAV8, AAV9, AAV10, AAV11, AAV12, AAV13, AAV14, AAV15, AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other AAV serotypes.

Any combination of vectors can be used to introduce AAV rep and cap genes, AAV helper genes, and rAAV genome to a cell in which rAAV particles are to be produced or packaged. In some embodiments of a method disclosed herein, a first plasmid vector encoding an rAAV genome comprising a gene of interest flanked by AAV inverted terminal repeats (ITRs), a second vector encoding AAV rep and cap genes, and a third vector encoding helper genes can be used. In some embodiments, a mixture of the three vectors is co-transfected into a cell. In some embodiments, a combination of transfection and infection is used by using both plasmid vectors as well as viral vectors.

In some embodiments, one or more of rep and cap genes, and AAV helper genes are constitutively expressed by the cells and does not need to be transfected or transduced into the cells. In some embodiments, the cell constitutively expresses rep and/or cap genes. In some embodiments, the cell constitutively expresses one or more AAV helper genes. In some embodiments, the cell constitutively expresses Ela. In some embodiments, the cell comprises a stable transgene encoding the rAAV genome.

In some embodiments, AAV rep, cap, and helper genes (e.g., E1a gene, E1b gene, E4 gene, E2a gene, or VA gene) can be of any AAV serotype. Similarly, AAV ITRs can also be of any AAV serotype. For example, in some embodiments, AAV ITRs are from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other AAV serotypes (e.g., a hybrid serotype harboring sequences from more than one serotype). In some embodiments, AAV cap gene is from AAV8 or AAV9 cap gene. In some embodiments, an AAV cap gene is from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, AAV.HSC16, AAV.rh74, AAV.hu31, AAV.hu32, or AAV.hu37 or other AAV serotypes (e.g., a hybrid serotype harboring sequences from more than one serotype). In some embodiments, AAV rep and cap genes for the production of a rAAV particle are from different serotypes. For example, the rep gene is from AAV2 whereas the cap gene is from AAV8. In another example, the rep gene is from AAV2 whereas the cap gene is from AAV9.

In some embodiments, the rep gene is from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other AAV serotypes (e.g., a hybrid serotype harboring sequences from more than one serotype). In other embodiments, the rep and the cap genes are from the same serotype. In still other embodiments, the rep and the cap genes are from the same serotype, and the rep gene comprises at least one modified protein domain or modified promoter domain. In certain embodiments, the at least one modified domain comprises a nucleotide sequence of a serotype that is different from the capsid serotype. The modified domain within the rep gene may be a hybrid nucleotide sequence consisting fragments different serotypes.

Hybrid rep genes provide improved packaging efficiency of rAAV particles, including packaging of a viral genome comprising a microdystrophin transgene greater than 4 kb, greater than 4.1 kb, greater than 4.2 kB, greater than 4.3 kb, greater than 4.4 kB, greater than 4.5 kb, or greater than 4.6 kb. AAV rep genes consist of nucleic acid sequences that encode the non-structural proteins needed for replication and production of virus. Transcription of the rep gene initiates from the p5 or p19 promoters to produce two large (Rep78 and Rep68) and two small (Rep52 and Rep40) nonstructural Rep proteins, respectively. Additionally, Rep78/68 domain contains a DNA-binding domain that recognizes specific ITR sequences within the ITR. All four Rep proteins have common helicase and ATPase domains that function in genome replication and/or encapsidation (Maurer A C, 2020, DOI: 10.1089/hum.2020.069). Transcription of the cap gene initiates from a p40 promoter, which sequence is within the C-terminus of the rep gene, and it has been suggested that other elements in the rep gene may induce p40 promoter activity. The p40 promoter domain includes transcription factor binding elements EF1A, MLTF, and ATF, Fos/Jun binding elements (AP-1), Sp1-like elements (Sp1 and GGT), and the TATA element (Pereira and Muzyczka, Journal of Virology, June 1997, 71(6):4300-4309). In some embodiments, the rep gene comprises a modified p40 promoter. In some embodiments, the p40 promoter is modified at any one or more of the EF1A binding element, MLTF binding element, ATF binding element, Fos/Jun binding elements (AP-1), Sp I-like elements (Sp1 or GGT), or the TATA element. In other embodiments, the rep gene is of serotype 1, 3, 4, 5, 6, 7, 8, 9, 10, 11, 12, 13, 14, 15, 16, rh8, rh10, rh20, rh39, rh.74, RHM4-1, or hu37, and the portion or element of the p40 promoter domain is modified to serotype 2. In still other embodiments, the rep gene is of serotype 8 or 9, and the portion or element of the p40 promoter domain is modified to serotype 2.

ITRs contain A and A' complimentary sequences, B and B' complimentary sequences, and C and C' complimentary sequences; and the D sequence is contiguous with the ssDNA genome. The complimentary sequences of the ITRs form hairpin structures by self-annealing (Berns K I. The Unusual Properties of the AAV Inverted Terminal Repeat. Hum Gene Ther 2020). The D sequence contains a Rep Binding Element (RBE) and a terminal resolution site (TRS), which together constitute the AAV origin of replication. The ITRs are also required as packaging signals for genome encapsidation following replication. In some embodiments, the ITR sequences and the cap genes are from the same serotype, except that one or more of the A and A' complimentary sequences, B and B' complimentary sequences, C and C' complimentary sequences, or the D sequence may be modified to contain sequences from a different serotype than the capsid. In some embodiments, the modified ITR sequences are from the same serotype as the rep gene. In other embodiments, the ITR sequences and the cap genes are from different serotypes, except that one or more of the ITR sequences selected from A and A' complimentary sequences, B and B' complimentary sequences, C and C' complimentary sequences, or the D sequence are from the same serotype as the capsid (cap gene), and one or more of the ITR sequences are from the same serotype as the rep gene.

In some embodiments, the rep and the cap genes are from the same serotype, and the rep gene comprises a modified Rep78 domain, DNA binding domain, endonuclease domain, ATPase domain, helicase domain, p5 promoter domain, Rep68 domain, p5 promoter domain, Rep52 domain, p19 promoter domain, Rep40 domain or p40 promoter domain. In other embodiments, the rep and the cap genes are from the same serotype, and the rep gene comprises at least one protein domain or promoter domain from a different serotype. In one embodiment, an rAAV comprises a transgene flanked by AAV2 ITR sequences, an AAV8 cap, and a hybrid AAV2/8 rep. In another embodiment, the AAV2/8 rep comprises serotype 8 rep except for the p40 promoter domain or a portion thereof is from serotype 2 rep. In other embodiments, the AAV2/8 rep comprises serotype 2 rep except for the p40 promoter domain or a portion thereof is from serotype 8 rep. In some embodiments, more than two serotypes may be utilized to construct a hybrid rep/cap plasmid.

Any suitable method known in the art may be used for transfecting a cell may be used for the production of rAAV particles according to a method disclosed herein. In some embodiments, a method disclosed herein comprises transfecting a cell using a chemical based transfection method. In some embodiments, the chemical-based transfection method uses calcium phosphate, highly branched organic compounds (dendrimers), cationic polymers (e.g., DEAE dextran or polyethylenimine (PEI)), lipofection. In some embodiments, the chemical-based transfection method uses cationic polymers (e.g., DEAE dextran or polyethylenimine (PEI)). In some embodiments, the chemical-based transfection method uses polyethylenimine (PEI). In some embodiments, the chemical-based transfection method uses DEAE dextran. In some embodiments, the chemical-based transfection method uses calcium phosphate.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

Nucleic acid sequences of AAV-based viral vectors, and methods of making recombinant AAV and AAV capsids, are taught, e.g., in U.S. Pat. Nos. 7,282,199; 7,790,449; 8,318,480; 8,962,332; and PCT/EP2014/076466, each of which is incorporated herein by reference in its entirety.

In preferred embodiments, the rAAVs provide transgene delivery vectors that can be used in therapeutic and prophylactic applications, as discussed in more detail below.

5.4. Therapeutic Utility

Provided are methods of assaying the constructs, including recombinant gene therapy vectors, encoding microdystrophins, as disclosed herein, for therapeutic efficacy. Methods include both in vitro and in vivo tests in animal models as described herein or using any other methods known in the art for testing the activity and efficacy of microdystrophins.

5.4.1 In Vitro Assays

5.4.1.1 In Vitro Infection System for Muscle Cells

Provided are methods of testing of the infectivity of a recombinant vector disclosed herein, for example rAAV particles. For example, the infectivity of recombinant gene therapy vectors in muscle cells can be tested in C2C12 myoblasts as described in Example 2, herein. Several muscle or heart cell lines may be utilized, including but not limited to T0034 (human), L6 (rat), MM14 (mouse), P19 (mouse), G-7 (mouse), G-8 (mouse), QM7 (quail), H9c2(2-1) (rat), Hs 74.Ht (human), and Hs 171.Ht (human) cell lines. Vector copy numbers may be assess using polymerase chain reaction techniques and level of microdystrophin expression may be tested by measuring levels of microdystrophin mRNA in the cells.

5.4.2 Animal Models

The efficacy of a viral vector containing a transgene encoding a microdystrophin as described herein may be tested by administering to an animal model to replace mutated dystrophin, for example, by using the mdx mouse and/or the golden retriever muscular dystrophy (GRMD) model and to assess the biodistribution, expression and therapeutic effect of the transgene expression. The therapeutic effect may be assessed, for example, by assessing change in muscle strength in the animal receiving the microdystrophin transgene. Animal models using larger mammals as well as nonmammalian vertebrates and invertebrates can also be used to assess pre-clinical therapeutic efficacy of a vector described herein. Accordingly, provided are compositions and methods for therapeutic administration comprising a dose of a microdystrophin encoding vector disclosed herein in an amount demonstrated to be effective according to the methods for assessing therapeutic efficacy disclosed here.

5.4.2.1 Murine Models

The efficacy of gene therapy vectors may be assessed in murine models of DMD. The mdx mouse model (Yucel, N., et al, Humanizing the mdx mouse model of DMD: the long and the short of it, Regenerative Medicine volume 3, Article number: 4 (2018)), carries a nonsense mutation in exon 23, resulting in an early termination codon and a truncated protein (mdx). Mdx mice have 3-fold higher blood levels of pyruvate kinase activity compared to littermate controls. Like the human DMD disease, mdx skeletal muscles exhibit active myofiber necrosis, cellular infiltration, a wide range of myofiber sizes and numerous centrally nucleated regenerating myofibers. This phenotype is enhanced in the diaphragm, which undergoes progressive degeneration and myofiber loss resulting in an approximately 5-fold reduction in muscle isometric strength. Necrosis and regeneration in hind-limb muscles peaks around 3-4 weeks of age, but plateaus thereafter. In mdx mice and mdx mice crossed onto other mouse backgrounds (for example DBA/2J), a mild but significant decrease in cardiac ejection fraction is observed (Van Westering, Molecules 2015, 20, 8823-8855). Such DMD model mice with cardiac functional defects may be used to assess the cardioprotective effects or improvement or maintenance of cardiac function or attenuation of cardiac dysfunction of the gene therapy vectors described herein. Example 3 herein details use of the mdx mouse model to assess gene therapy vectors encoding microdystrophins.

Additional mdx mouse models: A number of alternative versions in different genetic backgrounds have been generated including the mdx2cv, mdx3cv, mdx4cv, and mdx5cv lines (C57BL/6 genetic background). These models were created by treating mice with N-ethyl-N-nitrosourea, a chemical mutagen. Each strain carries a different point mutation. As a whole, there are few differences in the presentation of disease phenotypes in the mdxcv models compared to the mdx mouse. Additional mouse models have been created by crossing the mdx line to various knock-out mouse models (e.g. Myod1$^{-/-}$, α-Integrin7$^{-/-}$, α-Dystrobrevin$^{-/-}$, and Utrophin$^{-/-}$). All mouse models which are currently used to study DMD have been described in detail by Yucel, N., et al, Humanizing the mdx mouse model of DMD: the long and the short of it, npj Regenerative Medicine volume 3, Article number: 4 (2018), which is incorporated herein by reference.

5.4.2.2 Canine

Most canine studies are conducted in the golden retriever muscular dystrophy (GRMD) model (Korneygay, J. N., et al, The golden retriever model of Duchenne muscular dystrophy. *Skelet Muscle.* 2017; 7: 9, which is incorporated by reference in its entirety). Dogs with GRMD are afflicted with a progressive, fatal disease with skeletal and cardiac muscle phenotypes and selective muscle involvement—a severe phenotype that more closely mirrors that of DMD. GRMD dogs carry a single nucleotide change that leads to exon skipping and an out-of-frame DMD transcript. Phenotypic features in dogs include elevation of serum CK, CRDs on EMG, and histopathologic evidence of grouped muscle fiber necrosis and regeneration. Phenotypic variability is frequently observed in GRMD, as in humans. GRMD dogs develop paradoxical muscle hypertrophy which seems to play a role in the phenotype of affected dogs, with stiffness at gait, decreased joint range of motion, and trismus being common features. Objective biomarkers to evaluate disease progression include tetanic flexion, tibiotarsal joint angle, % eccentric contraction decrement, maximum hip flexion angle, pelvis angle, cranial sartorius circumference, and quadriceps femoris weight.

5.5. Methods of Treatment

Provided are methods of treating human subjects for any muscular dystrophy disease that can be treated by providing a functional dystrophin. DMD is the most common of such disease, but the gene therapy vectors that express microdystrophin provided herein can be administered to treat Becker muscular dystrophy (BMD), myotonic muscular dystrophy (Steinert's disease), Facioscapulohumeral disease (FSHD), limb-girdle muscular dystrophy, X-linked dilated cardiomyopathy, or oculopharyngeal muscular dystrophy. The microdystrophin of the present disclosure may be any microdystrophin described herein, including those that have the domains in an N-terminal to C-terminal order of ABD-H1-R1-R2-R3-H3-R24-H4-CR, ABD-H1-R1-R2-R3-H3-R24-H4-CR-CT, ABD-H1-R1-R2-R16-R17-R24-H4-CR, or ABD-H1-R1-R2-R16-R17-R24-H4-CR-CT, wherein ABD is an actin-binding domain of dystrophin, H1 is a hinge 1 region of dystrophin, R1 is a spectrin 1 region of dystrophin, R2 is a spectrin 2 region of dystrophin, R3 is a spectrin 3 region of dystrophin, H3 is a hinge 3 region of dystrophin, R16 is a spectrin 16 region of dystrophin, R17 is a spectrin 16 region of dystrophin, R24 is a spectrin 24 region of dystrophin, CR is a cysteine-rich region of dystrophin and CT is at least a portion of a C-terminal region of dystrophin comprising a a1-syntrophin binding site and/or an a-dystrobrevin binding site. In embodiments, the microdystrophin has an amino acid sequence of SEQ ID Nos: 1, 2, 79, 91, 92, or 93. The vectors encoding the microdystrophin include those having a nucleic acid sequence of SEQ ID NO: 20, 21, 81, 101, 102 or 103, in certain embodiments, operably linked to regulatory elements for constitutive, muscle-specific (including skeletal, smooth muscle and cardiac muscle-specific) expression, or CNS specific expression, and other regulatory elements such as poly A sites. Such nucleic acids may be in the context of an rAAV genome, for example, flanked by ITR sequences, particularly, AAV2 ITR sequences. In certain embodiments, the methods and compositions comprising administering to a subject in need thereof, an rAAV comprising the construct having a nucleic acid sequence of SEQ ID NO: 53, 54, 55, 56, 82, 104, 105, or 106. In embodiments, the patient has been diagnosed with and/or has symptom(s) associated with DMD. Recombinant vectors used for delivering the transgene encoding the microdystrophin are described in Section 5.3.4.1. Such vectors should have a tropism for human muscle cells (including skeletal muscle, smooth muscle and/or cardiac muscle) and can include non-replicating rAAV, particularly those bearing an AAV8 capsid. The recombinant vectors, such as those shown in FIG. 1A and FIG. 22, can be administered in any manner such that the recombinant vector enters the muscle tissue or CNS, preferably by introducing the recombinant vector into the bloodstream.

Subjects to whom such gene therapy is administered can be those responsive to gene therapy mediated delivery of a microdystrophin to muscles. In particular embodiments, the methods encompass treating patients who have been diagnosed with DMD or other muscular dystrophy disease, such as, Becker muscular dystrophy (BMD), myotonic muscular dystrophy (Steinert's disease), Facioscapulohumeral disease (FSHD), limb-girdle muscular dystrophy, X-linked dilated cardiomyopathy, or oculopharyngeal muscular dystrophy, or have one or more symptoms associated therewith, and identified as responsive to treatment with microdystrophin, or considered a good candidate for therapy with gene mediated delivery of microdystrophin. In specific embodiments, the patients have previously been treated with synthetic version of dystrophin and have been found to be responsive to one or more of synthetic versions of dystrophin. To determine responsiveness, the synthetic version of dystrophin (e.g., produced in human cell culture, bioreactors, etc.) may be administered directly to the subject.

Therapeutically effective doses of any such recombinant vector should be administered in any manner such that the recombinant vector enters the muscle (e.g., skeletal muscle or cardiac muscle), preferably by introducing the recombinant vector into the bloodstream. In specific embodiments, the vector is administered subcutaneously, intramuscularly or intravenously. Intramuscular, subcutaneous, or intravenous administration should result in expression of the soluble transgene product in cells of the muscle (including skeletal muscle, cardiac muscle, and/or smooth muscle) and/or the CNS. The expression of the transgene product results in delivery and maintenance of the transgene product in the muscle and/or the CNS. Alternatively, the delivery may result in gene therapy delivery and expression of the microdystrophin in the liver, and the soluble microdystrophin product is then carried through the bloodstream to the muscles where it can impart its therapeutic effect. In other embodiments, the recombinant vector may be administered such that it is delivered to the CNS, for example, but not limited to, intrathecally, intracerebroventricularly, intranasally or suprachoroidally.

The actual dose amount administered to a particular subject can be determined by a clinician, considering parameters such as, but not limited to, physical and physiological factors including body weight, severity of condition, type of disease, previous or concurrent therapeutic interventions, idiopathy of the subject, and/or route of administration.

Doses can range from $1\times10^{8}$ vector genomes per kg (vg/kg) to $1\times10^{15}$ vg/kg. Therapeutically effective amounts can be achieved by administering single or multiple doses during the course of a treatment regimen (i.e., days, weeks, months, etc.).

Pharmaceutical compositions suitable for intravenous, intramuscular, subcutaneous or hepatic administration comprise a suspension of the recombinant vector comprising the transgene encoding microdystrophin in a formulation buffer comprising a physiologically compatible aqueous buffer. The formulation buffer can comprise one or more of a polysaccharide, a surfactant, polymer, or oil.

The gene therapy vectors provided herein may be administered in combination with other treatments for muscular dystrophy, including corticosteroids, beta blockers and ACE inhibitors.

5.5.1 Muscle Degeneration/Regeneration

Deletion of dystrophin results in mechanical instability causing myofibers to weaken and eventually break during contraction. Patients with DMD first display skeletal muscle weakness in early childhood, which progresses rapidly to loss of muscle mass, spinal curvature known as kyphosis, paralysis and ultimately death from cardiorespiratory failure before 30 years of age. Skeletal muscles of DMD patients also develop muscle hypertrophy, particularly of the calf, evidence of focal necrotic myofibers, abnormal variation in myofiber diameter, increased fat deposition and fibrosis, as well as lack of dystrophin staining in immunohistological sections.

The goal of gene therapy treatment provided herein is to slow or arrest the progression of DMD, or other muscular dystrophy disease, or to reduce the severity of one or more symptoms associated with DMD, or other muscular dystrophy disease. In particular, the goal of gene therapy provided herein is to reduce muscle degeneration, induce/improve muscle regeneration, and/or prevent/reduce downstream pathologies including inflammation and fibrosis that interfere with muscle regeneration and cause loss of movement, orthopedic complications, and, ultimately, respiratory and cardiac failure.

Efficacy may be monitored by measuring changes from baseline in gross motor function using the North Star Ambulatory Assessment (NSAA) (scale is ordinal with 34 as the maximum score indicating fully-independent function) or an age-appropriate modified assessment, by assessing changes in ambulatory function (e.g. 6-min (distance walked<300m, between 300 and 400m, or >400m)), by performing a timed function test to measure changes from baseline in time taken to stand from a supine position (1 to 8 s (good), 8 to 20 s (moderate), and 20 to 35 s (poor)), by performing time to climb (4 steps) and time to run/walk assessments (10 meters), as well as myometry to evaluate changes from baseline in strength of upper and lower extremities [Mazzone et al, North Star Ambulatory Assessment, 6-minute walk test and timed items in ambulant boys with Duchenne muscular dystrophy, Neuromuscular Disorders 20 (2010) 712-716].

Efficacy may also be monitored by measuring changes (reduction) from baseline in serum creatine kinase (CK) levels (normal: 35-175 U/L, DMD: 500-20,000 U/L), an enzyme that is found in abnormally high levels when muscle is damaged, serum or urine creatinine levels (DMD: 10-25 μmol/L, mild BMD: 20-30 μmol/L, normal >53 μmol/L, DMD) and microdystrophin protein levels in muscle biopsies. Magnetic Resonance Imaging (MRI) may also be performed to assess fatty tissue infiltration in skeletal muscle (fat fraction) (Burakiewicz, J. et al. "Quantifying fat replacement of muscle by quantitative MRI in muscular dystrophy." *Journal of Neurology* vol. 264,10 (2017): 2053-2067. doi: 10.1007/s00415-017-8547-3).

Accordingly, provided are nucleic acid compositions and methods of administering those compositions that improve gross motor function or slow the loss of gross motor function, for example, as measured using the North Start Ambulatory Assessment to assess ambulatory function as compared to an untreated control or to the subject prior to treatment with the nucleic acid composition. Alternatively, the nucleic acid compositions described herein and the methods of administering nucleic acid compositions results in an improvement in gross motor function or reduction in the loss of gross motor function as assessed by a timed function test to measure time taken to stand from a supine position, myometry, or reduction in serum creatinine kinase (CK) levels or reduction in fatty tissue infiltration. Serum creatinine kinase levels may be further separated into its isoenzyme fractions, MM-CPK (skeletal muscle), BB-CPK (brain), and MB-CPK (heart).

Also provided are compositions comprising an amount of a nucleic acid composition, including, in particular, gene cassette containing vectors, viral vectors, and AAV vectors, comprising a nucleic acid sequence encoding a microdystrophin described herein that is effective to improve gross motor function or slow the loss of gross motor function, for example, as measured using the North Start Ambulatory Assessment to assess ambulatory function as compared to an untreated control or to the subject prior to treatment with the nucleic acid composition; or as assessed by a timed function test to measure time taken to stand from a supine position, or to demonstrate improvement by myometry, or reduction in serum creatinine kinase levels.

5.5.2 Cardiac Output

Although skeletal muscle symptoms are considered the defining characteristic of DMD, patients most commonly die of respiratory or cardiac failure. DMD patients develop dilated cardiomyopathy (DCM) due to the absence of dystrophin in cardiomyocytes, which is required for contractile function. This leads to an influx of extracellular calcium, triggering protease activation, cardiomyocyte death, tissue necrosis, and inflammation, ultimately leading to accumulation of fat and fibrosis. This process first affects the left ventricle (LV), which is responsible for pumping blood to most of the body and is thicker and therefore experiences a greater workload. Atrophic cardiomyocytes exhibit a loss of striations, vacuolization, fragmentation, and nuclear degeneration Functionally, atrophy and scarring leads to structural instability and hypokinesis of the LV, ultimately progressing to general DCM. DMD may be associated with various ECG changes like sinus tachycardia, reduction of circadian index, decreased heart rate variability, short PR interval, right ventricular hypertrophy, S-T segment depression and prolonged QTc.

Gene therapy treatment provided herein can slow or arrest the progression of DMD and other dystrophinopathies, particularly to reduce the progression of or attenuate cardiac dysfunction and/or maintain or improve cardiac function. Efficacy may be monitored by periodic evaluation of signs and symptoms of cardiac involvement or heart failure that are appropriate for the age and disease stage of the trial population, using serial electrocardiograms, and serial noninvasive imaging studies (e.g., echocardiography or cardiac magnetic resonance imaging (CMR)). CMR may be used to monitor changes from baseline in forced vital capacity (FVC), forced expiratory volume (FEV1), maximum inspiratory pressure (MIP), maximum expiratory pressure (MEP), peak expiratory flow (PEF), peak cough flow, left ventricular ejection fraction (LVEF), left ventricular fractional shortening (LVFS), inflammation, and fibrosis. ECG may be used to monitor conduction abnormalities and arrythmias. In particular, ECG may be used to assess normalization of the PR interval, R waves in V1, Q waves in V6, ventricular repolarization, QS waves in inferior and/or upper lateral wall, conduction disturbances in right bundle branch, QT C, and QRS.

Accordingly, provided are nucleic acid compositions, including compositions comprising gene expression cassettes and viral vectors, comprising a nucleic acid encoding a microdystrophin protein disclosed herein, and methods of administering those compositions that improve or maintain cardiac function or slow the loss of cardiac function, for example, by preventing reductions in decreasing LVEF below 45% and/or normalization of function (LVFS>28%) as measured by serial electrocardiograms, and/or serial noninvasive imaging studies (e.g., echocardiography or cardiac magnetic resonance imaging (CMR)). Measurements may be compared to an untreated control or to the subject prior to treatment with the nucleic acid composition. Alternatively, the nucleic acid compositions described here in and the methods of administering nucleic acid compositions results in an improvement in cardiac function or reduction in the loss of cardiac function as assessed by monitoring changes from baseline in forced vital capacity (FVC), forced expiratory volume (FEV1), maximum inspiratory pressure (MIP), maximum expiratory pressure (MEP), peak expiratory flow (PEF), peak cough flow, left ventricular ejection fraction (LVEF), left ventricular fractional shortening (LVFS), inflammation, and fibrosis. ECG may be used to monitor conduction abnormalities and arrythmias. In particular, ECG may be used to assess normalization of the PR interval, R waves in V1, Q waves in V6, ventricular repolarization, QS waves in inferior and/or upper lateral wall, conduction disturbances in right bundle branch, QT C, and QRS.

5.5.3 Central Nervous System

A portion of patients with DMD can also have epilepsy, learning and cognitive impairment, dyslexia, neurodevelopment disorders such as attention deficit hyperactive disorder (ADHD), autism, and/or psychiatric disorders, such as obsessive-compulsive disorder, anxiety or sleep disorders.

The goal of gene therapy treatments disclosed herein can be to improve cognitive function or alleviate symptoms of epilepsy and/or psychiatric disorders. Efficacy may be assessed by periodic evaluation of behavior and cognitive function that are appropriate for the age and disease stage of the trial population and or by quantifying and qualifying seizure events.

Accordingly, provided are nucleic acid compositions and methods of administering the microdystrophin gene therapy compositions that improve cognitive function, reduce the occurrence or severity of seizures, alleviate symptoms of ADHD, obsessive-compulsive disorder, anxiety and/or sleep disorders.

5.5.4 Patient Primary Endpoints

The efficacy of the compositions, including the dosage of the composition, and methods described herein may be assessed in clinical evaluation of subjects being treated. Patient primary endpoints may include monitoring the change from baseline in forced vital capacity (FVC), forced expiratory volume (FEV1), maximum inspiratory pressure (MIP), maximum expiratory pressure (MEP), peak expiratory flow (PEF), peak cough flow, left ventricular ejection fraction (LVEF), left ventricular fractional shortening (LVFS), change from baseline in the NSAA, change from baseline in the Performance of Upper Limp (PUL) score, and change from baseline in the Brooke Upper Extremity Scale score (Brooke score), change from baseline in grip strength, pinch strength, change in cardiac fibrosis score by MRI, change in upper arm (bicep) muscle fat and fibrosis assessed by MRI, measurement of leg strength using a dynamometer, walk test 6-minutes, walk test 10-minutes, walk analysis—3D recording of walking, change in utrophin membrane staining via quantifiable imaging of immunostained biopsy sections, and a change in regenerating fibers by measuring (via muscle biopsy) a combination of fiber size and neonatal myosin positivity. See, for example, Mazzone E et al, North Star Ambulatory Assessment, 6-minute walk test and timed items in ambulant boys with Duchenne muscular dystrophy. Neuromuscular Disorders 20 (2010) 712-716; Abdelrahim Abdrabou Sadek, et al, Evaluation of cardiac functions in children with Duchenne Muscular Dystrophy: A prospective case-control study. Electron Physician (2017) November; 9(11): 5732-5739; Magrath, P. et al, Cardiac MRI biomarkers for Duchenne muscular dystrophy. BIOMARKERS IN MEDICINE (2018) VOL. 12, NO. 11; Pane, M. et al, Upper limb function in Duchenne muscular dystrophy: 24 month longitudinal data. PLoS One. 2018 Jun. 20; 13(6):e0199223.

6. EXAMPLES

6.1 Example 1—Construction Microdystrophin (DMD) Gene Expression Cassettes for Insertion of Cis Plasmids DMD constructs with a similar backbone: 5'-ABD-H1-R1-R2-R3-H3-R24-H4-CR-3' (FIG. 1). The four constructs are distinct in promoter lengths, one without a C-terminus (RGX-DYS3), one without an intron (RGX-DYS1), and one having a truncated muscle-specific promoter (RGX-DYS4). All were cloned into Cis plasmids flanked by ITRs. All DNA sequences encoding the DMD genes are codon-optimized and CpG depleted.

6.1.1. Recombinant Engineering of RGX-DYS1 and RGX-DYS2 Transgenes

In brief, the human codon-optimized and CpG depleted nucleotide sequence of a microdystrophin construct in RGX-DYS1 and RGX-DYS2 as shown in FIG. 1A encoding N-terminal-ABD1-H1-R1-R2-R3-H3-R24-H4-CR-CT-C-terminal was synthesized using GeneArt Gene Synthesis (Invitrogen, Thermo Fisher, Waltham, MA). The desired C-terminus was made by site directed mutagenesis using the following two primers: 5': TGA CTC GAG AGG CCT AAT AAA GAG C (SEQ ID NO: 43), 3': CCT TGG AGA CTG TGG AGA GGT G (SEQ ID NO: 44). To generate RGX-DYS2 having the VH4 intron sequence (see Section 6.1.4 below), a fragment containing the nucleotide sequence encoding the microdystrophin was cohesively ligated to a backbone plasmid containing AAV ITRs, origin of replication, and antibiotic resistance, to form the RGX-DYS2 plasmid construction. Sequence analysis revealed an extra cytosine (C) in the 5' splicing site of the intron, therefore, the extra C nucleotide was removed by site-directed mutagenesis method, and the resulting construct RGX-DYS2 contains the VH4 intron. Similarly, site-directed mutagenesis was employed to remove the VH4 intron, and the resulting in RGX-DYS1.

6.1.2. Recombinant Engineering of RGX-DYS3 and RGX-DYS4 Transgenes

A construct RGX-DYS3 (FIG. 1A) was engineered encoding the microdystrophin of the RGX-DYS1 and RGX-DYS2 constructs detailed above without the CT domain. This construct includes the VH4 intron at the 5'end of the construct.

RGX-DYS4 (FIG. 1A) contains a cassette encoding the microdystrophin and VH4 intron as in RGX-DYS2 linked to a minimal SPc5-12 promoter (SEQ ID NO: 40; see Section 6.1.3) rather than the full length SPc5-12 promoter.

6.1.3. Recombinant Engineering of RGX-DYS5

A construct RGX-DYS5 (FIG. 1A) was engineered encoding a microdystrophin, named DYS5 (amino acid sequence of SEQ ID NO: 79), having a C-terminal domain of 140 amino acids in length (truncated C-Terminal Domain having an amino acid sequence of SEQ ID NO: 83) and containing an α1-syntrophin binding site but not a dystrobrevin binding site. The plasmid encodes the human codon-optimized and CpG depleted version of microdystrophin DYS5 transgene, a synthetic muscle promoter (e.g. spc5-12), and a small poly(A) signal sequence, and is flanked by ITRs (nucleotide sequence of SEQ ID NO. 82).

Plasmid RGX-DYS5 was created by replacing the long version of C-terminus of DYS1 in plasmid RGX-DYS1 with an intermediate length version of the C-terminus tail. In brief, a gBlock-DMD-1.5 tail was synthesized from Integrated DNA technologies containing the intermediate version of the C-terminus flanked by EcoRV and NheI sites and 17 bp of the overlapping sequence of the RGX-DYS1 plasmid. The source plasmid RGX-DYS1 was digested with restriction enzymes NheI and EcoRV (New England Biolabs), and then in-fusion ligated with the gBlock-DMD1.5 Tail. The final plasmid RGX-DYS5 was confirmed by enzyme digestion and subsequent sequencing.

The length and expression of the protein was confirmed by western blot. Towards this end, different plasmids were transfected into a myoblast cell line C2C12 cells. Four days after differentiation, the cells were harvested in lysis buffer. 20 μg of cell lysis from each plasmid sample was loaded on the SDS-PAGE gel. An antibody (1c7) against dystrophin (MANEX1011B, Developmental Studies Hybridoma Bank) was used to detect the microdystrophin protein band. The microdystrophin protein band generated from plasmid RGX-DYS5 (expressing DYS5) was significantly shorter than RGX-DYS1 (expressing DYS1), and longer than DYS3 (FIGS. 1B and C.). DYS3 transgene was driven by ubiquitous CB promoter, whereas DYS1 and DYS5 transgene expression driven by muscle-specific promoter in the experiment generating FIG. 1B. α-Actin protein control was used as a measure of consistent total protein recovery (FIG. 1C).

To examine the packaging efficiency of RGX-DYS5, RGX-DYS5 was packaged into AAV8 vector using HEK293 cells, and the titer of the vector RGX-DYS5 was determined following shake flask culture and affinity purification. Average titer was higher than AAV8 packaged RGX-DYS1 and comparable to AAV8 packaged RGX-DYS3 in these bench-top production runs. (Data not shown.)

6.1.4. VH4 Intron and minSPc5-12 Promoter

The VH4 intron in RGX-DYS2, RGX-DYS3 and RGX-DYS4 is obtained from a human immunoglobulin heavy chain variable region (SEQ ID NO: 41; GenBank Accession No. AB019438.1). The splicing efficiency and accuracy of the VH4 intron was tested in vitro in C2C12 cells First, sequencing of the reverse-transcriptional PCR product was conducted to test whether the correct splicing event occurred. RGX-DYS2 plasmid was transfected into C2C12 myoblasts and cells were cultured in differentiation media for three days. Cells were then subjected to RNA extraction, cDNA synthesis and PCR. The primers used for PCR were: Primer 1: GGC CCA CGA GCT ACC CGG AG (SEQ ID NO: 45), Primer 2: CTT CCA GCA GAT CCA GCA GCC (SEQ ID NO: 46). The expected PCR product was gel purified and subjected to sanger sequencing. Sequencing results revealed that accurate splicing events occurred. The function of the VH4 intron was then tested in a construct in which the microdystrophin coding sequence was replaced with the coding sequence for GFP reporter protein. Also tested were AAV8 vectors containing GFP gene driven by the SPc5-12 promoter with or without the VH4 intron in differentiated C2C12 cells at various dosages. Images were taken, and quantitation was done using Cytation 5 cell imaging multi-mode reader. The quantitation and image data all indicated that the VH4 intron increased GFP expression nearly 5-fold (FIGS. 2A-F and FIG. 3).

6.2 Example 2—In Vitro Potency Assay for Microdystrophin Vectors Using Differentiated C2C12 Cells An in vitro assay for testing the potency of microdystrophin vectors was developed by assaying the infectivity of AAV8-CAG-GFP vector in HEK293 cells. After three days of infection (1×10E5 vg/cell), few GFP-positive HEK293 cells were observed (data not shown) indicating that the infectivity of HEK293 cells with AAV8 vector was low. The ability of AAV8-CAG-GFP vector to transduce C2C12 myoblasts was then tested in the same manner. Undifferentiated C2C12 myoblasts were infected with AAV8-CAG-GFP vector (1×10e6 vg/cell), then differentiated for three days. Similar to HEK293 cells, very few GFP-positive cells were observed, demonstrating that undifferentiated C2C12 myoblast cells display low infectivity by rAAV8 (data not shown). Infectivity was tested in differentiated C2C12 cells by culturing the C2C12 cells in differentiation media (DMEM+2% horse serum) for 3 days, and then infecting them with AAV8-CAG-GFP. Images were taken three days post infection, and three days post differentiation. Many GFP positive cells were visible, suggesting that differentiated myotubes are susceptible to transduction by AAV8 vector (FIGS. 4A-C).

Following the successful establishment of an in vitro infection system for muscle cells, the potency of the microdystrophin vectors was assayed. For example, the potency of two batches of vectors (RGX-DYS1-RS and RGX-DYS1-03) generated several months apart using the same production process was tested in differentiated C2C12 cells. The primary antibody used was a monoclonal antibody against human dystrophin (DSHB Cat No. MANHINGE1A(6F11)). JMP software was used to analyze the data. Relative potency of the tested vector (RGX-DYS1-03) was 81.47% of the reference control (RGX-DYS1-RS, 100%) indicating that the infectivity of those two vectors was very similar (FIGS. 5A-H).

Batches of recombinant AAV packaging DYS1, DYS2, DYS3, or DYS4 vectors were produced, and their relative infectivity compared in the differentiated muscle cell line C2C12 cells, as a measure of vector potency (FIG. 6). Briefly, mouse muscle cell line C2C12 cells were seeded at 2×10E5 cells/well in 6-well plates cultured with 10% fetal bovine serum (FBS) in Dulbecco's modified eagle medium (DMEM). Then the cells were changed to a differentiation medium (DMEM with 2% horse serum supplemented with insulin (1 ug/ml)) on the second day. After three days of differentiation, the cells were infected with different DMD vectors at the dosage of 2.5E4 vg/cell. Three days after infection, the infected cells were harvested and subjected to DNA extraction followed by Q-PCR. The DNeasy Blood and Tissue kit (Cat No: 69504, Qiagen) was used to extract the DNA. Tagman assay was used for both endogenous control (glucagon gene) and AAV vectors. The mouse glucagon gene as an endogenous control allowed normalization of vector copy numbers. The sequences for mouse glucagon primers and probes were as follows: Glucagon-real-F (mouse): AAGGGACCTTTACCAGTGATGTG (SEQ ID NO: 47); Glucagon-real-R (mouse): ACTTACTCTCGCCTTCCTCGG (SEQ ID NO: 48); Taqman mouse glucagon probe: FAM-CAGCAAAGGAATTCA-MGB (SEQ ID NO: 49). For the target AAV vectors, primers and probes were designed to recognize the micro-dys sequence and were as follows: Dys-C-F: TGG GCC TGC TCC TGC ATG (SEQ ID NO: 50); Dys-C-R: ATC TCA GGC TTG GCA AAC (SEQ ID NO: 51); Dys-C-probe: FAM-CAA TAT TGA GCC ATC AGT C-MGB (SEQ ID NO: 52). The copy number per diploid cell was calculated as:

$$\frac{\text{vector copy number}}{\text{endogenous control}} \times 2.$$

The DYS1-RS batch was considered as reference control (set to 1.0), and all other vectors were compared against it (vector copy number/reference control (fold-change)). As shown in FIG. 6, the infectivity of all AAV8 vectors was comparable (ranging from 50 to 150% infectivity is acceptable), demonstrating good quality vectors.

The RNA expression level of the microdystrophin gene was determined after infection of differentiated C2C12 cells with the various AAV8 vectors at two different dosages (1e5 vg/cell and 5e4 vg/cell). Cells transfected with RGX-DYS3 vectors had 2-3 fold higher mRNA levels of the microdystrophin compared to microdystrophin mRNA levels in cells transfected with RGX-DYS1 vectors (FIG. 7). This difference is likely due to the presence of VH4 intron in RGX-DYS3 stabilizing mRNA.

6.3 Example 3—Gene Therapy Administration to a Mdx Mouse Model

6.3.1. Study Methods

RGX-DYS1 was packaged into AAV8 vector using HEK293 cells, and the titer of the vector RGX-DYS1 was 4.6E13 vg/ml. Briefly, the RGX-DYS1 AAV8 vector was systemically delivered into 5 week-old male mdx mice by tail vein injection at 2E14 vg/kg dosage (n=13). The mice were weighed periodically. The muscle grip strength was measured at 5 weeks post treatment, and the in vitro muscle contractile function assays were performed at 6-weeks post injection. Results are shown in Table 11.

TABLE 11

Outline of mdx mouse model analysis

| | Weeks of Treatment (Weeks of Age) | | | | | |
|---|---|---|---|---|---|---|
| | 1(5) | 2(6) | 3(7) | 4(8) | 5(9) | 6(10) |
| Bodyweights | + | + | + | + | + | + |
| Clinical Observations | + | + | + | + | + | + |
| Drug Administration | + | − | − | − | − | − |
| Forelimb Grip Strength | − | − | − | + | + | − |
| In Vitro Force Tissue Collection | − | − | − | − | − | + |

6.3.2. Body Weights and Tissue Weights

Because of the pathogenesis of degeneration and regeneration of skeletal muscle, mdx mice are usually heavier than wild-type mice. As revealed in FIG. 8, the treatment with the RGX-DYS1 vector significantly decreased the body weight. In fact, the body weight of the treated mice was similar to the wild-type counterparts at 2 weeks post treatment.

All mice were euthanized at 6 weeks post injection and various organs and muscles were weighed. RGX-DYS1-treated mice displayed a significant reduction in organ and muscle weight including soleus, quadriceps, and triceps muscles and the tibialis anterior (TA) (FIGS. 9A and 9B).

6.3.3. Grip Strength

To measure the grip strength mice were acclimated to the testing room for approximately 10 minutes before beginning the procedure. Experimenter was blinded to the treatment and the mouse to be measured was handed over to the experimenter by another person. The mouse was gently placed on top of the forelimb wire grid so that only its front paws were allowed to grip one of the horizontal bars. After ensuring both the front paws were grasping the same bar and the torso horizontal to the ground and parallel to the bar, the mouse was pulled back steadily with uniform force down the complete length of the grid until the grip was released. 5 good pulls for each animal over five consecutive days for acclimation and testing. The single best-recorded value (maximal force) was calculated for analysis of maximal strength of individual mice. Normalized strength (KGF/kg) was calculated based on the body weight.

The grip strength measurement at 5 weeks post treatment revealed that the treatment significantly increased the muscle force of RGX-DYS1-treated mice compared to diseased vehicle controls ($p<0.001$) (FIG. 10).

6.3.4. In Vitro Force

The mice were anesthetized using Ketamine and Xylazine. The EDL muscle of the right hindlimb were removed from each mouse and immersed in an oxygenated bath (95% 02, 5% CO2) that contains Ringer's solution (pH 7.4) at 25° C. Using non-fatiguing twitches, the muscle was adjusted to the optimal length for force generation. The muscles were stimulated with electrode to elicit tetanic contractions that were separated by 2-minute rest intervals. With each subsequent tetanus, the stimulation frequency was increased in steps of 20, 30 or 50 Hz until the force reached a plateau which usually occurred around 250 Hz. The cross-sectional area of the muscles was measured based on muscle mass, fiber length, and tissue density. Finally, the muscle specific force (kN/m2) was calculated based on the cross-sectional area of the muscle.

Vehicle mdx mice (n=13) showed a significant reduction in maximal and specific force compared to healthy BL10 mice (historical data, n=14). Treatment of mdx mice with RGX-DYS1 resulted in a significant improvement of both maximal and specific force at 6 weeks compared to vehicle controls (FIG. 11).

6.3.5. Cardiac Function

To measure the blood pressure (BP) mice are sedated using 1.5% isofluorane with constant monitoring of the plane of anesthesia and maintenance of the body temperature at 36.5-37.58 C. The heart rate is maintained at 450-550 beats/min. A BP cuff is placed around the tail, and the tail is then placed in a sensor assembly for noninvasive BP monitoring during anesthesia. Ten consecutive BP measurements are taken. Qualitative and quantitative measurements of tail BP, including systolic pressure, diastolic pressure and mean pressure, are made offline using analytic software. See, for example, Wehling-Henricks et al, Human Molecular Genetics, 2005, Vol. 14, No. 14; Uaesoontrachoon et al, Human Molecular Genetics, 2014, Vol. 23, No. 12.

To monitor ECG wave heights and interval durations in awake, freely moving mice, radio telemetry devices are used. Transmitter units are implanted in the peritoneal cavity of anesthetized mice and the two electrical leads are secured near the apex of the heart and the right acromion in a lead II orientation. Mice are housed singly in cages over antenna receivers connected to a computer system for data recording. Unfiltered ECG data is collected for 10 seconds each hour for 35 days. The first 7 days of data are discarded to allow for recovery from the surgical procedure and ensure any effects of anesthesia has subsided. Data waveforms and parameters are analyzed with the DSI analysis packages (ART 3.01 and Physiostat 4.01) and measurements are compiled and averaged to determine heart rates, ECG wave heights and interval durations. Raw ECG waveforms are scanned for arrhythmias by two independent observers.

Picro-Sirius red staining is performed to measure the degree of fibrosis in the heart of trial mice. In brief, at the end of trial, directly following euthanasia, the heart muscle is removed and fixed in 10% formalin for later processing. The heart is sectioned and paraffin sections are deparaffinized in xylene followed by nuclear staining with Weigert's hematoxylin for 8 min. They are then washed and then stained with Picro-Sirius red (0.5 g of Sirius red F3B, saturated aqueous solution of picric acid) for an additional 30 min. The sections are cleared in three changes of xylene and mounted in Permount. Five random digital images are taken using an Eclipse E800 (Nikon, Japan) microscope, and blinded analysis is done using Image J (NIH).

Blood samples are taken via cardiac puncture when the animals are euthanized, and the serum collected is used for the measurement of muscle CK levels.

6.4 Example 4 Vector Biodistribution

Vehicle- and RGX-DYS1-treated mdx mice were sacrificed at 6 weeks after treatment, and the vector copy numbers were assessed on various tissues including skeletal muscle, cardiac muscle, and liver cells using Naica crystal digital PCR system from Stilla Technologies.

RGX-DYS1 vector was administered into four-weeks-old male muscular dystrophic mdx mice via tail vein injection. Six weeks post injection, the mice were sacrificed, and tissues were subjected to total DNA extraction and ddPCR assay for vector copy numbers.

Total DNA from collected tissues was extracted with the DNeasy Blood & Tissue Kit and the DNA concentration was measured using a Nanodrop spectrophotometer. To determine the vector copy numbers in the tissues, digital PCR was performed with Naica Crystal Digital PCR system (Stilla technologies). Two color multiplexing system were applied here to simultaneously measure the dystrophin transgene and endogenous control gene. In brief, the dystrophin probe was labelled with FAM (6-carboxyfluorescein) dye while the endogenous control glucagon probe was labelled with VIC fluorescent dye. The sequences for mouse glucagon primers and probes were as follows: Glucagon-real-F (mouse): AAG GGA CCT TTA CCA GTG ATG TG (SEQ ID NO: X); Glucagon-real-R (mouse): ACT TAC TCT CGC CTT CCT CGG; Taqman mouse glucagon probe: VIC-CAG CAA AGG AAT TCA-MGB. For the AAV vectors, primers and probes were designed to recognize the C-terminus of dystrophin gene: Dys-dd-F2: ACA GAT ACC TGT TCA AGC AAG TGG C (SEQ ID NO: 122); Dys-dd-R2: TCA ATC TCA GGC TTG GC (SEQ ID NO: 123); Dys-C-Probe: FAM-CAA TAT TGA GCC ATC AGT C-MGB (SEQ ID NO: 124). The copy number of delivered vector in a specific tissue per diploid cell was calculated as:

$$\frac{\text{vector copy number}}{\text{endogenous control}} \times 2.$$

RGX-DYS1 administration resulted in the highest vector copy numbers in liver tissue (437±78 copies/cell, n=13). Cardiac muscle (23±9, n=13) and skeletal muscle (Tibialis anterior (TA) 28±10 copies/cell, Extensor digitorum longus (EDL) muscle 23±11 copies/cell, Diaphragm muscle 28±29 copies/cell, Triceps muscle 49±22 copies/cell) and all exhibited significant of vector distribution (FIG. 12).

6.5 Example 5—Restoration of DAPC Including nNOS

The dystrophin-associated proteins together with dystrophin form a complex known as the dystrophin associated protein complex (DAPC), which, acting as a bridge, connects the intracellular cytoskeletal actin to the basal lamina through the extracellular matrix. Sadoulet-Puccio, H. M., et al, Dystrobrevin and dystrophin: an interaction through coiled-coil motifs. (1997) Proc Natl Acad Sci USA 94:12413-8. The DAPC is comprised of several subcomplexes: dystroglycan, sacroglycan, and syntrophin/dystrobrevin, which are collectively attributed to maintaining fiber integrity during repeated cycles of contraction and relaxation and in cell signaling. Id. (FIG. 13). In wild-type dystrophin, the β-dystroglycan binding site is located at hinge 4 and cysteine-rich (CR) domain. The WW domain of dystrophin requires EF-hands region to interact with beta-dystroglycan (Rentschler, S., et al. 1999, Biol Chem 380: 431-42). RGX-DYS1 includes a portion of the C-terminus (SEQ ID NO: 16), which contains dystrobrevin and syntrophin binding domains (see Table 1). One of the important functions of syntrophin is to anchor signaling proteins such as neuronal nitric oxide synthase (nNOS) to the sarcolemma. Adams, M. E., et al, 2000. Absence of α1-syntrophin leads to structurally aberrant neuromuscular synapses deficient in utrophin. J Cell Biol 150:1385-98. Therefore, expression of the microdystrophin from RGX-DYS1 in mdx mouse muscle would be expected to restore dystrobrevin, syntrophins, and nNOS to the muscle membrane.

Immunofluorescent staining against dystrophin, nNOS, α1-syntrophin, α-dystrobrevin was performed on cry-thin-section of the treated and control gastrocnemius muscle. Reagents and antibodies used for the experimental procedure are listed in Tables 12 and 13.

TABLE 12

| Staining reagents | | |
|---|---|---|
| **Description** | **Catalog Number** | **Vendor/Supplier** |
| DAPI nucleic acids stain, FluoroPure Grade | D21490 | Thermo Fisher/Invitrogen |
| Horse Serum (New Zealand Origin) | 16050-130 | Thermo Fisher/Gibco |
| Mouse on Mouse (M.O.M) blocking reagent | VWR Catalog 101098-256, Vector Labs catalog MKB-2213 | VWR/Vector Laboratories |
| Apex Superior Adhesive slides | VWR Catalog 10015-146, Leica Catalog 3800080 | VWR/Leica |
| SlowFade Gold Antifade Mountant | S36937 | Thermo Fisher/Invitrogen |
| Cover Glass | VWR Catalog 75810-254, Leica Catalog 3800150ACS | VWR/Leica |
| PAP Pen liquid blocker, small | VWR catalog 100502-806, Electron Microscopy Service catalog 71312 | VWR/Electron Microscopy Service |
| PBS | 20012-027 | Thermo Fisher/ Gibco |
| Ultra pure distiller water | 10977-015 | Thermo Fisher/Invitrogen |

Freshly isolated mouse tissue was snap frozen by immediate immersion in isopentane/liquid nitrogen double bath and afterwards stored at −80 degrees. Tissue was affixed to cutting block by adding a few drops of OCT (Optimal cutting temperature) compound and then placing the tissue on the block in the desired cutting orientation. OCT and tissue were frozen in place in cryostat (hold tissue in desired orientation until OCT is solid) and tissue was sectioned at 10 μm (8-10 μm acceptable). Four to six sections were arranged on each slide and store at −80 degrees.

Muscle cryo-section slides were removed from −80 degrees storage and air dried for 10 minutes at room temperature (RT). Marks are then made around the tissue section area with a PAP pen. If the primary antibody is from mouse monoclonal antibody, two blocking steps are required. First the sample is blocked by adding an appropriate volume of 1× M.O.M to cover the full area enclosed by the PAP pen by pipette and incubated for 1.5 hours at RT. M.O.M. is the removed by aspiration and subsequently blocked with 10% horse serum (in PBS) for 1 hour at RT. If the primary antibody is not from mouse origin, samples is directly blocked with 10% horse serum (in PBS) by using a pipette to add an appropriate volume of PBS to cover the full area enclosed by the PAP pen and subsequently incubated for 1 hour at RT.

Primary antibodies were diluted in 2% horse serum (in PBS) and samples were incubated for 1-2 hours at RT. Slides were then washed with 1×PBS by adding an appropriate volume of PBS to cover the full area enclosed by the PAP pen followed by incubation for 3 minutes at RT and aspiration. Repeated for total of 3 to 4 times. The secondary antibody (CY3, equivalent such as Alexa Fluor 594, or 488 conjugated antibody) was diluted in 2% horse serum in PBS and slides were incubated for 1 hour at RT. Slides were washed 3-4 times with 1×PBS for 3 minutes at RT. Counterstain was performed with DAPI to display nuclei by incubating the slides with 1×DAPI diluted in PBS for 5 to 8 minutes at RT. Slides were washed with 1×PBS for 3 minutes at RT after DAPI staining and then mounted with 1-2 drops/slide of anti-fade mount medium at RT. Slide were air dried at RT after mounting and protected from light. Fluorescence was analyzed using a fluorescent microscope and images were taken.

TABLE 13

Primary and secondary antibodies used for DAPC analysis

| Description | Catalog Number | Vendor/ Supplier | Recommended Dilutions |
|---|---|---|---|
| Mouse anti-dystrophin monoclonal antibody | MANEX1011B (1C7) Supernatant | Developmental Studies Hy bridoma Bank /University of Iowa | 1:100 |
| Mouse anti-beta-dystroglycan monoclonal antibody | MANDAG2 (7D11) Supernatant | Developmental Studies Hybridoma Bank (University of Iowa) | 1:3000 |
| Mouse anti-NOS1 monoclonal antibody | SC-5302 | Santa Cruz Biotechnology | 1:50 |
| Rabbit anti-Syntrophin alpha 1, polyclonal antibody | Ab11187 | Abcam | 1:3000 |
| Mouse anti-Dystrobrevin monoclonal antibody | 610766 | BD Biosciences | 1:100 |
| Goat Anti-Mouse IgG polyclonal antibody, Cy3 conjugate | AP124C | Millipore Sigma | 1:500 |
| Goat anti-rabbit IgG (H + L) polyclonal antibody, Cy3 conjugate | A10520 | Thermo Fisher/Invitrogen | 1:500 |

As shown in FIG. 14, except for a few revertant fibers, the dystrophin protein and examined DAPC proteins were all absent in mdx mouse muscle untreated with RGX-DYS1. Systemic delivery of RGX-DYS1 efficiently restored dystrophin expression, as well as anchored α1-syntrophin, α-dystrobrevin, β-dystroglycan and nNOS to the sarcolemma (Table 14). To note, two commercial antibodies were used for nNOS staining. In both instances, nNOS expression was significantly restored to the muscle membrane as compared to the untreated control group. In conclusion, the RGX-DYS1 microdystrophin was able to restore dystrophin-associated protein complexes, including nNOS, to the sarcolemma in vivo.

TABLE 14

Anchoring of DAPC members

| | β-Dystroglycan | α-Dystrobrevin | α1-Syntrophin | nNOS |
|---|---|---|---|---|
| Wild type dystrophin | +++ | +++ | +++ | +++ |
| DYS1 | +++ | +++ | +++ | ++ |
| DYS3 | +++ | + | + | − |
| DYS5 | +++ | + | +++ | ++ |

6.6 Example 6—Gene Therapy Administration to a Mdx Mouse Model

In vivo testing of AAV8-RGX-DYS3 and AAV8-RGX-DYS5 vectors was performed in 13 male C57BL/10ScSn-Dmd$^{mdx}$/J (mdx) mice. All vectors were systemically delivered into the 5-weeks-old mdx mice by tail vein injection at 2E14 vg/kg dosage (n=5 for group 1, AAV8-RGX-DYS3; n=5 for group 2, AAV8-RGX-DYS5; n=3, mdx negative (no dosing) control). Animals ranged from 15.9 g to 22.0 g in weight on the day of dosing. At 6 weeks post-vector administration, blood was collected for serum and animals were euthanized and underwent necropsy for collection of tissues. Major skeletal muscles including gastrocnemius (Gas), tibialis anterior (TA), diaphragm, triceps, quadriceps, heart, liver and major organs were collected and snap frozen in isopentane/liquid nitrogen double bath and placed into pre-chilled cryotubes.

The body weights for each animal were recorded two times weekly, and the average change in weight for each group was calculated. All animals gained weight, as expected, over the 7 week period except animal #12 (R13-35-012).

TABLE 15

Change in individual and group body weights from Day 0 to 42

| Animal Number | Group | Change in Weight (g) | Mean change in group weight (g) |
|---|---|---|---|
| R13-135-001 | 1 | 9.5 | 5.9 |
| R13-135-002 | 1 | 7.7 | |
| R13-135-005 | 1 | 1.7 | |
| RI 3-135-006 | 1 | 5.2 | |
| R13-135-007 | 1 | 5.4 | |
| R13-135-008 | 2 | 9.7 | 7.3 |
| R13-135-009 | 2 | 3.8 | |
| R13-135-011 | 2 | 8.0 | |
| R13-135-012 | 2 | Sick animal | |
| R13-135-013 | 2 | 7.7 | |
| R13-135-003 | Neg control | 13.8 | 13.2 |
| R13-135-004 | Neg control | 12.7 | |
| R13-135-010 | Neg control | 13.0 | |

The pathogenesis of degeneration and regeneration of skeletal muscle in mdx mice typically results in heavier than wild-type mice. As seen in Table 15, mdx mice treated with RGX-DYS3 or RGX-DYS5 vector resulted in significantly less changes in body weight compared to mdx mice receiving no treatment.

6.7 Example 7—Assessment of Microdystrophin (μ-Dys) Protein Expression in Treated Mdx Mice

6.7.1 μ-Dys Expression Comparisons by Western Blot, mRNA Expression and DNA Vector Copy Numbers.

Data and samples described in this example related to RGX-DYS1 experiments were collected following treatment as described in Section 6.3 infra (n=13 mice dosed with AAV8-RGX-DYS1). Data and samples described hereinbelow related to experiments with animals administered AAV8-RGX-DYS3 and AAV8-RGX-DYS5 were collected following treatment as described in Section 6.6 hereinabove (n=5 each treated mdx mouse group). Experiments were performed at different facilities.

Microdystrophin protein expression from gastrocnemius muscle, as collected from treated mdx mice, was examined by western blot. Briefly, 20 to 30 mg of tissues were homogenized in protein lysis buffer (15% SDS, 75 mM Tri-HCl pH6.8, proteinase inhibitor, 20% glycerol, 5% beta-mercaptoethanol) (Bead Mill homogenizer Bead Ruptor 12, SKU:19050A, OMNI International). After homogenizing, the samples were spun down for 5 mins at top speed at room temperature, and the supernatants were subjected to protein quantification. The protein stock supernatants were quantified using Qubit protein assay kit (Catalog #Q33211, ThermoFisher Scientific). Total protein concentration per stock was calculated, then 20 μg of protein stock supernatant was loaded onto an SDS-PAGE gel. Western blot was performed using a primary anti-dystrophin antibody (MANEX1011B (1C7), Developmental Studies Hybridoma Bank) at 1:1000 dilution, and the secondary antibody applied was goat anti-mouse IgG2a conjugate to horseradish peroxidase (HRP) (Thermo Fisher Scientific, Cat. No. 62-6520). α1-actin serves as the loading control in each lane of the gel. For anti-al-actin blot, rabbit polyclonal anti-al-actin antibody (PA5-78715, Thermo Fisher) was used at a dilution factor of 1:10,000, and the secondary goat anti-rabbit antibody (Thermo Fisher Scientific, Cat. No. 31460) was used at 1:20,000. Protein signal was detected using ECL Prime Western Blotting Detection Reagent (per Manufacturer's instructions; AMERSHAM, RPN2232) and quantified by densitometry guided by Image Lab software (Bio-Rad).

Western blot results (FIG. 15) revealed several observations: First, the estimated size of each μ-dystrophin protein corresponds well to its observed migration on the gel, e.g. RGX-DYS1 μ-dystrophin protein was 148 kDa, while the size of RGX-DYS5 and RGX-DYS3 proteins were 142 kDa and 132 kDa, respectively. Second, the intensity of the bands was different for each protein present in the gastrocnemius muscle tissue. The longer version μ-dystrophin, RGX-DYS1 vector, displayed the strongest transgene expression, followed by the intermediate version RGX-DYS5 and shorter version RGX-DYS3 (FIG. 15 and FIG. 16A). The difference in μ-dystrophin expression level among those three constructs could be due to either variation in AAV vector genome level or protein stability of different lengths of μ-dystrophin constructs.

To elucidate genome copies per cell, ddPCR was performed to examine AAV-μ-dys vector genome copy numbers in those tissues, using the method described previously in Section 6.4 (Example 4). As displayed in FIG. 16B, the RGX-DYS1 vector-delivered tissues indeed had higher vector genome copy numbers (50±14 gc/cell) than RGX-DYS5 (17±4 gc/cell) and RGX-DYS3 (16±5 gc/cell) vector-delivered tissues (values were normalized to glucagon genome copies). The relative μ-dystrophin expression was then compared to vector copy numbers. As shown in FIG. 16C, the expression of relative μ-dystrophin in RGX-DYS1-treated muscle (1.33±0.39) and RGX-DYS5-treated muscle (1.774±0.40) were all significantly higher than the RGX-DYS3-treated muscle (0.77±0.22, $p<0.05$, n=3 to 5). This data indicates that the longer versions of μ-dystrophin (having a C-terminus) generated by RGX-DYS1 and RGX-DYS3 vectors render better stability of μ-dystrophin protein in muscle cells in vivo.

Additionally, the mRNA expression of μ- and wild-type (WT)-dystrophin in skeletal muscle in untreated wild-type B6 and mdx mice, compared to treated mice, was measured with ddPCR. Total RNA were extracted from the muscle tissue using RNeasy Fibrous Tissue Mini Kit (REF 74704, Qiagen). cDNA was synthesized using High-capacity cDNA reverse transcription kit with RNAse inhibitor (Ref 4374966, Applied Biosystems by Thermo Fisher Scientific). The RNA concentration was measured using a Nanodrop spectrophotometer. The copy numbers of μ-dystrophin, WT-dystrophin, and endogenous control Glyceraldehyde 3-phosphate dehydrogenase (GAPDH) mRNA were measured using digital PCR (Naica Crystal Digital PCR system, Stilla technologies). Primers and probe against mouse WT-dystrophin (mm01216951_m1, Thermo Fisher Scientific)(also described in the biodistribution study above in Section 6.4 (Example 4)), and mouse GAPDH (mm99999915_g1, Thermo Fisher Scientific) were commercially available. As shown in FIG. 17A, the relative WT-dystrophin transcript in the naïve B6 mice was 1±0.64, and the WT-dystrophin mRNA expression in mdx mice was 1.55±0.77 ($p=0.15$, n=4). The relative μ-dystrophin mRNA in treated animals were as follows: RGX-DYS1-treated muscle, 22.66±11.6 ($p<0.01$, n=5); RGX-DYS5-treated, 16.83±11.07 ($p=0.06$, n=3) and RGX-DYS3 treated muscle, 11.87±7.90 ($p<0.05$, n=4). This data indicated that delivery of the μ-dystrophin vectors in RGX-DYS1, RGX-DYS5, and RGX-DYS3 groups all generated much higher μ-dystrophin transcripts than the wild-type level. Furthermore, μ-dystrophin mRNA copy numbers were normalized to AAV vector genome copy numbers per cell, and WT-dystrophin mRNA was normalized to genome copy numbers per cell (2 copies/cell), in addition to GAPDH normalization. As shown in FIG. 17B, all groups displayed essentially similar levels of mRNA expression on a per genome basis (n=3 to 5, $p>0.05$). This indicated that the muscle-specific Spc5-12 promoter driving expression of the AAV-μ-dystrophin transgenes was as potent as the native dystrophin promoter in mouse skeletal muscle cells.

6.7.2 μ-Dystrophin Expression by Immunofluorescence (IF) Staining and Dystrophin-Associated Protein Complex (DAPC) Association Next, immunofluorescent (IF) staining was performed to examine expression of dystrophin and dystrophin associated protein complexes including dystrobrevin, β-dystroglycan, syntrophin, and nNos on gastrocnemius muscles from different groups. The IF staining protocol and antibodies applied were as previously described in Section 6.5 hereinabove (Example 5). As shown in FIG. 18, the dystrophin protein and examined DAPC proteins were all absent in the untreated mdx muscle, while they were strongly present on the wild-type B6 muscle membrane. For all three treated groups, μ-dystrophin protein was expressed on nearly 100% muscle fibers and they were indistinguishable amongst the different treatment groups. The three treatment groups displayed restoration of dystrobrevin expression on muscle membranes with a very similar pattern observed. For β-dystroglycan staining, the muscles in the RGX-DYS1-treated group displayed a more uniform and more intense (3-dystroglycan staining (expression).

Figure 19A:
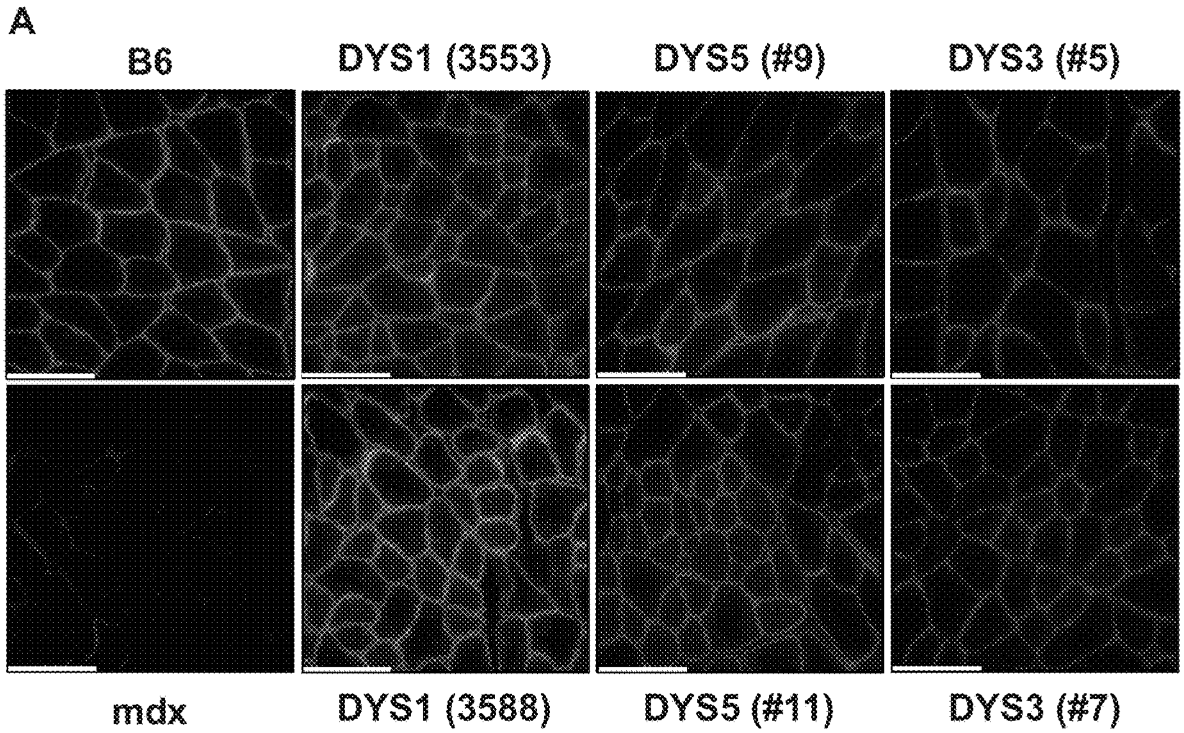
Figure 19B:
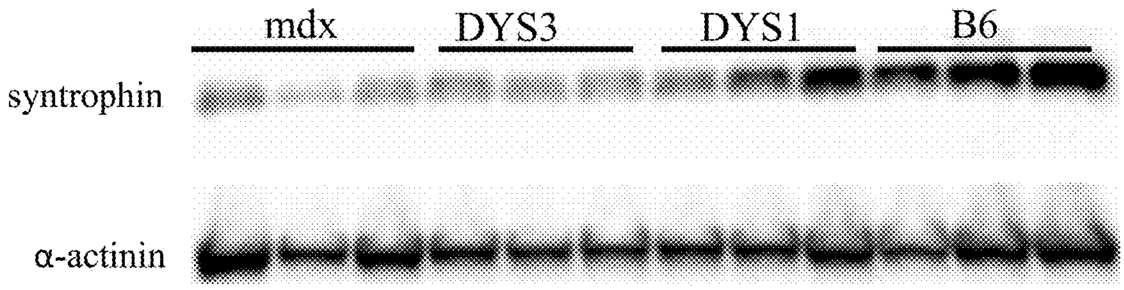
Figure 19C:
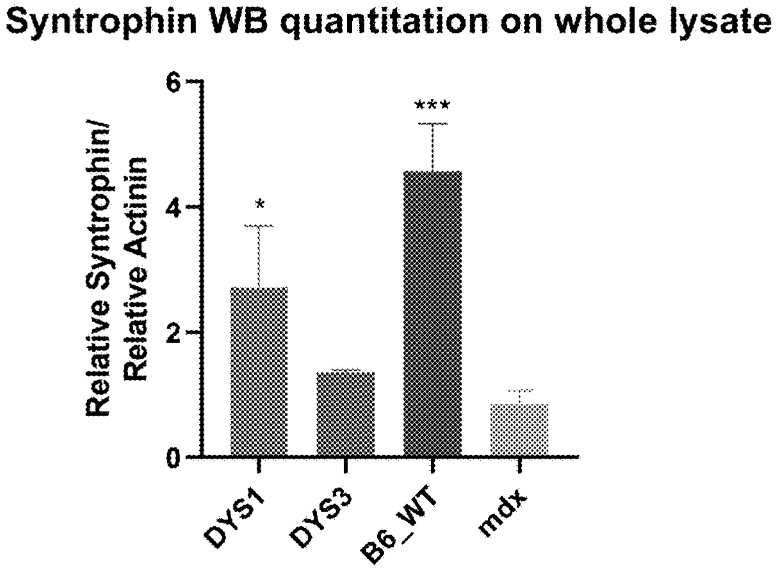
Figure 19D:
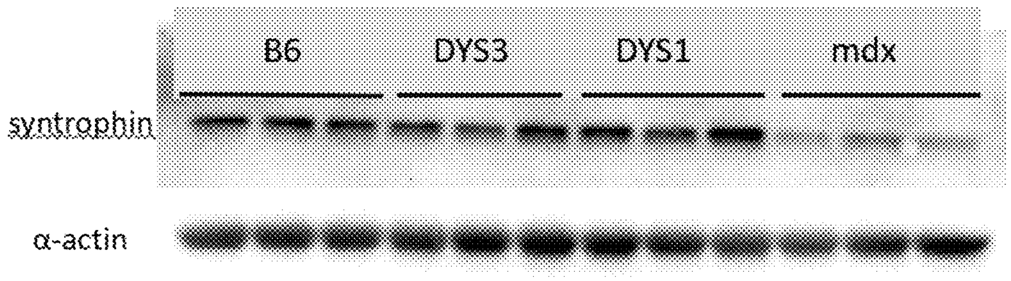
Figure 19E:
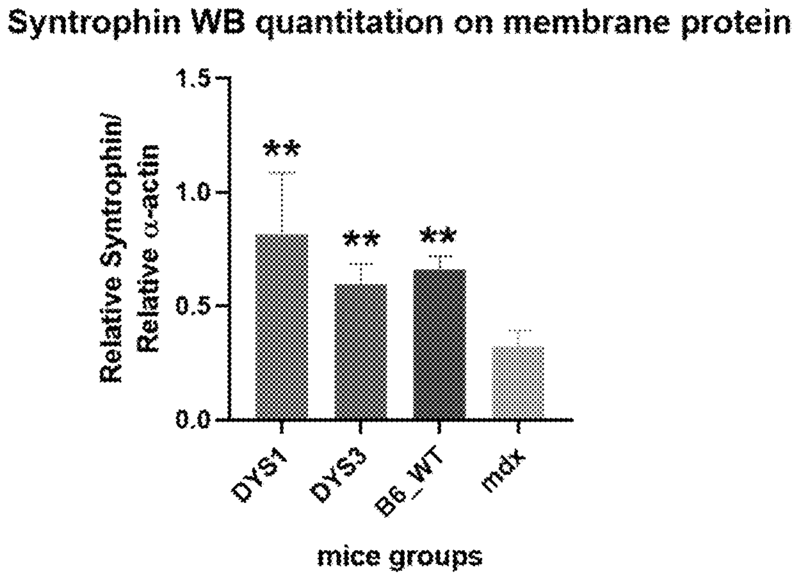

The more dramatic difference amongst the treatment groups was observed in syntrophin staining. The expression of syntrophin on muscle membrane was much enhanced in RGX-DYS1 group which contains longer length of μ-dystrophin, followed by RGX-DYS5 and RGX-DYS3 (FIG. 18 and FIG. 19A). The same trend was further substantiated by western blot analysis on muscle lysates (FIG. 19B). Western blot against syntrophin was performed on skeletal muscle tissue lysate (gastrocnemius muscle tissue from 3 each of the mdx treated and untreated groups, and one gastrocnemius and two triceps were from the B6 mice group). The polyclonal anti-syntrophin antibody (Abcam, ab11187) was used at 1:10,000, incubation at room temperature for 1 hour. Rabbit monoclonal against α-actinin (ab68167, Abcam) was applied at 1:5000 dilution. Secondary goat anti-rabbit antibody (Thermo Fisher Scientific, Cat. No. A-10685) was applied. The ratio of syntrophin expression to the endogenous control actinin expression in WT muscle was 4.56±0.76 (n=3, $p<0.001$ by one-way ANOVA) as compared with mdx group (0.84±0.22). The ratio in RGX-DYS1 and RGX-DYS5 groups were 2.72±0.97 (n=3, $p<0.05$ as compared with mdx group) and 1.35±0.03, respectively (FIG. 19C). The level of syntrophin expression in skeletal muscle was additionally examined on total muscle membrane extracts by western blot. Total skeletal muscle protein was extracted using Mem-Per Plus membrane protein extraction kit (Cat #89842, Thermo Fisher) (gastrocnemius muscle tissue from each of the mdx treated and untreated groups, and quadriceps from the B6 mice group). 20 μg of total membrane protein was loaded into each lane (FIG. 19D). The polyclonal anti-syntrophin antibody (Abcam, ab11187) was used at 1:10,000 incubation at 4° C. overnight. The loading control polyclonal anti-actin (PA5-78715, Thermo Fisher) was applied at 1:10,000 dilution for overnight incubation at 4° C. Slightly different from the whole lysate western experiment where WT muscle displayed the highest syntrophin expression level, the total membrane protein western blot displayed highest relative syntrophin expression in RGX-DYS1 group (0.81±0.26, n=3), followed by B6_WT group (0.6623±0.05, n=3), RGX-DYS3 group (0.59±0.08), and mdx group (0.32±0.07, n=3), as seen in FIG. 19E. These results clearly indicated that the μ-dystrophins generated by the μ-dystrophin vectors were able to restore muscle membrane syntrophin expression, and the longer version of RGX-DYS1 had superior ability to anchor syntrophin to muscle membrane than the shorter version RGX-DYS3.

nNOS western blots were prepared analogously using muscle membranes (gastrocnemius muscle tissue/mdx, and quadriceps/B6 groups). Total muscle membrane protein was extracted using Mem-Per Plus membrane protein extraction kit (Cat #89842, Thermo Fisher). 20 μg of total membrane protein was loaded into each lane of an SDS-PAGE gel. The primary antibody against nNOS (SC-5302, Santa Cruz Biotechnology) was used at 1:500, and polyclonal anti-actin (PA5-78715, Thermo Fisher) was applied at 1:10,000 dilution. Secondary goat anti-Mouse IgG antibody, HRP (62-6520, ThermoFisher) was applied. With respect to nNOS expression, we observed a noticeable difference between the RGX-DYS1 and RGX-DYS3 group images following IF staining (FIG. 20A). However, western blot results did not reveal any significant difference among RGX-DYS1, RGX-DYS3, and untreated mdx group (FIGS. 20B-C), indicating the restoration of nNOS by RGX-DYS1 vector was low.

Overall, delivery of RGX-DYS1, RGX-DYS3, and RGX-DYS5 vectors in mdx mice all resulted in robust μ-dystrophin expression and restoration of dystrophin associated protein complexes (DAPCs). The longer version of RGX-DYS1 vector enhanced restoration of DAPCs particularly for syntrophin and β-dystroglycan. The ability of restoration of nNOS to the membrane DAPC by RGX-DYS1 vector was low but visible upon IF staining.

6.8 Example 8—Transduction of Satellite Cells and Amelioration of Regeneration of Muscular Dystrophic Muscle by RGX-DYS1 Vector Skeletal muscle stem cells, or satellite cells (SCs), are normally quiescent and located between the basal lamina and sarcolemma of the myofiber. During growth and after muscle damage, a myogenic program of SCs is activated, and SCs self-renew to maintain their pool and/or differentiate to form myoblasts and eventually myofibers. Adeno-associated viral (AAV) vectors are well-known for transduction of differentiated myofibers, so we investigated whether satellite cells could be transduced by AAV vectors. Satellite cells are small with very little cytoplasm, so it is technically challenging to study transgene expression in these cells. Here, we applied RNAscope to investigate whether AAV could transduce satellite cells. RNAscope is a cutting-edge in situ hybridization (ISH) technology that enables simultaneous signal amplification and background noise suppression, which allows for the visualization of single molecule gene expression directly in intact tissue with single cell resolution. RNAscope multiplex fluorescent analysis was utilized with AAV μ-dystrophin probe labelled with fluorophore, Opal 570, and muscle satellite cell marker, pax7, labelled with fluorophore, Opal 520. The RNAscope multiplex fluorescent analysis of AAV transgene and Pax7 mRNA expression was performed at Advanced Cell Diagnostics Inc (Newark, CA). Total RNA was extracted from skeletal muscles using RNeasy® Fibrous Tissue Mini Kit (Qiagen Cat. No. 74704), and cDNA was synthesized with High-Capacity cDNA Reverse Transcription Kit with RNase Inhibitor (Applied Biosystems Cat. No. 4374966). The absolute copy numbers of μ-dystrophin mRNA and endogenous control GAPDH mRNA were measured using digital PCR (Naica Crystal Digital PCR system, Stilla technologies). The primers and probe against μ-dystrophin was the same as previously described. The mouse pax7 primers and probe set (TaqMan™ MGB Probe, Applied Biosystems Cat. No. 4316034) was bought commercially.

Figures 21A, 21B:
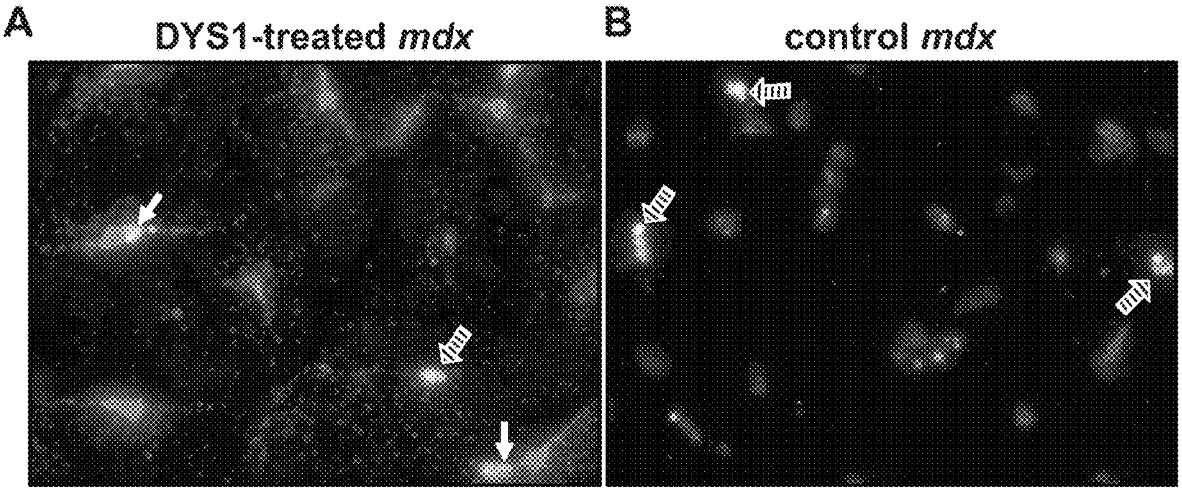
Figure 21C:
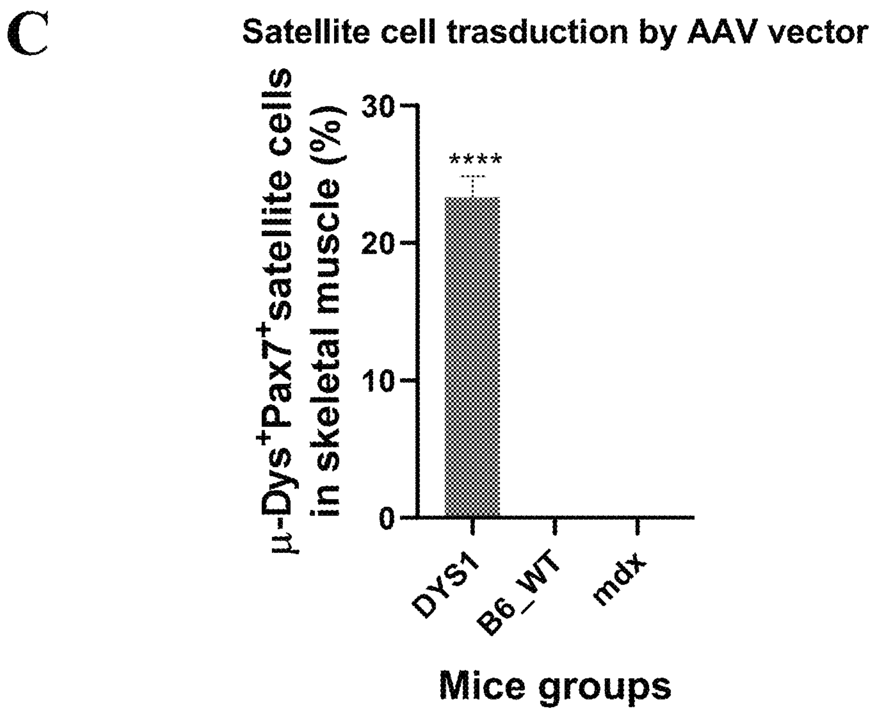

As shown in FIGS. 21A-B, staining indicated u-dystrophin signal (either mRNA expression or the presence of AAV genome), and pax7+ satellite cells. DAPI staining (FIGS. 21A-B) indicated nucleus staining. The colocalization of pax7+, μ-dystrophin, and DAPI (white arrows) represented AAV-DMD vector transduction of muscle satellite cells, while pax7+ and DAPI only cells (white arrow with black lines) indicated satellite cells without AAV transduction. The μ-dystrophin transduced satellite cells were counted, and the satellite cell transduction rate was calculated. In AAV-μ-dys transduced skeletal muscles, the transduction rate of satellite cells was 23±1.5% (FIG. 21C). This indicated AAV vector was able to transduce muscle satellite cells although at much lower transduction rate than mature myofibers.

Figure 21D:
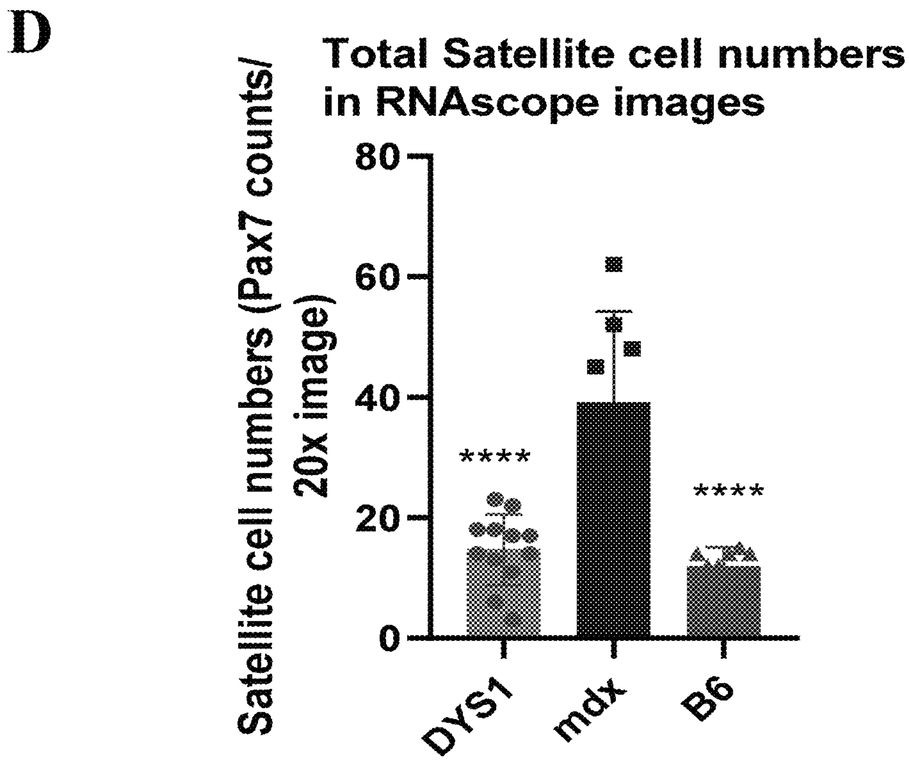

Total pax7+ satellite cell numbers were then counted in the RNAscope images to investigate whether the numbers of satellite cells were similar in the different treatment groups. As shown in FIG. 21D, pax7 positive cell counts per image in the untreated mdx was 39.12±15.14, and the positive cell counts in the wild-type B6 mice and DMD vector treated mice were 11.87±3.23 (8 images were counted, $p<0.0001$ by one way ANOVA) and 14.66±5.91 (12 images were counted, $p<0.0001$ by one way ANOVA), respectively. The increase of satellite cell numbers in the untreated mdx muscle indicated the regenerative nature of muscular dystrophic muscle. Delivery of μ-dystrophin with the RGX-DYS1 vector reversed this pathology and alleviated muscle regeneration.

Figure 21E:
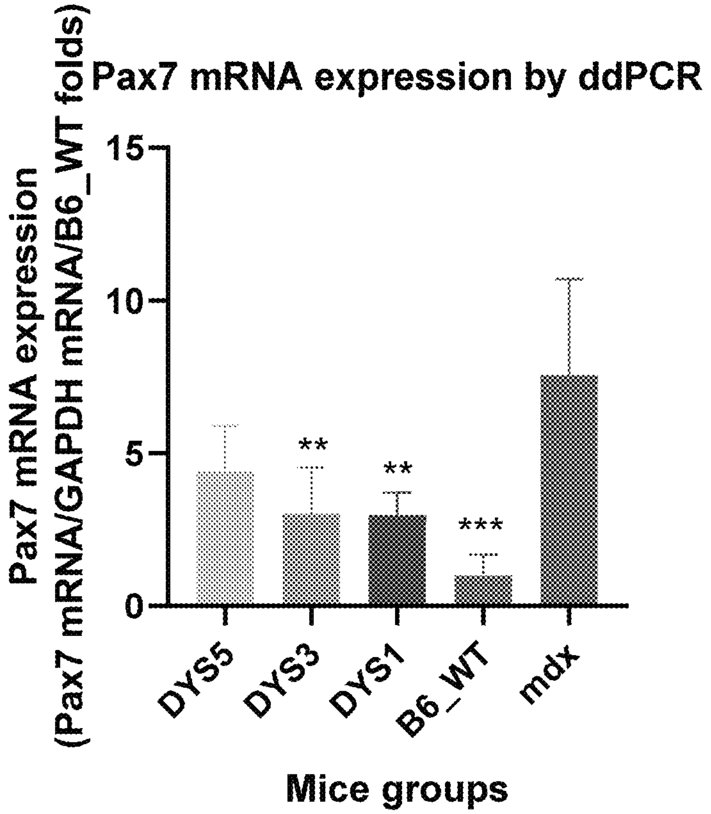

In addition to RNAscope technology analysis, we extracted total muscle RNA and performed cDNA synthesis. Total RNA was extracted from skeletal muscles using RNeasy® Fibrous Tissue Mini Kit (Qiagen Cat. No. 74704), and cDNA was synthesized with High-Capacity cDNA Reverse Transcription Kit with RNase Inhibitor (Applied Biosystems Cat. No. 4374966). The samples were subjected to ddPCR analysis using mouse pax7 specific primers and probe sets (available commercially: mm01354484_m1 Pax7, Thermo Fisher Scientific; and TaqMan™ MGB Probe from Applied Biosystems Cat. No. 4316034, respectively). The mouse GAPDH primers and probe set were used to normalize the RNA and cDNA input. The absolute copy numbers of μ-dystrophin mRNA and endogenous control GAPDH mRNA were measured using digital PCR (Naica Crystal Digital PCR system, Stilla technologies). The ratio of pax7 mRNA copy numbers to GAPDH mRNA copy numbers were compared among groups (FIG. 21E). As expected, the relative expression of pax7 expression in mdx mice was 7.56±3.14, which was much higher than the WT-B6 mice (1±0.68, n=5, $p<0.001$ by one-way ANOVA). The relative pax7 expression in three different μ-dystrophin vector-treated groups were much reduced (4.40±1.50 for RGX-DYS5 (n=3, p=0.06), 3.12±0.74 for RGX-DYS3 group (n=5, $p<0.01$), 2.98±0.68 for RGX-DYS1 (n=5, $p<0.01$). The reduction of pax7 mRNA expression by ddPCR method was consistent with the RNAscope technology finding, further proving one of the therapeutic mechanisms mediated by the present μ-dystrophin vectors in muscular dystrophic muscle was through amelioration of muscle regeneration.

6.9 Example 9—Construction of Additional Microdystrophin (DMD) Gene Expression Cassettes To potentially further improve the function of μ-dystrophin and decrease the overall transgene size (kB), several additional μ-dystrophin constructs were recombinantly engineered (FIG. 22). For RGX-DYS6 (SEQ ID NO: 91), approx. 50 amino acids in the cysteine-rich (CR short, SEQ ID NO: 90) domain were removed to reduce AAV genome size for efficient packaging. For RGX-DYS7 (SEQ ID NO: 92), the nNOS-anchoring spectrin repeat domains R16 and R17 (SEQ ID NO: 86 and 87) were inserted between R2 and R24 region using the previous constructs as a scaffold for recombinant engineering. RGX-DYS8 (SEQ ID NO: 93) is similar to RGX-DYS7 in that the nNOS-anchoring domains R16 and R17 were inserted but the C-terminal domain (CT) was removed to reduce the size of AAV vector.

All μ-dystrophin Cis plasmids were packaged into AAV8 vectors, and the vectors ($2\times10^5$ gc/cell) were infected on differentiated C2C12 myotubes as described in Section 6.2 (Example 2). Five days after infection, the cells were harvested and subjected to western blot analysis using anti-dystrophin primary antibody (MANEX1011B(1C7) as described herein to detect μ-dystrophin protein. All methods used are analogous to those describe in Section 6.7 (Example 7). As shown in FIG. 23A, AAV vector carrying different versions of μ-dystrophin generated different lengths of μ-dystrophin proteins and their sizes migrated as expected. Two noteworthy observations: 1) In general, the longer versions of μ-dystrophin proteins had stronger bands (FIGS. 23A-B). The μ-dystrophin mRNA expression level examined by ddPCR (FIG. 23C) did not correlate with the protein expression level, indicating the stronger bands generated by longer version of μ-dystrophin was not due to increased mRNA expression, rather likely because of the increased stability of the protein. 2) μ-dystrophin RGX-DYS6 was particularly not stable as compared with others. We reasoned that the deletion of the 50 amino acids in the CR domain might affect the stability of μ-dystrophin.

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties.

The discussion herein provides a better understanding of the nature of the problems confronting the art and should not be construed in any way as an admission as to prior art nor should the citation of any reference herein be construed as an admission that such reference constitutes "prior art" to the instant application.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of treating a dystrophinopathy in a human subject in need thereof, the method comprising:

administering to the subject a therapeutically effective amount of a pharmaceutical composition comprising a recombinant adeno-associated virus (rAAV) particle, wherein the rAAV particle comprises a) a nucleic acid comprising a nucleotide sequence encoding a microdystrophin protein comprising an amino acid sequence at least 97% identical to the amino acid sequence of SEQ ID NO: 79, or the reverse complement of the nucleotide sequence, wherein the microdystrophin protein comprises an H3 domain and a C-terminal (CT) domain, wherein the CT domain comprises an α1-syntrophin binding site, and b) a capsid comprising a capsid protein, wherein the administration results in delivery of a microdystrophin protein to the muscle of the subject.

2. The method of claim 1, wherein the nucleotide sequence encoding the microdystrophin protein a nucleotide sequence at least 85% identical to the nucleotide sequence of SEQ ID NO: 81, or the reverse complement thereof.

3. The method of claim 1, wherein the nucleic acid comprises a transcription regulatory element that promotes expression in muscle, wherein the transcription regulatory element is operably linked to the nucleotide sequence encoding the microdystrophin protein.

4. The method of claim 3, wherein the transcription regulatory element is a SPc5-12 promoter or a transcriptionally active portion thereof.

5. The method of claim 3, wherein the nucleic acid comprises a nucleotide sequence comprising from 5' to 3':

a first adeno-associated virus (AAV) inverted terminal repeat (ITR) sequence—the transcription regulatory element sequence—the nucleotide sequence encoding the microdystrophin protein-a polyadenylation sequence-a second AAV ITR sequence.

6. The method of claim 5, wherein the AAV ITR sequence is an AAV2 ITR sequence.

7. The method of claim 1, wherein the capsid protein comprises a) an amino acid sequence that is at least 95% identical to SEQ ID NO: 77, b) the amino acid sequence of SEQ ID NO: 77, c) an amino acid sequence that is at least 95% identical to SEQ ID NO: 78, or d) the amino acid sequence of SEQ ID NO: 78.

8. The method of claim 7, wherein the capsid protein comprises the amino acid sequence of SEQ ID NO: 77.

9. The method of claim 1, wherein the dystrophinopathy is Duchenne muscular dystrophy (DMD), Becker muscular dystrophy (BMD), X-linked dilated cardiomyopathy, or wherein the subject is a female carrier of DMD or BMD.

10. A method of treating a dystrophinopathy in a human subject in need thereof, the method comprising:

administering to the subject a therapeutically effective amount of a pharmaceutical composition comprising an rAAV particle, wherein the rAAV particle comprises a) a nucleic acid comprising a nucleotide sequence encoding a microdystrophin protein comprising an amino acid sequence at least 97% identical to the amino acid sequence of SEQ ID NO: 1, or the reverse complement of the nucleotide sequence, wherein the microdystrophin protein comprises an H3 domain and a C-terminal (CT) domain, wherein the CT domain comprises an α1-syntrophin binding site, and b) a capsid comprising a capsid protein, wherein the administration results in delivery of a microdystrophin protein to the muscle of the subject.

11. The method of claim 10, wherein the nucleotide sequence encoding the microdystrophin protein comprises a nucleotide sequence at least 85% identical to the nucleotide sequence of SEQ ID NO: 20, or the reverse complement thereof.

12. The method of claim 10, wherein the nucleic acid comprises a transcription regulatory element that promotes expression in muscle, wherein the transcription regulatory element is operably linked to the nucleotide sequence encoding the microdystrophin protein.

13. The method of claim 12, wherein the transcription regulatory element is a SPc5-12 promoter or a transcriptionally active portion thereof.

14. The method of claim 12, wherein the nucleic acid comprises a nucleotide sequence comprising from 5' to 3':

a first adeno-associated virus (AAV) inverted terminal repeat (ITR) sequence—the transcription regulatory element sequence—the nucleotide sequence encoding the microdystrophin protein—a polyadenylation sequence—a second AAV ITR sequence.

15. The method of claim 14, wherein the AAV ITR sequence is an AAV2 ITR sequence.

16. The method of claim 10, wherein the capsid protein comprises a) an amino acid sequence that is at least 95% identical to SEQ ID NO: 77, b) the amino acid sequence of SEQ ID NO: 77, c) an amino acid sequence that is at least 95% identical to SEQ ID NO: 78, or d) the amino acid sequence of SEQ ID NO: 78.

17. The method of claim 16, wherein the capsid protein comprises the amino acid sequence of SEQ ID NO: 77.

18. The method of claim 10, wherein the dystrophinopathy is Duchenne muscular dystrophy (DMD), Becker muscular dystrophy (BMD), X-linked dilated cardiomyopathy, or wherein the subject is a female carrier of DMD or BMD.

19. A method of delivering a nucleic acid encoding a microdystrophin protein to a cell, the method comprising contacting the cell with an rAAV particle comprising the nucleic acid encoding the microdystrophin protein, wherein the microdystrophin protein comprises an amino acid sequence at least 97% identical to the amino acid sequence of SEQ ID NO: 79, wherein the microdystrophin protein comprises an H3 domain and a C-terminal (CT) domain, wherein the CT domain comprises an α1-syntrophin binding site, and wherein the nucleic acid encoding the microdystrophin protein is delivered to the cell.

20. A method of delivering a nucleic acid encoding a microdystrophin protein to a cell, the method comprising contacting the cell with an rAAV particle comprising the nucleic acid encoding the microdystrophin protein, wherein the microdystrophin protein comprises an amino acid sequence at least 97% identical to the amino acid sequence of SEQ ID NO: 1, wherein the microdystrophin protein comprises an H3 domain and a C-terminal (CT) domain, wherein the CT domain comprises an α1-syntrophin binding site, —and wherein the nucleic acid encoding the microdystrophin protein is delivered to the cell.

21. The method of claim 5, wherein the transcription regulatory element is SPc5-12, the AAV ITR sequences are AAV2 ITR sequences, and the capsid protein comprises an amino acid sequence of SEQ ID NO: 77.

22. The method of claim 21, wherein the dystrophinopathy is Duchenne muscular dystrophy (DMD), Becker muscular dystrophy (BMD), X-linked dilated cardiomyopathy, or wherein the subject is a female carrier of DMD or BMD.

23. The method of claim 1, wherein the H3 domain is coupled to an R24 domain via a linker L4 (SEQ ID NO: 12).

24. The method of claim 14, wherein the transcription regulatory element is SPc5-12, the AAV ITR sequences are AAV2 ITR sequences, and the capsid protein comprises an amino acid sequence of SEQ ID NO: 77.

25. The method of claim 24, wherein the dystrophinopathy is Duchenne muscular dystrophy (DMD), Becker muscular dystrophy (BMD), X-linked dilated cardiomyopathy, or wherein the subject is a female carrier of DMD or BMD.

26. The method of claim 10, wherein the H3 domain is coupled to an R24 domain via a three amino acid linker.

27. The method of claim 20, wherein the H3 domain is coupled to an R24 domain via a three amino acid linker.

28. The method of claim 1, wherein the H3 domain is coupled to an R24 domain via a linker L4 (SEQ ID NO: 12).

29. The method of claim 10, wherein the H3 domain is coupled to an R24 domain via a linker L4 (SEQ ID NO: 12).

30. The method of claim 20, wherein the H3 domain is coupled to an R24 domain via a linker L4 (SEQ ID NO: 12).

31. A method of treating a dystrophinopathy in a human subject in need thereof, said method comprising:

administering to the subject a therapeutically effective amount of a pharmaceutical composition comprising a recombinant adeno-associated virus (rAAV) particle, wherein the rAAV particle comprises a) a nucleic acid comprising i) a nucleotide sequence encoding a microdystrophin protein comprising the amino acid sequence of SEQ ID NO: 1, and ii) a transcription regulatory element comprising the nucleotide sequence of SEQ ID NO: 39; and b) a capsid comprising a capsid protein, wherein said administration results in delivery of a microdystrophin protein to the muscle of said subject.

32. The method of claim 31, wherein the capsid protein comprises a) an amino acid sequence that is at least 95% identical to SEQ ID NO: 77, b) the amino acid sequence of SEQ ID NO: 77, c) an amino acid sequence that is at least 95% identical to SEQ ID NO: 78, or d) the amino acid sequence of SEQ ID NO: 78.

33. The method of claim 32, wherein the capsid protein comprises the amino acid sequence of SEQ ID NO: 77.

34. The method of claim 32, wherein the dystrophinopathy is Duchenne muscular dystrophy (DMD), Becker muscular dystrophy (BMD), or X-linked dilated cardiomyopathy, or the subject is a female carrier of DMD or BMD.

35. The method of claim 34, wherein the dystrophinopathy is DMD.

36. A method of treating a dystrophinopathy in a human subject in need thereof, said method comprising:

administering to the subject a therapeutically effective amount of a pharmaceutical composition comprising a recombinant adeno-associated virus (rAAV) particle, wherein the rAAV particle comprises a) a nucleic acid comprising from 5' to 3': (i) a first AAV2 ITR comprising the nucleotide sequence of SEQ ID NO: 73, (ii) a SPc5-12 promoter comprising the nucleotide sequence of SEQ ID NO: 39, (iii) a nucleotide sequence encoding a microdystrophin protein comprising the amino acid sequence of SEQ ID NO: 1, (iv) a polyadenylation nucleotide sequence of SEQ ID NO: 42, and (v) a second AAV2 ITR comprising the nucleotide sequence of SEQ ID NO: 74; and b) a capsid comprising a capsid protein, wherein said administration results in delivery of a microdystrophin protein to the muscle of said subject.

37. The method of claim 36, wherein the capsid protein comprises a) an amino acid sequence that is at least 95% identical to SEQ ID NO: 77, b) the amino acid sequence of SEQ ID NO: 77, c) an amino acid sequence that is at least 95% identical to SEQ ID NO: 78, or d) the amino acid sequence of SEQ ID NO: 78.

38. The method of claim 37, wherein the capsid protein comprises the amino acid sequence of SEQ ID NO: 77.

39. The method of claim 37, wherein the dystrophinopathy is Duchenne muscular dystrophy (DMD), Becker muscular dystrophy (BMD), or X-linked dilated cardiomyopathy, or the subject is a female carrier of DMD or BMD.

40. The method of claim 39, wherein the dystrophinopathy is DMD.

41. A method of delivering a nucleic acid encoding a microdystrophin protein to a cell, the method comprising contacting the cell with an rAAV particle comprising the nucleic acid encoding the microdystrophin protein and an SPc5-12 promoter comprising the nucleotide sequence of SEQ ID NO: 39, wherein the microdystrophin protein comprises the amino acid sequence of SEQ ID NO: 1, and wherein the nucleic acid encoding the microdystrophin protein and the SPc5-12 promoter is delivered to the cell.

42. The method of claim 41, wherein the capsid protein comprises a) an amino acid sequence that is at least 95% identical to SEQ ID NO: 77, b) the amino acid sequence of SEQ ID NO: 77, c) an amino acid sequence that is at least 95% identical to SEQ ID NO: 78, or d) the amino acid sequence of SEQ ID NO: 78.

43. The method of claim 42, wherein the capsid protein comprises the amino acid sequence of SEQ ID NO: 77.

44. A method of delivering a nucleic acid encoding a microdystrophin protein to a cell, the method comprising contacting the cell with an rAAV particle wherein the rAAV particle comprises a) the nucleic acid comprising from 5' to 3': (i) a first AAV2 ITR comprising the nucleotide sequence of SEQ ID NO: 73, (ii) a SPc5-12 promoter comprising the nucleotide sequence of SEQ ID NO: 39, (iii) a nucleotide sequence encoding a microdystrophin protein comprising the amino acid sequence of SEQ ID NO: 1, (iv) a polyadenylation nucleotide sequence of SEQ ID NO: 42, and (v) a second AAV2 ITR comprising the nucleotide sequence of SEQ ID NO: 74 and b) a capsid comprising a capsid protein, wherein the nucleic acid encoding the microdystrophin protein is delivered to the cell.

45. The method of claim 44, wherein the capsid protein comprises a) an amino acid sequence that is at least 95% identical to SEQ ID NO: 77, b) the amino acid sequence of SEQ ID NO: 77, c) an amino acid sequence that is at least 95% identical to SEQ ID NO: 78, or d) the amino acid sequence of SEQ ID NO: 78.

46. The method of claim 44, wherein the capsid protein comprises the amino acid sequence of SEQ ID NO: 77.

* * * * *